United States Patent
Xia et al.

(10) Patent No.: US 10,828,305 B2
(45) Date of Patent: Nov. 10, 2020

(54) NITROGENOUS HETEROCYCLIC COMPOUND, PREPARATION METHOD, INTERMEDIATE, COMPOSITION AND USE

(71) Applicant: SHANGHAI PHARMACEUTICALS HOLDING CO., LTD., Shanghai (CN)

(72) Inventors: Guangxin Xia, Shanghai (CN); Di Li, Shanghai (CN); Hongjian Zuo, Shanghai (CN); Guangsheng Wu, Shanghai (CN); Lingjun Duan, Shanghai (CN); Jing Zhang, Shanghai (CN); Yu Mao, Shanghai (CN); Yanjun Liu, Shanghai (CN)

(73) Assignee: Shanghai Pharmaceuticals Holding Co., Ltd., Shanghai (CN)

( * ) Notice: Subject to any disclaimer, the term of this patent is extended or adjusted under 35 U.S.C. 154(b) by 0 days.

(21) Appl. No.: 16/081,558

(22) PCT Filed: Mar. 1, 2017

(86) PCT No.: PCT/CN2017/075332
§ 371 (c)(1),
(2) Date: Aug. 31, 2018

(87) PCT Pub. No.: WO2017/148391
PCT Pub. Date: Sep. 8, 2017

(65) Prior Publication Data
US 2019/0091226 A1     Mar. 28, 2019

(30) Foreign Application Priority Data
Mar. 1, 2016    (CN) .......................... 2016 1 0116045

(51) Int. Cl.
| | |
|---|---|
| A61K 31/519 | (2006.01) |
| A61K 31/5377 | (2006.01) |
| C07D 487/04 | (2006.01) |
| A61P 35/00 | (2006.01) |
| A61K 31/5355 | (2006.01) |
| A61K 31/541 | (2006.01) |

(52) U.S. Cl.
CPC ........ *A61K 31/519* (2013.01); *A61K 31/5355* (2013.01); *A61K 31/5377* (2013.01); *A61K 31/541* (2013.01); *A61P 35/00* (2018.01); *C07D 487/04* (2013.01); *Y02P 20/55* (2015.11)

(58) Field of Classification Search
CPC ........................... A61K 31/519; C07D 487/04
USPC ........................................ 514/259.1; 544/263
See application file for complete search history.

(56) References Cited

U.S. PATENT DOCUMENTS

| | | | |
|---|---|---|---|
| 6,828,320 B2 | 12/2004 | Cockerill et al. | |
| 6,890,924 B2 | 5/2005 | Kath et al. | |
| 7,332,493 B2 | 2/2008 | Kath et al. | |
| 7,713,973 B2 * | 5/2010 | Dong | C07D 487/04 514/243 |
| 2003/0149056 A1 | 8/2003 | Wissner et al. | |
| 2005/0159435 A1 | 7/2005 | Kath et al. | |
| 2008/0319011 A1 | 12/2008 | Wissner et al. | |

FOREIGN PATENT DOCUMENTS

| | | |
|---|---|---|
| CA | 2413424 A1 | 12/2001 |
| CA | 2467573 A1 | 6/2003 |
| CN | 1659145 A | 8/2005 |
| CN | 101348467 A | 1/2009 |
| CN | 103965202 B | 1/2016 |
| CN | 107141293 A | 9/2017 |
| EP | 3424928 A1 | 1/2019 |
| JP | 2004501139 A | 1/2004 |
| JP | 2005514384 A | 5/2005 |

(Continued)

OTHER PUBLICATIONS

Registry (STN) [online], Jan. 12, 2014, CAS Registration No. 1517629-03-6.
Registry (STN) [online], Jan. 8, 2014, CAS Registration No. 1514655-62-9.
Registry (STN) [online], Jan. 6, 2014, CAS Registration No. 1512520-03-4.
Notice of Reasons for Refusal and Search Report issued in Japanese patent application No. 2018-545994 dated Jun. 25, 2019.

(Continued)

*Primary Examiner* — Jeffrey H Murray
(74) *Attorney, Agent, or Firm* — Piloff Passino & Cosenza LLP; Sean A. Passino; Rachel K. Piloff

(57) ABSTRACT

Disclosed are a nitrogenous heterocyclic compound, intermediates, a preparation method, a composition and use thereof. The nitrogenous heterocyclic compound in the present invention is as shown in formula I. The compound has a high inhibitory activity towards ErbB2 tyrosine kinase and a relatively good inhibitory activity towards human breast cancer BT-474 and human gastric cancer cell NCI-N87 which express ErbB2 at a high level, and at the same time has a relatively weak inhibitory activity towards EGFR kinase. Namely, the compound is a highly selective small-molecule inhibitor targeted at ErbB2, and hence it has a high degree of safety, and can effectively enlarge the safety window in the process of taking the drug.

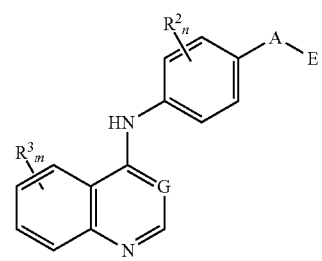

17 Claims, No Drawings

(56) References Cited

FOREIGN PATENT DOCUMENTS

| JP | 2009515988 A | 4/2009 |
|---|---|---|
| WO | 03050090 A1 | 6/2003 |
| WO | 2005028443 A2 | 3/2005 |
| WO | 2007059257 A2 | 5/2007 |
| WO | 2013056108 A2 | 4/2013 |
| WO | 0198277 A2 | 6/2019 |

OTHER PUBLICATIONS

Extended European search report issued in European patent application No. 17759242.5 dated Sep. 5, 2019.
Priority Application—Chinese patent application CN 201610116045.4, filed Mar. 1, 2016 (Not published).
International Search Report and Written Opinion for PCT/CN2017/075332, dated Jun. 8, 2017.

* cited by examiner

NITROGENOUS HETEROCYCLIC COMPOUND, PREPARATION METHOD, INTERMEDIATE, COMPOSITION AND USE

The present application claims the benefit of the Chinese Patent Application No. CN201610116045.4 filed on Mar. 1, 2016, the content of which is incorporated herein by reference in its entirety.

FIELD OF INVENTION

The present invention relates to a nitrogenous heterocyclic compound, an intermediate, a preparation method, a composition and a use thereof.

PRIOR ARTS

The epidermal growth factor receptor (EGFR, also known as ErbB or HER) family includes four receptor tyrosine kinases: EGFR (ErbB1 or HER1), ErbB2 (HER2), ErbB3 (HER3) and ErbB4 (HER4). Some researchers have demonstrated the role of EGFR and ErbB2 in the progression of cancer, and the high expression level of EGFR in head, neck, and lung squamous cell carcinoma. ErbB2 overexpression occurs in 30% of all breast cancers and it is also associated with other human cancers such as colon, ovarian, bladder, stomach, esophagus, lung, uterus and prostate cancer. ErbB2 overexpression is also associated with poor prognosis of other cancers, including metastasis and early recurrence.

The epidermal growth factor receptor family has become an active field of anticancer research, for example, U.S. Pat. No. 6,828,320 disclosed some substituted quinoline and, quinazoline compounds as protein tyrosine kinase inhibitors. In 1998, Herceptin (a humanized anti-ErbB2 monoclonal antibody) was approved for breast cancer in the United States. The small molecule EGFR inhibitors such as Iressa, Itaiwa, Tekpo have been approved for market. Currently, ErbB2 has become a therapeutic target for breast cancer and gastric/esophageal cancer, and other studies have shown that ErbB2 is a potential therapeutic target for ovarian cancer. Meanwhile, there are ongoing trials on single or combined treatment of several new ErbB2-targeted drugs, which are expected to bring about new changes for ErbB2-targeted therapy in the near future.

The treatment for ErbB2-positive breast cancer is still mainly based on antibody therapy, there are still no very effective small molecule inhibitors (although lapatinib has been approved for market earlier, its efficacy is not satisfactory). Since the ErbB2 inhibitors which have been on the market or are currently under research usually have inhibitory activity on EGFR at the same time, they may produce some toxic side effects associated with the target: gastrointestinal toxic side effects such as diarrhea, skin-related toxic side effects such as rashes. These toxic side effects have been detection value in clinical trials of cetuximab, gefitinib, erlotinib, lapatinib and neratinib, which are generally thought to be triggered by inhibition of EGFR activity. Reducing the inhibitory activity of the compound on EGFR and improving the selectivity of the compound on ErbB2 can effectively alleviate the aforementioned toxic side effects.

Therefore, there is a need for a selective small molecule inhibitor of ErbB2 in the art.

CONTENT OF THE PRESENT INVENTION

The technical problem to be solved in the present invention is to cure the defects of the existing compounds such as poor selectivity, various toxic side effects and low safety. Thus, the present invention provides a nitrogenous heterocyclic compound, an intermediate, a preparation method, a composition and a use thereof. These compounds exhibit a high inhibitory activity against ErbB2 tyrosine kinase and a relatively good inhibitory activity against human breast cancer BT-474 and human gastric cancer cell NCI-N87 which express ErbB2 at a high level, and exhibit a relatively weak inhibitory activity against EGFR kinase at the same time, that is, these compounds are highly selective small-molecule inhibitors targeted ErbB2, and hence they have a high degree of safety, and can effectively enlarge the safety window during drug administration.

The present invention provides a nitrogenous heterocyclic compound represented by formula I, a pharmaceutically acceptable salt, an enantiomer, a diastereomer, a tautomer, a solvate, a metabolite or a prodrug thereof;

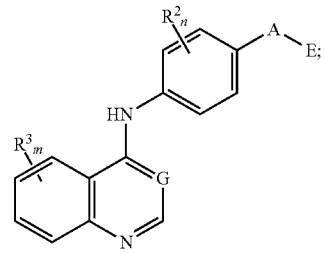

wherein, A is —O—, —S—, —C(=O)—, —SO— or —SO$_2$—;

G is N or C—CN;

E is

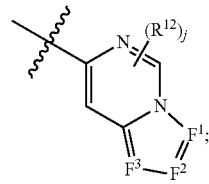

in the definition of E, F$^1$, F$^2$ and F$^3$ are independently N or CR$^{19}$;

in the definition of E, j is 0, 1 or 2 (when j is 1, E is

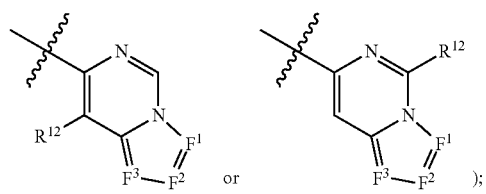

in the definition of E, each R$^{12}$ is independently selected from the group consisting of halogen (e.g. fluorine, chlorine, bromine or iodine), cyano, nitro, haloalkyl (the halogen comprised in the "haloalkyl" is, for example, fluorine, chlorine or bromine; the number of halogen can be one or more than one; the alkyl comprised in the "haloalkyl" is preferably C$_1$-C$_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen comprised in the "haloalkoxy" is, for example, fluorine, chlorine or bromine; the number of halogen can be one or more than one; the alkoxy comprised in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, $-SR^{18}$, $-OR^{15}$, $-C(=O)R^{15}$, $-C(=O)OR^{15}$, $-NR^{15}C(=O)OR^{18}$, $-OC(=O)R^{15}$, $-OC(=O)NR^{15}R^{13}$, $-NR^{15}SO_2R^{18}$, $-SO_2NR^{15}R^{14}$, $-NR^{14}C(=O)R^{15}$, $-C(=O)NR^{15}R^{14}$, $-NR^{14}C(=O)NR^{15}R^{13}$, $-NR^{14}SO_2NR^{15}R^{13}$, $-NR^{14}C(=N-CN)NR^{15}R^{13}$, $-NR^{15}R^{14}$, alkyl (e.g. $C_1$-$C_6$ alkyl, e.g. $C_1$-$C_4$ alkyl, e.g. methyl or ethyl), alkenyl, alkynyl, saturated or partially unsaturated cycloalkyl, cycloalkylalkyl, $-S(=O)_p$(alkyl), $-S(=O)_p(CR^{13}R^{14})_q$-aryl, aryl, arylalkyl, heteroaryl, heteroarylalkyl, saturated or partially unsaturated heterocyclyl, heterocyclylalkyl, $-O(CR^{13}R^{14})_q$-aryl, $-NR^{15}(CR^{13}R^{14})_q$-aryl, $-O(CR^{13}R^{14})_q$-heteroaryl, $-NR^{15}(CR^{13}R^{14})_q$-heteroaryl, $-O(CR^{13}R^{14})_q$-heterocyclyl and $-NR^{15}(CR^{13}R^{14})_q$-heterocyclyl;

in the definition of $R^{12}$, the alkyl, alkenyl, alkynyl, cycloalkyl, aryl, arylalkyl, heteroaryl, heteroarylalkyl, heterocyclyl and heterocyclylalkyl can be independently substituted with the substituent selected from the group consisting of oxo, halogen, cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_4$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, $-NR^{15}SO_2R^{18}$, $-SO_2NR^{15}R^{13}$, $-C(=O)R^{15}$, $-C(=O)OR^{15}$, $-OC(=O)R^{15}$, $-OC(=O)NR^{15}R^{13}$, $-NR^{15}C(=O)OR^{18}$, $-NR^{13}C(=O)R^{15}$, $-C(=O)NR^{15}R^{13}$, $-NR^{15}R^{13}$, $-NR^{14}C(=O)NR^{15}R^{13}$, $-NR^{14}SO_2NR^{15}R^{13}$, $-NR^{14}C(=N-CN)NR^{15}R^{13}$, $-OR^{15}$, aryl, heteroaryl, arylalkyl, heteroarylalkyl, saturated or partially unsaturated heterocyclyl, and heterocyclylalkyl, when there are more than one substituents, the substituents are the same or different; wherein the aryl, heteroaryl, arylalkyl, heteroarylalkyl, heterocyclyl or heterocyclylalkyl can be independently substituted with the substituent selected from the group consisting of halogen, hydroxy, cyano, nitro, azido, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), alkyl, alkenyl, alkynyl, saturated or partially unsaturated cycloalkyl, saturated or partially unsaturated heterocyclyl, $-NR^{15}R^{13}$ and $-OR^{15}$, when there are more than one substituents, the substituents are the same or different:

in the definition of E, each $R^{19}$ is independently selected from the group consisting of H, halogen, cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, $-SR^{18}$, $-OR^{15}$, $-C(=O)R^{15}$, $-C(=O)OR^{15}$, $-NR^{15}C(=O)OR^{18}$, $-OC(=O)R^{15}$, $-OC(=O)NR^{15}R^{13}$, $-NR^{15}SO_2R^{18}$, $-SO_2NR^{15}R^{14}$, $-NR^{14}C(=O)R^{15}$, $-C(=O)NR^{15}R^{14}$, $-NR^{14}C(=O)NR^{15}R^{13}$, $-NR^{14}SO_2NR^{15}R^{13}$, $-NR^{14}C(=N-CN)NR^{15}R^{13}$, $-NR^{15}R^{14}$, alkyl, alkenyl, alkynyl, saturated or partially unsaturated cycloalkyl, cycloalkylalkyl, $-S(O)_p$(alkyl), $-S(O)_p(CR^{13}R^{14})_q$-aryl, aryl, arylalkyl, heteroaryl, heteroarylalkyl, saturated or partially unsaturated heterocyclyl, heterocyclylalkyl, $-O(CR^{13}R^{14})_q$-aryl, $-NR^{15}(CR^{13}R^{14})_q$-aryl, $-O(CR^{13}R^{14})_q$-heteroaryl, $-NR^{15}(CR^{13}R^{14})_q$-heteroaryl, $-O(CR^{13}R^{14})_q$-heterocyclyl and $-NR^{15}(CR^{13}R^{14})_q$-heterocyclyl;

in the definition of $R^{19}$, the alkyl, alkenyl, alkynyl, cycloalkyl, aryl, arylalkyl, heteroaryl, heteroarylalkyl, heterocyclyl, and heterocyclylalkyl can be independently substituted with the substituent selected from the group consisting of oxo, halogen, cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, $-NR^{15}SO_2R^{18}$, $-SO_2NR^{15}R^{13}$, $-C(=O)R^{15}$, $-C(=O)OR^{15}$, $-OC(=O)R^{15}$, $-OC(=O)NR^{15}R^{13}$, $-NR^{15}C(=O)OR^{18}$, $-NR^{13}C(=O)R^{15}$, $-C(=O)NR^{15}R^{13}$, $-NR^{15}R^{13}$, $-NR^{14}C(=O)NR^{15}R^{13}$, $-NR^{14}SO_2NR^{15}R^{13}$, $-NR^{14}C(=N-CN)NR^{15}R^{13}$, $-OR^{15}$, aryl, heteroaryl, arylalkyl, heteroarylalkyl, saturated or partially unsaturated heterocyclyl, and heterocyclylalkyl, when there are more than one substituents, the substituents are the same or different; wherein the aryl, heteroaryl, arylalkyl, heteroarylalkyl, heterocyclyl or heterocyclylalkyl can be further independently substituted with the substituent selected from the group consisting of halogen, hydroxy, cyano, nitro, azido, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), alkyl, alkenyl, alkynyl, saturated or partially unsaturated cycloalkyl, saturated or partially unsaturated heterocyclyl, $-NR^{15}R^{13}$ and $-OR^{15}$, when there are more than one substituents, the substituents are the same or different:

each $R^2$ is independently selected from the group consisting of halogen (e.g. fluorine, chlorine, bromine or iodine), cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, —$SR^{18}$, —OBIS, —C(=O)$R^{15}$, —C(=O)O$R^{15}$, —$NR^{15}$C(=O)O$R^{18}$, —OC(=O)$R^{15}$, —OC(=O)$NR^{15}R^{13}$, —$NR^{15}SO_2R^{18}$, —$SO_2NR^{15}R^{1a}$, —$NR^{14}$C(=O)$R^{15}$, —C(=O)$NR^{15}R^{14}$, —$NR^{14}$C(=O)$NR^{15}R^{13}$, —$NR^{14}SO_2NR^{15}R^{13}$, —$NR^{1a}$C(=N—CN)$NR^{15}R^{13}$, —$NR^{15}R^{14}$, alkyl (e.g. $C_1$-$C_6$ alkyl; the "$C_1$-$C_6$ alkyl" such as $C_1$-$C_4$ alkyl; the "$C_1$-$C_4$ alkyl" such as methyl or ethyl), alkenyl, alkynyl, saturated or partially unsaturated cycloalkyl, cycloalkylalkyl, —S(O)$_p$(alkyl), —S(O)$_p$(C$R^{13}R^{14}$)$_q$-aryl, aryl, arylalkyl, heteroaryl, heteroarylalkyl, saturated or partially unsaturated heterocyclyl, heterocyclylalkyl, —O(C$R^{13}R^{14}$)$_q$-aryl, —$NR^{15}$(C$R^{13}R^{14}$)$_q$-aryl, —O(C$R^{13}R^{14}$)$_q$-heteroaryl, —$NR^{15}$(C$R^{13}R^{14}$)$_q$-heteroaryl, —O(C$R^{13}R^{14}$)$_q$-heterocyclyl and —$NR^{15}$(C$R^{13}R^{14}$)$_q$-heterocyclyl;

in the definition of $R^2$, the alkyl, alkenyl, alkynyl, cycloalkyl, aryl, arylalkyl, heteroaryl, heteroarylalkyl, heterocyclyl, and heterocyclylalkyl can be independently substituted with the substituent selected from the group consisting of oxo, halogen, cyano, nitro, haloalkyl, haloalkoxy, azido, —$NR^{15}SO_2R^{18}$, —$SO_2NR^{15}R^{13}$, —C(=O)$R^{15}$, —C(=O)O$R^{15}$, —OC(=O)$R^{15}$, —OC(=O)$NR^{15}R^{13}$, —$NR^{15}$C(=O)O$R^{18}$, —$NR^{13}$C(=O)$R^{15}$, —C(=O)$NR^{15}R^{13}$, —$NR^{15}R^{13}$, —$NR^{14}$C(=O)$NR^{15}R^{13}$, —$NR^{14}SO_2NR^{15}R^{16}$, —$NR^{14}$C(=N—CN)$NR^{15}R^{13}$, —O$R^{15}$, aryl, heteroaryl, arylalkyl, heteroarylalkyl, saturated and partially unsaturated heterocyclyl, and heterocyclylalkyl, when there are more than one substituents, the substituents are the same or different; wherein the aryl, heteroaryl, arylalkyl, heteroarylalkyl, heterocyclyl or heterocyclylalkyl can be independently substituted with the substituent selected from the group consisting of halogen, hydroxy, cyano, nitro, azido, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), alkyl, alkenyl, alkynyl, saturated and partially unsaturated cycloalkyl, saturated and partially unsaturated heterocyclyl, —$NR^{15}R^{13}$ and —O$R^{15}$, when there are more than one substituents, the substituents are the same or different;

each $R^3$ is independently selected from the group consisting of Z, "5 to 6 membered heterocycle having 1 to 4 heteroatom(s) selected from the group consisting of N, O, S, SO and $SO_2$, substituted with -$M_1$-$M_2$-$M_3$-$M_4$ or -$M_1$-$M_4$" (the 5 to 6 membered heterocycle can be substituted with $C_1$-$C_4$ alkyl; the 5 to 6 membered heterocycle is, for example, pyrrolyl, thienyl or furyl; and for example, 1-methyl-pyrrol-2-yl, pyrrol-2-yl, pyrrol-1-yl, thiophen-2-yl or furan-2-yl), aryl substituted with -$M_1$-$M_2$-$M_3$-$M_4$ or -$M_1$-$M_5$ (the "aryl" is, for example, $C_6$-$C_{10}$ aryl; the $C_6$-$C_{10}$ aryl is, for example, phenyl), —(C$R^{13}R^{14}$)$_s$—C≡C—(C$R^{13}R^{14}$)$_r$$R^{14}$, —(C$R^{13}R^{14}$)$_s$—C=C—(C$R^{13}R^{14}$)$_r$—$R^{14}$, —(C$R^{13}R^{14}$)$_s$—C=C—(C$R^{13}R^{14}$)$_k$—$R^5$, (C$R^{13}R^{14}$)$_s$—C≡C—(C$R^{13}R^{14}$)$_k$—$R^5$, halogen (e.g. fluorine, chlorine, bromine or iodine), cyano, nitro, alkyl, alkenyl (e.g. $C_2$-$C_6$ alkenyl; the $C_2$-$C_6$ alkenyl is, for example, vinyl), alkynyl, heteroalkyl, heteroalkenyl, heteroalkynyl, saturated or partially unsaturated cycloalkyl, saturated or partially unsaturated heterocyclyl (e.g. 5 to 6 membered heterocyclyl having 1 to 2 heteroatom(s) selected from the group consisting of N and O, and e.g. dihydropyridinyl, and e.g. 3,6-dihydropyridin-4(2H)-yl or 5,6-dihydropyridin-4(2H)-yl), cycloalkylalkyl, heterocyclylalkyl, aryl (e.g. $C_6$-$C_{10}$ aryl; the $C_6$-$C_{10}$ aryl is, for example, phenyl), arylalkyl, heteroaryl (e.g. 5 to 6 membered heteroaryl having 1 to 2 heteroatom(s) selected from the group consisting of N and O, and e.g. isoxazolyl, pyridazinyl, pyrrolyl, furyl or pyridinyl, and e.g. isoxazol-5-yl, pyridazin-3-yl, pyrrol-1-yl, pyrrol-3-yl, furan-2-yl, furan-3-yl, pyridin-4-yl or pyridin-3-yl), heteroarylalkyl, haloalkyl, haloalkoxy, —O$R^{15}$, —$NR^{15}R^{16}$, —$NR^{15}OR^{16}$, —$NR^{15}$C(=O)O$R^{18}$, —$NR^{15}$C(=O)S$R^{18}$, —$NR^{15}$C(=O)$R^{16}$, —$NR^{15}SO_2R^{18}$, —$SO_2NR^{15}R^{16}$, —S$R^{15}$, —$SO_2R^{15}$, —$SO_2R^{15}$, —C(=O)$R^{15}$, —C(=O)O$R^{15}$, —OC(=O)$R^{15}$, —OC(=O)O$R^{15}$, —OS$O_2R^{15}$, —OS$O_2NR^{15}R^{13}$, —OC(=O)$NR^{15}R^{13}$, —C(=O)$NR^{15}R^{16}$, —$NR^{15}$C(=O)$NR^{16}R^{17}$, —$NR^{15}SO_2NR^{16}R^{17}$, —$NR^{15}$C(=S)$NR^{16}R^{17}$, —$NR^{15}$C(=S)$R^{16}$, —$NR^{15}$C(=N—CN)$NR^{16}R^{17}$, —$NR^{15}$C(=N—CN)$R^{16}$, —S(O)$_p$(C$R^{13}R^{14}$)$_q$-aryl, —O(C$R^{13}R^{14}$)$_q$-aryl, —$NR^{15}$(C$R^{13}R^{14}$)$_q$-aryl, —O(C$R^{13}R^{14}$)$_q$-heteroaryl, —$NR^{13}$(C$R^{13}R^{14}$)$_q$-heteroaryl, —O(C$R^{13}R^{14}$)$_q$-heterocyclyl and —$NR^{15}$(C$R^{13}R^{14}$)$_q$-heterocyclyl;

in the definition of $R^3$, the alkyl, alkenyl, alkynyl, heteroalkyl, heteroalkenyl, heteroalkynyl, cycloalkyl, heterocyclyl, aryl, arylalkyl, heteroaryl, heteroarylalkyl can be independently substituted with the substituent selected from the group consisting of halogen (e.g. fluorine, chlorine, bromine or iodine), oxo, cyano, nitro, alkyl (e.g. $C_1$-$C_6$ alkyl; the "$C_1$-$C_6$ alkyl" is, for example, $C_1$-$C_4$ alkyl; the "$C_1$-$C_4$ alkyl" is, for example, methyl or ethyl), alkenyl, alkynyl, aryl, arylalkyl, heteroaryl, heteroarylalkyl, haloalkyl, haloalkoxy, —O$R^{15}$, —$NR^{15}R^{16}$, —$NR^{15}OR^{16}$, —$NR^{15}$C(=O)O$R^{18}$, —$NR^{15}$C(=O)$R^{16}$, —$NR^{15}SO_2R^{18}$, —$SO_2NR^{15}R^{16}$, —S$R^{15}$, —SO$R^{15}$, —$SO_2R^{15}$, —C(=O)$R^{15}$, —C(=O)O$R^{15}$, —OC(=O)$R^{15}$, —OC(=O)O$R^{15}$, —OS$O_2R^{15}$, —OS$O_2NR^{15}R^{13}$, —OC(=O)$NR^{15}R^{13}$, —C(=O)$NR^{15}R^{16}$, —$NR^{15}$C(=O)$NR^{16}R^{17}$, —$NR^{15}SO_2NR^{16}R^{17}$, —$NR^{15}$C(=S)$NR^{16}R^{17}$, —$NR^{15}$C(=S)$R^{16}$, —$NR^{15}$C(=N—CN)$NR^{16}R^{17}$, —$NR^{15}$C(=N—CN)$R^{16}$, —($C_1$-$C_4$ alkyl)$NR^aR^b$ and —$NR^{15}$C(=O)$CH_2OR^a$; when there are more than one substituents, the substituents are the same or different:

in the definition of $R^3$, $M_1$ is $C_1$-$C_4$ alkylene (e.g. —$CH_2$— or —$CH_2CH_2$—), wherein, —$CH_2$— can be replaced with —C(=O)— (e.g. —C(=O)— or —$CH_2$C(=O)—); $M_2$ is $NR^e$—, —O— or —C$R^eR^f$—; $M_3$ is $C_1$-$C_4$ alkylene (e.g. methylene, ethylene or propylene); Ma is —CN, —$NR^eS$(=O)$_{0-2}R^f$, —S(=O)$_{0-2}NR^gR^h$, —C(=O)$NR^gR^h$, —S(=O)$_{0-2}R^f$, —$CO_2R^f$, —P(=O)$R^eR^f$, —$NR^eP$(=O)$R^eR^f$ or —P(=O)$R^f$/$NR^gR^h$; and $M_5$ is —OH or —$NR^gR^h$; wherein, each of $R^e$, $R^f$, $R^g$ and $R^h$ is independently H, $C_1$-$C_6$ alkyl (e.g. $C_1$-$C_4$ alkyl; the $C_1$-$C_4$ alkyl is, for example, methyl or ethyl), $C_3$-$C_6$ cycloalkyl or aryl (e.g. $C_6$-$C_{10}$ aryl, and e.g. phenyl), or, $R^g$ and $R^h$ together with the N atom attached form a 5 to 6 membered heterocyclyl having 1 to 3 heteroatom selected from the group consisting of N, O, S, SO and $SO_2$ (e.g. piperazinyl or

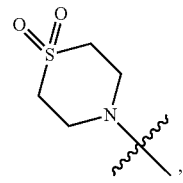 [SMILES: *N1CCS(=O)(=O)CC1]

and e.g. piperazin-1-yl), wherein any nitrogen atom on the ring can be substituted with $C_1$-$C_4$ alkyl (e.g. methyl or ethyl) or —S(=O)$_p$alkyl (e.g. $C_1$-$C_6$ alkyl; the "$C_1$-$C_6$ alkyl" is, for example, methyl or ethyl), and the ring can have one or two oxo or thioxo substituent(s);

in the definition of $R^3$, Z is selected from:

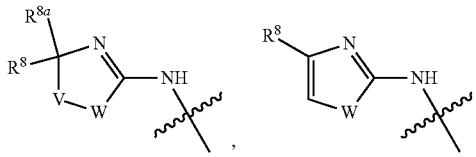

or a tautomer thereof;

in the definition of Z, W and V are independently —O—, —NR$^6$—, —S—, —SO—, —SO$_2$—, —CR$^7$R$^8$—, —CR$^8$R$^9$— or —C(=O)—;

the requirement is that when W is —O—, —NR$^6$—, —S—, —SO— or —SO$_2$—, V is —CR$^7$R$^8$— or —CR$^8$R$^9$—, and when V is —O—, —NR$^6$—, —S—, —SO— or —SO$_2$—, W is —CR$^7$R$^8$— or —CR$^8$R$^9$—;

in the definition of Z, each of $R^8$, $R^{8a}$ and $R^9$ is independently hydrogen, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), alkyl (e.g. $C_1$-$C_6$ alkyl; the "$C_1$-$C_6$ alkyl" is, for example, isopropyl, methyl or ethyl), saturated or partially unsaturated cycloalkyl, cycloalkylalkyl, saturated or partially unsaturated heterocyclyl, aryl, arylalkyl, heteroaryl, heteroarylalkyl, or heterocyclylalkyl;

in the definition of $R^8$, $R^{8a}$ and $R^9$, the alkyl, cycloalkyl, cycloalkylalkyl, heterocyclyl, aryl, arylalkyl, heteroaryl, heteroarylalkyl, and heterocyclylalkyl can be independently substituted with the substituent selected from the group consisting of oxo, halogen, alkyl, alkenyl, alkynyl, saturated or partially unsaturated cycloalkyl, saturated or partially unsaturated heterocyclyl, cycloalkylalkyl, cyano, nitro, —OR$^{15}$, —NR$^{15}$R$^{16}$, —SR$^{15}$, —SOR$^{15}$, —SO$_2$R$^{15}$, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, aryl, heteroaryl, arylalkyl, heteroarylalkyl, and heterocyclylalkyl; when there are more than one substituents, the substituents are the same or different;

in the definition of Z, $R^7$ is selected from the group consisting of hydrogen, halogen, cyano, nitro, alkyl, alkenyl, alkynyl, saturated or partially unsaturated cycloalkyl, saturated or partially unsaturated heterocyclyl, cycloalkylalkyl, aryl, arylalkyl, heteroaryl, heteroarylalkyl, heterocyclylalkyl, —NR$^{15}$SO$_2$R$^{16}$, —SO$_2$NR$^{15}$R$^{16}$, —C(=O)R$^{15}$, —C(=O)OR$^{15}$, —OC(=O)R$^{15}$, —OC(=O)NR$^{15}$R$^{13}$, —NR$^{15}$C(=O)OR$^{18}$, —NR$^{15}$C(=O)R$^{16}$, —C(=O)NR$^{15}$R$^{16}$, —NR$^{15}$R$^{16}$, —NR$^{15}$C(=O)NR$^{16}$R$^{17}$, —OR$^{15}$, —S(=O)R$^{15}$, —SO$_2$R$^{15}$ and —SR$^{15}$;

in the definition of $R^7$, the alkyl, alkenyl, alkynyl, cycloalkyl, heterocyclyl, cycloalkylalkyl, aryl, arylalkyl, heteroaryl, heteroarylalkyl, and heterocyclylalkyl can be independently substituted with the substituent selected from the group consisting of oxo, halogen, alkyl, alkenyl, alkynyl, saturated or partially unsaturated cycloalkyl, saturated or partially unsaturated heterocyclyl, cycloalkylalkyl, cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, —NR$^{15}$SO$_2$R$^{16}$, —SO$_2$NR$^{15}$R$^{16}$, —C(=O)R$^{15}$, —C(=O)OR$^{15}$, —OC(=O)R$^{15}$, —OC(=O)NR$^{15}$R$^{13}$, —NR$^{15}$C(=O)OR$^{18}$, —NR$^{15}$C(=O)R$^{16}$, —C(=O)NR$^{15}$R$^{16}$, —NR$^{15}$R$^{16}$, —NR$^{15}$C(=O)NR$^{16}$R$^{17}$, —OR$^{15}$, —S(=O)R$^{15}$, —SO$_2$R$^{15}$, —SR$^{15}$ aryl, heteroaryl, arylalkyl, heteroarylalkyl, and heterocyclylalkyl, when there are more than one substituents, the substituents are the same or different; or, in the definition of Z, $R^8$ and $R^{8a}$ together with the atom attached form a 3 to 6 membered carbocycle (e.g. cyclopentyl, cyclopropyl or cyclobutyl), or, a 3 to 10 membered saturated or partially unsaturated heterocyclyl (e.g. a 4 to 6 membered heterocyclyl having 1 to 3 heteroatom(s) selected from the group consisting of N, O, S, SO and SO$_2$, and e.g. oxahex-4-yl, piperidin-4-yl or azetidin-3-yl); wherein the carbocycle and heterocyclyl can be independently substituted with the substituent selected from the group consisting of oxo, halogen (e.g. fluorine, chlorine, bromine or iodine), alkyl (e.g. $C_1$-$C_6$ alkyl, and e.g. $C_1$-$C_4$ alkyl, and e.g. methyl or ethyl), alkenyl, alkynyl, saturated or partially unsaturated cycloalkyl, saturated or partially unsaturated heterocyclyl, cycloalkylalkyl, cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, aryl, —C(=O)OR$^{15}$, —C(=O)R$^{15}$, —OR$^{15}$, —NR$^{15}$R$^{16}$, —SR$^{15}$, heteroaryl, arylalkyl, heteroarylalkyl, and heterocyclylalkyl; when there are more than one substituents, the substituents are the same or different;

or, in the definition of Z, $R^7$ and $R^8$ together with the atom attached form a 3 to 10 membered saturated or partially unsaturated cycloalkyl or heterocyclyl; the heterocyclyl can have one or more heteroatom(s) selected from the group consisting of N, O, S, SO, SO$_2$ and NR$^6$, wherein the cycloalkyl and heterocyclyl can be independently substituted with the substituent selected from the group consisting of oxo, halogen, alkyl, alkenyl, alkynyl, saturated or partially unsaturated cycloalkyl, saturated or partially unsaturated heterocyclyl, cycloalkylalkyl, cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, aryl, —$OR^{15}$, —$NR^{15}R^{16}$, —$SR^{15}$, heteroaryl, arylalkyl, heteroarylalkyl, and heterocyclylalkyl; when there are more than one substituents, the substituents are the same or different;

or, in the definition of Z, $R^8$ and $R^9$ together with the atom attached form a 3 to 10 membered saturated or partially unsaturated cycloalkyl (e.g. a 3 to 6 membered saturated or partially unsaturated cycloalkyl, e.g. cyclobutyl) or heterocyclyl (e.g. a 5 to 6 membered heterocyclyl having 1 to 3 heteroatom(s) selected from the group consisting of N, O, S, SO and $SO_2$, e.g. azahex-4-yl, oxahex-4-yl, piperidin-4-yl or azetidin-3-yl); the heterocyclyl can have one or more heteroatom(s) selected from the group consisting of N, O, S, SO, $SO_2$ and $NR^6$, wherein the cycloalkyl and heterocyclyl can be independently substituted with the substituent selected from the group consisting of oxo, halogen, alkyl (e.g. $C_1$-$C_6$ alkyl, e.g. $C_1$-$C_4$ alkyl, e.g. methyl or ethyl), alkenyl, alkynyl, saturated or partially unsaturated cycloalkyl, saturated or partially unsaturated heterocyclyl, cycloalkylalkyl, cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, aryl, —$C(=O)OR^{15}$, —$C(=O)R^{15}$, —$OR^{15}$, —$NR^{15}R^{16}$, —$SR^{15}$, heteroaryl, arylalkyl, heteroarylalkyl, and heterocyclylalkyl; when there are more than one substituents, the substituents are the same or different:

in the definition of $R^3$, each $R^4$ is independently H, alkyl, alkenyl, alkynyl, heteroalkyl, heteroalkenyl, heteroalkynyl, saturated or partially unsaturated cycloalkyl, saturated or partially unsaturated heterocyclyl, aryl, arylalkyl, heteroaryl or heteroarylalkyl; the heterocyclyl can have one or more heteroatom(s) selected from the group consisting of N, O, S, SO, $SO_2$ and $NR^6$;

in the definition of $R^4$, the alkyl, alkenyl, alkynyl, heteroalkyl, heteroalkenyl, heteroalkynyl, cycloalkyl, heterocyclyl, aryl, arylalkyl, heteroaryl, heteroarylalkyl can be independently substituted with the substituent selected from the group consisting of alkyl, alkenyl, alkynyl, saturated or partially unsaturated cycloalkyl, saturated or partially unsaturated heterocyclyl, cycloalkylalkyl, aryl, heteroaryl, arylalkyl, heteroarylalkyl, and heterocyclylalkyl, halogen, cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, oxo, —$OR^{15}$, —$NR^{15}R^{16}$, —$NR^{15}OR^{16}$, —$NR^{15}C(=O)OR^{18}$, —$NR^{15}C(=O)R^{16}$, —$SO_2NR^{15}R^{16}$, —$SR^{15}$, —$SOR^{15}$, —$SO_2R^{15}$, —$C(=O)R^{15}$, —$C(=O)OR^{15}$, —$OC(=O)R^{15}$, —$OC(=O)NR^{15}R^{13}$, —$OC(=O)OR^{15}$, —$OSO_2R^{15}$, —$OSO_2NR^{15}R^{13}$, —$C(=O)NR^{15}R^{16}$, —$NR^{15}C(=O)NR^{16}R^{17}$, —$NR^{15}SO_2R^{18}$, —$NR^{15}SO_2NR^{16}R^{17}$, —$NR^{15}C(=S)NR^{16}R^{17}$, —$NR^{15}C(=S)R^{16}$, —$NR^{15}C(=N—CN)NR^{16}R^{17}$, —$NR^{15}C(=N—CN)R^{16}$, —($C_1$-$C_4$ alkyl)$NR^aR^b$ and —$NR^{15}C(=O)CH_2OR^a$; when there are more than one substituents, the substituents are the same or different;

in the definition of $R^3$, each $R^5$ is independently —$NR^{15}R^{13}$, —$NR^{15}OR^{16}$, —$NR^{15}C(=O)OR^{18}$, —$NR^{15}C(=O)R^{16}$, —$NR^{15}C(=O)NR^{16}R^{17}$, —$NR^{15}SO_2R^{18}$, —$NR^{15}SO_2NR^{16}R^{17}$, —$OR^{15}$, —$OC(=O)R^{15}$, —$OC(=O)OR^{15}$, —$OSO_2R^{15}$, —$OSO_2NR^{15}R^{13}$, —$OC(=O)NR^{15}R^{13}$;

each of $R^{13}$ and $R^{14}$ is independently hydrogen or alkyl (e.g. $C_1$-$C_6$ alkyl, and e.g. $C_1$-$C_4$ alkyl, and e.g. methyl or ethyl), or, $R^{13}$ and $R^{14}$ together with the atom attached form a saturated or partially unsaturated cycloalkyl (e.g. $C_3$-$C_6$ cycloalkyl, and e.g. cyclopropyl or cyclobutyl), or, a saturated or partially unsaturated heterocyclyl; wherein, the alkyl, cycloalkyl and heterocyclyl can be independently substituted with the substituent selected from the group consisting of halogen, cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, oxo, —$OR^a$, —$NR^aR^b$, —$NR^aOR^b$, —$NR^aCO_2R^b$, —$NR^aCOR^b$, —$SO_2NR^aR^b$, —$SR^a$, —$SOR^a$, —$SO_2R^a$, —S—S—$R^a$, —$C(=O)R^a$, —$C(=O)OR^a$, —$OC(=O)R^a$, —$OC(=O)OR^a$, —$OSO_2R^a$, —$OSO_2NR^aR^b$, —$OC(=O)NR^aR^b$, —$C(=O)NR^aR^b$, —$NR^aC(=O)R^b$, —$NR^aSO_2R^b$, —$NR^aSO_2NR^bR^c$ and —$NR^aC(=O)NR^bR^c$; when there are more than one substituents, the substituents are the same or different;

each of $R^{15}$, $R^{16}$ and $R^{17}$ is independently selected from the group consisting of H, alkyl (e.g. $C_1$-$C_6$ alkyl, e.g. $C_1$-$C_4$ alkyl, e.g. methyl, ethyl,

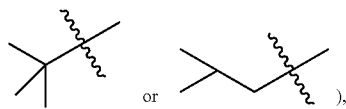

alkenyl (e.g. $C_2$-$C_6$ alkenyl, e.g. vinyl or propenyl, e.g. propen-1-yl or propen-2-yl), alkynyl, heteroalkyl (e.g. —O—($C_1$-$C_6$ alkyl),

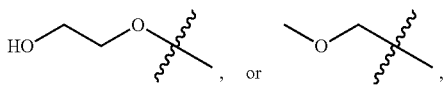, or

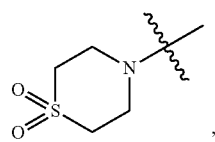 [SMILES: *N1CCS(=O)(=O)CC1], e.g. ethoxy), heteroalkenyl, heteroalkynyl, saturated or partially unsaturated cycloalkyl (e.g. $C_3$-$C_6$ cycloalkyl, e.g. cyclopropyl), saturated or partially unsaturated heterocyclyl (e.g. a 5 to 6 membered heterocyclyl having 1 to 2 heteroatom(s) selected from the group consisting of N and O, e.g. tetrahydropyrimidinyl, dihydroisoxazolyl, dihydrooxazinyl, pyrrolidinyl, piperazinyl, morpholinyl or piperidinyl, and e.g. 1,4,5,6-tetrahydropyrimidin-2-yl, piperazin-1-yl, 4,5-dihydroisoxazol-5-yl, 5,6-dihydro-4H-1,3-oxazin-2-yl, morpholin-1-yl or piperidin-4-yl), cycloalkylalkyl, aryl, arylalkyl, heteroaryl (e.g. a 5 to 6 membered heteroaryl having 1 to 2 heteroatom(s) selected from the group consisting of N and O, e.g. oxazolyl, pyrazolyl or isoxazolyl, and e.g. oxazol-2-yl, pyrazol-3-yl, isoxazol-3-yl or isoxazol-4-yl), heteroarylalkyl, —C(=O)$R^a$, O$R^a$, and heterocyclylalkyl;

in the definition of $R^{15}$, $R^{16}$ and $R^{17}$, the alkyl, alkenyl, alkynyl, heteroalkyl, cycloalkyl, heterocyclyl, cycloalkylalkyl, aryl, arylalkyl, heteroaryl, heteroarylalkyl, and heterocyclylalkyl can be independently substituted with the substituent selected from the group consisting of alkyl (e.g. $C_1$-$C_6$ alkyl; the $C_1$-$C_6$ alkyl is, for example, methyl or ethyl), alkenyl, alkynyl, heteroalkyl, heteroalkenyl, heteroalkynyl, saturated or partially unsaturated cycloalkyl (e.g. $C_3$-$C_6$ cycloalkyl, e.g. cyclopropyl), saturated or partially unsaturated heterocyclyl substituted with $C_1$-$C_6$ alkyl or unsubstituted (e.g. a 5 to 6 membered heterocyclyl having 1 to 2 heteroatom(s) selected from the group consisting of N and O, e.g. tetrahydropyrrolyl, e.g. tetrahydropyrrol-2-yl), aryl, heteroaryl (e.g. a 5 to 6 membered heteroaryl having 1 to 2 heteroatom(s) selected from the group consisting of N and O, e.g. pyridinyl, e.g. pyridin-3-yl), halogen (e.g. fluorine, chlorine, bromine or iodine), haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), oxo, cyano, —O$R^a$, —N$R^a R^b$, —N$R^a$O$R^b$, —N$R^a$CO$_2 R^b$, —N$R^a$CO$R^b$, —SO$_2$N$R^a R^b$, —S$R^a$, —SO$R^a$, —SO$_2 R^a$, —S—S—$R^a$, —C(=O)$R^a$, —C(=O)O$R^a$, —OC(=O)$R^a$, —OC(=O)O$R^a$, —OSO$_2 R^a$, —OSO$_2$N$R^a R^b$, —OC(=O)N$R^a R^b$, —C(=O)N$R^a R^b$, —N$R^a$C(=O)$R^b$, —N$R^a$C(=O)N$R^b R^c$, —N$R^a$SO$_2 R^b$, —N$R^a$SO$_2$N$R^b R^c$, —OC(=O)N$R^a R^b$, —C(=O)—C$R^a$=C$R^a R^b$, —C(=O)—C≡C—(C$R^a R^b$)$_{1-3}$N$R^a R^b$, —(CH$_2$)$_{1-3}$C(=O)N$R^a$, —C(=O)(CH$_2$)$_{1-3}$O$R^a$ and —(C$R^a R^b$)$_{1-3}$N$R^a R^b$; when there are more than one substituents, the substituents are the same or different;

or, any two of $R^{15}$, $R^{16}$ and $R^{17}$ together with the atom attached form a heterocycle (e.g. a 5 to 6 membered heterocyclyl having 1 to 2 heteroatom(s) selected from the group consisting of N and O, a 5 to 6 membered heterocyclyl having a second heteroatom selected from N and O or and e.g. morpholinyl or piperazinyl, and e.g. morpholin-4-yl or piperazin-1-yl); the heterocycle can have one or more heteroatom(s) selected from the group consisting of N, O, S, SO, SO$_2$ and N$R^6$, wherein the heterocycle can be substituted with the substituent selected from the group consisting of oxo, halogen, alkyl (e.g. $C_1$-$C_6$ alkyl), alkenyl, alkynyl, saturated or partially unsaturated cycloalkyl, saturated or partially unsaturated heterocyclyl, cycloalkylalkyl, cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, aryl, —O$R^a$, —N$R^a R^b$, —S$R^a$, heteroaryl, arylalkyl, heteroarylalkyl, and heterocyclylalkyl; when there are more than one substituents, the substituents are the same or different;

or, $R^{13}$ and $R^{15}$ together with the atom attached form a saturated or partially unsaturated heterocyclyl; wherein, the heterocyclyl can be independently substituted with the substituent selected from the group consisting of halogen, cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, oxo, —O$R^a$, —N$R^a R^b$, —N$R^a$O$R^b$, —N$R^a$CO$_2 R^b$, —N$R^a$CO$R^b$, —SO$_2$N$R^a R^b$, —S$R^a$, —SO$R^a$, —SO$_2 R^a$, —S—S—$R^a$, —C(=O)$R^a$, —C(=O)O$R^a$, —OC(=O)$R^a$, —C(=O)N$R^a R^b$, —OC(=O)O$R^a$, —OSO$_2 R^a$, —OSO$_2$N$R^a R^b$, —OC(=O)N$R^a R^b$, —N$R^a$C(=O)$R^b$, —N$R^a$SO$_2 R^b$, —N$R^a$SO$_2$N$R^b R^c$ and —N$R^a$C(=O)N$R^b R^c$; when there are more than one substituents, the substituents are the same or different;

each $R^{18}$ is independently H, —CF$_3$, alkyl (e.g. $C_1$-$C_6$ alkyl, and e.g. $C_1$-$C_4$ alkyl, and e.g. methyl or ethyl), alkenyl, alkynyl, heteroalkyl, heteroalkenyl, heteroalkynyl, saturated or partially unsaturated cycloalkyl, saturated or partially unsaturated heterocyclyl, cycloalkylalkyl, aryl (e.g. $C_6$-$C_{10}$ aryl, and e.g. phenyl), arylalkyl, heteroaryl, heteroarylalkyl, or heterocyclylalkyl (e.g. a 4 to 6 membered heterocyclylalkyl, the heterocyclyl has 1 or 2 heteroatom(s) on the ring independently selected from the group consisting of N, O, and SO$_2$, the alkyl is $C_1$-$C_4$ alkyl; and e.g.

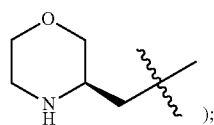 [SMILES: *C[C@@H]1COCCN1]

in the definition of $R^{18}$, the alkyl, alkenyl, alkynyl, cycloalkyl, saturated or partially unsaturated heterocyclyl, cycloalkylalkyl, aryl, arylalkyl, heteroaryl, heteroarylalkyl and heterocyclylalkyl can be independently substituted with the substituent selected from the group consisting of alkyl, alkenyl, alkynyl, heteroalkyl, heteroalkenyl, heteroalkynyl, saturated or partially unsaturated cycloalkyl (e.g. $C_3$-$C_6$ cycloalkyl, and e.g. cyclopropyl), saturated or partially unsaturated heterocyclyl, aryl, heteroaryl, halogen, oxo, —$OR^a$, —$NR^aR^b$, —$NR^aOR^b$, —$NR^aCO_2R^b$, —$NR^aCOR^b$, —$SO_2NR^aR^b$, —$SR^a$, —$SOR^a$, —$SO_2R^a$, —S—S—$R^a$, —C(=O)$R^a$, —C(=O)$OR^a$, —OC(=O)$R^a$, —OC(=O)$OR^a$, —$OSO_2R^a$, —$OSO_2NR^aR^b$, —OC(=O)$NR^aR^b$, —C(=O)$NR^aR^b$, —$NR^aC$(=O)$R^b$, —$NR^aC$(=O)$NR^bR^c$, —$NR^aSO_2R^b$, and —$NR^aSO_2NR^bR^c$; when there are more than one substituents, the substituents are the same or different:

or, $R^{15}$ and $R^{18}$ together with the atom attached form saturated or partially unsaturated heterocyclyl; wherein, the heterocyclyl can be independently substituted with the substituent selected from the group consisting of halogen, cyano, nitro, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, oxo, —$OR^a$, —$NR^aR^b$, —$NR^aOR^b$, —$NR^aCO_2R^b$, —$NR^aCOR^b$, —$SO_2NR^aR^b$, —$SR^a$, —$SOR^a$, —$SO_2R^a$, —S—S—$R^a$, —C(=O)$R^a$, —C(=O)$OR^a$, —OC(=O)$R^a$, —OC(=O)$OR^a$, —$OSO_2R^a$, —$OSO_2NR^aR^b$, —OC(=O)$NR^aR^b$, —C(=O)$NR^aR^b$, —$NR^aC$(=O)$R^b$, —$NR^aSO_2R^b$, —$NR^aSO_2NR^bR^c$ and —$NR^aC$(=O)$NR^bR^c$; when there are more than one substituents, the substituents are the same or different;

each $R^6$ is independently hydrogen, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), alkyl, saturated or partially unsaturated cycloalkyl, saturated or partially unsaturated heterocyclyl, aryl, arylalkyl, heteroaryl, heteroarylalkyl, or heterocyclylalkyl;

in the definition of $R^6$, the alkyl, cycloalkyl, heterocyclyl, aryl, arylalkyl, heteroaryl, heteroarylalkyl, and heterocyclylalkyl can be independently substituted with the substituent selected from the group consisting of oxo, halogen, alkyl, alkenyl, alkynyl, saturated or partially unsaturated cycloalkyl, saturated or partially unsaturated heterocyclyl, cycloalkylalkyl, cyano, nitro, —$OR^{15}$, —$SR^{15}$, —$SOR^{15}$, —$SO_2R^{15}$, haloalkyl (the halogen in the "haloalkyl" is, for example, fluorine, chlorine or bromine; the number of halogen can be one or more than one; the alkyl in the "haloalkyl" is preferably $C_1$-$C_6$ alkyl, e.g. methyl, ethyl or propyl; the "haloalkyl" is preferably fluoroalkyl, e.g. trifluoromethyl, difluoromethyl or monofluoromethyl), haloalkoxy (the halogen in the "haloalkoxy" is, for example, fluorine, chlorine or bromine; the number of halogen can be one or more than one; the alkoxy in the "haloalkoxy" is preferably $C_1$-$C_6$ alkoxy, e.g. methoxy, ethoxy, or propoxy; the "haloalkoxy" is preferably fluoroalkoxy, e.g. trifluoromethoxy, difluoromethoxy or monofluoromethoxy), azido, aryl, heteroaryl, arylalkyl, heteroarylalkyl, and heterocyclylalkyl; when there are more than one substituents, the substituents are the same or different:

each $R^a$, $R^b$ and $R^c$ is independently H, halogen (e.g. fluorine, chlorine, bromine or iodine), alkyl (e.g. $C_1$-$C_6$ alkyl, e.g. methyl or tert-butyl), alkenyl (e.g. $C_2$-$C_6$ alkenyl, and e.g. vinyl), alkynyl, saturated or partially unsaturated cycloalkyl (e.g. $C_3$-$C_6$ cycloalkyl, and e.g. cyclopropyl), saturated or partially unsaturated heterocyclyl, aryl or heteroaryl, or, —$NR^aR^b$ forms a 5 to 6 membered heterocycle having 1 to 2 nitrogen atom(s) on the ring which can be substituted with $C_1$-$C_3$ alkyl (e.g. 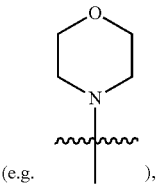 [SMILES: *N1CCOCC1] ), or, —$NR^bR^c$ forms a 5 to 6 membered heterocycle having 1 to 2 nitrogen atom(s) on the ring;

m is 1, 2, 3 or 4 (when m is 1, preferably, the compound I is

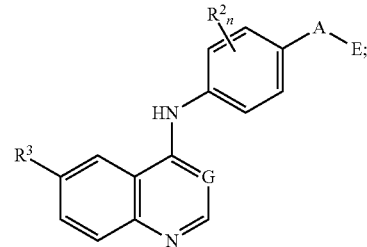

when m is 2, preferably, the compound I is

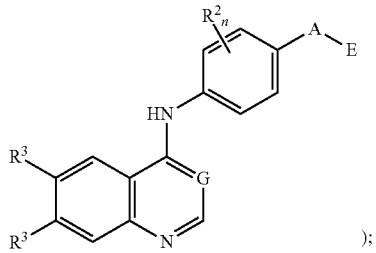

n is 0, 1, 2, 3 or 4 (when n is 1, preferably, the compound I is

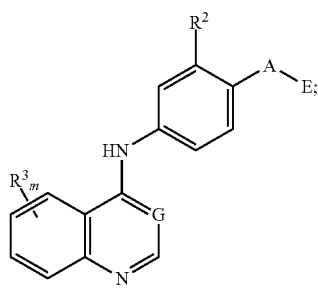

when n is 2, preferably, the compound I is

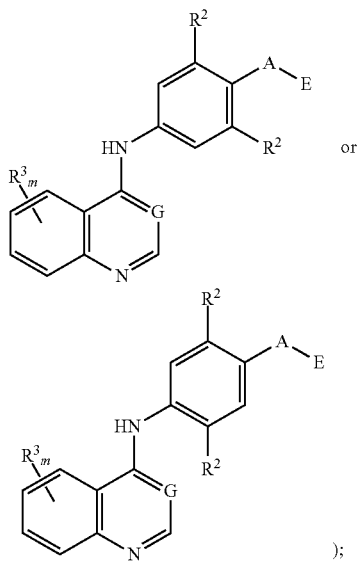

q is 0, 1, 2, 3, 4 or 5;
p is 0, 1 or 2;
s is 0, 1, 2 or 3;
k is 1, 2 or 3; and
t is 0, 1, 2, 3, 4 or 5.

In a certain embodiment of the compound represented by formula I, the definition of each group is as follows:
wherein, A is —O—;
G is N;
E is

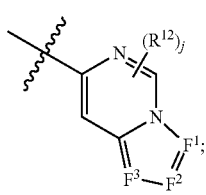

in the definition of E, $F^1$, $F^2$ and $F^3$ is independently N or $CR^{19}$;
in the definition of E, j is 0 or 1;
in the definition of E, each $R^{12}$ is independently halogen, —$OR^{15}$, alkyl;
in the definition of E, each $R^{19}$ is independently H;
each $R^2$ is independently halogen, haloalkyl or alkyl (e.g. methyl);

in the definition of $R^2$, the haloalkyl and alkyl can be substituted with one or more —$OR^{15}$, when there are more than one substituents, the substituents are the same or different;

each $R^3$ is independently Z, "a 5 to 6 membered heterocycle having 1 to 4 heteroatom(s) selected from the group consisting of N, O, S, SO and $SO_2$, and substituted with -$M_1$-$M_2$-$M_3$-$M_4$ or -$M_1$-$M_5$", aryl substituted with -$M_1$-$M_2$-$M_3$-$M_4$ or -$M_1$-$M_5$, —$(CR^{13}R^{14})_s$—C≡C—$(CR^{13}R^{14})_k$—$R^5$, halogen, alkenyl, saturated or partially unsaturated heterocyclyl, aryl, heteroaryl, —$OR^{15}$, —$NR^{15}R^{16}$, —$NR^{15}C(=O)OR^{18}$, —$NR^{15}C(=O)R^{16}$, —$OC(=O)R^{15}$, —$NR^{15}C(=O)NR^{16}R^{17}$ or $NR^{15}C(=S)NR^{16}R^{17}$;

in the definition of $R^3$, the alkenyl, heterocyclyl, aryl and heteroaryl can be independently substituted with the substituent selected from the group consisting of halogen, alkyl, —$NR^{15}R^{16}$, —$NR^{15}C(=O)OR^{18}$, —$NR^{15}C(=O)R^{16}$, —$C(=O)R^{15}$, —$C(=O)NR^{15}R^{16}$, —$NR^{15}C(=O)NR^{16}R^{17}$, —$(C_1$-$C_4$ alkyl)$NR^aR^b$ and —$NR^{15}C(=O)CH_2OR^a$; when there are more than one substituents, the substituents are the same or different;

in the definition of $R^3$, $M_1$ is $C_1$-$C_4$ alkylene; $M_2$ is —$NR^e$—; $M_3$ is $C_1$-$C_4$ alkylene; $M_4$ is —$NR^eS(=O)_{0-2}R^f$, —$S(=O)_{0-2}NR^gR^h$ or —$S(=O)_{0-2}R^f$; and $M_5$ is —OH or —$NR^gR^h$; wherein, each of $R^e$, $R^f$, $R^g$ and $R^h$ is independently H or $C_1$-$C_6$ alkyl, or, $R^g$ and $R^h$ together with the nitrogen atom attached form a 5 to 6 membered heterocyclyl having 1 to 3 heteroatom(s) selected from the group consisting of N, O, S, SO and $SO_2$, wherein any N atom on the ring can be substituted with $C_1$-$C_4$ alkyl or —$S(=O)_p$alkyl;

in the definition of $R^3$, Z is

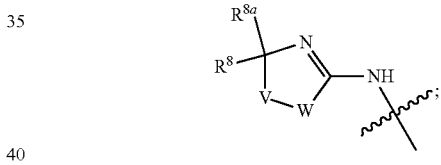

in the definition of Z, W and V are independently —O—, —$NR^6$—, —S— or —$CR^8R^9$—;
the requirement is that when W is —O—, —$NR^6$—, —S—, —SO— or —$SO_2$—, V is —$CR^7R^8$— or —$CR^8R^9$—, and
when V is —O—, —$NR^6$—, —S—, —SO— or —$SO_2$—, W is —$CR^7R^8$— or —$CR^8R^9$—;
in the definition of Z, each of $R^8$, $R^{8a}$ and $R^9$ is independently hydrogen or alkyl;
in the definition of $R^8$, $R^{8a}$ and $R^9$, the alkyl can be substituted with one or more —$OR^{15}$, when there are more than one substituents, the substituents are the same or different;
or, in the definition of Z, $R^8$ and $R^{8a}$ together with the atom attached form a 3 to 6 membered carbocycle, or, a 3 to 10 membered saturated or partially unsaturated heterocyclyl; wherein the carbocycle and heterocyclyl can be independently substituted with the substituent selected from the group consisting of halogen, alkyl, —$C(=O)OR^{15}$ or —$C(=O)R^{15}$; when there are more than one substituents, the substituents are the same or different;
or, in the definition of Z, $R^8$ and $R^9$ together with the atom attached form a 3 to 10 membered saturated or partially unsaturated cycloalkyl or heterocyclyl; the cycloalkyl and heterocyclyl can be independently substituted with the substituent selected from the group consisting of alkyl, —C(=O)OR$^{15}$ and —C(=O)R$^{15}$; when there are more than one substituents, the substituents are the same or different:

in the definition of R$^3$, each R$^5$ is independently —NR$^{15}$R$^{13}$, —NR$^{15}$C(=O)R$^{16}$ or —NR$^{15}$C(=O)NR$^{16}$R$^{17}$;

each of R$^{13}$ and R$^{14}$ is independently hydrogen or alkyl;

each of R$^{15}$, R$^{16}$ and R$^{17}$ is independently H, alkyl, alkenyl, heteroalkyl, saturated or partially unsaturated cycloalkyl, saturated or partially unsaturated heterocyclyl, heteroaryl, OR$^a$ or —C(=O)R$^a$;

in the definition of R$^{15}$, R$^{16}$ and R$^{17}$, the alkyl, alkenyl, heteroalkyl, cycloalkyl, heterocyclyl, heteroaryl can be independently substituted with the substituent selected from the group consisting of alkyl, saturated or partially unsaturated cycloalkyl, saturated or partially unsaturated heterocyclyl substituted with C$_1$-C$_6$ alkyl or unsubstituted, heteroaryl, halogen, cyano, —OR$^a$, —NR$^a$R$^b$, —NR$^a$CO$_2$R$^b$, —SO$_2$R$^a$, —C(=O)R$^a$, —C(=O)OR$^a$, —C(=O)—CR$^a$=CR$^a$R$^b$, —C(=O)—C≡C—(CR$^a$R$^b$)$_{1-3}$NR$^a$R$^b$ and —(CH$_2$)$_{1-3}$C(=O)NR$^a$; when there are more than one substituents, the substituents are the same or different;

or, any two of R$^{15}$, R$^{16}$ and R$^{17}$ together with the atom attached form heterocycle;

each R$^{18}$ is independently alkyl, aryl or heterocyclylalkyl;

in the definition of R$^{18}$, the alkyl, aryl and heterocyclylalkyl can be substituted with one or more saturated or partially unsaturated cycloalkyl(s), when there are more than one substituents, the substituents are the same or different;

each R$^6$ is independently hydrogen;

each of R$^a$, R$^b$ and R$^c$ is independently H, halogen, alkyl or alkenyl;

m is 1 or 2;

n is 1 or 2 (e.g. 1);

p is 2;

s is 0;

k is 1.

In some embodiments of the compound represented by formula I, s and t are not 0 at the same time.

In some embodiments of the compound represented by formula I, A is —O—.

In some embodiments of the compound represented by formula I, G is N.

In some embodiments of the compound represented by formula I, F$^1$, F$^2$ and F$^3$ are independently N or CH, j is 0, namely, E can be selected from the following bicyclic heteroaryl:

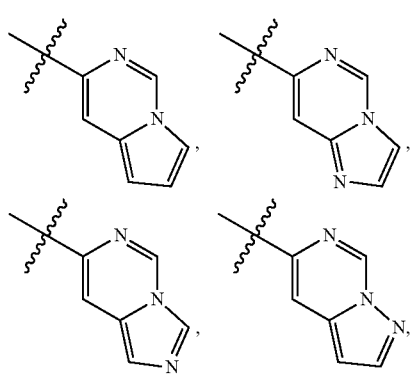

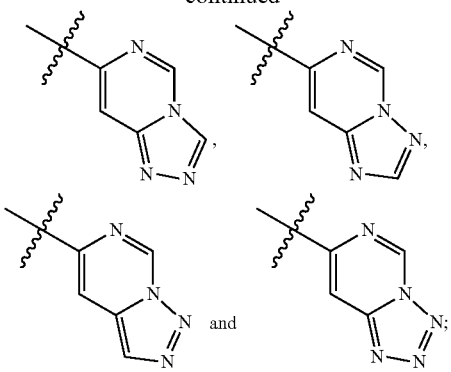

preferably, E is selected from the following structures:

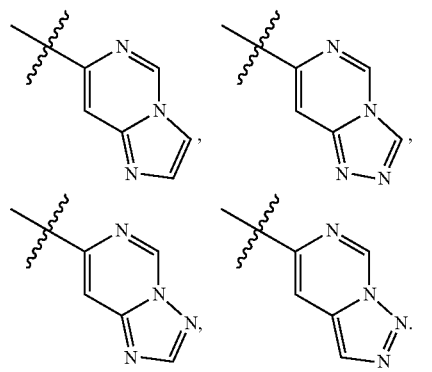

In some embodiments of the compound represented by formula I, n is 1 or 2.

In some embodiments of the compound represented by formula I, each R$^2$ is independently halogen, —CN, trifluoromethyl, difluoromethyl, monofluoromethyl, C$_1$-C$_4$-alkyl, C$_1$-C$_4$-alkoxy, or cycloalkyl.

In some embodiments of the compound represented by formula I, m is 1.

In some embodiments of the compound represented by formula I, when each R$^3$ is independently —NR$^{15}$C(=O)NR$^{16}$R$^{17}$, wherein R$^{15}$ is H or C$_1$-C$_6$ alkyl, meanwhile R$^{16}$ and R$^{17}$ together with the nitrogen atom attached form a 5 to 6 membered heterocycle having a second heteroatom selected from N and O (e.g. morpholinyl and piperazinyl). In some embodiments, the heterocycle is substituted with C$_1$-C$_6$ alkyl. Specific examples of R$^3$ include:

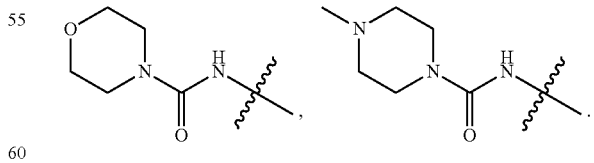

In some embodiments of the compound represented by formula I, each R$^3$ is independently —NR$^{15}$C(=O)NR$^{16}$R$^{17}$, wherein R$^{15}$ is H or C$_1$-C$_6$ alkyl, meanwhile R$^{16}$ and R$^{17}$ are independently selected from the group consisting of H, C$_1$-C$_6$ alkyl, —O—(C$_1$-C$_6$ alkyl) and "alkyl substituted with —NR$^a$R$^b$, wherein the alkyl can be

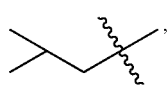 [SMILES: *CC(C)C]

$R^a$ and $R^b$ are independently H or $C_1$-$C_6$ alkyl". Specific examples of $R^3$ include:

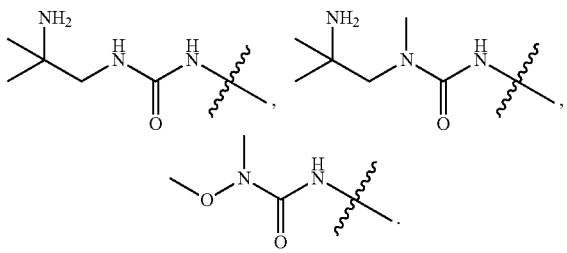

In some embodiments of the compound represented by formula I, each $R^3$ is independently —NR$^{15}$C(=O)OR$^{18}$, wherein $R^{15}$ is H or $C_1$-$C_6$ alkyl, meanwhile $R^{18}$ is a 4 to 6 membered heterocyclylalkyl or aryl (e.g. phenyl), the heterocyclyl has 1 or 2 heteroatom(s) on the ring independently selected from the group consisting of N, O, and SO$_2$. Examples of $R^3$ include:

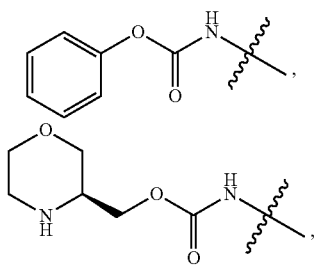

In some embodiments of the compound represented by formula I, each $R^3$ is independently —NR$^{15}$C(=O)R$^{16}$. Examples of $R^{16}$ include but not limited to alkyl, alkenyl or alkynyl, wherein the alkyl, alkenyl and alkynyl can be substituted with —NR$^a$R$^b$, halogen.

In some embodiments of the compound represented by formula I, each $R^3$ is independently —NR$^{15}$C(=O)R$^{16}$, wherein $R^{15}$ is H or methyl, meanwhile $R^{16}$ is $C_2$-$C_6$ alkenyl, which can be substituted with the substituent selected from the group consisting of —NR$^a$R$^b$, halogen (e.g. fluorine) and $C_1$-$C_6$ alkyl. Examples of $R^3$ include —NR$^{15}$C(=O)—CX=CH$_2$R$^{16a}$, wherein, $R^{16a}$ is H or —CH$_2$N(CH$_3$)$_2$, X is H or halogen. Specific examples of $R^3$ include:

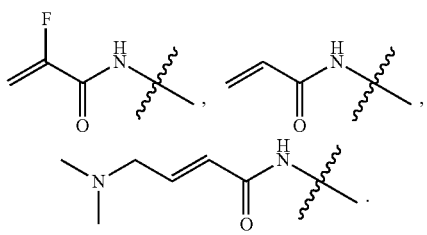

In some embodiments of the compound represented by formula I, each $R^3$ is independently —NR$^{15}$C(=O)R$^{16}$, wherein $R^{15}$ is H or methyl, meanwhile $R^{16}$ is $C_2$-$C_6$ alkenyl, which can be substituted with the substituent selected from the group consisting of cyano and —(CR$^a$R$^b$)$_{1-3}$NR$^a$R$^b$. Specific examples of $R^3$ include:

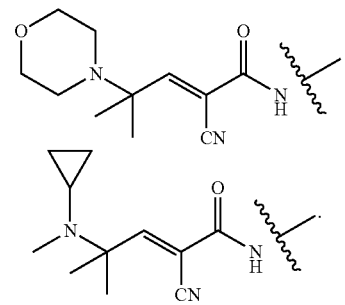

In some embodiments of the compound represented by formula I, each $R^3$ is independently —NR$^{15}$C(=O)R$^{16}$, wherein $R^{15}$ is H or methyl, and $R^{16}$ is $C_1$-$C_6$ alkyl, which can be substituted with the substituent selected from the group consisting of $C_1$-$C_6$ alkyl and —OR$^a$. In some embodiments, $R^a$ is H or $C_1$-$C_6$ alkyl. Specific examples of $R^3$ include:

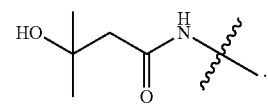 [SMILES: *NC(=O)CC(C)(C)O]

In some embodiments of the compound represented by formula I, each $R^3$ is independently halogen. Specific example of $R^3$ is bromine.

In some embodiments of the compound represented by formula I, each $R^3$ is independently —NR$^{15}$C(=S)NR$^{16}$R$^{17}$, wherein $R^{15}$ is H or methyl, $R^{17}$ is H, and $R^{16}$ is alkyl (e.g. methyl, ethyl, or

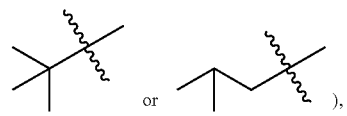

wherein the alkyl can be substituted with the substituent selected from the group consisting of alkyl, hydroxy, amino, —NH—C(=O)OR$^{16b}$, wherein $R^{16b}$ is $C_1$-$C_6$ alkyl (e.g. tert-butyl), when there are more than one substituents, the substituents are the same or different. Specific examples of $R^3$ are:

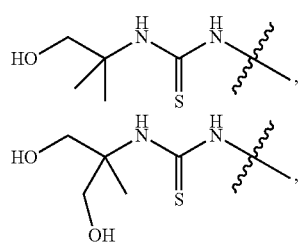

-continued

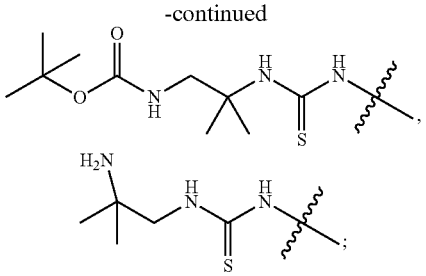

In some embodiments of the compound represented by formula I, each $R^3$ can be independently Z. In some embodiments, Z is selected from:

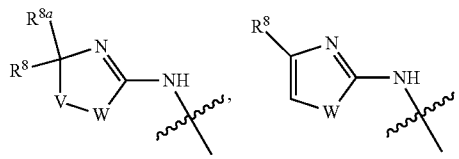

or a tautomer thereof.

In some embodiments, W is —O— or —S—.

In some embodiments, V is —$CR^8R^9$—.

In some embodiments, $R^8$ and $R^{8a}$ are independently H or $C_1$-$C_6$ alkyl, the $C_1$-$C_6$ alkyl can be substituted with $OR^{15}$, wherein $R^{15}$ is H or $C_1$-$C_6$ alkyl. In some embodiments, $R^8$ and $R^{8a}$ together with the atom attached form $C_3$-$C_6$ carbocycle.

In some embodiments, Z is selected from:

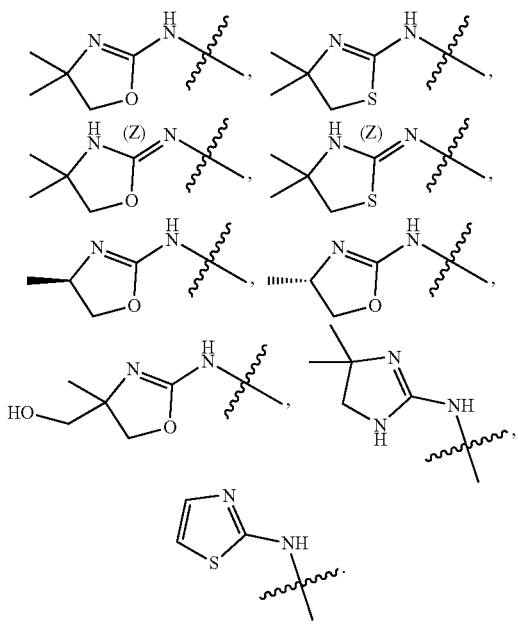

In some embodiments, $M_1$ is —$CH_2$—, —$CH_2CH_2$—, —C(=O)—, or —$CH_2C$(=O)—. In a specific embodiment, $M_1$ is —$CH_2$—.

In some embodiments, $M_2$ is —O—, —NH— or —N($C_1$-$C_6$ alkyl)-. In a specific embodiment, $M_2$ is —NH— or —NMe-.

In some embodiments, $M_3$ is methylene, ethylene or propylene.

In some embodiments, $M_4$ is —$SOR^f$, —$SO_2R^f$, —$NR^eSO_2R^f$, —$SO_2NR^gR^h$, —$CO_2R^f$, —$CONR^gR^h$ or —$NR^ePOR^eR^f$, wherein $R^e$, $R^f$, $R^g$ and $R^h$ are independently H, $C_1$-$C_4$ alkyl or phenyl.

In some embodiments, $M_5$ is —$NR^gR^h$, wherein $R^g$ and $R^h$ are independently H or $C_1$-$C_4$ alkyl.

When $R^3$ is a 5 to 6 membered heterocycle substituted with $M_1$-$M_2$-$M_3$-$M_4$, specific examples of $R^3$ include:

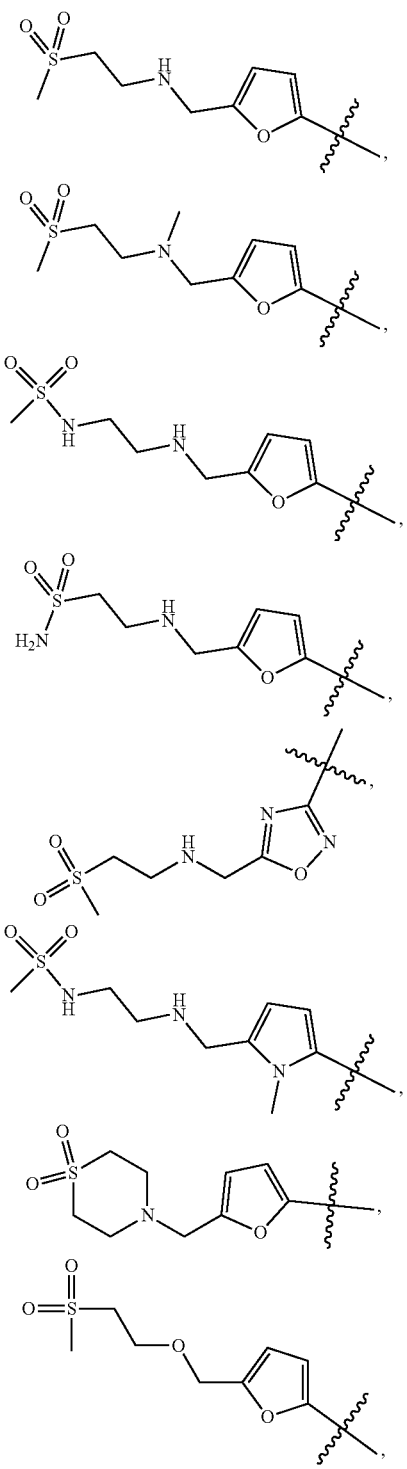

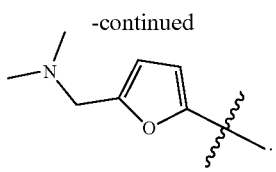

In a specific embodiment, $R^3$ is

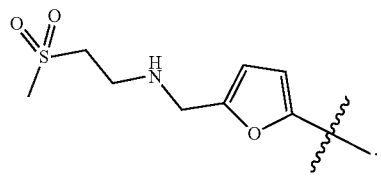 [SMILES: *c1ccc(CNCCS(C)(=O)=O)o1]

In some embodiments, $R^3$ is —$(CR^{13}R^{14})$S—C≡C—$(CR^{13}R^{14})_k R^5$. $R^5$ is —$NR^{15}C(=O)R^{16}$, wherein, $R^{15}$ is H or methyl, meanwhile $R^{16}$ is $C_1$-$C_6$ alkyl, the $C_1$-$C_6$ alkyl can be substituted with the substituent selected from the group consisting of $C_1$-$C_6$ alkyl and —$OR^a$. In some embodiments, $R^{13}$ and $R^{14}$ are all H, s is 0, k is 1, $R^a$ is $C_1$-$C_6$ alkyl. Specific example of $R^3$ is:

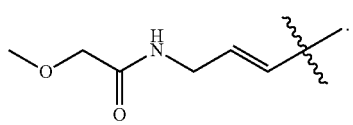 [SMILES: */C=C/CNC(=O)COC]

In some embodiments of the compound represented by formula I, m is 2.

In some embodiments of the compound represented by formula I, $R^3$ is $OR^{15}$. In some embodiments, $R^{15}$ is independently alkyl, alkenyl or alkynyl, wherein the alkyl, alkenyl, alkynyl can be independently substituted with the substituent selected from the group consisting of saturated or partially unsaturated cycloalkyl, heteroaryl, saturated or partially unsaturated heterocyclyl, —$OR^a$, —$SO_2R^a$, and —$NR^a R^b$, when there are more than one substituents, the substituents are the same or different.

In some embodiments of the compound represented by formula I, when m is 2, each $R^3$ is independently —$OR^{15}$; each $R^{15}$ is independently: $C_1$-$C_6$ alkyl, or, a 5 to 6 membered heterocycle having a heteroatom selected from N and O which can be substituted with —$C(=O)R^a$, $C_1$-$C_6$ alkyl, oxo, —$C(=O)NR^a R^b$, —$SO_2R^a$, —$(CH_2)_{1-3}C(=O)NR^a$, or —$C(=O)CH_2OR^a$. Examples of $R^{15}$ include $CH_3$—, $CH_3CH_2$—, pyrrolidinyl and piperidinyl, the pyrrolidinyl and piperidinyl can be independently substituted with the substituent selected from the group consisting of —$C(=O)$($C_1$-$C_6$ alkyl), oxo, $C_1$-$C_6$ alkyl, —$C(=O)N(C_1$-$C_6$ alkyl$)_2$, —$SO_2(C_1$-$C_6$ alkyl), —$(CH_2)_{1-3}C(=O)N(C_1$-$C_6$ alkyl) and —$C(=O)CH_2O(C_1$-$C_6$ alkyl). Specific examples include:

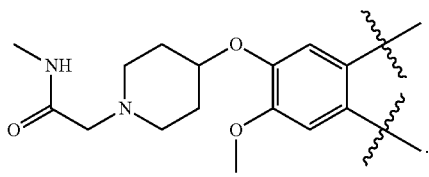 [SMILES: *c1cc(OC)c(OC2CCN(CC(=O)NC)CC2)cc1*]

In some embodiments of the compound represented by formula I, when m is 2, each $R^3$ is independently —$OR^{15}$ or —$OC(=O)R^{15}$, each $R^{15}$ is independently $C_1$-$C_6$ alkyl or a 5 to 6 membered heterocycle having 1 to 2 heteroatom(s) selected from the group consisting of N and O, the heterocycle can be substituted with one or more $C_1$-$C_6$ alkyl. Examples of $R^{15}$ include $CH_3$—, $CH_3CH_2$—, morpholinyl or piperazinyl. In some embodiments, the heterocycle is substituted with $C_1$-$C_6$ alkyl. Specific examples include:

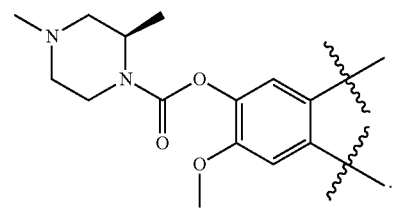 [SMILES: *c1cc(OC)c(OC(=O)N2CCN(C)C[C@H]2C)cc1*]

In some embodiments, when m is 2, each $R^3$ is independently $OR^{15}$ and —$NR^{15}C(=O)R^{16}$, wherein each $R^{15}$ is independently H, methyl or ethyl, meanwhile each $R^{16}$ is $C_2$-$C_6$ alkenyl, the $C_2$-$C_6$ alkenyl can be substituted with $NR^a R^b$. Examples of $R^3$ include $CH_3O$—, $CH_3CH_2O$—, and —$NR^{15}C(=O)$—CH=CHCH$_2R^{16c}$, wherein $R^{16c}$ is —$NCH_3CH_3$. Specific examples include:

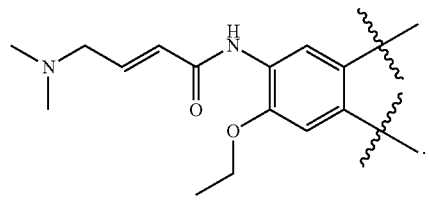 [SMILES: *c1cc(NC(=O)/C=C/CN(C)C)c(OCC)cc1*]

In some embodiments of the compound represented by formula I, when m is 2, one of $R^3$ is Z, the other $R^3$ is halogen. A specific example is:

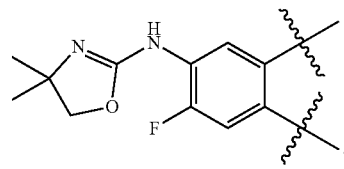

For the selectivity of EGFR/ErbB2, the above substituents are further preferably as follows:

In the compound I, preferably, A is O.
In the compound I, preferably, G is N.
In the compound I, preferably, E is

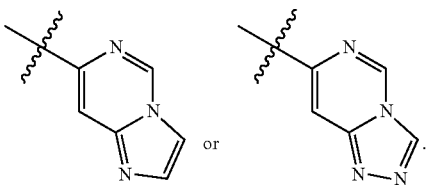 [SMILES: *c1cc2nccn2cn1 ; *c1cc2nncn2cn1]

In the compound I, preferably, $R^2$ is methyl or halogen.
In the compound I, preferably, n is 1.
In the compound I, preferably, $R^3$ is

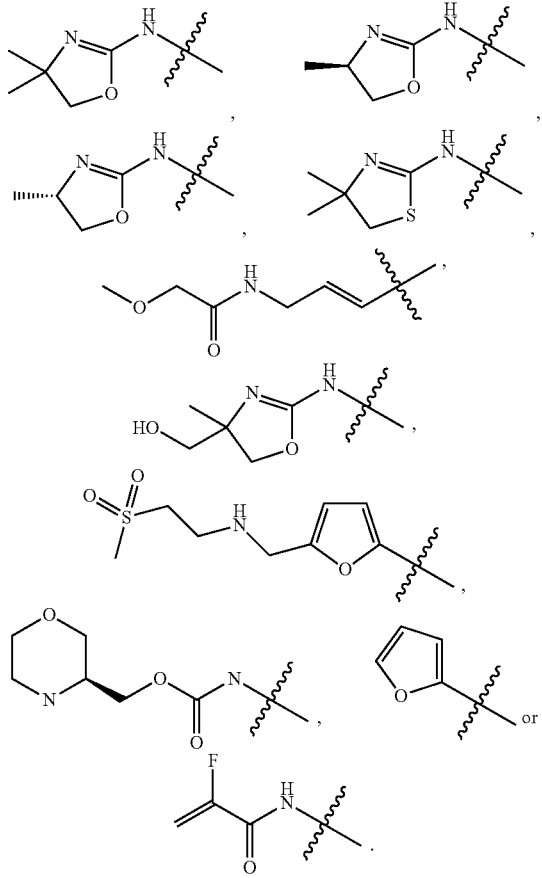

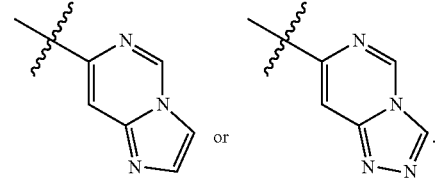 [SMILES: *c1cc2nccn2cn1 ; *c1cc2nncn2cn1]

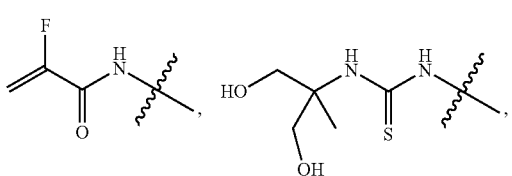

In the compound I, preferably, m is 1.
For ErbB2, the above substituents are further preferably as follows:
In the compound I, preferably, A is O.
In the compound I, preferably, G is N.
In the compound I, preferably, E is

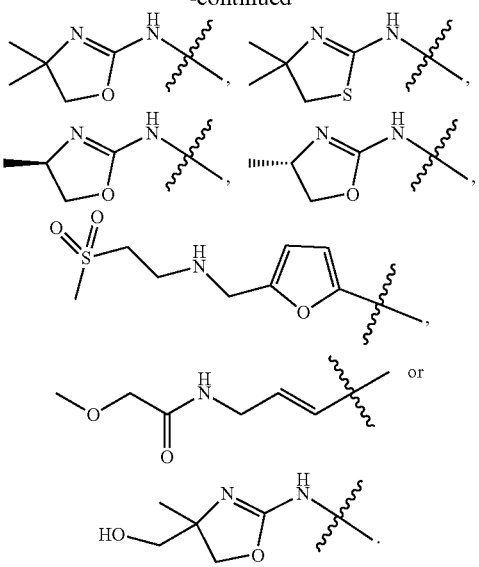

In the compound I, preferably, $R^2$ is methyl.
In the compound I, preferably, n is 1.
In the compound I, preferably, $R^3$ is -continued

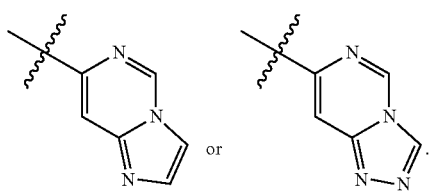 [SMILES: *c1cc2nccn2cn1 ; *c1cc2nncn2cn1]

In the compound I, preferably, m is 1.
For N87, the above substituents are further preferably as follows:
In the compound I, preferably, A is O.
In the compound I, preferably, G is N.
In the compound I, preferably, E is

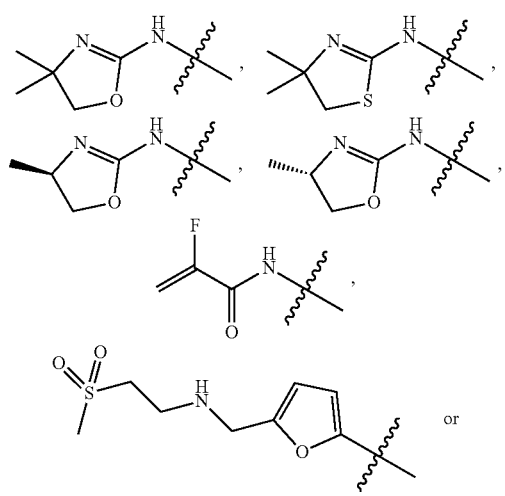

In the compound I, preferably, $R^2$ is methyl.
In the compound I, preferably, n is 1.
In the compound I, preferably, $R^3$ is

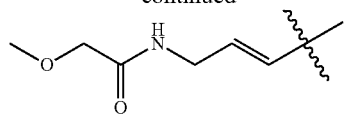

In the compound I, preferably, m is 1.
For BT-474, the above substituents are each further preferably as follows:
In the compound I, preferably, A is O.
In the compound I, preferably, G is N.
In the compound I, preferably, E is

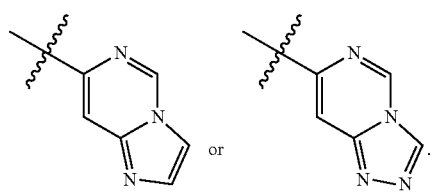 [SMILES: *c1cc2nccn2cn1 ; *c1cc2nncn2cn1]

In the compound I, preferably, $R^2$ is methyl.
In the compound I, preferably, n is 1.
In the compound I, preferably, $R^3$ is

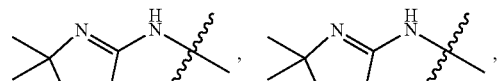

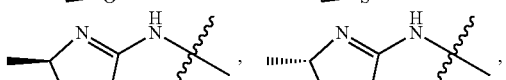

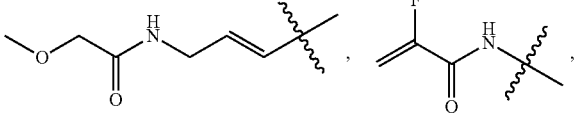

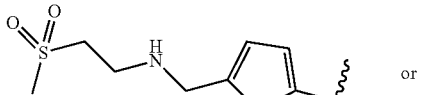

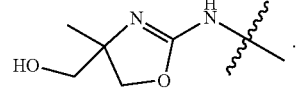

In the compound I, preferably, m is 1.
Preferably, in the present invention, the compound I is any one of the following compounds:

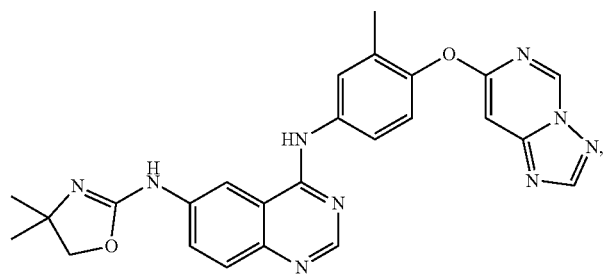

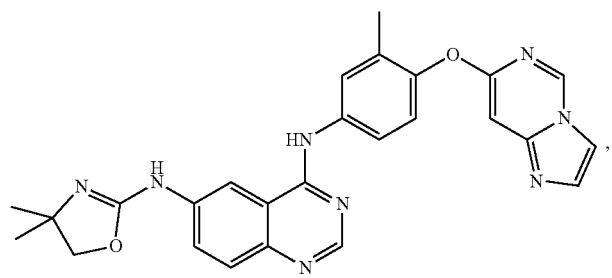

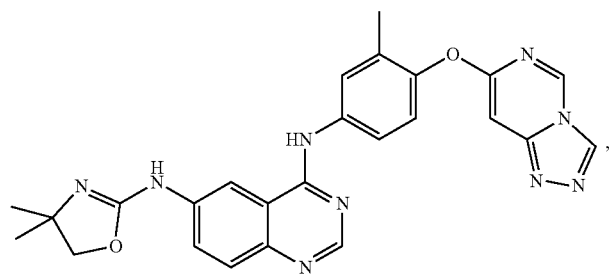

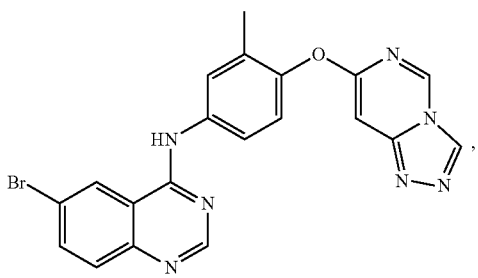

-continued
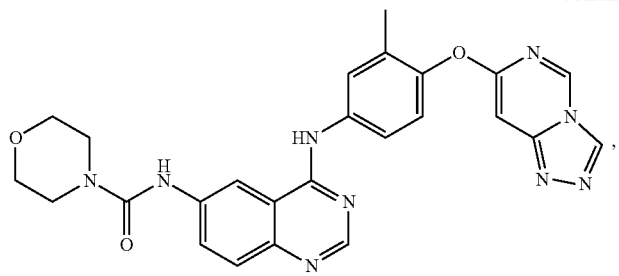
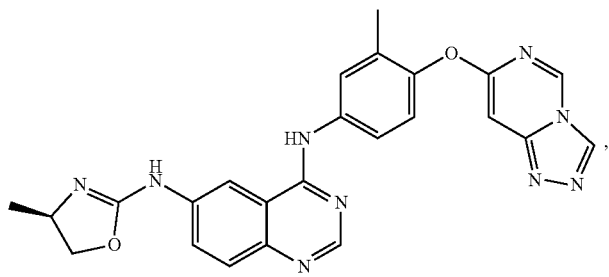
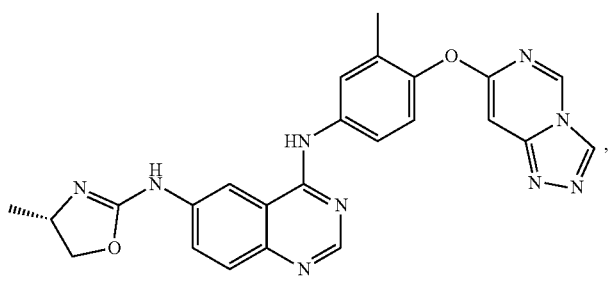
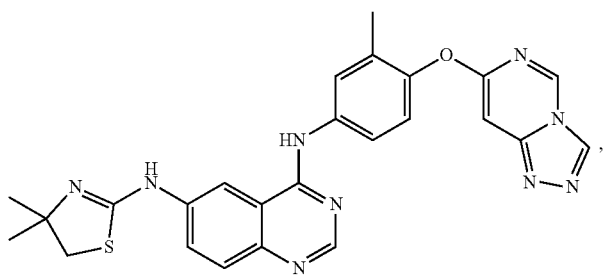
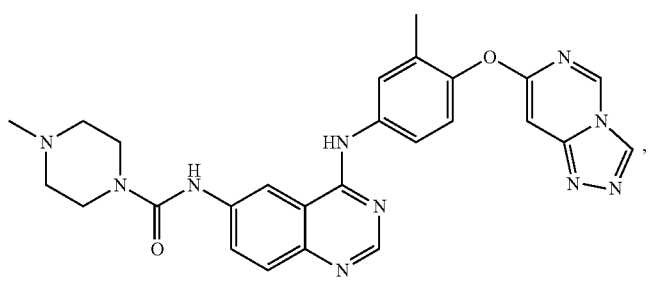
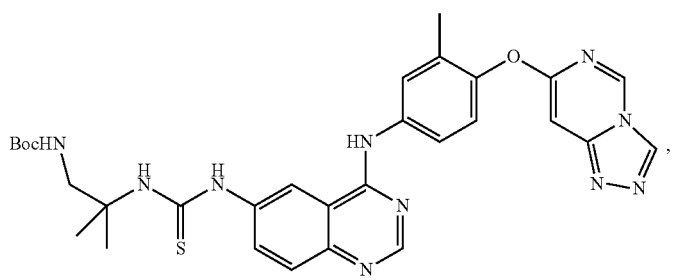

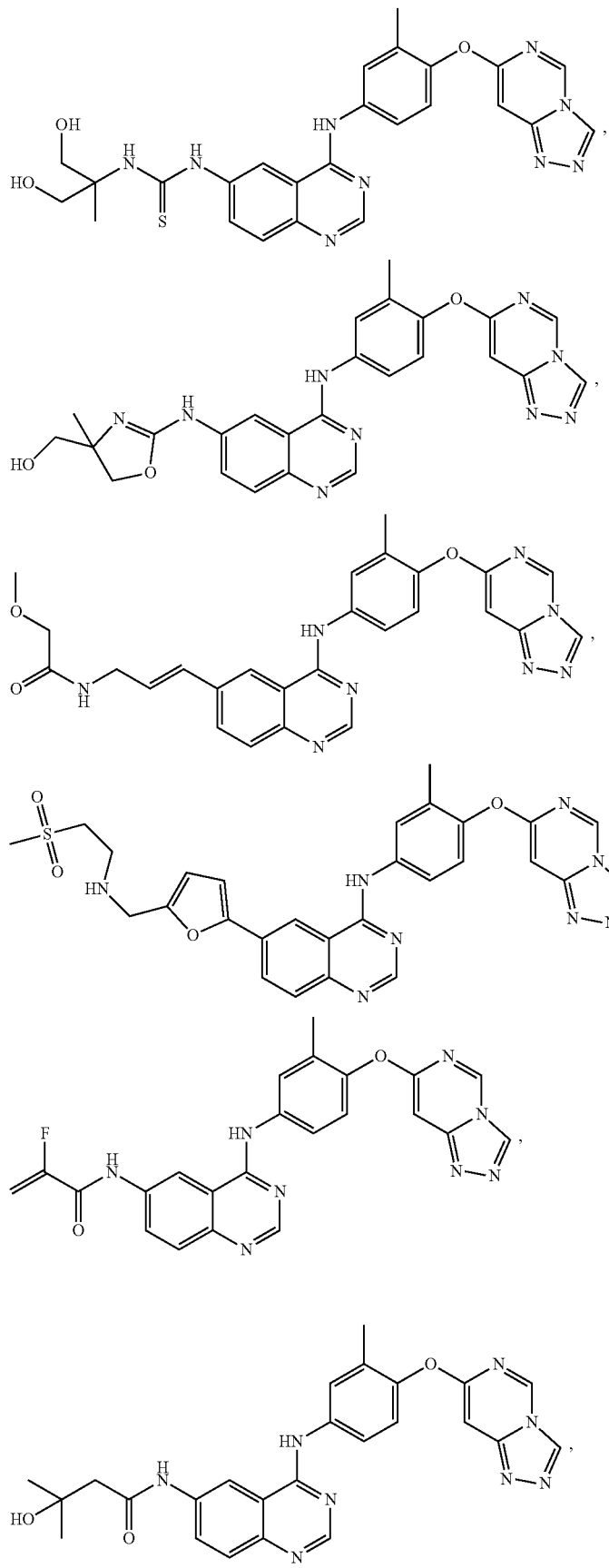

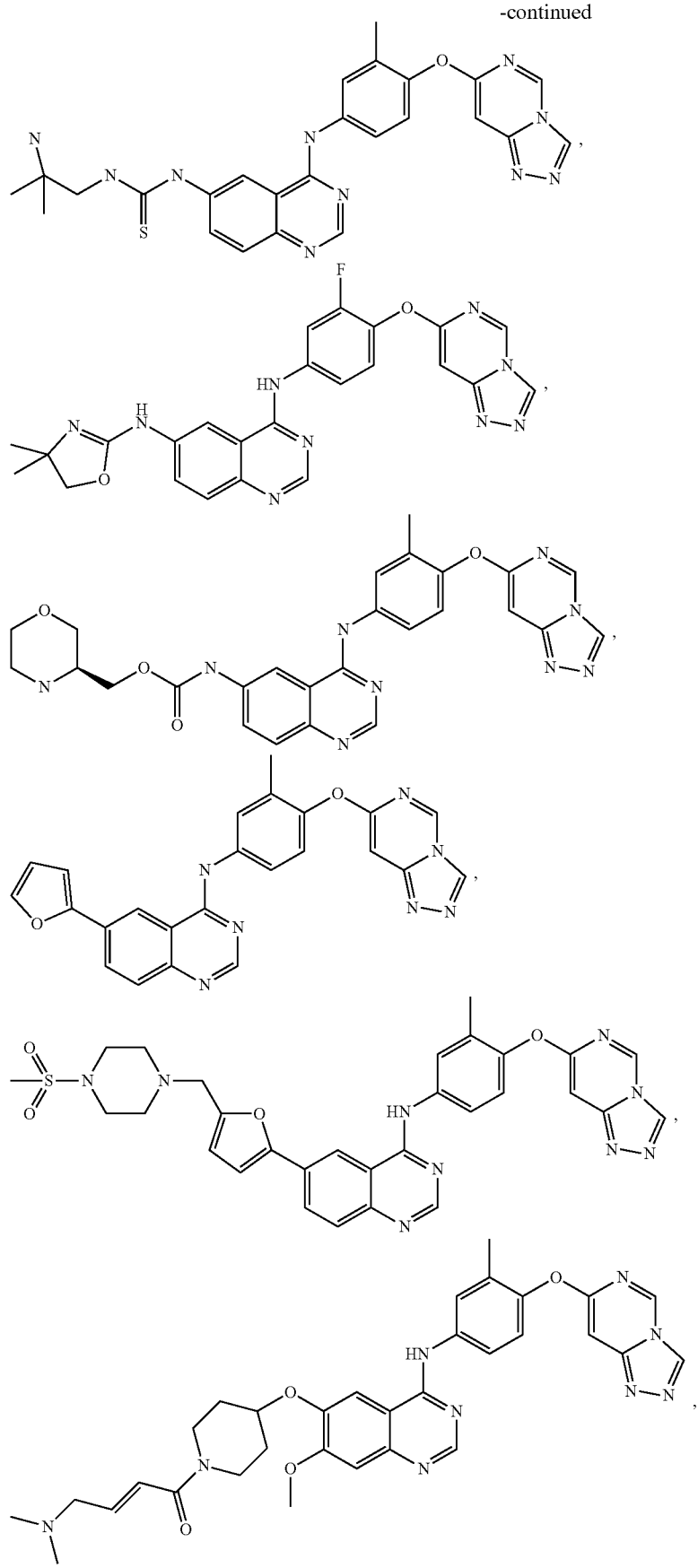

-continued
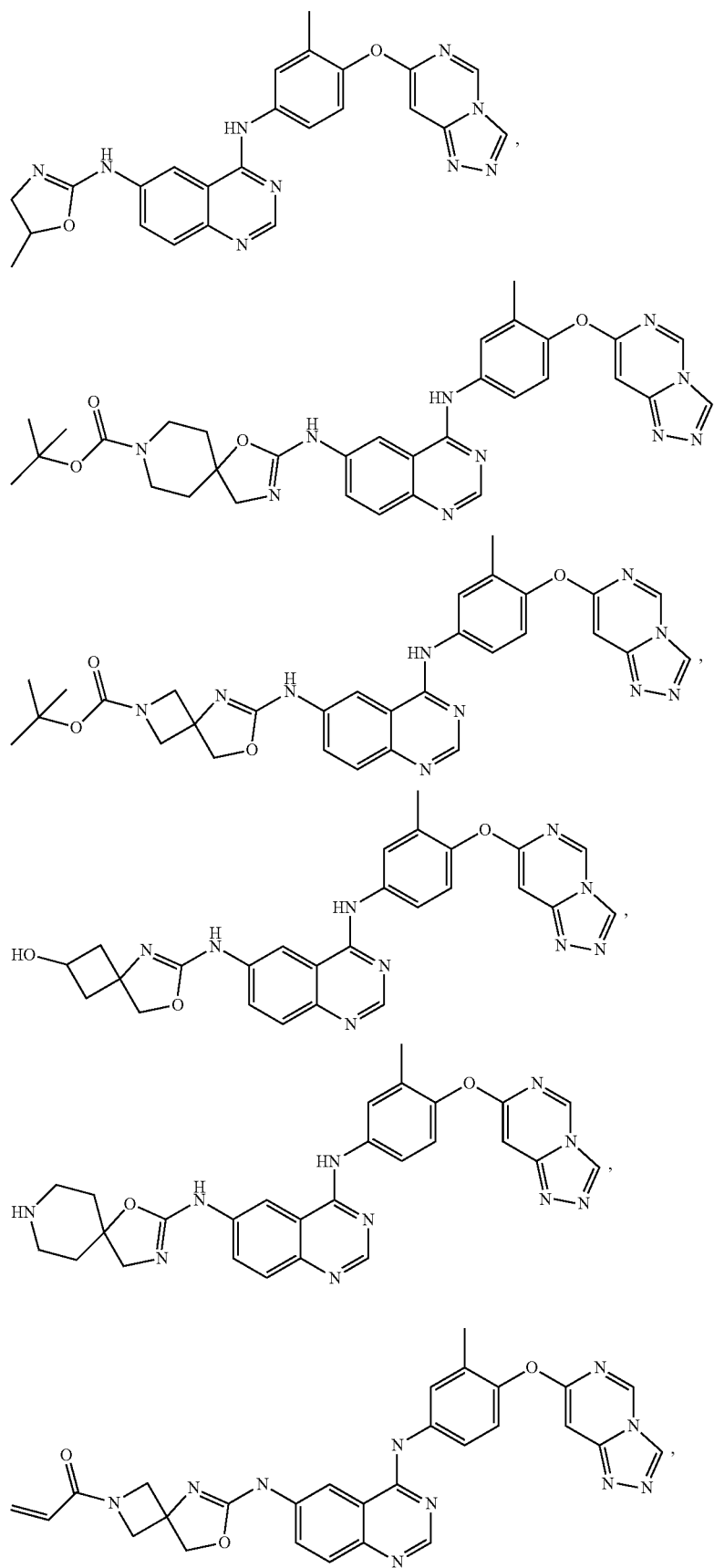

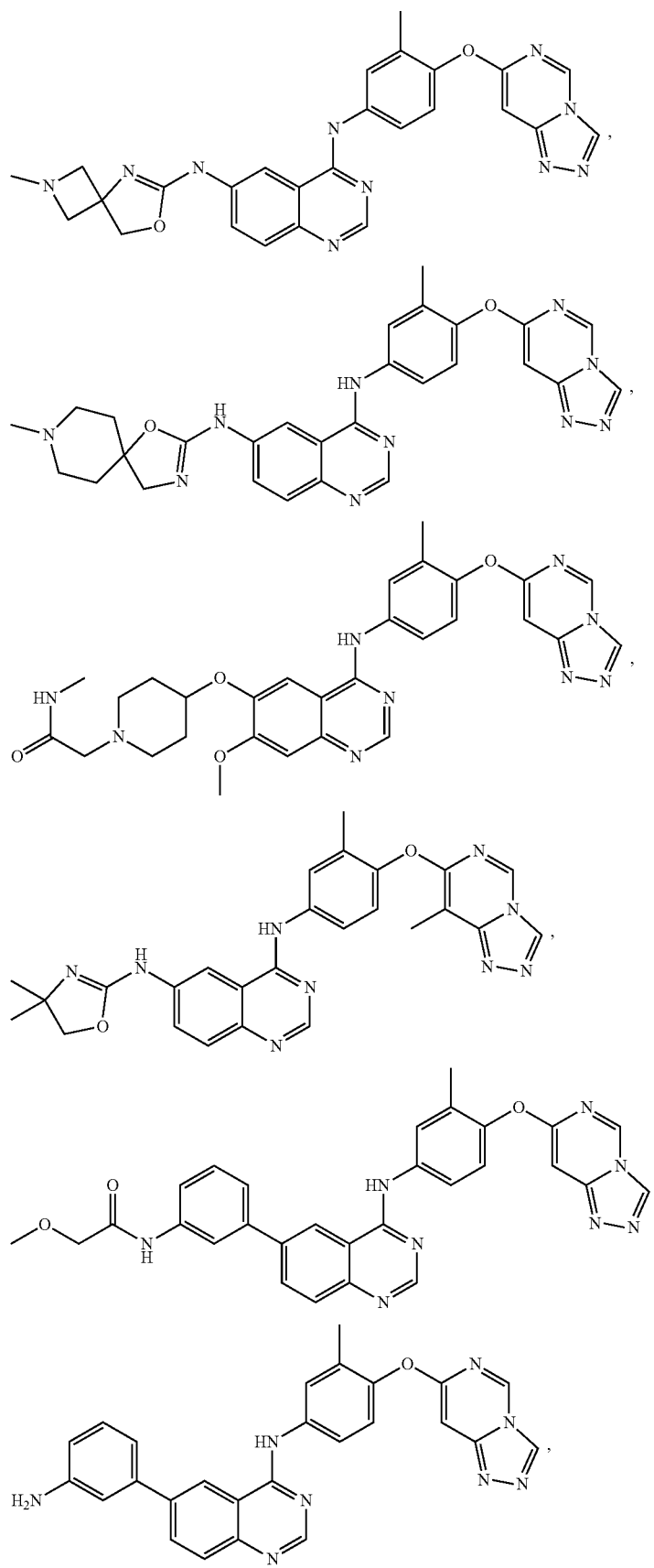

-continued
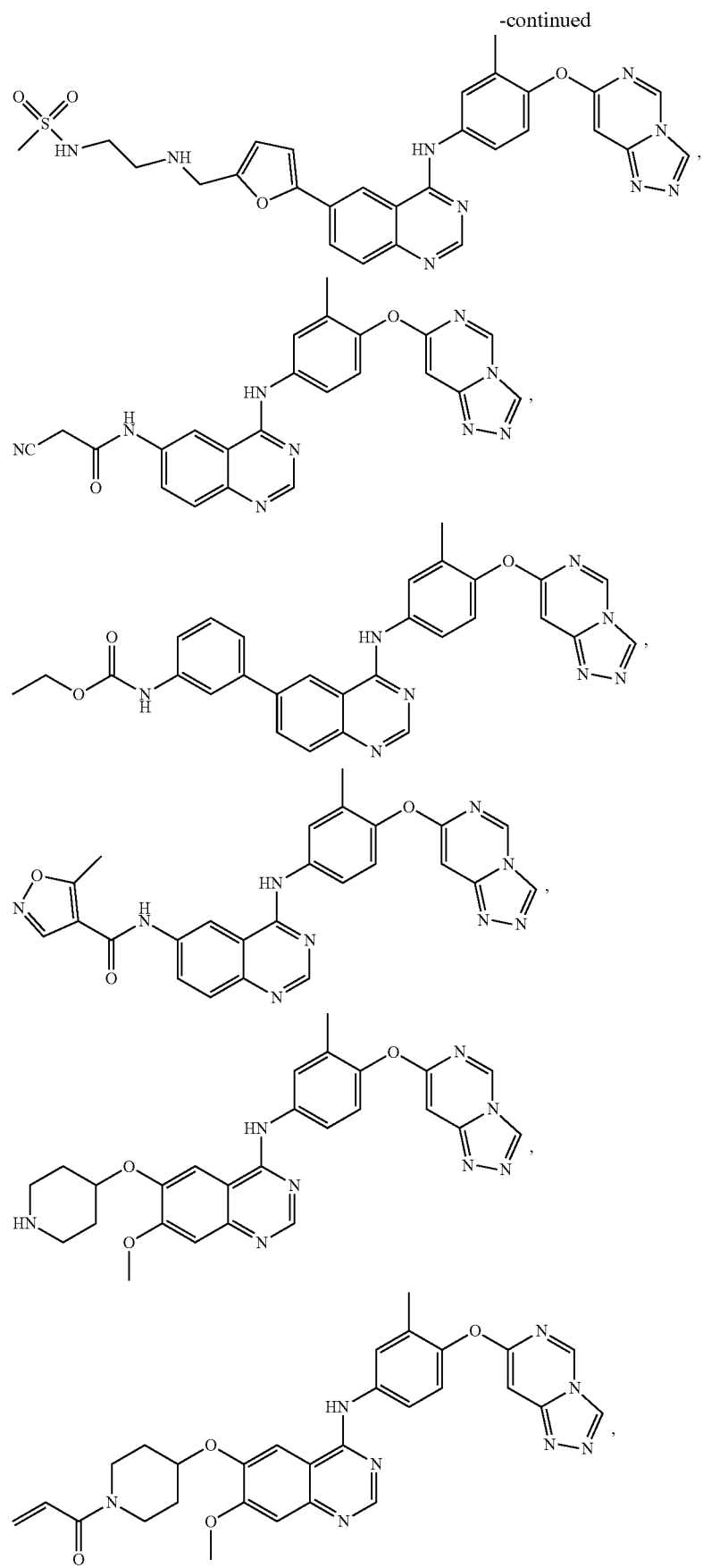

-continued
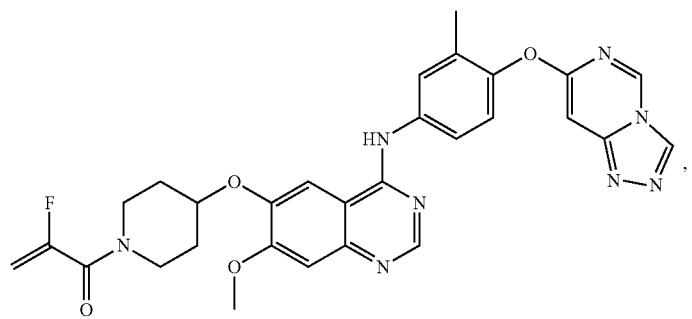
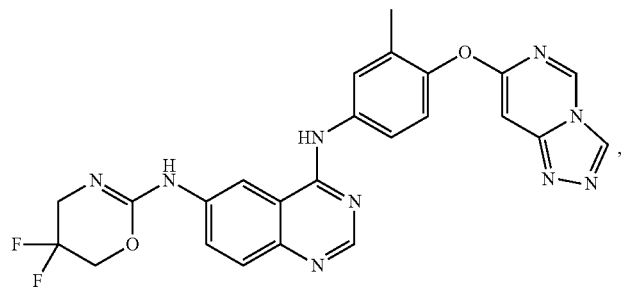
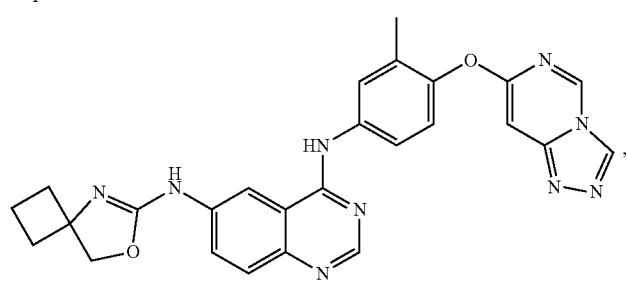
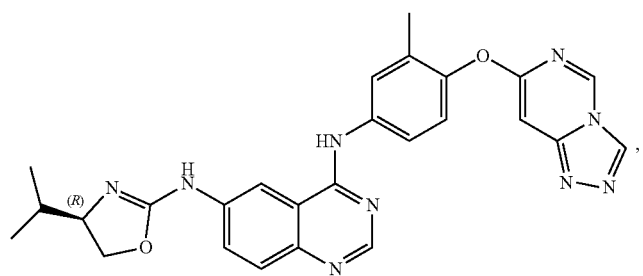
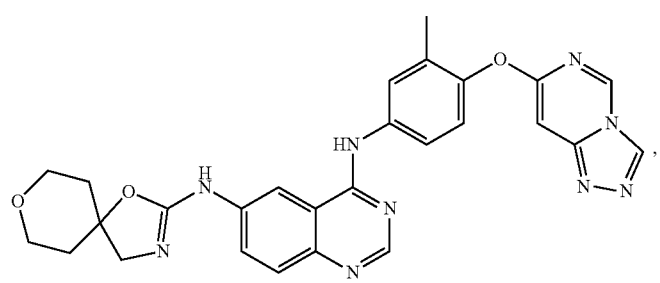
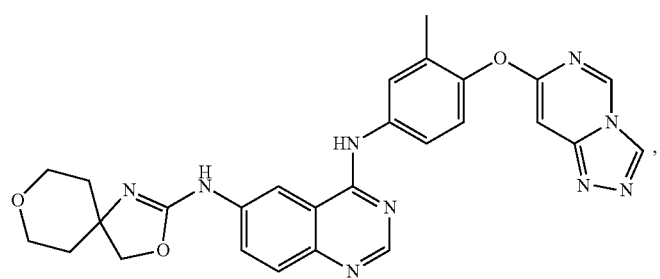

-continued
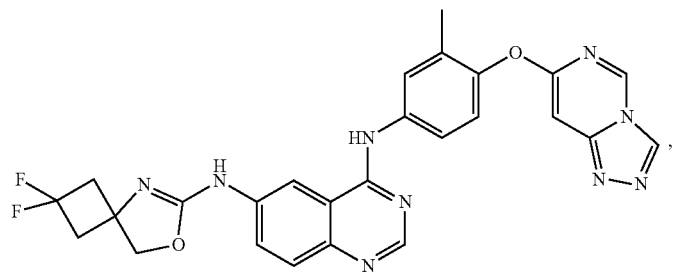
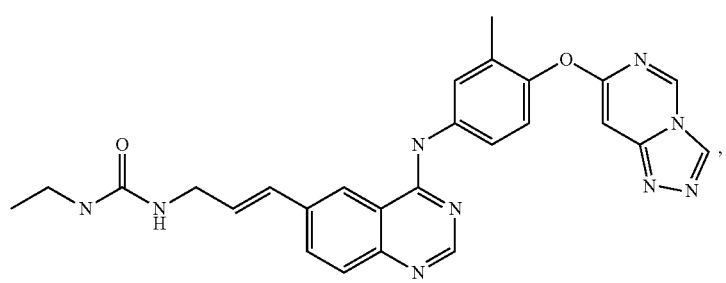
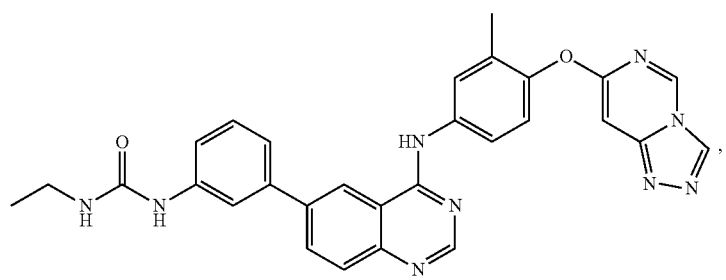
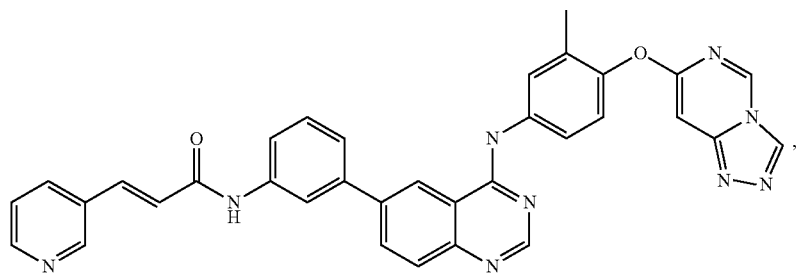
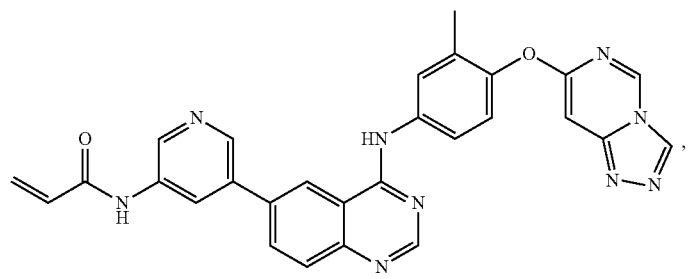
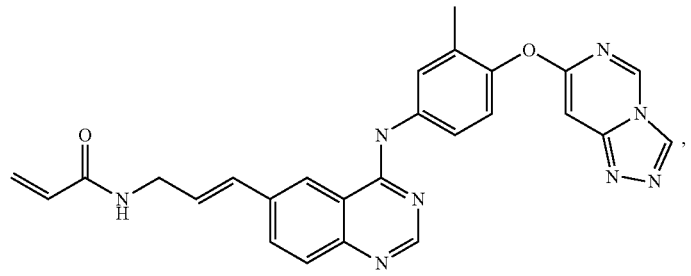

-continued
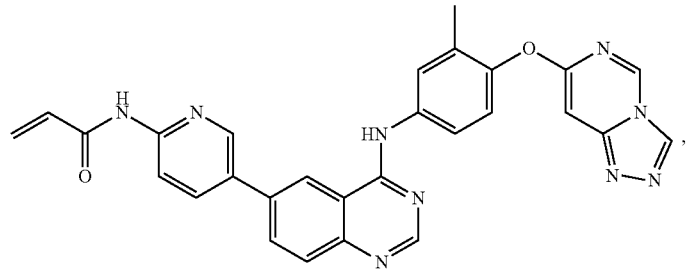
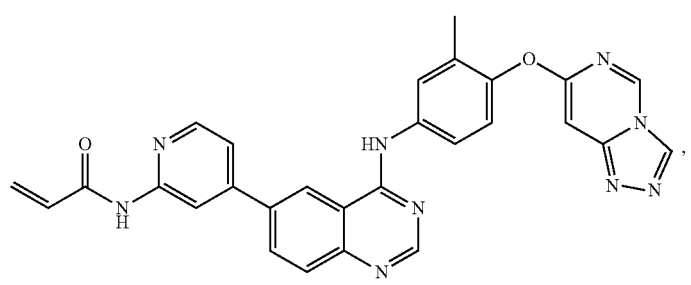
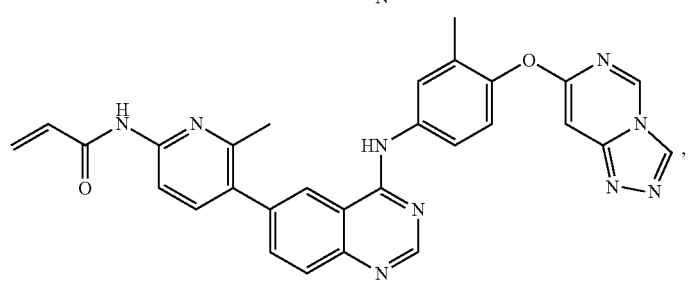
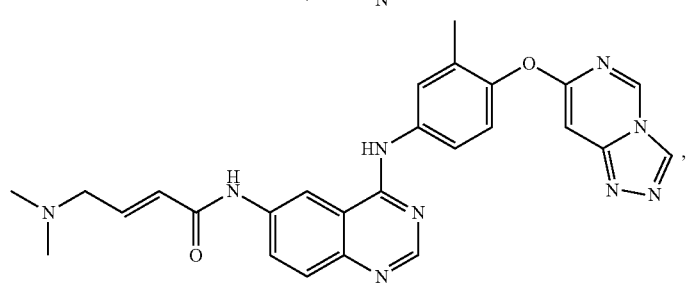
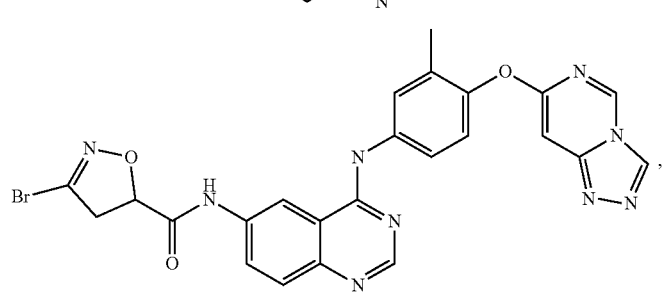
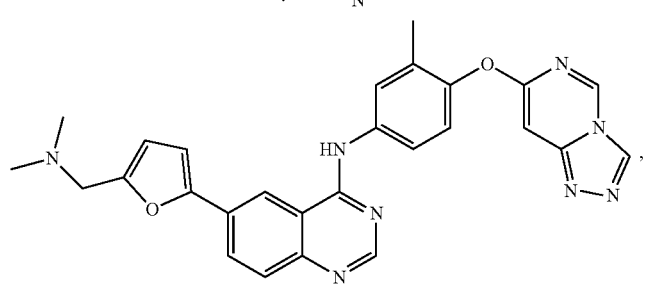

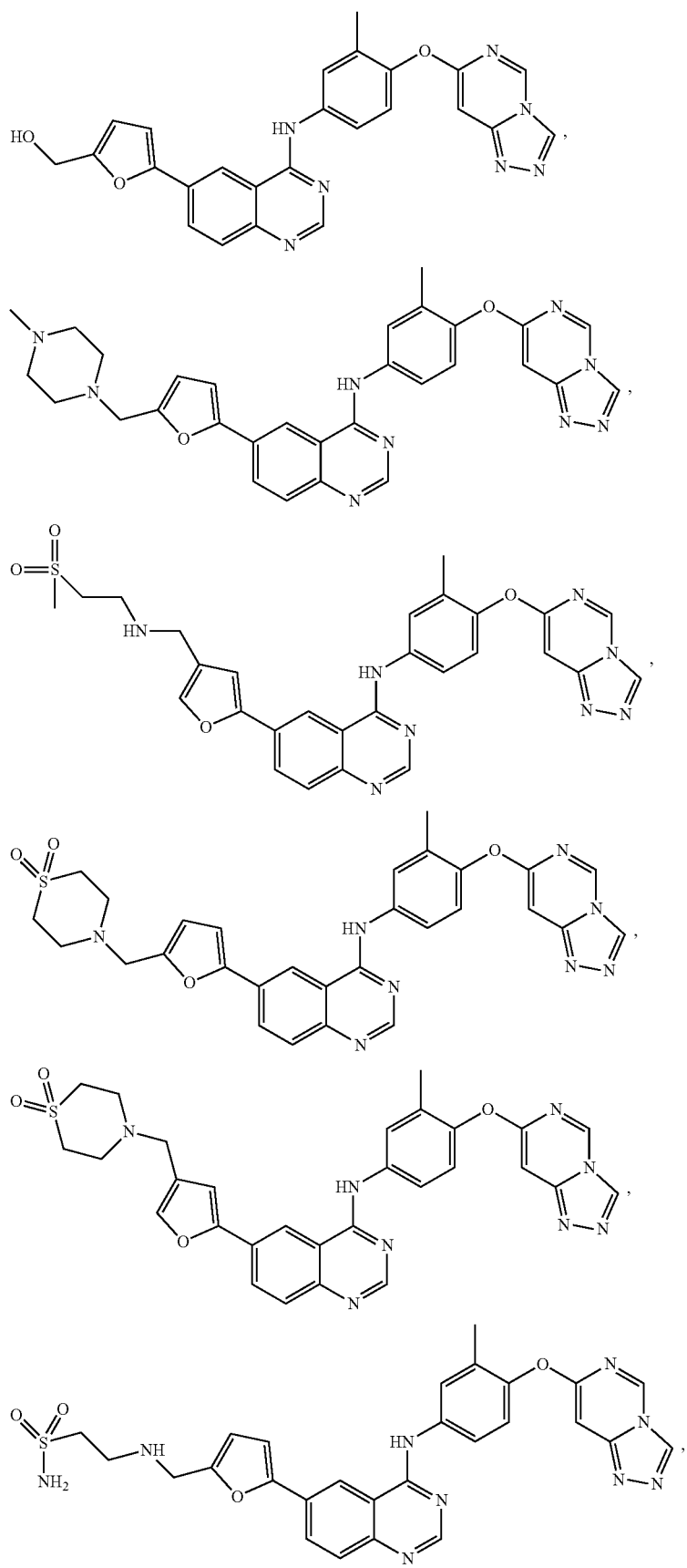

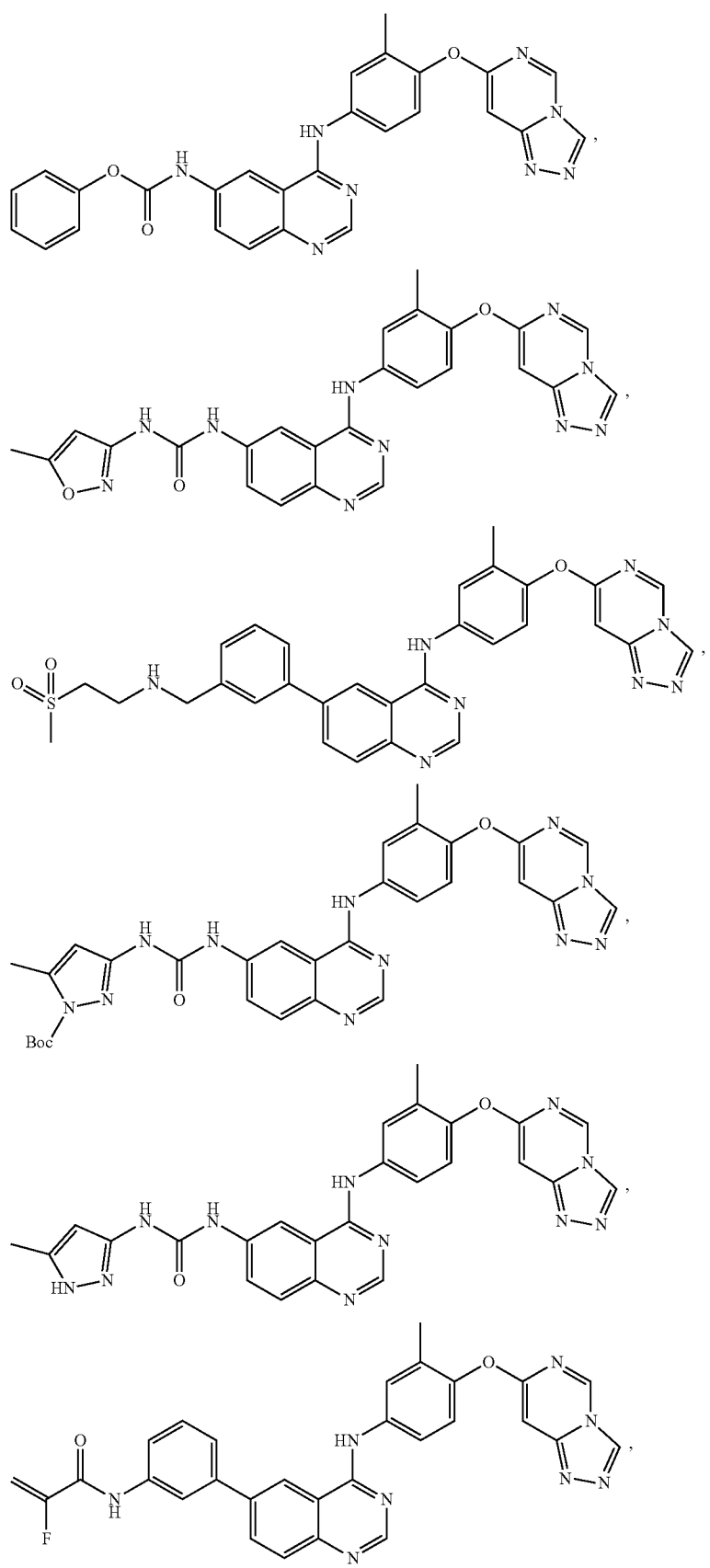

-continued
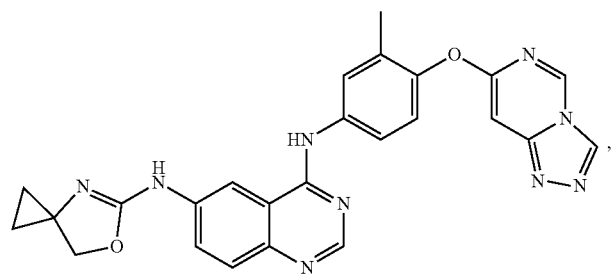
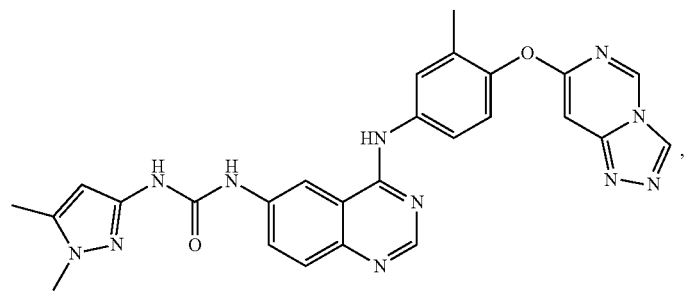
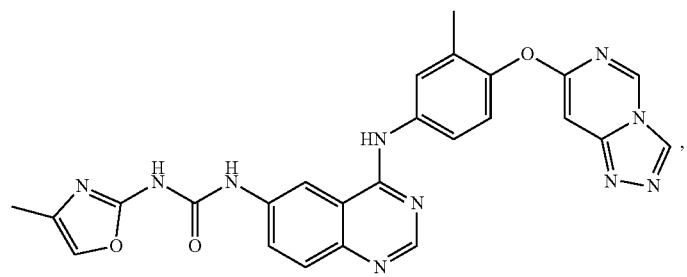
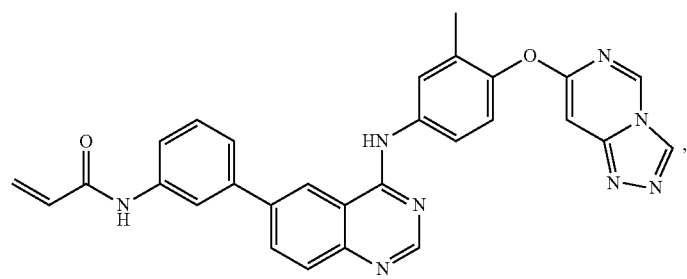
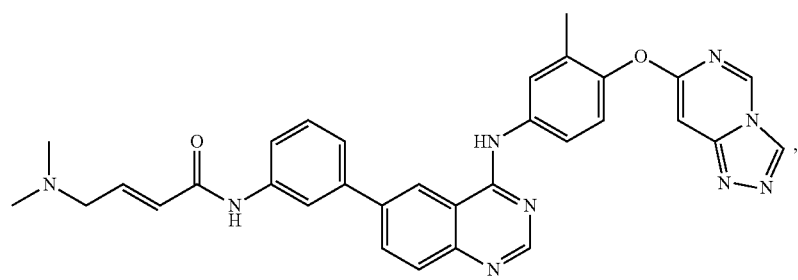
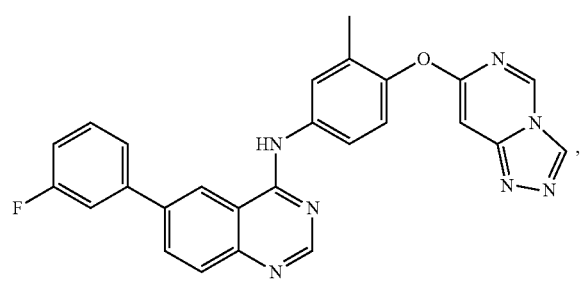
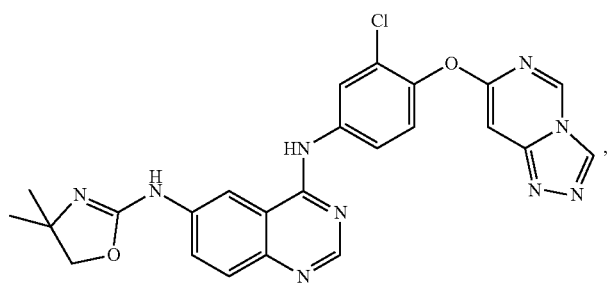

-continued
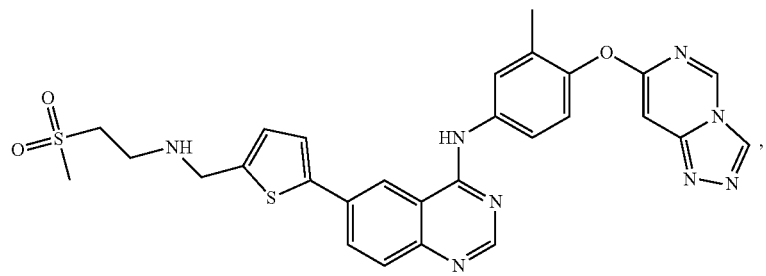
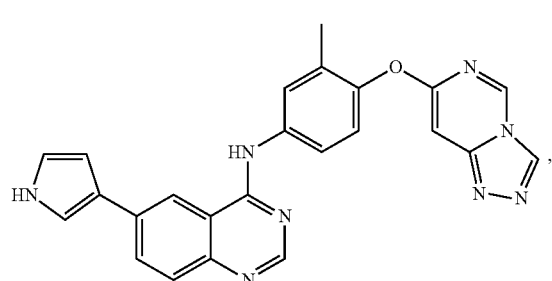
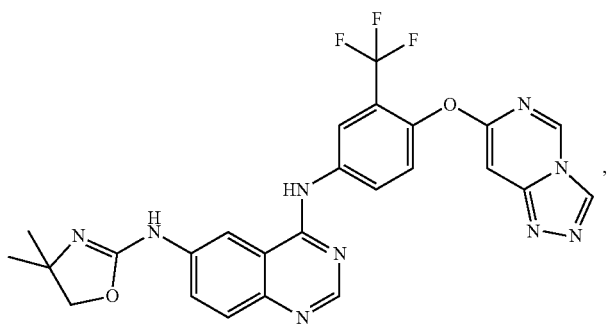
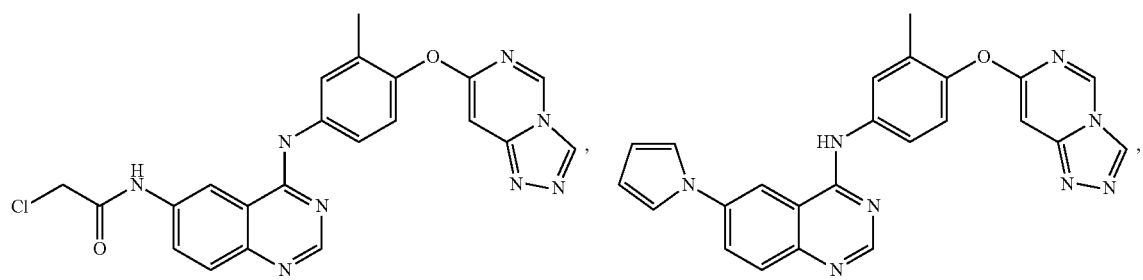
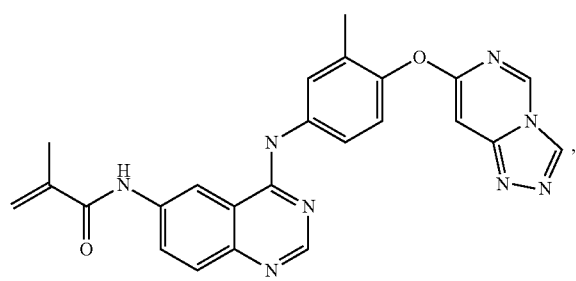
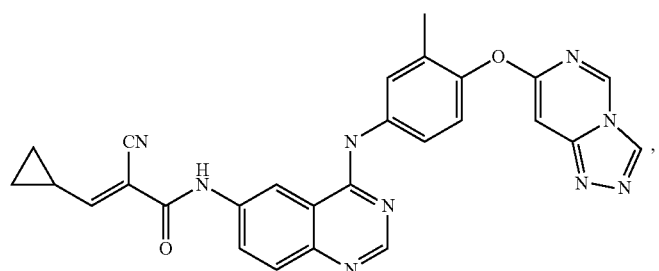
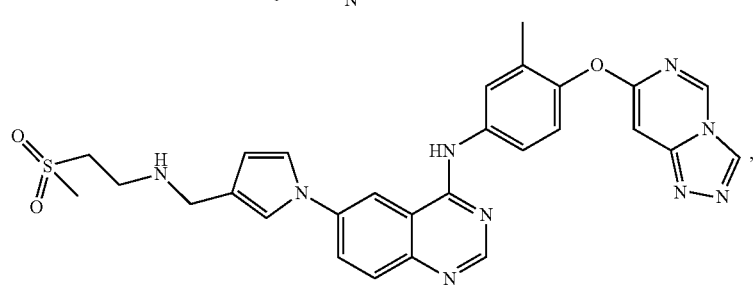

-continued
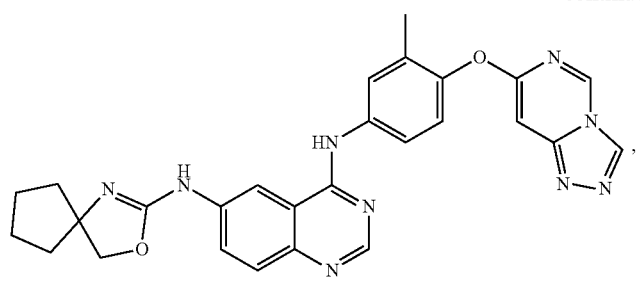
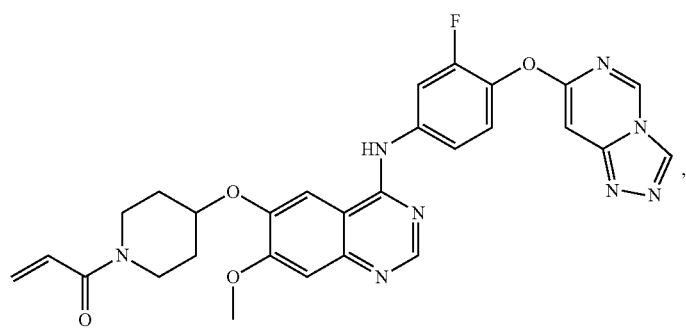
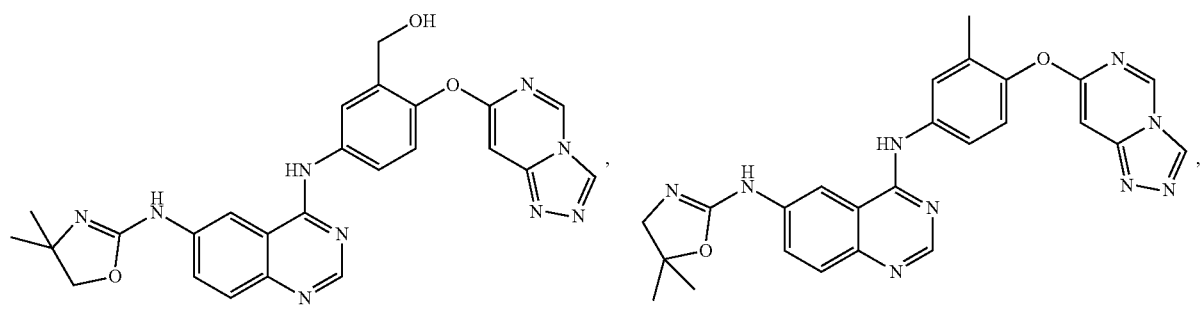
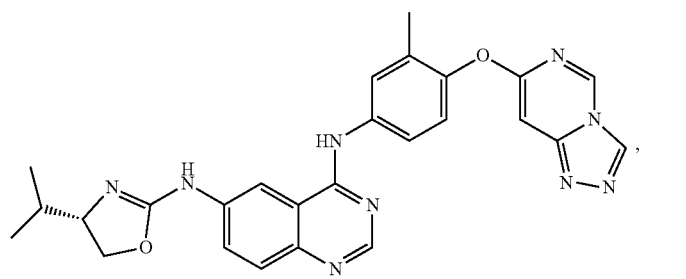
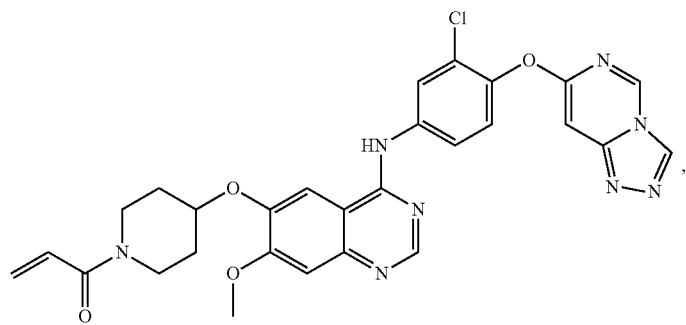

-continued
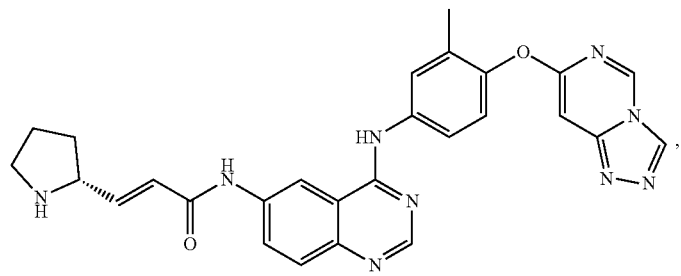
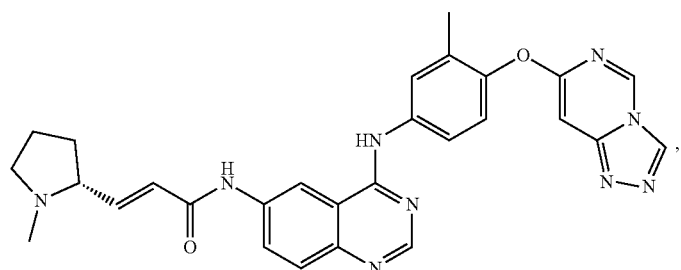
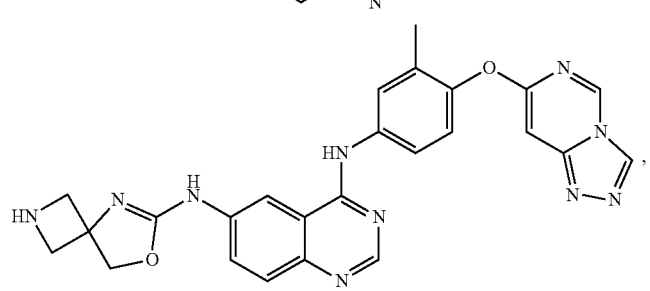
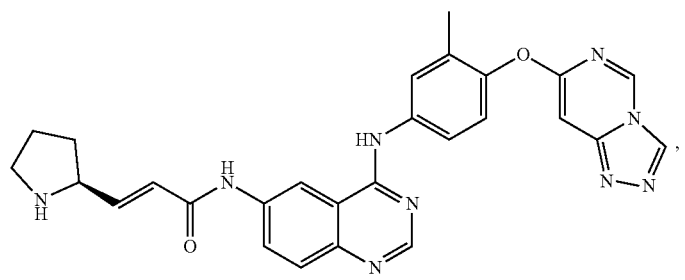
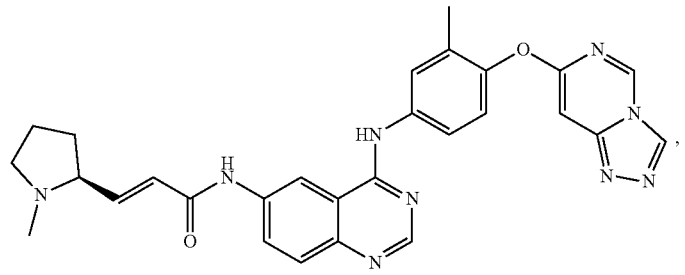
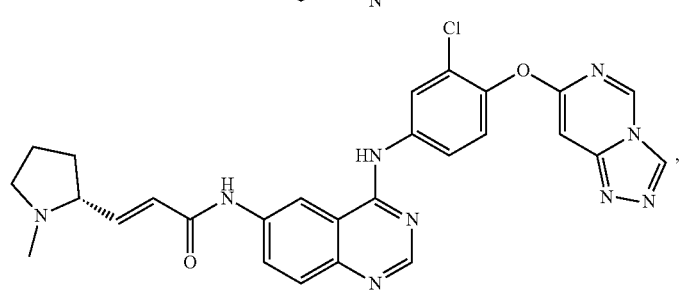

-continued
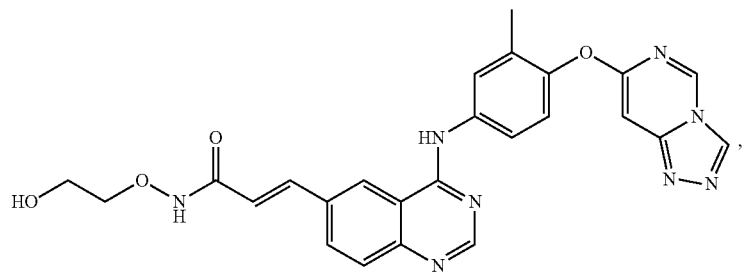
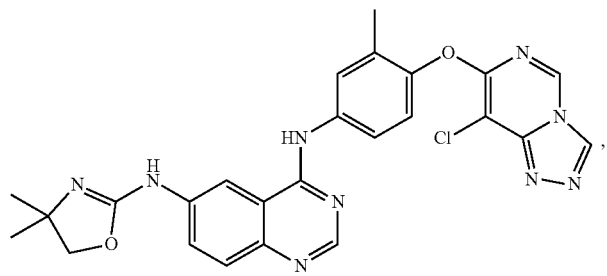
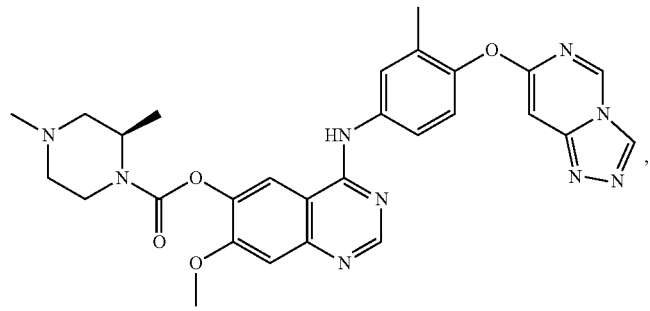
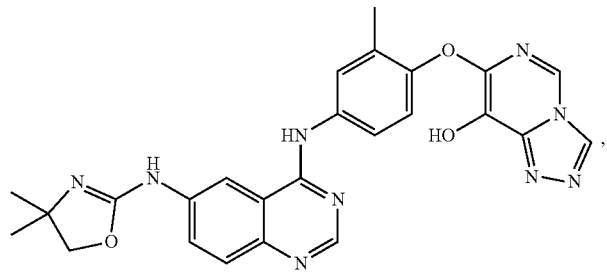
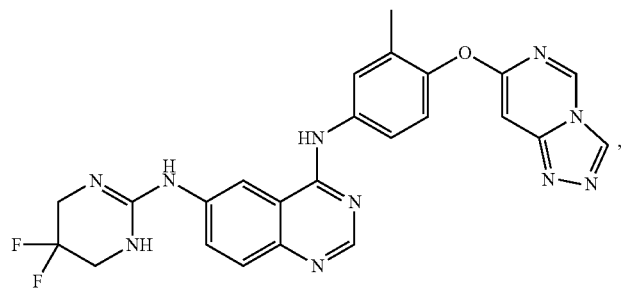
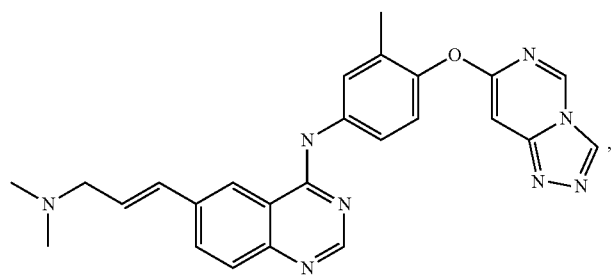

-continued
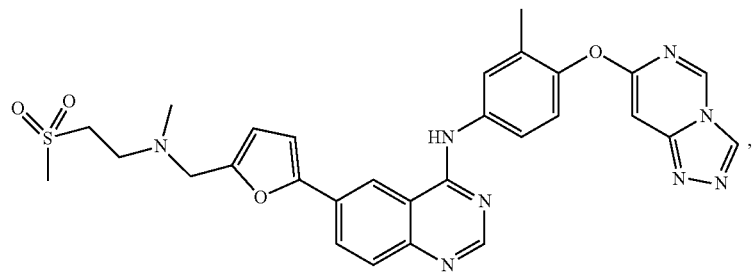
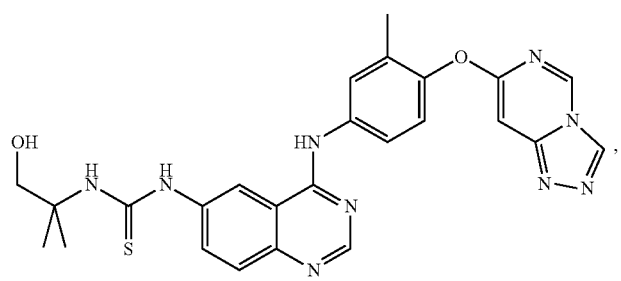
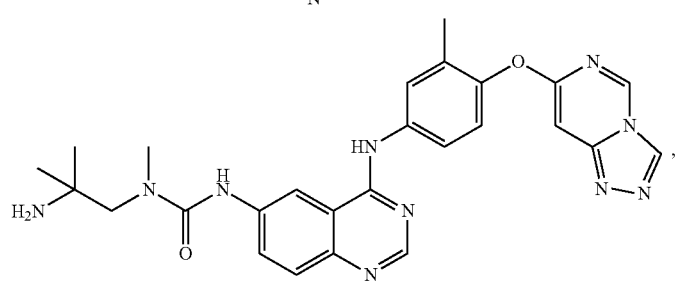
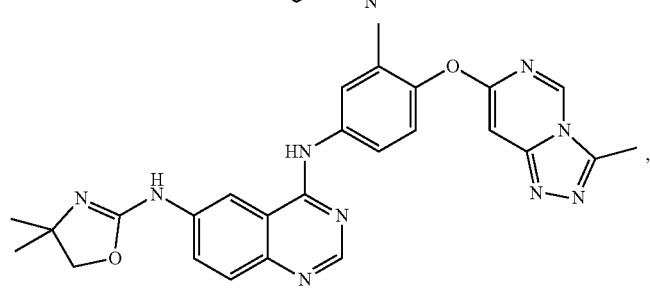
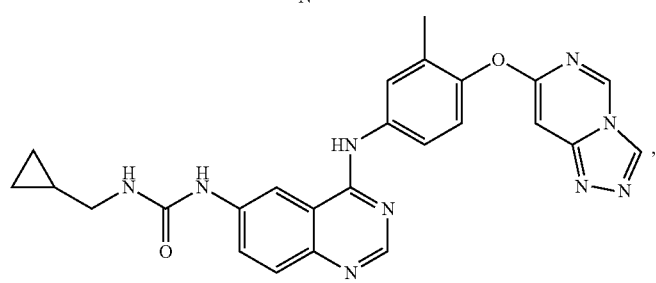
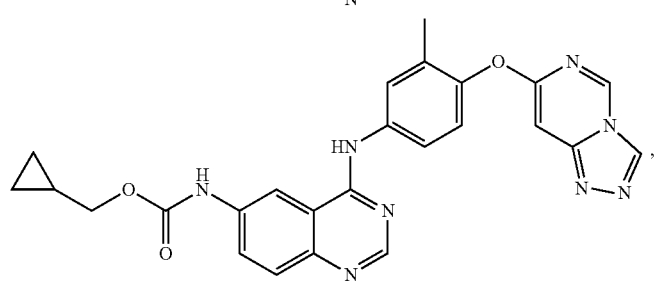

-continued
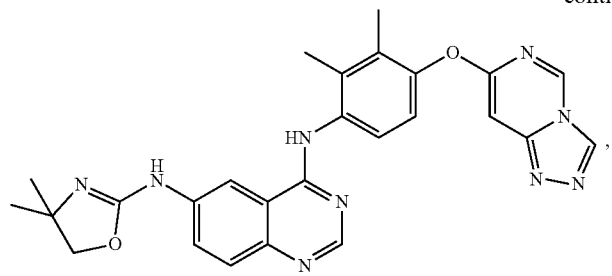
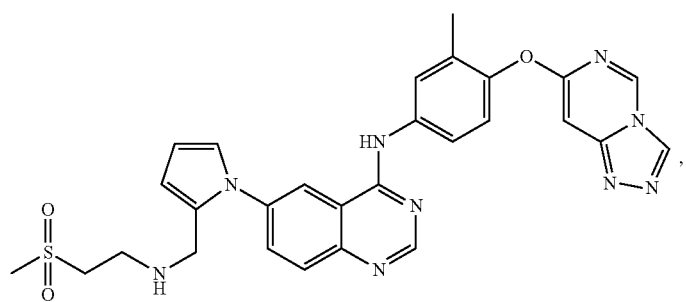
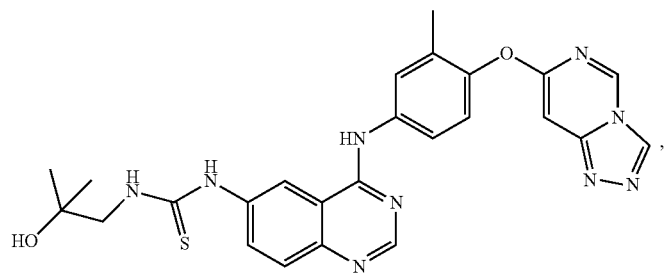
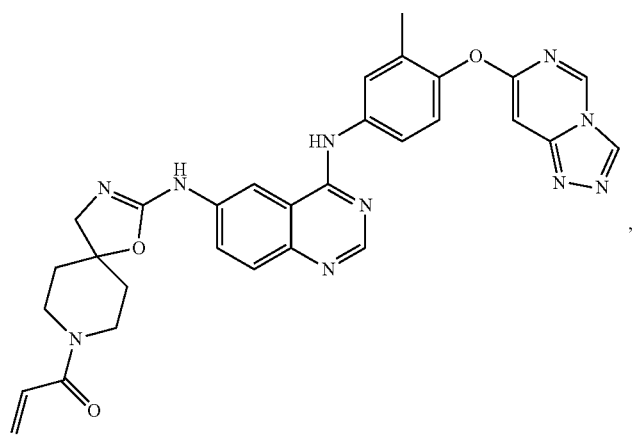
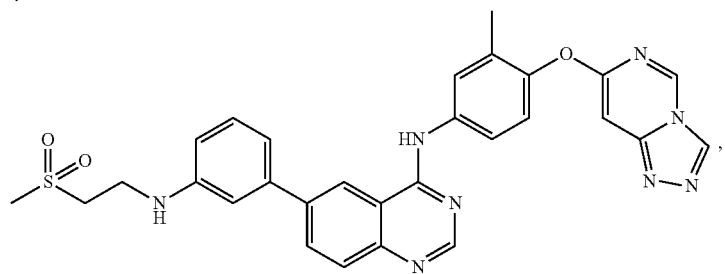

-continued
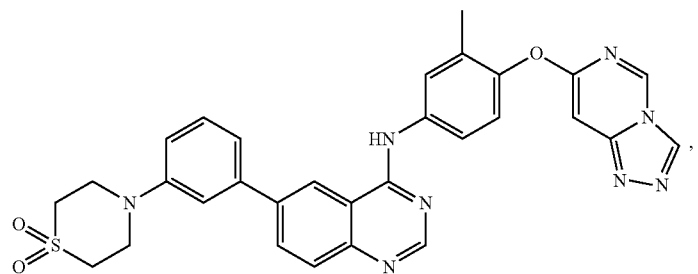
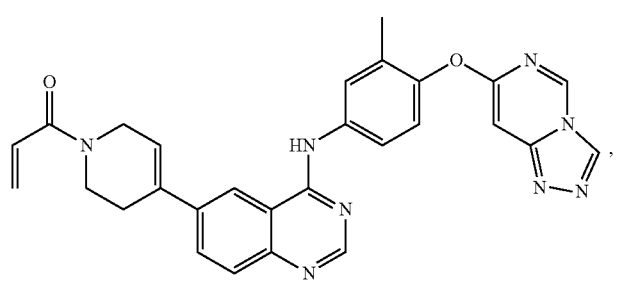
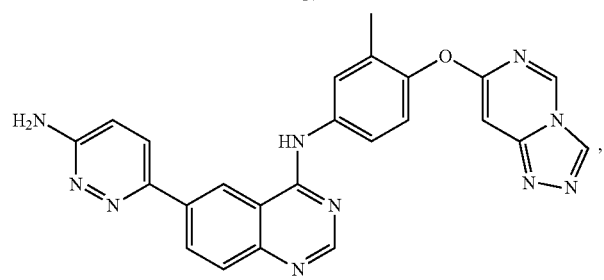
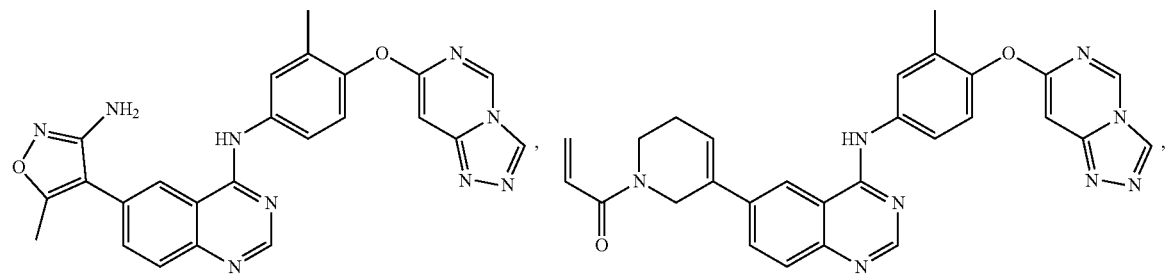
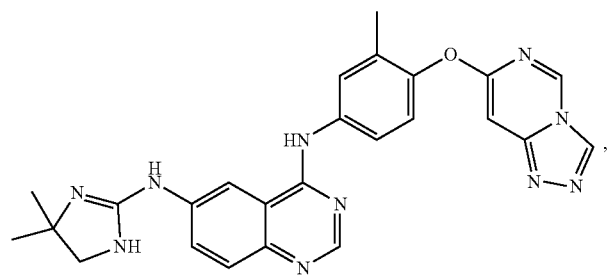
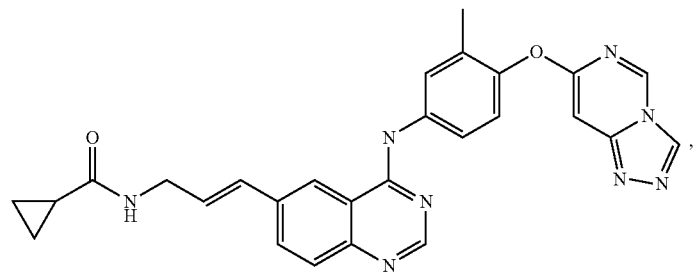

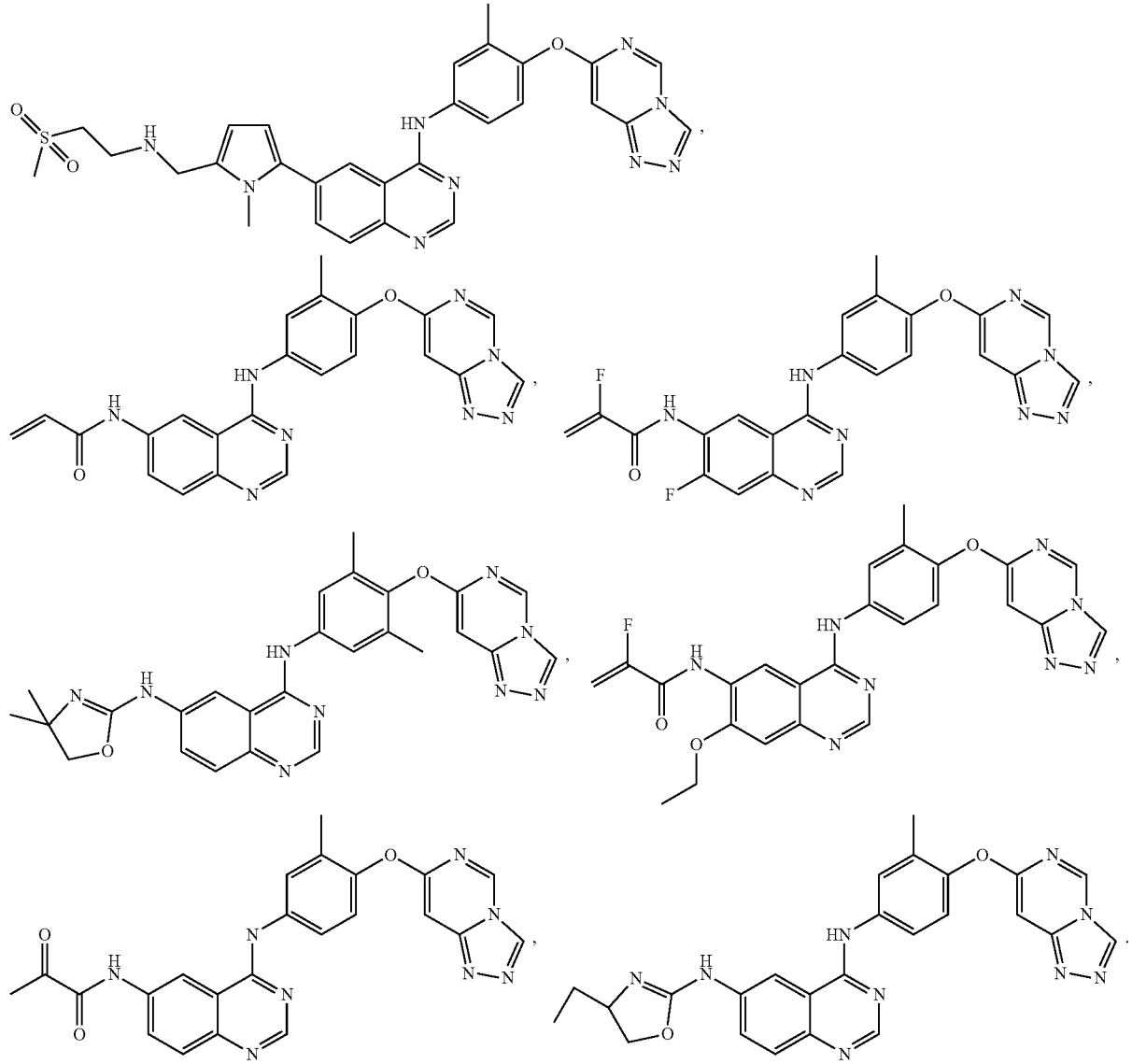

The nitrogenous heterocyclic compounds involved in the present invention may exhibit tautomerism, structural isomerism and stereoisomerism. The present invention includes any tautomeric or structural isomeric or stereoisomeric forms thereof and mixtures thereof.

Compound I can be synthesized by methods similar to those known in the field of chemistry, particularly according to the description herein. The raw materials are usually available from commercial sources such as Alirich or can be easily prepared by methods well known to those skilled in the art (obtained from SciFinder, Reaxys online database).

For illustrative purpose, schemes 1-8 show general methods for preparing the compounds of the present invention and key intermediates. For a more detailed description of each reaction step, the Embodiment Section below can be referred. The person skilled in the art understands that there are other synthetic routes that can be used to synthesize the compounds of the present invention. Although specific raw materials and reagents are described in the following methods and discussions below, they can be easily replaced with other raw materials and reagents in order to provide various derivatives and/or reaction conditions. In addition, a variety of the compounds prepared by the methods described below can be further modified according to the disclosure of the present invention through conventional chemical methods known to those skilled in the art.

The present invention also provides a method for preparing the compound I, which is any one of the following schemes:

Scheme 1

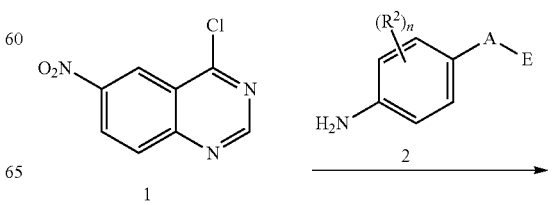

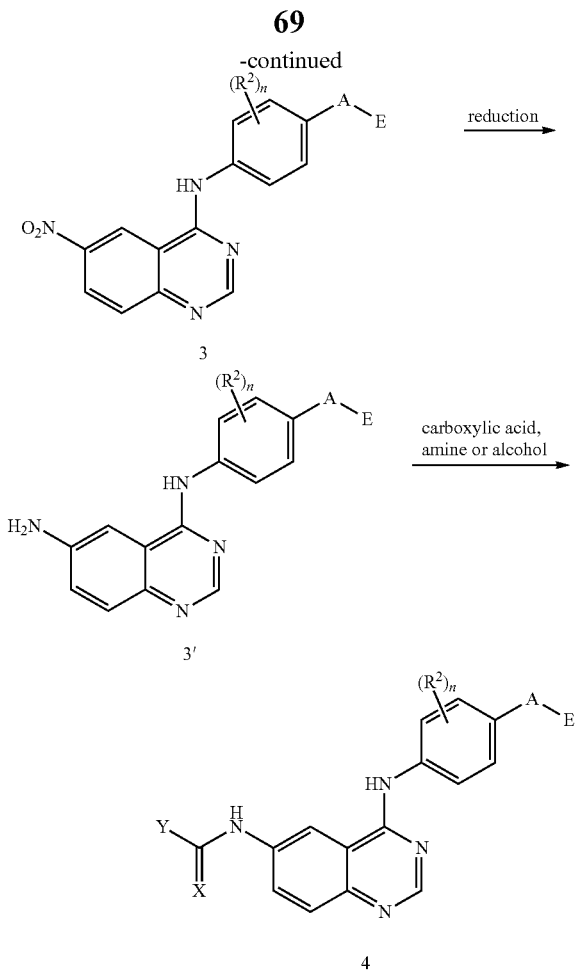

wherein,

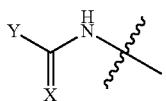

is part of the groups of $R^3$ described above (e.g. —$NR^{15}C(=O)OR^{18}$, —$NR^{15}C(=O)SR^{18}$, —$NR^{15}C(=O)R^{16}$, —$NR^{15}C(=O)NR^{16}R^{17}$, —$NR^{15}C(=S)NR^{16}R^{17}$ or $NR^{15}C(=S)R^{16}$), e.g. amido, ureido, thioureido or alkoxycarbonylamino.

Scheme 1 illustrates the synthesis of a "N-linked" quinazoline compound (4) of the present invention, wherein A and E are defined as above. According to scheme 1, 4-anilino-6-nitro-quinazoline (3) can be prepared by reaction of an appropriate aniline (2) with a quinazoline (1) which is substituted with a suitable leaving group such as a chloride at the 4-position under standard coupling condition. The coupling reaction can be conducted in various solvents such as isopropanol, acetonitrile or DMF, and a high temperature and a base such as DIEA, potassium carbonate may be required. The reduction of the nitro of compound (3) can be conducted by various standard reduction methods known in the art, e.g. Pd/C with $H_2$, Pd/C with hydrazine, Ni with $H_2$, Ni with hydrazine, Pt/C with NaOH, and $H_2$ with Zn/AcOH, Zn/$NH_4$Cl, or Fe/HOAc. In one embodiment, reduction is conducted by Ni with $H_2$. When $R^2$ is a halogen, reduction can be achieved by Pt/C with NaOH and $H_2$ or Zn/$NH_4$Cl. The obtained aniline (3') can undergo a condensation reaction with a carboxylic acid to give an amide, or a reaction with another aliphatic amine in the presence of a thio agent to give a thiourea, or a reaction with another aliphatic amine in the presence of carbonyldiimidazole to give a urea, then compound (4) is obtained. A suitable base and/or a high temperature may be required in these reactions.

That is to say the method for preparing compound 4 comprises the following step: conducting an amidation reaction of compound 3' with a carboxylic acid to give compound 4; or, conducting a substitution reaction of compound 3' with an amine or an alcohol in the presence of a thio agent (e.g. thiocarbonyldiimidazole) or carbonyldiimidazole to give compound 4.

Scheme 2

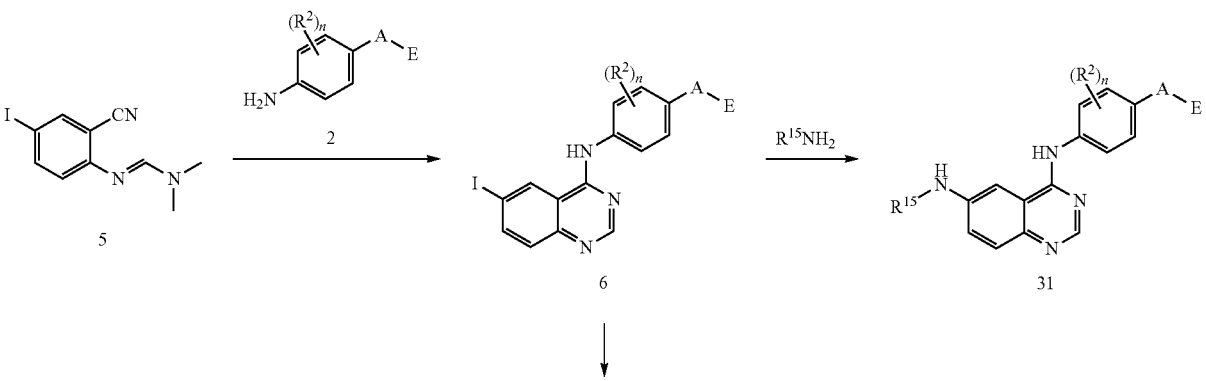

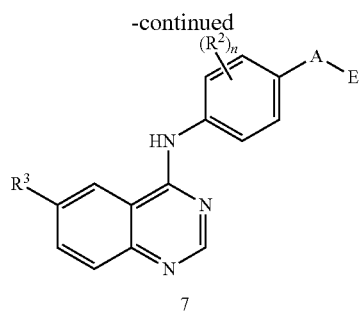

In the compound 7, $R^3$ is preferably a group that can be connected through standard Suzuki, Heck or Stille reaction.

Scheme 2 illustrates an alternative synthetic route for the "N-linked" quinazoline compound (31) of the present invention, wherein A and E are defined as herein. According to scheme 2, 4-anilino-6-iodo-quinazoline (6) can be prepared by reaction of (E)-N-(2-cyano-4-iodophenyl)-N,N-dimethylformamidine (5) with compound (2). Compound 31 can be prepared by a palladium-mediated cross-coupling reaction of the iodoquinazoline (6) obtained with a suitable amine $R^{15}NH_2$, which can be conducted through a palladium catalyst such as $Pd(OAc)_2$, $Pd(PPh_3)_4$, $Pd(dppf)_2Cl_2$, $Pd_2(dba)_3$, a phosphine ligand and a base in a suitable organic solvent such as THF, DME, DMF or toluene. Scheme 2 also illustrates the preparation of C-linked compound (7). These analogues can be prepared from compound (6) by a palladium-mediated cross-coupling reaction with a boronic acid, olefin, or organotin compound under standard Suzuki, Heck, or Stille reaction conditions well known in the art.

That is to say that the method for preparing compound 31 comprises the following step: conducting a coupling reaction of compound 6 with $R^{15}NH_2$ in an organic solvent (e.g. THF, DME, DMF, or toluene) in the presence of a palladium catalyst (e.g. $Pd(OAc)_2$, $Pd(PPh_3)_4$, $Pd(dppf)_2Cl_2$ or $Pd_2(dba)_3$), a phosphine ligand and a base to give the compound 31;

the method for preparing compound 7 comprises the following step: conducting a coupling reaction of compound 6 with "boronic acid, olefin, or organotin compound" in the presence of a palladium catalyst to give compound 7;

Scheme 3 illustrates the synthetic route for the "N-linked" dihydrooxazole-quinazoline compound (10), wherein A and E are defined as herein. According to scheme 3, thiourea (9) can be prepared by a condensation reaction of amidine (8) with a suitable aniline (2) in the presence of an acid such as HOAc in a suitable organic solvent such as isopropyl acetate (IPAc). Dihydrooxazol-quinazoline compounds (10) can be prepared by a cyclization reaction of thiourea (9) under various conditions, for example, the cyclization reaction can be conducted in TI-IF (water can be contained therein) in the presence of TsCl and NaOH.

That is to say the method for preparing compound 10 comprises the following step: conducting a cyclization reaction of compound 9 to give compound 10; preferably, conducting a cyclization reaction of compound 9 in THF (water can be contained therein) in the presence of TsCl and NaOH to give compound 10.

Scheme 3

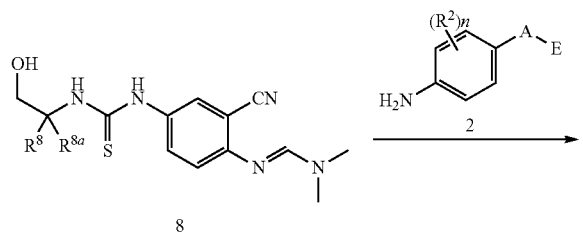

Scheme 4

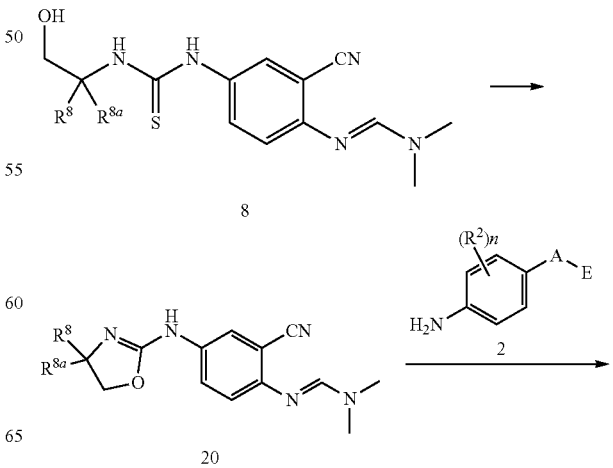

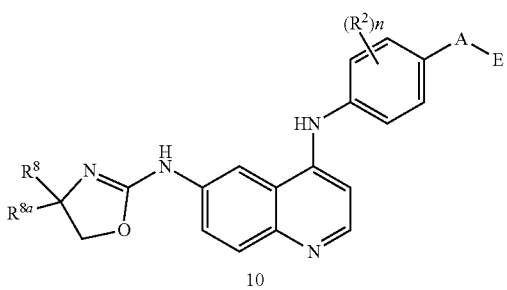

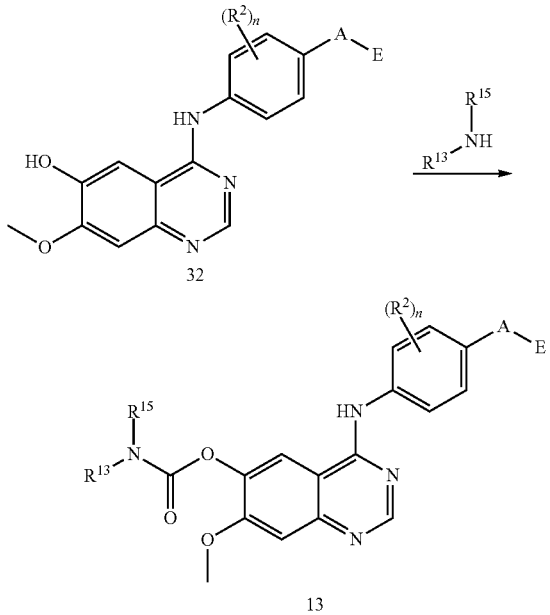

wherein, $R^y$ is a hydroxy protecting group (e.g. acyl).

Scheme 4 illustrates an alternative synthetic route for the "N-linked" dihydrooxazole-quinazoline compound (10), wherein A and E are defined as herein. According to method 4, firstly amidine (8) can be cyclized to prepare an oxazole ring under various conditions, for example, amidine (8) is dissolved in THF, a NaOH aqueous solution and TsCl are added, and the mixture is stirred at room temperature for several hours, then a condensation reaction with a suitable aniline (2) is conducted in the presence of an acid such as HOAc in a suitable organic solvent such as isopropyl acetate (IPAc) to give the dihydrooxazole-quinazoline compound (10). The advantages of scheme 4 includes avoiding the destruction of the base-labile E ring of compound (2), saving the amount of the compound (2) that is relatively difficult to be prepared, making the reaction of dihydrooxazole-quinazoline compound (10) cleaner, easier to be separated and purified, and improving the yield.

That is to say that the method for preparing compound 10 comprises the following step: conducting a cyclization reaction of compound 20 and compound 2 in an organic solvent (e.g. isopropyl acetate) in the presence of an acid (e.g. acetic acid) to give compound 10;

Scheme 5 illustrates the synthesis of the oxygen-linked quinazoline (13) of the present invention, wherein A and E are defined as herein. According to scheme 5, compound (12) can be prepared by a coupling condition of 4-chloro-6-oxy-7-methoxyquinazoline (11) with a suitable aniline (2) under standard coupling conditions as described in scheme 1. The oxygen moiety of compound (11) can be substituted with various $R^y$ groups, wherein $R^y$ is a suitable alcohol protecting group such as acyl. After the reaction with aniline, the optional protecting group can be removed under suitable conditions to give compound (32), for example in the case of an acetate protecting group, the protecting group can be removed with a base such as potassium carbonate in methanol. Compound (13) can be prepared by a reaction of the hydroxy of compound (32) with a suitable amine (namely

in the presence of triphosgene and a suitable base such as triethylamine in an organic solvent such as dichloromethane.

That is to say that the method for preparing compound 13 comprises the following step: conducting a substitution reaction of

with compound 32 in the presence of triphosgene and a base (e.g. triethylamine) in an organic solvent (e.g. dichloromethane) to give compound 13.

Scheme 5

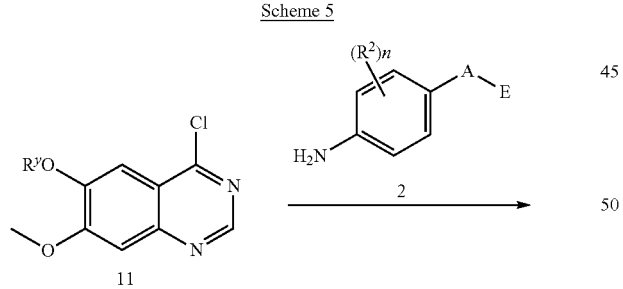

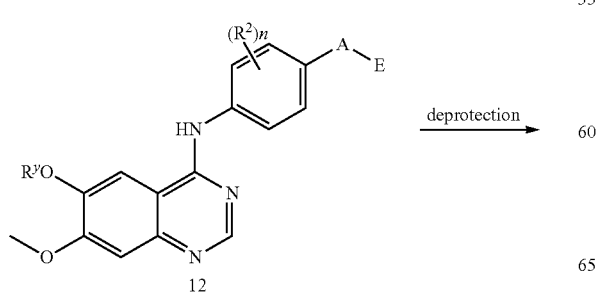

Scheme 6

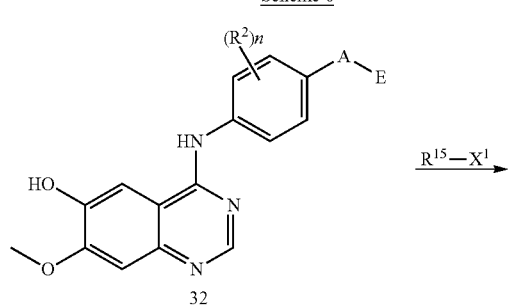

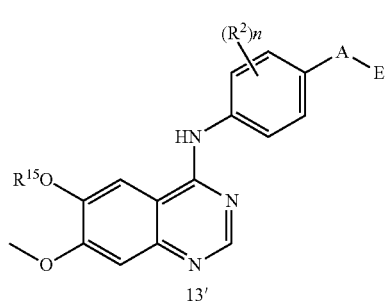

wherein, $X^1$ is H or a leaving group (e.g. tosyloxy).

Scheme 6 illustrates the reaction of the phenolic hydroxy of compound 32 with $R^{15}$—$X^1$ to give compound 13'.

That is to say that the method for preparing compound 13' comprises the following step: conducting a substitution reaction of compound 32 with $R^{15}$—$X^1$ to give compound 13'.

Scheme 7

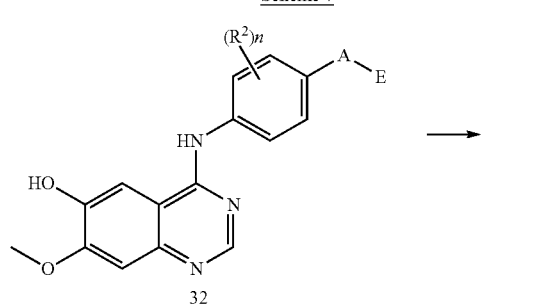

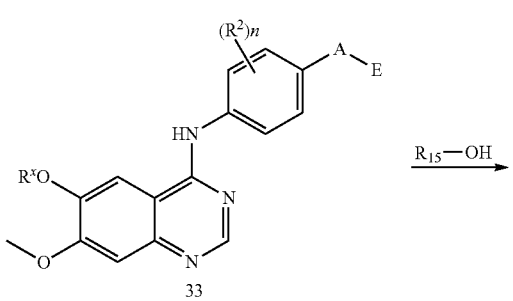

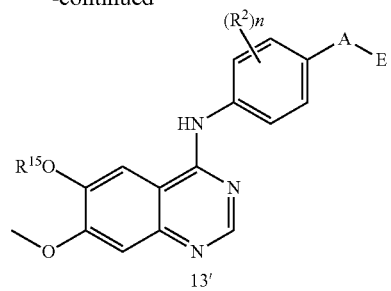

wherein, $R^xO$— is a leaving group (e.g. tosyloxy).

Scheme 7 illustrates that the phenolic hydroxy of compound 32 is converted to an activated leaving group such as tosyloxy, then compound 33 is reacted with $R^{15}$—OH to give compound 13'.

That is to say that the method for preparing compound 13' comprises the following step: conducting a substitution reaction of compound 33 with $R^{15}$—OH to give the compound 13'.

Scheme 8

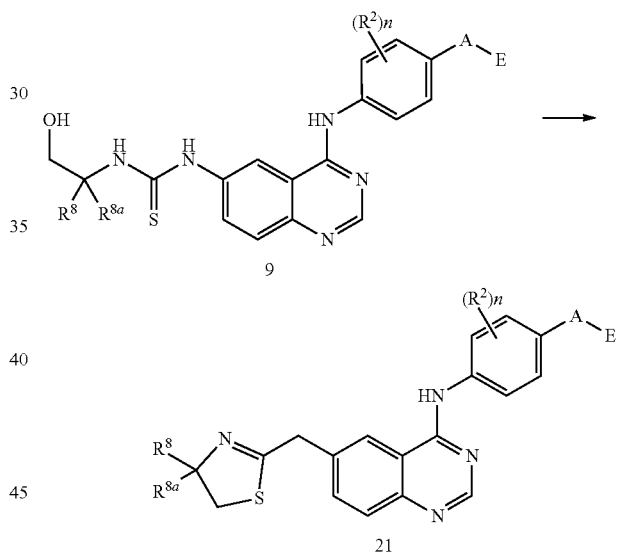

Scheme 8 illustrates the synthetic route for the "N-linked" dihydrothiazole-quinazoline compound (21), wherein A and E are defined as herein. According to the synthesis methods reported in the references, the dihydrothiazole-quinazoline compound (21) can be prepared by a cyclization reaction of thiourea (9) under various conditions, for example, thiourea (9) is treated in THE with TsCl and NaOH aqueous solution. However, in practical operation, a dihydrooxazole ring or a small amount of a dihydrothiazole ring is usually obtained with the method comprising TsCl and NaOH aqueous solution. At the same time, considering the stability of the E-ring under other acidic or basic reaction conditions, the Mitsunobu reaction method of DIAD/PPh$_3$ is used, this method is conducted in a mild reaction condition which does not affect the stability of the E-ring, and can give dihydrothiazole-quinazoline compound (21) with a better yield.

That is to say that the method for preparing compound 21 comprises the following step: conducting a cyclization reaction of compound 9 in the presence of DIAD (diisopropyl azodicarboxylate) and PPh₃ to give compound 21; preferably the solvent of the cyclization reaction is DMF.

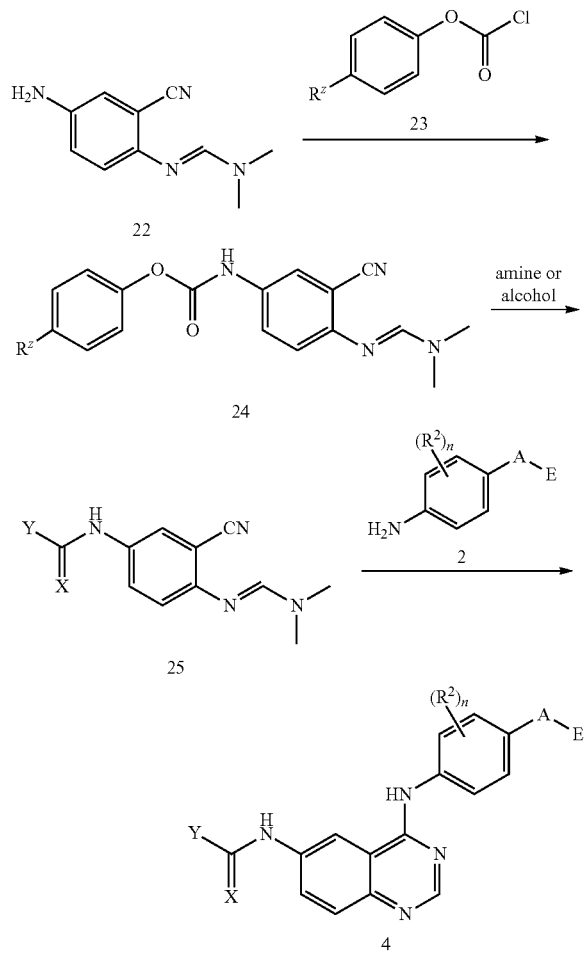

wherein,

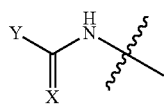

is part of the groups of R³ described above (e.g. —NR¹⁵C(=O)OR¹⁸, —NR¹⁵C(=O)R¹⁶, —NR¹⁵C(=O)NR¹⁶R¹⁷, —NR¹⁵C(=S)NR¹⁶R¹⁷ or —NR¹⁵C(=O)SR¹⁸, NR¹⁵C(=S)R¹⁶), e.g. amido, ureido, thioureido or alkoxyaminoacyl.

R¹ is H or nitro.

Scheme 9 illustrates an alternative route of quinazoline compound (4) substituted with urea or carbamate, wherein A and E are defined as herein. According to the method described in scheme 9, the active intermediate (24) can be prepared by reaction of amidine (22) with benzoyl chloride (23) substituted with Rᵃ. Amidine (25) substituted with urea or carbamate can be prepared by reaction of compound (24) with an amine or an alcohol under a suitable condition (a high temperature is required in reaction with alcohol).

According to the method described in scheme 3 above, quinazoline compound (4) can be prepared by a condensation reaction of amidine (25) with a suitable aniline (2) in the presence of an acid such as HOAc in a suitable organic solvent such as isopropyl acetate (IPAc). This scheme is an effective supplement to scheme 1. The advantage of this synthetic route includes: reducing the amount of the E-ring which is difficult to be prepared; avoiding the instability of the E-ring under high-temperature reaction condition; and avoiding the destruction of E ring in the preparation of urea and thiourea using a strong amine as raw material.

That is to say the method for preparing compound 4 comprises the following step: conducting a cyclization reaction of compound 25 and compound 2 in the presence of an acid (e.g. acetic acid) in an organic solvent (e.g. isopropyl acetate) to give compound 4.

The method for preparing compound I can further comprise scheme a or scheme b:

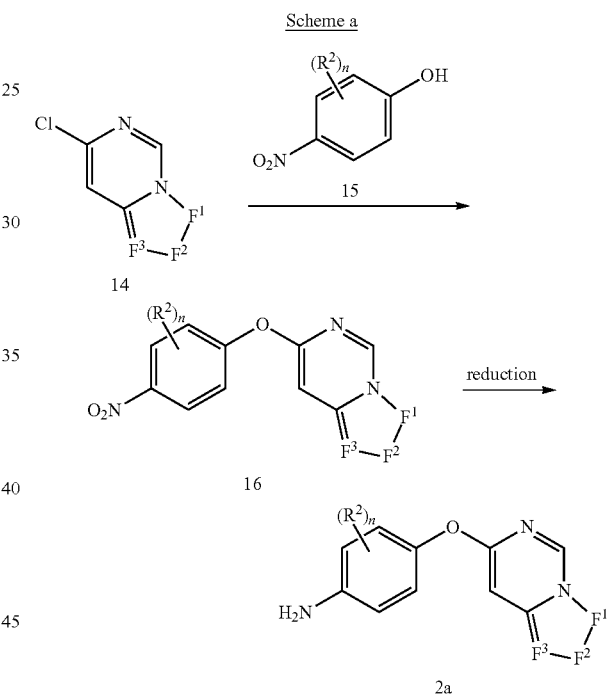

Scheme a illustrates the preparation of aniline intermediate (2a) suitable for use in schemes 1-8 from chloro compound (14) and 4-hydroxynitrobenzene (15) respectively. Chloro compound (14) and nitrophenol (15) are either commercially available or known in the literature, or can be prepared through standard methods by the person skilled in the art. Coupling product (16) can be prepared by reaction of chloro compound (14) with an optionally substituted 4-hydroxynitrobenzene (15) and a suitable base such as sodium carbonate, potassium carbonate or cesium carbonate in a polar organic solvent such as DMF, DMSO at a high temperature. The nitro of the compound (16) can be reduced by standard reduction methods such as Pd/C with H₂, Pd/C with hydrazine, Ni with H₂, Ni with hydrazine, Pt/C with NaOH, and H₂ with Zn/AcOH, Zn/NH₄C₁ or Fe/HOAc. When R₂ is halogen, the reduction can be achieved by Pt/C with NaOH and H₂ or Zn/NH₄Cl.

Scheme b

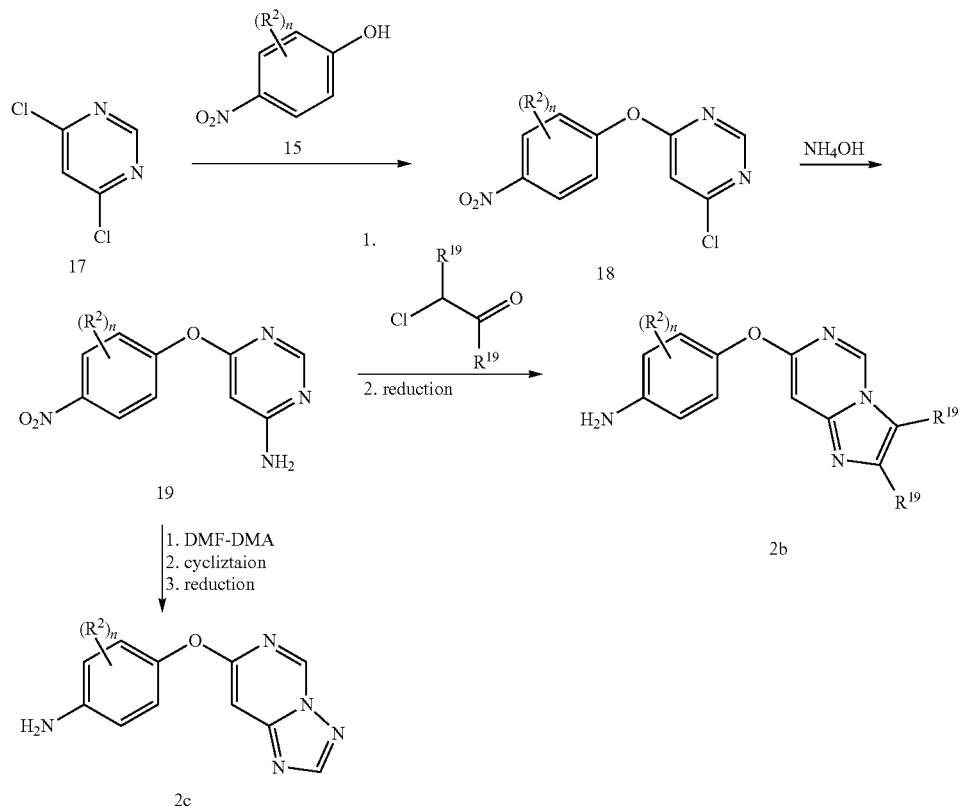

Scheme b illustrates the preparation of aniline intermediates (2b) and (2c) suitable for use in schemes 1-8. According to the method described in scheme b, the coupling product (18) can be prepared by reaction of dichloropyrimidine (17) with optionally substituted 4-hydroxynitrobenzene (15). The reaction of compound (18) with aqueous ammonia under a high temperature condition gives the 2-aminopyrimidine compound (19) which can be converted to an imidazolopyrimidine derivative by the reaction with an appropriately substituted 2-halo-carbonyl compound. For example, compound (19) can react with chloroacetaldehyde under heating. The conversion from compound (19) to the triazolopyrimidine can be achieved by a two-step process which comprises conducting a condensation reaction of (19) with dimethylformamide dimethyl acetal to give a N,N-dimethylformamidine derivative, followed by the reaction with hydroxyaminosulfonic acid to give the triazolopyrimidine. The reduction of the nitro can be achieved as described in scheme a to give compounds (2b) and (2c).

The scheme a can further comprise scheme i:

scheme i

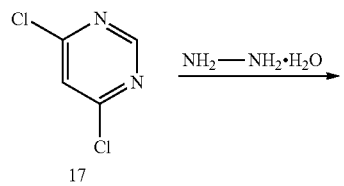

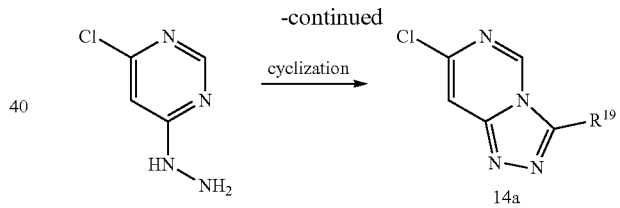

Scheme i illustrates a method for preparing chloro intermediate (14a) suitable for use in scheme a. The reaction of the substituted dichloropyrimidine (17) with hydrazine can be conducted in an alcohol solvent. The compound obtained is subjected to a reaction with an equivalent of carboxylic acid such as triethyl orthoformate or trimethyl orthoformate and an acid such as HCl, HOAc, or p-toluenesulfonic acid. In one embodiment, the cyclization reaction is conducted using trimethyl orthoformate and p-toluenesulfonic acid to give a triazole.

In any methods for preparing compound I, it may be advantageous to separate the reaction products from one another or from the raw material. The desired products in each step or series of steps are separated and/or purified to the desired degree of homogeneity by techniques conventional in the art. The separation involves multi-phase extraction, crystallization from a solvent or a mixture of solvents, or chromatographic separation. The chromatographic separation can involve a variety of methods including: normal phase and reverse phase, high pressure, medium pressure, and low pressure liquid chromatography methods and devices; preparative thin layer or thick layer chromatography.

A suitable separation method depends on the nature of the compound, for example, the chromatographic separation depends on the presence or absence of a polar functional group, the multi-phase extraction in an acidic and basic media depends on the stability of the substance, etc. The person skilled in the art will employ the technique by which the desired separation is most likely to be achieved. The enantiomer can be separated by chiral HPLC column.

The present invention also provides compound 2, 3, 3', 6, 9, 12, 32 or 33 as shown below:

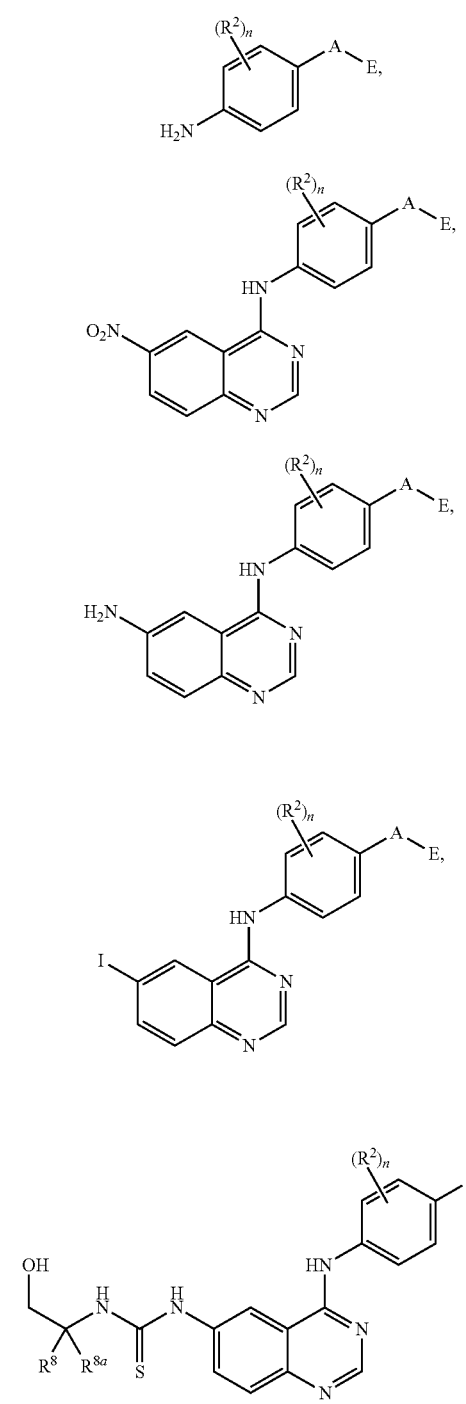

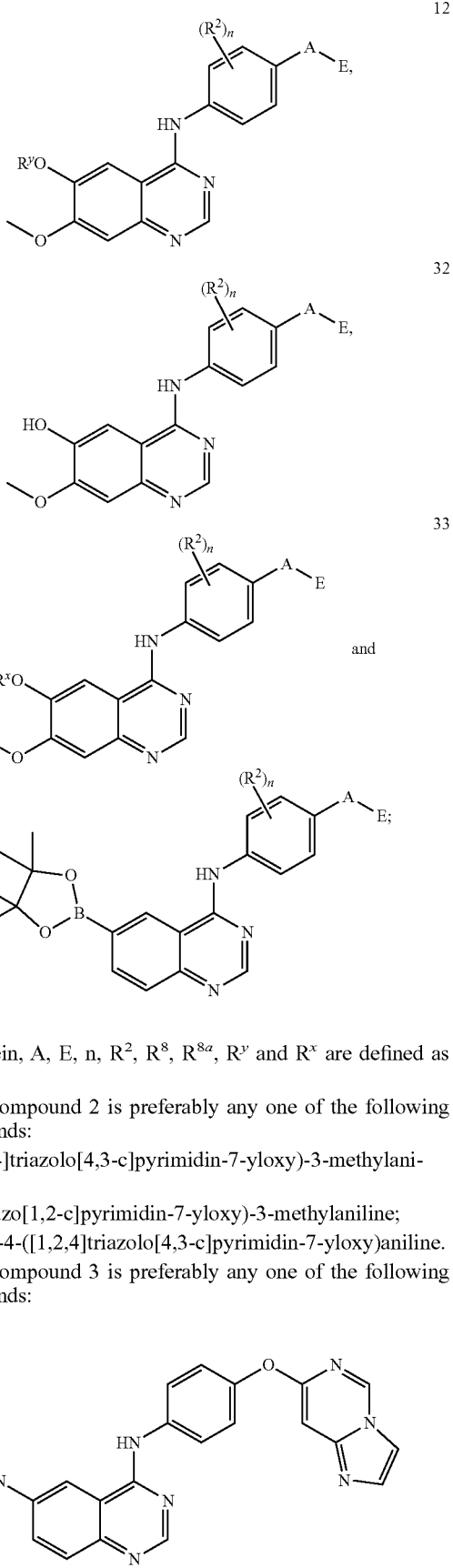

wherein, A, E, n, $R^2$, $R^8$, $R^{8a}$, $R^y$ and $R^x$ are defined as above.

The compound 2 is preferably any one of the following compounds:
4-([1,2,4]triazolo[4,3-c]pyrimidin-7-yloxy)-3-methylaniline;
4-(imidazo[1,2-c]pyrimidin-7-yloxy)-3-methylaniline;
3-fluoro-4-([1,2,4]triazolo[4,3-c]pyrimidin-7-yloxy)aniline.

The compound 3 is preferably any one of the following compounds:

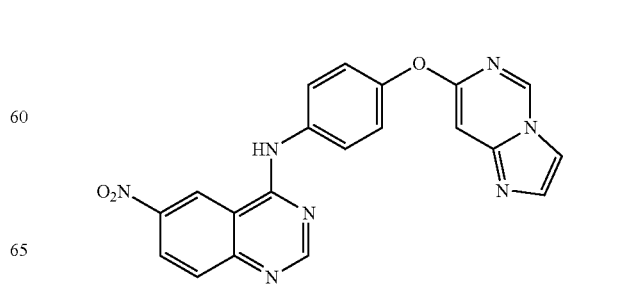

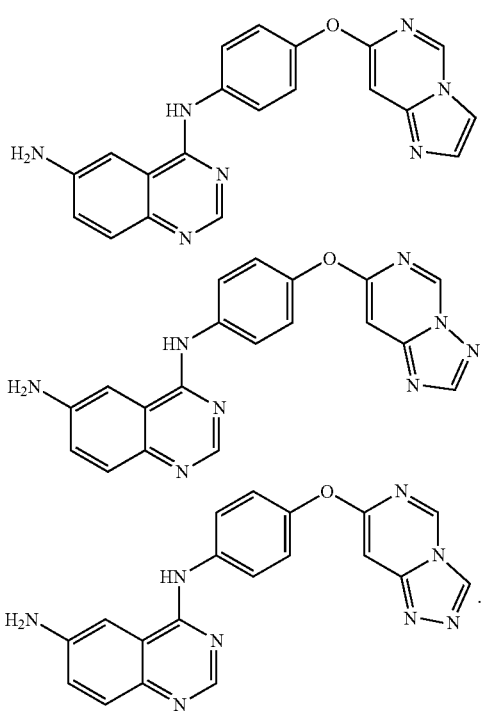

The compound 3' is preferably any one of the following compounds:

The compound 6 is preferably any one of the following compounds:
N-(4-([1,2,4]triazolo[4,3-c]pyrimidin-7-yloxy)-3-methylphenyl)-6-iodoquinazolin-4-amine.

The compound 9 is preferably any one of the following compounds:

1-(1-hydroxy-2-methylpropan-2-yl)-3-(4-((4-(imidazo[1,2-c]pyrimidin-7-yloxy)-3-methylphenyl)amino)quinazolin-6-yl)thiourea;

1-(4-((4-([1,2,4]triazolo[4,3-c]pyrimidin-7-yloxy)-3-methylphenyl)amino)quinazolin-6-yl)-3-(1-hydroxy-2-methylpropan-2-yl)thiourea.

The present invention also provides a use of the nitrogenous heterocyclic compound, the pharmaceutically acceptable salt, the enantiomer, the diastereomer, the tautomer, the solvate, the metabolite or the prodrug thereof in manufacturing a medicament, the medicament is used for a disease treated by inhibiting EGFR and/or ErbB2 receptor tyrosine kinase. Preferably, the medicament is used for a disease treated by selectively inhibiting ErbB2 receptor tyrosine kinase. The "disease treated by selectively inhibiting ErbB2 receptor tyrosine kinase" can be breast cancer, gastric cancer and the like (for example, neratinib for treating breast cancer is an oral irreversible EGFR/ErbB2 inhibitor, referring to ExteNet and NEfERTT clinical trials).

The present invention also provides a use of the nitrogenous heterocyclic compound, the pharmaceutically acceptable salt, the enantiomer, the diastereomer, the tautomer, the solvate, the metabolite or the prodrug thereof in manufacturing an inhibitor for EGFR and/or ErbB2 receptor tyrosine kinase, preferably, in manufacturing a selective inhibitor for ErbB2 receptor tyrosine kinase.

The present invention also provides a pharmaceutical composition, which comprises the nitrogenous heterocyclic compound, the pharmaceutically acceptable salt, the enantiomer, the diastereomer, the tautomer, the solvate, the metabolite or the prodrug thereof, and at least a pharmaceutical excipient.

The dose of the nitrogenous heterocyclic compound, the pharmaceutically acceptable salt, the enantiomer, the diastereomer, the tautomer, the solvate, the metabolite or the prodrug thereof can be a therapeutically effective amount.

The pharmaceutical excipient, the selection of which varies depending on the routes of administration and the characteristic of action, can generally be fillers, diluents, adhesives, wetting agents, disintegrants, lubricants, emulsifiers, suspending agents and the like that are conventional in the art.

The pharmaceutical composition can be administered by oral administration, injection (intravenous, intramuscular, subcutaneous and intracoronary), sublingual administration, buccal administration, rectal administration, transurethral administration, transvaginal administration, nasal administration, inhalation or topical administration, preferably oral administration.

In the present invention, unless otherwise specified, the following terms in the description and the claims of the invention have the following meanings:

The term "alkyl" refers to a saturated linear or branched monovalent hydrocarbon group having one to twelve carbon atoms (e.g. $C_1$-$C_6$ alkyl, e.g. $C_1$-$C_4$ alkyl). Examples of alkyl include but not limited to methyl, ethyl, 1-propyl, 2-propyl, 1-butyl, 2-methyl-1-butyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl.

The term "alkenyl" refers to a linear or branched monovalent hydrocarbon group having two to twelve carbon atoms with at least one unsaturated position i.e. carbon-carbon $sp^2$ double bond (e.g. $C_2$-$C_6$ alkenyl, e.g. $C_2$-$C_4$ alkenyl), which includes the group orientated as "cis" and "trans" or "E" and "Z". Examples of alkenyl include but are not limited to vinyl, allyl, 1-cyclopent-1-enyl, 1-cyclopent-2-enyl, 1-cyclopent-3-enyl, 5-hexenyl, 1-cyclohex-1-enyl, 1-cyclohex-2-enyl, and 1-cyclohex-3-enyl.

The term "alkynyl" refers to a linear or branched monovalent hydrocarbon group having two to twelve carbon atoms with at least one unsaturated position i.e. carbon-carbon sp triple bond (e.g. $C_2$-$C_6$ alkynyl, e.g. $C_2$-$C_4$ alkynyl). Examples of alkynyl include but are not limited to ethynyl and propynyl.

The terms "cycloalkyl", "carbocyclyl", and "carbocycle" are used interchangeably herein, and refer to a non-aromatic saturated or partially unsaturated monovalent cyclic hydrocarbon group having three to ten carbon atoms (e.g. $C_3$-$C_6$ cycloalkyl). Examples of monocyclic carbocycle group include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl cyclononyl, cyclodecyl, cycloundecyl and cyclododecyl. The term "cycloalkyl" also includes polycyclic (e.g. bicyclic and tricyclic) cycloalkyl, wherein the polycyclic structure optionally includes saturated or partially unsaturated cycloalkyl fused with saturated or partially unsaturated cycloalkyl or heterocyclyl or aryl or heteroaryl. Bicyclic carbocycle having 7 to 12 atoms can be arranged as bicyclo[4,5], [5,5], [5,6] or [6,6] system, or as bridged ring system such as bicyclo[2.2.1]heptane, bicyclo[2.2.2]octane and bicyclo[3.2.2]nonane.

The term "heteroalkyl" refers to a saturated linear or branched monovalent hydrocarbon group having one to twelve carbon atoms (e.g. $C_1$-$C_6$ heteroalkyl, e.g. $C_1$-$C_4$ heteroalkyl), wherein at least one carbon atom is replaced with a heteroatom selected from the group consisting of N, O, and S, and wherein the group can be a carbon group or a heteroatom group (i.e. the heteroatom can be located in the middle or at the end of the group). The term "heteroalkyl" includes alkoxy and heteroalkoxy.

The term "heteroalkenyl" refers to a linear or branched monovalent hydrocarbon group having two to twelve carbon atoms and at least one double bond, e.g. vinyl, propenyl etc., wherein at least one carbon atom is replaced with the heteroatom selected from the group consisting of N, O, and S, and wherein the group can be a carbon group or a heteroatom group (i.e. the heteroatom can be located in the middle or at the end of the group). "Heteroalkenyl" includes a group orientated as "cis" and "trans" or "E" and "Z".

The term "heteroalkynyl" refers to a linear or branched monovalent hydrocarbon group having two to twelve carbon atoms and at least one triple bond. Examples of heteroalkynyl include but are not limited to ethynyl, propynyl and the like, wherein at least one carbon atom is replaced with the heteroatom selected from the group consisting of N, O, and S, wherein the group can be a carbon group or a heteroatom group (i.e. the heteroatom can be located in the middle or at the end of the group).

The terms "heterocycle" and "heterocyclyl" can be used interchangeably herein and refer to a saturated and partially unsaturated carbocyclic group having 3 to 8 ring atoms, wherein at least one ring atom is independently the heteroatom selected from the group consisting of N, O, S, SO, and $SO_2$, and the remaining ring atoms are C. The group can be a carbon group or a heteroatom group. The term "heterocyclyl" includes heterocycloalkoxy. "Heterocyclyl" also includes a group wherein a heterocycle group is fused with a saturated, partially unsaturated, or completely unsaturated (i.e. aromatic) carbocyclic or heterocyclic ring. Examples of heterocyclyl include but are not limited to pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, 4-thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyco[3.1.0]hexanyl, 3-azabicyclo[4.1.0]heptanyl, and azabicyclo[2.2.2]hexanyl, 3H-indolyl, quinolizinyl and N-pyridinyl urea. A Spiro moiety is also included within the scope of this definition. Heterocyclyl can be C-attached or N-attached as long as it is possible. For example, a group derived from pyrrole can be pyrrol-1-yl (N-attached) or pyrrol-3-yl (C-attached). In addition, a group derived from imidazole can be imidazol-1-yl (N-attached) or imidazol-3-yl (C-attached). Examples of heterocyclyl of which two carbon atoms on the ring are partially substituted with an oxo (=O) are dihydroisoindol-1,3-dionyl and 1,1-dioxothiomorpholinyl.

By way of example and not limitation, a carbon bonded heterocycle is bonded at position 2, 3, 4, 5, or 6 of a pyridine; at position 3, 4, 5, or 6 of a pyridazine, at position 2, 4, 5, or 6 of a pyrimidine; at position 2, 3, 5, or 6 of a pyrazine; at position 2, 3, 4, or 5 of a furan, tetrahydrofuran, thiophene, pyrrole or tetrahydropyrrole; at position 2, 4, or 5 of an oxazole, imidazole or thiazole; at position 3, 4, or 5 of an isoxazole, pyrazole, or isothiazole; at position 2 or 3 of an aziridine; at position 2, 3, or 4 of an azetidine, at position 2, 3, 4, 5, 6, 7, or 8 of a quinoline or at position 1, 3, 4, 5, 6, 7, or 8 of an isoquinoline. Additional examples of carbon bonded heterocycle include 2-pyridinyl, 3-pyridinyl, 4-pyridinyl, 5-pyridinyl, 6-pyridinyl, 3-pyridazinyl, 4-pyridazinyl, 5-pyridazinyl. 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, a nitrogen bonded heterocycle is bonded at position 1 of an aziridine, azetidine, pyrrole, pyrrolidine, 2-pyrroline, 3-pyrroline, imidazole, imidazoline, 2-imidazoline, 3-imidazoline, pyrazole, pyrazoline, 2-pyrazoline, 3-pyrazoline, piperidine, piperazine, indole, indoline, 1H-indazole, position 2 of an isoindole or dihydroisoindoline, position 4 of a morpholine, and position 9 of a carbazole or β-carboline. More typically, the nitrogen bonded heterocycle includes 1-aziridine, 1-azetidinyl, 1-pyrrolyl, 1-imidazolyl, 1-pyrazolyl, and 1-piperidinyl.

The term "aryl" (used alone or included in other groups) refers to any stable monocyclic or bicyclic carbon ring which can have up to 7 atoms in each ring, wherein at least one ring is aromatic. Examples of the above aryl include phenyl, naphthyl, tetrahydronaphthyl, 2,3-dihydroindenyl, biphenyl, phenanthryl, anthryl or acenaphthyl. It is to be understood that when the aryl is a bicyclic substituent and one of the rings is non-aromatic, the linkage is made through the aromatic ring.

The term "aromatic hetero group" or "heteroaryl" (used alone or included in other groups) used herein refers to a stable monocyclic ring or bicyclic ring which can have up to 7 atoms in each ring, and at least one of the rings is an aromatic ring having 1 to 4 heteroatoms selected from the group consisting of O, N and S. The heteroaryl defined herein includes but not limited to acridinyl, carbazolyl, cinnolinyl, quinoxalinyl, pyrazolyl, indolyl, benzotriazolyl, furanyl, thienyl, benzothienyl, benzofuranyl, quinolinyl, isoquinolyl, oxazolyl, isoxazolyl, indolyl, pyrazinyl, pyridazinyl, pyridinyl, pyrimidyl, pyrryl, tetrahydroquinoline. As defined in the "heterocycloalkyl", "heteroaryl" can also be understood to include the N-oxide derivative of any nitrogenous heteroaryl. When the heteroaryl is a bicyclic substituent and one of the rings is non-aromatic or without any heteroatom, it can be understood, the linkage is through the aromatic ring or the heteroatom on the ring.

The term "arylalkyl" refers to an alkyl moiety (as defined above) substituted with one or more than one aryl moiety (as defined above). Examples of arylalkyl group include aryl-$C_{1-3}$-alkyl, for example but not limited to benzyl, phenylethyl and the like.

The term "heteroarylalkyl" refers to an alkyl moiety (as defined above) substituted with a heteroaryl moiety (as defined above). Examples of heteroarylalkyl include 5- or 6-membered heteroaryl-$C_{1-3}$-alkyl, e.g. but not limited to oxazolylmethyl, pyridinylethyl and the like.

The term "heterocyclylalkyl" refers to an alkyl moiety (as defined above) substituted with a heterocyclyl moiety (as defined above). Examples of heterocyclylalkyl include 5- or 6-membered heterocyclyl-$C_{1-3}$-alkyl, for example but not limited to, tetrahydropyranylmethyl.

The term "cycloalkylalkyl" refers to an alkyl moiety (as defined above) substituted with a cycloalkyl moiety (as defined above). Examples of cycloalkylalkyl include 5- or 6-membered cycloalkyl-$C_{1-3}$-alkyl, for example but not limited to, cyclopropylmethyl.

The term "halogen" includes F, $C_1$, Br, I.

The term "oxo" refers to —$CH_2$— is replaced with

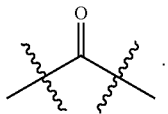

In the present invention, the term "a/an" refers to one or more.

In the present invention, when a term such as $(CR^{13}R^{14})_q$ is used, $R^{13}$ and $R^{14}$ may vary with each repetition when q exceeds 1 For example, when q is 2, the term $(CR^{13}R^{14})_q$ can be —$CH_2CH_2$— or —$CH(CH_3)C(CH_2CH_3)(CH_2CH_2CH_3)$— or any number of similar parts falling within the definition of $R^{13}$ and $R^{14}$.

The term "pharmaceutically acceptable salt" refers to a salt formed by a suitable non toxic organic acid, inorganic acid, organic base or inorganic base with compound I, which retains the biological activity of compound I. The organic acid can be various conventional organic acids capable of salt formation in the art, preferably selected from the group consisting of methanesulfonic acid, p-toluenesulfonic acid, maleic acid, fumaric acid, citric acid, tartaric acid, malic acid, lactic acid, formic acid, acetic acid, propionic acid, trifluoroacetic acid, oxalic acid, succinic acid, benzoic acid, isethionic acid, naphthalenesulfonic acid and salicylic acid. The inorganic acid can be various conventional inorganic acid capable of salt formation in the art, preferably selected from the group consisting of hydrochloric acid, sulfuric acid and phosphoric acid. The organic base can be various conventional organic base capable of salt formation in the art, preferably selected from the group consisting of pyridines, imidazoles, pyrazines, indoles, purines, tertiary amines and anilines. The tertiary amine organic base is preferably triethylamine and/or N,N-diisopropylethylamine. The aniline organic base is preferably N,N-dimethylaniline. The pyridine organic base is preferably selected from the group consisting of pyridine, methylpyridine, 4-dimethylaminopyridine and 2-methyl-5-ethylpyridine. The inorganic base can be various conventional inorganic base capable of salt formation in the art, preferably selected from the group consisting of alkali metal hydride, alkali metal hydroxide, alkali metal alkoxide, potassium carbonate, sodium carbonate, lithium carbonate, cesium carbonate, potassium bicarbonate and sodium bicarbonate. The alkali metal hydride is preferably sodium hydride and/or potassium hydride. The alkali metal hydroxide is preferably selected from the group consisting of sodium hydroxide, potassium hydroxide and lithium hydroxide. The alkali metal alkoxide is preferably selected from the group consisting of sodium methoxide, sodium ethoxide, potassium tert-butoxide and sodium tert-butoxide.

The term "solvate" refers to a substance formed by the compound I with a suitable solvent. The solvent is preferably water or an organic solvent.

Without violating the common sense in the art, the above preferred conditions can be arbitrarily combined, then preferred embodiments of the present invention are obtained.

The reagents and raw materials used in the present invention are commercially available.

The positive and progressive effect of the present invention is that the compound exhibits a high inhibitory activity against ErbB2 tyrosine kinase and a relatively good inhibitory activity against human breast cancer BT-474 and human gastric cancer cell NCI-N87 which express ErbB2 at a high level, and a relatively weak inhibitory activity against EGFR kinase at the same time. Namely, the compound is a highly selective small-molecule inhibitor targeted at ErbB2, and hence may reduce EGFR-related side effects of drugs in clinical applications, and can effectively enlarge the safety window during drug administration.

DETAILED DESCRIPTION OF THE PREFERRED EMBODIMENT

Preparation Embodiment

For the sake of illustrating the invention, the following embodiments are provided. However, it should be understood that these embodiments do not imply any limitation of the present invention but merely present methods of practicing the invention. The person skilled in the art will recognize that the chemical reactions described herein can be readily modified to prepare many of the other compounds of the present invention, and alternative methods for preparing the compounds of the invention are considered to be within the scope of the invention. For example, the compounds which are not illustrated in the present invention can be successfully prepared by changes apparent to those skilled in the art, examples of the changes include suitable protection for interfering groups, using other different suitable reagents known in the art, and/or conventional changes to reaction conditions. Alternatively, the reactions disclosed herein or other reactions known in the art may be applicable to preparation of the other compounds of the present invention.

In the following embodiments, unless otherwise specified, the temperature is stated in degrees Celsius. Reagents were purchased from commercial suppliers such as Aldrich, TCI, or Sinopharm Group and used without further purification unless otherwise stated. Tetrahydrofuran (THF), N,N-dimethylformamide (DMF), dichloromethane (DCM), toluene, dioxane were purchased from Aldrich in sealed bottles and used as they were.

The reaction described below was generally carried out in an anhydrous solvent under a positive pressure of nitrogen, argon or with a drying tube (unless otherwise stated). The glassware was oven dried and/or dried by heating.

Column chromatography was performed on a Biotage system with a silica gel column. ¹HNMR spectrum was recorded in a 400 MHz Varian device. ¹HNMR spectrum was obtained in a solution of CDCl₃, CD₃OD or d₆-DMSO (reported as ppm) by using TMS as a reference standard (0.0 ppm). The following abbreviations are used to report peak multiplicity: s (singlet), d (doublet), t (triplet), m (multiplet), br (broad), dd (double doublet). The coupling constant is reported in Hertz (Hz) when given.

Embodiment 2

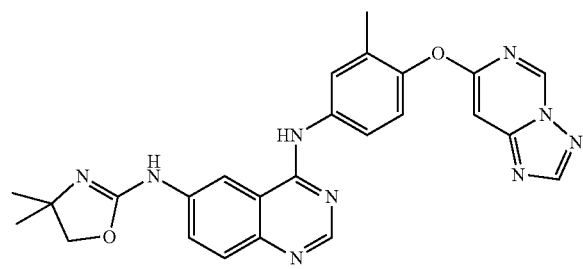 [SMILES: Cc1cc(Nc2ncnc3ccc(NC4=NC(C)(C)CO4)cc23)ccc1Oc1cc2ncnn2cn1]

Synthesis of N⁴-(4-([1,2,4]triazolo[1,5-c]pyrimidin-7-yloxy)-3-methylphenyl)-N⁶-(4,4-dimethyl-4,5-dihydrooxazol-2-yl)quinazoline-4,6-diamine Step A: preparation of (E)-N'-(2-cyano-4-nitrophenyl)-N,N-dimethylformamidine: 2-amino-5-nitrobenzyl nitrile (11.5 g, 2.91 mmol) was dissolved in N,N-dimethylformamide dimethylacetal (40 mL), the mixture was heated to 100° C. and stirred for 2 hours. After the reaction was completed, the mixture was evaporated to dryness under reduced pressure to give 15.1 g pale yellow solid, which was used directly in the next step.

Step B: preparation of (E)-N'-(4-amino-2-cyanophenyl)-N,N-dimethylformamidine: (E)-N'-(2-cyano-4-nitrophenyl)-N,N-dimethylformamidine (1.0 g, 4.58 mmol) was dissolved in a mixed solvent (60 mL) of methanol:cyclohexene (5:1), palladium on carbon (10%, 100 mg) was added. The mixture was heated to 80° C. under hydrogen atmosphere (balloon) and stirred for 18 hours. After the reaction was completed, the mixture was filtered, and evaporated to dryness under reduced pressure to give 845 mg pale brown solid, which was used directly in the next step.

Step C: preparation of (E)-N'-2-cyano-4-(3-(1-hydroxy-2-methylpropan-2-yl)thioureidophenyl)-N,N-dimethylformamidine: (E)-N'-(4-amino-2-cyanophenyl)-N,N-dimethylformamidine (5.30 g, 28.04 mmol) was suspended in tetrahydrofuran (40 mL), and the reaction solution was cooled to −5~0° C. A solution of thiocarbonyldiimidazole (5.10 g, 28.65 mmol) in tetrahydrofuran (30 mL) was added dropwise under stirring, and stirred at −5° C. to 0° C. for 0.5 hours. A solution of 2-amino-2-methyl-1-propanol (3.00 g, 33.71 mmol) in tetrahydrofuran (5 mL) was added dropwise, and after the addition was completed, the reaction solution was slowly warmed to room temperature and stirred for another 18 hours. The reaction was quenched by adding water and the mixture was extracted three times with ethyl acetate. The organic phase was dried over anhydrous sodium sulfate, filtered and concentrated. The residue was purified by column chromatography to give 4.20 g pale yellow solid with a yield of 46.72%.

Step D: preparation of 1-(4-((4-(((6-aminopyrimidin-4-yl)oxy)-3-methylphenyl)amino)quinazolin-6-yl)-3-(1-hydroxy-2-methylpropan-2-yl)thiourea: 6-(4-amino-2-methylphenoxy)pyrimidin-4-amine (100 mg, 0.462 mmol) and (E)-N'-2-cyano-4-(3-(1-hydroxy-2-methylpropan-2-yl)thioureidophenyl)-N,N-dimethylformamidine (147 mg, 0.460 mmol) was suspended in 2 mL isopropyl acetate, glacial acetic acid (0.5 mL) was added and the mixture was stirred at room temperature for 48 hours. A solid precipitated and was filtered under reduced pressure to give 130 mg brown solid with a yield of 57.3%.

Step E: preparation of N'-(4-(((6-aminopyrimidin-4-yl)oxy)-3-methylphenyl)-N⁶-(4,4-dimethyl-4,5-dihydrooxazol-2-yl)quinazolin-4,6-diamine: 1-(4-((4-(((6-aminopyrimidin-4-yl)oxy)-3-methylphenyl)amino)quinazolin-6-yl)-3-(1-hydroxy-2-methylpropan-2-yl)thiourea (80 mg, 0.346 mmol) was suspended in 5 mL tetrahydrofuran, sodium hydroxide (64 mg, 1.600 mmol) and p-toluenesulfonyl chloride (101 mg, 0.530 mmol) were added and the mixture was stirred at room temperature for 20 hours. Water (5 mL) was added and the mixture was extracted three times with ethyl acetate (10 mL). The organic phases were combined, washed once with saturated brine (10 mL), dried over anhydrous sodium sulfate, filtered and evaporated to dryness under reduced pressure to give a crude product, which was purified by column chromatography to give 50 mg orange solid with a yield of 41.3%.

Step F: preparation of (E)-N'-(6-(4-(((6-((4,4-dimethyl-4,5-dihydrooxazol-2-yl)amino)quinazolin-4-yl)amino)-2-methylphenoxy)pyrimidin-4-yl)-N,N-dimethylformamidine: N⁴-(4-(((6-aminopyrimidin-4-yl)oxy)-3-methylphenyl)-N⁶-(4,4-dimethyl-4,5-dihydrooxazol-2-yl)quinazolin-4,6-diamine (50 mg, 0.110 mmol) was suspended in 1 mL N,N-dimethylformamide dimethyl acetal, the reaction solution was heated to 100° C. and stirred for 2 hours, then evaporated to dryness under reduced pressure to give 47 mg orange solid, which was used directly in the next step.

Step G: preparation of N⁴-(4-([1,2,4]triazolo[1,5-c]pyrimidin-7-yloxy)-3-methylphenyl)-N⁶-(4,4-dimethyl-4,5-dihydrooxazol-2-yl)quinazoline-4,6-diamine: (L)-N'-(6-(4-((6-((4,4-dimethyl-4,5-dihydrooxazol-2-yl)amino)quinazolin-4-yl)amino)-2-methylphenoxy)pyrimidin-4-yl)-N,N-dimethylformamidine (47 mg, 0.092 mmol) was dissolved in 2 mL methanol, pyridine (37 mg, 0.468 mmol) and hydroxyaminosulfonic acid (11 mg, 0.098 mmol) were added at 0° C., and the mixture was stirred at room temperature for 48 hours, then filtered. The filter cake was washed three times with methanol (3 mL) and the filtrate was evaporated to dryness under reduced pressure to give a crude product, which was purified by column chromatography to give 3 mg yellow solid with a yield of 6.78%. LC-MS: 482.3 [M+H] detection value; ¹H-NMR (40 MHz, CD₃OD) δ 8.54 (s, 1H), 8.25 (m, 2H), 7.80-7.68 (m, 5H), 7.17 (d, 1H, J=8.0 Hz), 6.05 (s, 1H), 4.31 (s, 2H), 2.25 (s, 3H), 1.46 (s, 6H).

Embodiment 3

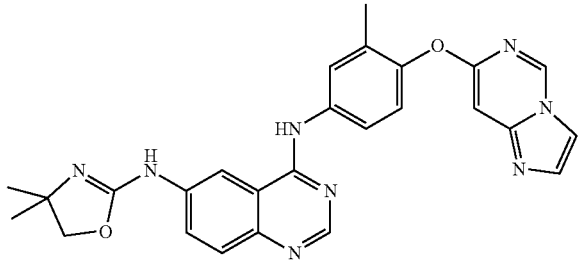 [SMILES: Cc1cc(Nc2ncnc3ccc(NC4=NC(C)(C)CO4)cc23)ccc1Oc1cc2nccn2cn1]

Synthesis of N⁶-(4,4-dimethyl-4,5-dihydrooxazol-2-yl)-N⁴-(4-(imidazo[1,2-c]pyrimidin-7-yloxy)-3-methylphenyl)quinazoline-4,6-diamine Step A: preparation of 4-chloro-6-(2-methyl-4-nitrophenoxy)pyrimidine: 4,6-dichloropyrimidine (1.5 g, 10.07 mmol) was dissolved in 30 mL N,N-dimethylformamide, 2-methyl-4-nitrophenol (1.5 g, 9.81 mmol) and potassium carbonate solid (1.5 g, 10.87 mmol) were added, the mixture was heated to 80° C. and stirred overnight. After the reaction was completed, 40 mL ethyl acetate was added, the mixture was stirred, filtered, and the filtrate was evaporated to dryness under reduced pressure. The residue was purified by column chromatography to give 2.3 g pale yellow solid with a yield of 88.46%.

Step B: preparation of 6-(2-methyl-4-nitrophenoxy)-4-aminopyrimidine: 4-chloro-6-(2-methyl-4-nitrophenoxy)pyrimidine (1.2 g, 4.51 mmol) was dissolved in 20 mL ethanol and 60 mL aqueous ammonia, the mixture was sealed and stirred at 120° C. for 18 hours. After the reaction was completed, the mixture was evaporated to dryness under reduced pressure to give a residue, which was purified by column chromatography to give 400 mg solid with a yield of 35.96%.

Step C: preparation of 7-(2-methyl-4-nitrophenoxy)imidazo[1,2-c]pyrimidine: 6-(2-methyl-4-nitrophenoxy)-4-aminopyrimidine (400 mg, 1.62 mmol) was added to 10 mL 1,4-dioxane and an aqueous solution of 400 mg chloroacetaldehyde, the mixture was heated to 130° C. and stirred for 3 hours. After the reaction was completed, the mixture was directly concentrated to give a residue, which was purified by column chromatography to give 220 mg solid with a yield of 50.12%.

Step D: preparation of 4-(imidazo[1,2-c]pyrimidin-7-yloxy)-3-methylaniline: 7-(2-methyl-4-nitrophenoxy)imidazo[1,2-c]pyrimidine (220 mg, 0.92 mmol) was dissolved in 30 mL of a mixed solvent of methanol:ethyl acetate (2:1), a small amount of Raney Ni was added, the mixture was stirred under hydrogen atmosphere (balloon) at room temperature for 2 hours. After the reaction was completed, the mixture was filtered, evaporated to dryness under reduced pressure to give 180 mg crude product, which was used directly in the next step.

Step E: preparation of 1-(1-hydroxy-2-methylpropan-2-yl)-3-(4-((4-(imidazo[1,2-c]pyrimidin-7-yloxy)-3-methylphenyl)amino)quinazolin-6-yl)thiourea: a mixture of 4-(imidazo[1,2-c]pyrimidin-7-yloxy)-3-methylaniline (180 mg, 0.75 mmol) and 2-cyano-4-(3-1-hydroxy-2-methylisopropyl-2-yl)thioureaphenyl-N,N-dimethylformamidine (240 mg, 0.75 mmol) was added to 1.5 mL acetic acid and 10 mL isopropyl acetate, and the mixture was stirred at room temperature for 18 hours. After the reaction was completed, a large amount of solid precipitated and was directly filtered. The filter cake was washed with a small amount of isopropyl acetate to give 110 mg purer product with a yield of 28.52%.

Step F: preparation of N⁶-(4,4-dimethyl-4,5-dihydrooxazol-2-yl)-N⁴-(4-(imidazo[1,2-c]pyrimidin-7-yloxy)-3-methylphenyl)quinazoline-4,6-diamine: 1-(1-hydroxy-2-methylpropan-2-yl)-3-(4-((4-(imidazo[1,2-c]pyrimidin-7-yloxy)-3-methylphenyl)amino)quinazolin-6-yl)thiourea (110 mg, 0.21 mmol) was dissolved in 30 mL tetrahydrofuran, sodium hydroxide (30 mg, 0.75 mmol) and p-toluenesulfonyl chloride (78 mg, 0.41 mmol) were added. The mixture was stirred at room temperature for 18 hours. After the reaction was completed, water was added and the mixture was extracted three times with ethyl acetate. The organic phase was washed with brine, dried over anhydrous sodium sulfate, filtered, concentrated to give a crude product, which was purified by column chromatography to give 11 mg purer product with a yield of 17.48%. LC-MS: 480.9 [M+H] detection value; $^1$H-NMR (400 MHz, CD$_3$OD) d 9.23 (s, 1H), 8.50 (s, 1H), 8.20 (br, s, 1H), 7.95 (s, 1H), 7.76-7.61 (m, 5H), 7.17 (d, 1H, J=8 Hz), 6.74 (s, 1H), 4.24 (s, 2H), 2.26 (s, 3H), 1.43 (s, 6H).

Embodiment 4

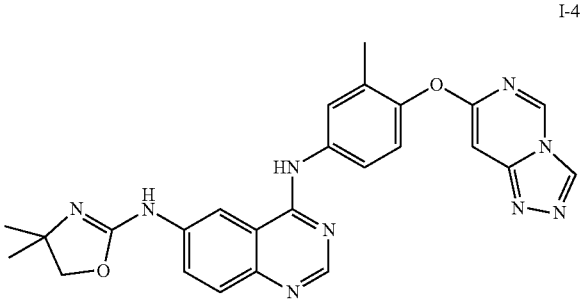 [SMILES: Cc1cc(Nc2ncnc3ccc(NC4=NC(C)(C)CO4)cc23)ccc1Oc1cc2nncn2cn1]

I-4

Preparation of N⁴-(4-([1,2,4]triazolo[4,3-c]pyrimidin-7-yloxy)-3-methylphenyl)-N⁶-(4,4-dimethyl-4,5-dihydrooxazol-2-yl)quinazoline-4,6-diamine Step A: preparation of 2-chloro-6-hydrazinopyrimidine: 2,6-dichloropyrimidine (25 g, 167.81 mmol) was dissolved in 350 mL isopropanol, hydrazine hydrate (29.5 g, 503.44 mmol, 85%) was slowly added dropwise at room temperature under stirring. During the dropwise addition, a white solid precipitated out and the mixture was stirred at room temperature for 1 hour. The mixture was evaporated under reduced pressure, the residue was mixed with water (50 mL) and stirred for 30 minutes. The mixture was filtered, and the filter cake was washed with water and dried to give 22.4 g white solid with a yield of 92.3%.

Step B: preparation of 7-chloro-[1,2,4]triazolo[4,3-c]pyrimidine: 2-chloro-6-hydrazinopyrimidine (21 g, 145.27 mmol) was dispersed in 210 mL trimethyl orthoformate, stirred at 60° C. overnight and the reaction solution became clear. p-Toluenesulfonic acid (0.6 g, 3.48 mmol) was added and the reaction was continued at 60° C. for another 1 hour.

The mixture was evaporated under reduced pressure, water (20 mL) was added, the resulting mixture was stirred for 30 minutes, then filtered, and the filter cake was washed with water and dried to give 9.2 g pale brown solid with a yield of 41%.

Step C: preparation of 7-(2-methyl-4-nitrophenoxy)-[1,2,4]triazolo[4,3-c]pyrimidine: 7-chloro-[1,2,4]triazolo[4,3-c]pyrimidine (450 mg, 2.91 mmol) was dissolved in 10 mL N,N-dimethylformamide, 2-methyl-4-nitrophenol (550 mg, 3.59 mmol) and sodium carbonate solid (500 mg, 4.72 mmol) were added, and the mixture was heated to 80° C. and stirred overnight. After the reaction was completed, 20 mL ethyl acetate was added, the mixture was stirred and then filtered. The filtrate was evaporated to dryness under reduced pressure, and the residue was purified by column chromatography to give 510 mg pale yellow solid with a yield of 64.46%.

Step D: preparation of 7-(2-methyl-4-aminophenoxy)-[1,2,4]triazolo[4,3-c]pyrimidine: 7-(2-methyl-4-nitrophenoxy)-[1,2,4]triazolo[4,3-c]pyrimidine (510 mg, 1.88 mmol) was dissolved in 60 mL of a mixed solvent of methanol:ethyl acetate (2:1), a small amount of Raney Ni was added, and the mixture was stirred under hydrogen atmosphere (balloon) at room temperature for 2 hours. After the reaction was completed, the mixture was filtered, evaporated to dryness under reduced pressure to give 410 mg crude product, which was directly used in the next step.

Step E: preparation of 1-(4-((4-([1,2,4]triazolo[4,3-c]pyrimidin-7-yloxy)-3-methylphenyl)amino)quinazolin-6-yl)-3-(1-hydroxy-2-methylpropan-2-yl)thiourea: a mixture of 7-(2-methyl-4-aminophenoxy)-[1,2,4]triazolo[4,3-c]pyrimidine (170 mg, 0.71 mmol) and (Z)—N'-(2-cyano-4-(3-(1-hydroxy-2-methylpropan-2-yl)thioureido)phenyl)-N,N-dimethylformimidamide (240 mg, 0.75 mmol) was added to 3 mL acetic acid and 30 mL isopropyl acetate, the mixture was stirred at room temperature for 18 hours. After the reaction was completed, a large amount of solid precipitated and was directly filtered. The filter cake was washed with a small amount of isopropyl acetate to give 245 mg purer product with a yield of 67.42%.

Step F: preparation of $N^4$-(4-([1,2,4]triazolo[4,3-c]pyrimidin-7-yloxy)-3-methylphenyl)-$N^6$-(4,4-dimethyl-4,5-dihydrooxazol-2-yl)quinazoline-4,6-diamine: 1-(4-((4-([1,2,4]triazolo[4,3-c]pyrimidin-7-yloxy)-3-methylphenyl)amino)quinazolin-6-yl)-3-(1-hydroxy-2-methylpropan-2-yl)thiourea (245 mg, 0.48 mmol) was dissolved in 50 mL tetrahydrofuran, sodium hydroxide (120 mg, 3.0 mmol) and p-toluenesulfonyl chloride (190 mg, 1.0 mmol) were added. The mixture was stirred at room temperature for 18 hours. After the reaction was completed, water was added and the mixture was extracted three times with ethyl acetate. The organic phase was washed with brine, dried over anhydrous sodium sulfate, filtered, concentrated to give a crude product, which was purified by column chromatography to give 40 mg purer product with a yield of 17.48%. LC-MS: 481.9 [M+H] detection value; H-NMR (400 MHz, $CD_3OD$) δ 9.46 (m, 1H), 8.48 (s, 1H), 8.44 (s, 1H), 8.19 (s, 1H), 7.76-7.72 (m, 3H), 7.63 (d, 1H, J=12 Hz), 7.22 (d, 1H, J=8 Hz), 6.96 (s, 1H), 4.18 (s, 2H), 2.28 (s, 3H), 1.43 (s, 6H).

Embodiment 5

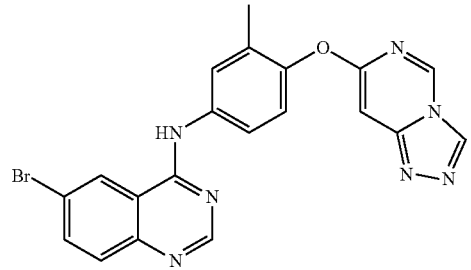 [SMILES: Cc1cc(Nc2ncnc3ccc(Br)cc23)ccc1Oc1cc2nncn2cn1]

Synthesis of N-(4-([1,2,4]triazolo[4,3-c]pyrimidin-7-yloxy)-3-methylphenyl)-6-bromoquinazolin-4-amine Step A: preparation of (E)-N'-(4-bromo-2-cyanophenyl)-N,N-dimethylformamidine: 6-(4-amino-2-methylphenoxy)pyrimidine-4-amine (100 mg, 0.462 mmol) and 2-cyano-4-(3-1-hydroxy-2-methylisopropyl-2-yl)thioureaphenyl-N,N-dimethylformamidine (147 mg, 0.460 mmol) were suspended in 2 mL isopropyl acetate, glacial acetic acid (0.5 mL) was added, and the mixture was stirred at room temperature for 48 hours. A solid precipitated and was filtered under reduced pressure to give 130 mg brown solid with a yield of 57.3%.

Step B: preparation of N-(4-([1,2,4]triazolo[4,3-c]pyrimidin-7-yloxy)-3-methylphenyl)-6-bromoquinazolin-4-amine: 4-([1,2,4]triazolo[4,3-c]pyrimidin-7-yloxy)-3-methylaniline (130 mg, 0.539 mmol) and glacial acetic acid (0.6 mL) were mixed in 2 mL ethyl acetate, then (E)-N'-(4-bromo-2-cyanophenyl)-N,N-dimethylformamidine (100 mg, 0.508 mmol) was added, and the mixture was stirred at room temperature for 20 hours. A solid precipitated and was filtered under reduced pressure to give a crude product, which was purified by column chromatography to give 10.62 mg off-white solid with a yield of 4.67%. LC-MS: 449.7 [M+H] detection value; $^1$H-NMR (400 MHz, DMSO-$d_6$) δ 8.96 (m, 1H), 8.89 (m, 1H), 8.65 (s, 1H), 8.58 (s, 1H), 8.02-8.00 (m, 1H), 7.82 (m, 1H), 7.81-7.78 (m, 1H), 7.77-7.74 (m, 1H), 7.21 (d, 1H, J=8.0 Hz), 7.14 (m, 1H), 2.20 (s, 3H).

Embodiment 6

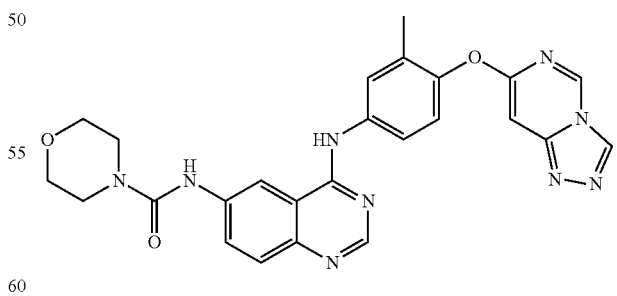

Synthesis of N-(4-((4-([1,2,4]triazolo[4,3-c]pyrimidin-7-yloxy)-3-methylphenyl)amino)quinazolin-6-carbamoylmorpholine Step A: preparation of phenyl (E)-(3-cyano-4-(((dimethylamino)methylene)amino)phenyl)carbamate: (E)-N'-(4- amino-2-cyanophenyl)-N,N-dimethylformamidine (1.0 g, 5.32 mmol) and sodium bicarbonate solid (500 mg, 5.95 mmol) were mixed in tetrahydrofuran (30 mL) and the reaction solution was cooled to 0° C. Phenyl chloroformate (780 mg, 5 mmol) was dissolved in tetrahydrofuran (10 mL) and the solution was added dropwise to the above mixture, then the reaction solution was stirred for 30 minutes under an ice bath and another 10 minutes at room temperature. Water was added to the reaction solution and the mixture was extracted with ethyl acetate. The organic phase was dried over anhydrous magnesium sulfate, filtered, concentrated and purified by column chromatography to give 1.2 g product with a yield of 73.26%.

Step B: preparation of (E)-N-(3-cyano-4-(((dimethylamino)methylene)amino)phenyl)-carbamoylmorpholine: phenyl (E)-(3-cyano-4-(((dimethylamino)methylene)amino)phenyl)carbamate (400 mg, 1.30 mmol) was dissolved in 20 mL tetrahydrofuran, morpholine (300 mg, 3.45 mmol) was added. The mixture was heated to 65° C. and stirred for 18 hours. After the reaction was completed, the mixture was evaporated under reduced pressure, and the residue was slurried with methyl tert-butyl ether to give 310 mg solid with a yield of 79.28%.

Step C: preparation of N-(4-((4-([1,2,4]triazolo[4,3-c]pyrimidin-7-yloxy)-3-methylphenyl)amino)quinazolin-6-carbamoylmorpholine: (E)-N-(3-cyano-4-(((dimethylamino)methylene)amino)phenyl)-carbamoylmorpholine (100 mg, 0.33 mmol) and 7-(2-methyl-4-aminophenoxy)-[1,2,4]triazolo[4,3-c]pyrimidine (50 mg, 0.21 mmol) were dissolved in 10 mL isopropyl acetate, and 1 mL acetic acid was added, and the mixture was stirred under nitrogen atmosphere at room temperature for 18 hours. After the reaction was completed, a solid precipitated out. The solid was filtrated and purified by preparative chromatography to give 27.25 mg product with a yield of 26.43%. LC-MS: 497.9 [M+H] detection value; $^1$H-NMR (400 MHz, DMSO-$d_6$) δ 9.40 (s, 1H), 8.50 (s, 1H), 8.40-8.39 (m, 2H), 7.76-7.69 (m, 4H), 7.18 (d, 1H, J=8 Hz), 6.94 (s, 1H), 3.80-3.77 (t, 4H, J=4 Hz), 3.62-3.60 (t, 4H, J=4 Hz), 2.28 (s, 3H).

Embodiment 7 at −5° C. to −8° C. for 30 minutes. A solution of (R)-2-amino-1-propanol (260 mg, 3.462 mmol) in tetrahydrofuran (1 mL) was added dropwise (1 mL), and the reaction solution was stirred overnight at room temperature, then evaporated under reduced pressure to give a crude product, which was purified by column chromatography to give 800 mg orange solid with a yield of 98.6%.

Step B: preparation of (R,E)-N'-(2-cyano-4-((4-methyl-4,5-dihydrooxazol-2-yl)amino)phenyl)-N,N-dimethylformamidine: (R,E)-N'-(2-cyano-4-(3-(1-hydroxypropyl-2-)thioureido)phenyl)-N,N-dimethylformamidine (150 mg, 0.491 mmol) was dissolved in 3 mL tetrahydrofuran, sodium hydroxide (118 mg, 2.950 mmol) and p-toluenesulfonyl chloride (187 mg, 0.981 mmol) were added, and the mixture was stirred at room temperature for 1 hour. Water (3 mL) was added and the mixture was extracted twice with ethyl acetate (5 mL). The organic phases were combined, dried over anhydrous sodium sulfate, filtered and evaporated under reduced pressure to give a crude product, which was purified by column chromatography to give 150 mg brown oil with a yield of 100%.

Step C: preparation of (R)—N$^4$-(4-([1,2,4]triazolo[4,3-c]pyrimidin-7-yloxy)-3-methylphenyl)-N$^6$-(4-methyl-4,5-dihydrooxazol-2-yl)quinazoline-4,6-diamine: (R,E)-N'-(2-cyano-4-((4-methyl-4,5-dihydrooxazol-2-yl)amino) phenyl)-N,N-dimethylformamidine (80 mg, 0.295 mmol) and glacial acetic acid (0.5 mL) were mixed in 3 mL of ethyl acetate, 3-methyl-4([1,2,4]triazolo[1,4,c]pyrimidin-7-oxy) aniline (71 mg, 0.294 mmol) and the mixture was stirred at room temperature overnight. The reaction solution was evaporated under reduced pressure to give a crude product, which was purified by column chromatography to give 2.15 mg pale yellow solid with a yield of 1.56%. LC-MS: 467.9 [M+H] detection value; $^1$H-NMR (400 MHz, CDCl$_3$) δ 8.92 (s, 1H), 8.70 (s, 1H), 8.35 (s, 1H), 8.13 (s, 1H), 7.82 (d, 1H, J=8 Hz), 7.77 (m, 1H), 7.70 (d, 1H, J=8 Hz), 7.51 (d, 1H, J=8 Hz), 7.13 (d, 1H, J=8 Hz), 6.90 (s, 1H), 4.57 (t, 1H, J=8 Hz), 4.29 (m, 1H), 4.01 (t, 1H, J=6 Hz), 2.25 (s, 3H), 1.40 (d, 3H, J=4 Hz).

Embodiment 8

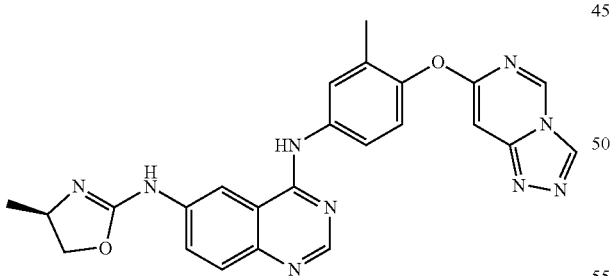

Synthesis of (R)—N$^4$-(4-([1,2,4]triazolo[4,3-c]pyrimidin-7-yloxy)-3-methylphenyl)-N$^6$-(4-methyl-4,5-dihydrooxazol-2-yl)quinazoline-4,6-diamine Step A: preparation of (R,E)-N'-(2-cyano-4-(3-(1-hydroxypropyl-2-)thioureido)phenyl)-N,N-dimethylformamidine: N'-(4-amino-2-cyanophenyl)-N,N-dimethylformamidine (500 mg, 2.656 mmol) was suspended in 5 mL tetrahydrofuran, thiocarbonyldiimidazole (713 mg, 4.001 mmol) was added at −8° C., the reaction solution was stirred

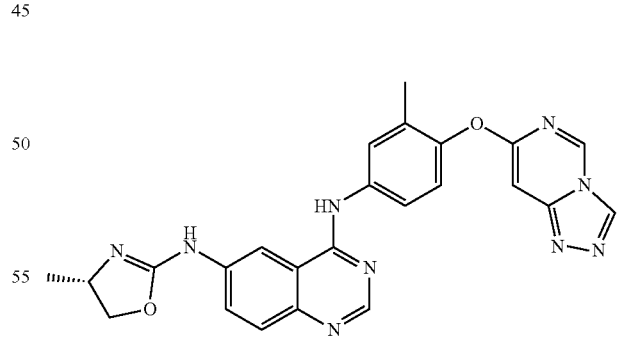

According to the preparation method of Embodiment 7, wherein (R)-2-amino-1-propanol was replaced with (S)-2-amino-1-propanol. LC-MS: 467.9 [M+H] detection value; $^1$H NMR (400 MHz, CD$_3$OD) d 9.45 (d, 1H, J=1.0 Hz), 8.44 (m, 2H), 8.20 (s, 1H), 7.78-7.72 (m, 3H), 7.61 (dd, 1H, J=9.0, 2.3 Hz), 7.20 (d, 1H, J=8.0 Hz), 6.94 (m, 1H), 4.56 (t, 1H, J=8.2 Hz), 4.27 (dd, 1H, J=14.4, 6.7 Hz), 4.08-3.95 (m, 1H), 2.26 (s, 3H), 1.35 (d, 3H, J=6.4 Hz).

Embodiment 9

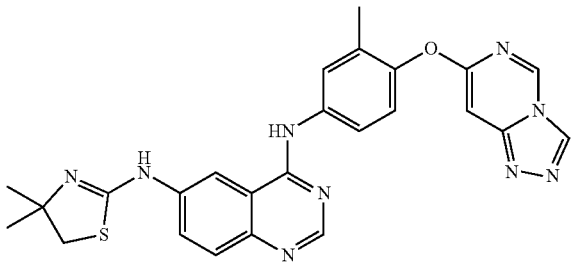 [SMILES: Cc1cc(Nc2ncnc3ccc(NC4=NC(C)(C)CS4)cc23)ccc1Oc1cc2nncn2cn1]

Synthesis of N⁴-(4-([1,2,4]triazolo[4,3-c]pyrimidin-7-yloxy)-3-methylphenyl)-N⁶-(4,4-dimethyl-4,5-dihydrothiazol-2-yl)quinazoline-4,6-diamine Step A: the corresponding thiourea was prepared according to the method of Embodiment 7, wherein (R)-2-amino-1-propanol was replaced with 2-amino-2-methyl-1-propanol.

Step B: the thiourea prepared in Step A (48 mg, 0.09 mmol), triphenylphosphine (36 mg, 0.14 mmol) were dissolved in 4 mL N,N-dimethylformamide under an ice bath, diisopropyl azodicarboxylate (28 mg, 0.14 mmol) was added and the mixture was stirred at room temperature for 16 h. Ethyl acetate (40 mL) was added, and the mixture was washed with 20 mL water and 20 mL saturated aqueous sodium chloride solution respectively for once. The organic phase was dried over anhydrous magnesium sulfate, filtered, and evaporated under reduced pressure to give a crude product, which was purified by thin layer chromatography to give 22 mg earthy yellow solid with a yield of 47.5%. LC-MS: 497.80 [M+H] detection value; $^1$H NMR (400 MHz, CDCl$_3$) δ 9.20 (m, 1H), 8.70 (s, 1H), 8.32 (s, 1H), 7.85 (d, 1H, J=8.9 Hz), 7.75-7.70 (m, 2H), 7.69 (dd, 1H, J=8.6, 2.5 Hz), 7.54 (dd, 1H, J=8.8, 2.1 Hz), 7.12 (d, 1H, J=8.6 Hz), 6.90 (m, 1H), 3.20 (s, 2H), 2.25 (s, 3H), 1.31 (s, 6H).

Embodiment 10

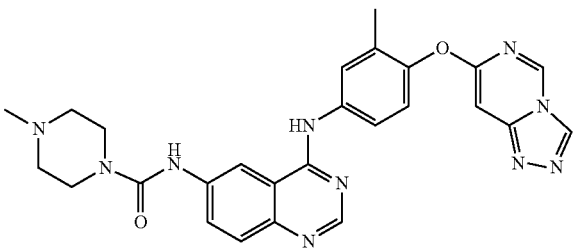 [SMILES: Cc1cc(Nc2ncnc3ccc(NC(=O)N4CCN(C)CC4)cc23)ccc1Oc1cc2nncn2cn1]

Synthesis of N-(4-((4-([1,2,4]triazolo[4,3-c]pyrimidin-7-yloxy)-3-methylphenyl)amino)quinazolin-6-yl)-4-methylpiperazine-1-carboxamide According to the method of Embodiment 6, wherein morpholine was replaced with N-methylpiperazine. LC-MS: 510.9 [M+H] detection value; $^1$H-NMR (400 MHz, DMSO-d$_6$) δ 9.46 (m, 1H), 8.48-8.40 (m, 3H), 7.79-7.70 (m, 4H), 7.22 (d, 1H, J=8 Hz), 6.97 (m, 1H), 3.68 (t, 4H, J=4 Hz), 2.58 (t, 4H, J=4 Hz), 2.40 (s, 3H), 2.28 (s, 3H).

Embodiment 11

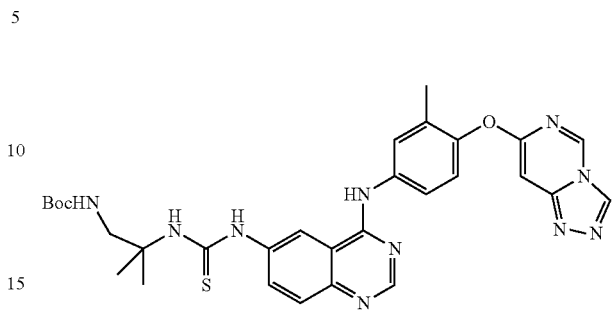

Synthesis of tert-butyl (2-(3-(4-((4-([1,2,4]triazolo[4,3-c]pyrimidin-7-yloxy)-3-methylphenyl)amino)quinazolin-6-yl)thioureido)-2-methylpropyl)carbamate Step A: preparation of tert-butyl (2-amino-2-methylpropyl)carbamate: 2-methylpropane-1,2-diamine (0.843 g, 9.56 mmol) was dissolved in 40 mL dichloromethane, a solution of di-tert-butyl dicarbonate (0.74 g, 4.2 mmol) in dichloromethane (37 mL) was slowly added dropwise under an ice bath during approximately one hour. The mixture was stirred at room temperature for 18 hours, then transferred to a separatory funnel, washed once with saturated brine (50 mL), and the aqueous phase was extracted twice with dichloromethane (30 mL). The organic phases were combined, dried over anhydrous sodium sulfate, filtered, and evaporated under reduced pressure to give 0.681 g pale yellow oil which was used directly in the next step.

Step B: preparation of tert-butyl (E)-2-(3-(3-cyano-4-(((dimethylamino)methylene)amino)phenyl)thioureido)-2-methylpropyl)carbamate: (E)-N'-(4-amino-2-cyanophenyl)-N,N-dimethylformamidine (300 mg, 1.954 mmol) was dissolved in 9 mL tetrahydrofuran, thiocarbonyldiimidazole (240 mg, 1.347 mmol) was added at −10° C. The mixture was stirred at −10° C. for 30 minutes, tert-butyl (2-amino-2-methylpropyl)carbamate (231 mg, 1.227 mmol) was added. The resulting mixture was slowly warmed to room temperature and stirred for 18 hours, then evaporated under reduced pressure to give a crude product, which was purified by column chromatography to give 455 mg orange oil with a yield of 88.6%.

Step C: Preparation of tert-butyl (2-(3-(4-((4-([1,2,4]triazolo[4,3-c]pyrimidin-7-yloxy)-3-methylphenyl)amino)quinazolin-6-yl)thioureido)-2-methylpropyl)carbamate:
tert-butyl (E)-2-(3-(3-cyano-4-(((dimethylamino)methylene)amino)phenyl)thioureido)-2-methylpropyl)carbamate (163 mg, 0.389 mmol) and glacial acetic acid (0.8 mL) were mixed in 2 mL ethyl acetate, 4-([1,2,4]triazolo[4,3-c]pyrimidin-7-yloxy)-3-methylaniline (94 mg, 0.556 mmol) was added and the mixture was stirred at room temperature for 38 hours. The mixture was evaporated under reduced pressure to give a crude product, which was purified by column chromatography to give 148.8 mg yellow solid with a yield of 62.2%. LC-MS: 614.8 [M+H] detection value; $^1$H-NMR (400 MHz, CD$_3$OD) δ 9.46 (s, 1H), 8.53 (s, 1H), 8.44 (s, 1H), 8.35 (s, 1H), 7.82-7.79 (m, 2H), 7.75 (m, 1H), 7.70 (d, 1H, J=8.0 Hz), 7.22 (d, 1H, J=8.0 Hz), 6.96 (m, 1H), 3.49 (s, 2H), 2.28 (s, 3H), 1.58 (s, 6H), 1.31 (s, 9H).

Embodiment 12

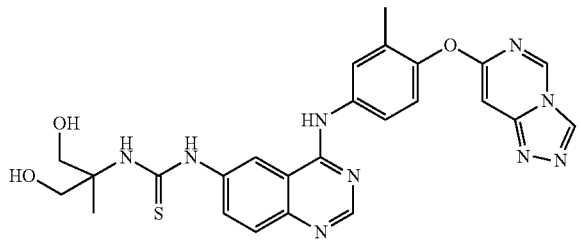 [SMILES: Cc1cc(Nc2ncnc3ccc(NC(=S)NC(C)(CO)CO)cc23)ccc1Oc1cc2nncn2cn1]

Synthesis of 1-(4-((4-([1,2,4]triazolo[4,3-c]pyrimidin-7-yloxy)-3-methylphenyl)amino)quinazoline-6-yl)-3-(1,3-dihydroxy-2-methylpropan-2-yl)thiourea Step A: preparation of (E)-N'-(2-cyano-4-(3-(1,3-dihydroxy-2-methylpropan-2-yl)thioureido)phenyl)-N,N-dimethylformamidine: according to the method of Embodiment 11, wherein tert-butyl (2-amino-2-methylpropyl)carbamate was replaced with 2-amino-2-methyl-1,3-propanediol.

Step B: preparation of 1-(4-((4-([1,2,4]triazolo[4,3-c]pyrimidin-7-yloxy)-3-methylphenyl)amino)quinazoline-6-yl)-3-(1,3-dihydroxy-2-methylpropan-2-yl)thiourea: according to the method of Embodiment 11, wherein tert-butyl (E)-(2-(3-(3-cyano-4-(((dimethylamino)methylene)amino)phenyl)thiourea)-2-methylpropyl)carbamate was replaced with (E)-N'-(2-cyano-4-(3-(1,3-dihydroxy-2-methylpropan-2-yl)thioureido)phenyl)-N,N-dimethylformamidine. LC-MS: 531.8 [M+H] detection value; $^1$H-NMR (400 MHz, CD$_3$OD) δ 9.46 (s, 1H), 8.53 (s, 1H), 8.44 (s, 1H), 8.42 (d, 1H, J=4.0 Hz), 7.93 (d, 1H, J=8.0 Hz), 7.80 (s, 1H), 7.78-7.76 (m, 1H), 7.71 (dd, 1H, J=4.0 Hz, 12.0 Hz), 7.21 (d, 1H, J=8.0 Hz), 6.96 (m, 1H), 3.88 (d, 1H, J=12.0 Hz), 3.81 (d, 2H, J=12.0 Hz), 2.27 (s, 3H), 1.53 (s, 3H).

Embodiment 13

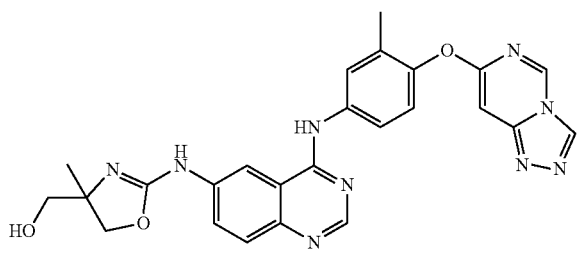 [SMILES: Cc1cc(Nc2ncnc3ccc(NC4=NC(C)(CO)CO4)cc23)ccc1Oc1cc2nncn2cn1]

Synthesis of (2-((4-((4-([1,2,4]triazolo[4,3-c]pyrimidin-7-yloxy)-3-methylphenyl)amino)quinazolin-6-yl)amino)-4-methyl-4,5-dihydrooxazol-4-yl)methanol Step A: preparation of (E)-N'-(2-cyano-4-((4-(hydroxymethyl)-4-methyl-4,5-dihydrooxazol-2-yl)amino)phenyl)-N,N-dimethylformamidine: (E)-N'-(2-cyano-4-(3-(1,3-dihydroxy-2-methylpropan-2-yl)thioureido)phenyl)-N,N-dimethylformamidine (600 mg, 1.79 mmol) was dissolved in 40 mL tetrahydrofuran, aqueous sodium hydroxide (1N, 0.75 mL) and p-toluenesulfonyl chloride (380 mg, 1.99 mmol) were added. The mixture was stirred at 18° C. for 3.5 hours, then washed once with saturated brine (10 mL). The organic phase was dried over anhydrous sodium sulfate, filtered, and evaporated to dryness under reduced pressure to give 540 mg white solid which was used directly in the next step.

Step B: preparation of (2-((4-((4-([1,2,4]triazolo[4,3-c]pyrimidin-7-yloxy)-3-methylphenyl)amino)quinazolin-6-yl)amino)-4-methyl-4,5-dihydrooxazol-4-yl)methanol: according to the method of Embodiment 11, wherein tert-butyl (E)-(2-(3-(3-cyano-4-(((dimethylamino)methylene)amino)phenyl)thioureido)-2-methylpropyl)carbamate was replaced with (E)-N'-(2-cyano-4-((4-(hydroxymethyl)-4-methyl-4,5-dihydrooxazol-2-yl)amino)phenyl)-N,N-dimethylformamidine. LC-MS: 497.9 [M+H] detection value; $^1$H-NMR (400 MHz, DMSO-d$_6$) δ 9.67 (s, 1H), 9.54 (s, 1H), 8.58 (s, 1H), 8.48 (s, 1H), 8.19 (s, 1H), 8.07 (s, 1H), 7.84 (s, 1H), 7.79 (d, 1H, J=8.0 Hz), 7.68-7.66 (m, 2H), 7.18 (d, 1H, J=8.0 Hz), 7.11 (s, 1H), 4.31 (d, 1H, J=8.0 Hz), 3.97 (d, 1H, J=8.0 Hz), 2.19 (s, 3H), 1.25-1.24 (m, 5H).

Embodiment 14

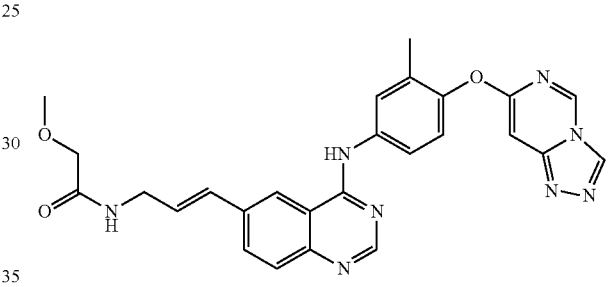

Synthesis of 2-methoxy-N-((E)-3-(4-(3-methyl-4-([1,2,4]triazolo[4,3-c]pyrimidin-7-yloxy)anilino)-6-quinazolinyl)allyl)acetamide Step A: preparation of N,N'-di-tert-butoxycarbonylallylamine: allylamine (I 0.9 g, 33.28 mmol) was dissolved in acetonitrile (13 mL), dimethylaminopyridine (40.6 mg, 0.33 mmol) and di-tert-butoxycarbonyl (8 g, 36.70 mmol) were successively added, and the mixture was stirred at room temperature for 5 h, then the reaction solution was evaporated to dryness under reduced pressure. Acetonitrile (13 mL) was added to dissolve the residue, then dimethylaminopyridine (40.6 mg, 0.33 mmol) and a solution of di-tert-butoxycarbonyl (8 g, 36.70 mmol) in acetonitrile (5 mL) were successively added, the mixture was heated to 60° C. and stirred for 48 hours. After the reaction mixture cooled to room temperature, dichloromethane (50 mL) was added, then washed with a saturated aqueous solution of sodium bicarbonate (20 mL). The aqueous phase was extracted with dichloromethane (20 mL×3). The organic phases were combined, washed once with saturated sodium chloride (20 ml), dried over anhydrous magnesium sulfate for 1 hour, filtered, evaporated to dryness under reduced pressure to give a crude product, which was purified by column chromatography (petroleum ether:ethyl acetate=90:10) to give 2 g colorless oil with a yield of 23%.

Step B: preparation of tert-butyl-N-tert-butoxycarbonyl-N-((E)-3-(4-(3-methyl-4-([1,2,4]triazolo[4,3-c]pyrimidin-7-yloxy)anilino)quinazolin-6-yl)allyl)carbamate: 6-iodo-N-(3-methyl-4-([1,2,4]triazolo[4,3-c]pyrimidin-7-yloxy)

phenyl)quinazolin-4-amine (250 mg, 0.50 mmol), N,N'-di-tert-butoxycarbonylallyl amide (170 mg, 0.66 mmol), tris(dibenzylideneacetone)dipalladium (5 mg, 0.005 mmol) and triethylamine (255 mg, 2.52 mmol) were mixed in a mixed solvent of isopropanol (2.5 mL) and N,N'-dimethylformamide (1.5 mL), the mixture was heated to 80° C. and stirred for 24 hours, then filtered through celite and evaporated to dryness under reduced pressure to give a crude product, which was purified by thin layer chromatography (dichloromethane:methanol=10:1) to give 140 mg colorless solid with a yield of 44.4%.

Step C: preparation of 6-((E)-3-amino-1-propenyl)-N-(3-methyl-4-([1,2,4]triazolo[4,3-c]pyrimidin-7-yloxo)phenyl)quinazolin-4-amine: tert-butyl-N-tert-butoxycarbonyl-N-((E)-3-(4-(3-methyl-4-([1,2,4]triazolo[4,3-c]pyrimidin-7-yloxy)anilino)quinazolin-6-yl)allyl)carbamate (140 mg, 0.22 mmol) was dissolved in 25 mL of 5% trifluoroacetic acid in dichloromethane. The mixture was stirred at room temperature for 16 hours, then concentrated under reduced pressure to give 93 mg crude product with a yield of 100%, which was used directly in the next step.

Step D: preparation of 2-methoxy-N-((E)-3-(4-(3-methyl-4-([1,2,4]triazolo[4,3-c]pyrimidin-7-yloxy)anilino)-6-quinazolinyl)allyl)acetamide: 6-((E)-3-amino-1-propenyl)-N-(3-methyl-4-([1,2,4]triazolo[4,3-c]pyrimidin-7-yloxo)phenyl)quinazolin-4-amine (93 mg, 0.22 mmol), 1-hydroxybenzotriazole (36 mmg, 0.27 mmol), 1-ethyl-(3-dimethylaminopropyl)carbodiimide hydrochloride (52 mg, 0.33 mmol) and N,N-diisopropylethylamine (145 mg, 1.12 mmol) were successively added to a solution of methoxyacetic acid (24 mg, 0.27 mmol) in dimethylformamide (5 mL) under an ice bath, the reaction solution was gradually warmed to room temperature and stirred for 16 hours. Ethyl acetate (50 mL) was added to the reaction solution, the resulting mixture was washed successively with water (30 mL) and saturated sodium chloride (30 mL), dried over anhydrous magnesium sulfate for 1 hour, filtered, and evaporated to dryness under reduced pressure to give a crude product which was slurried with 10 mL of a mixed solvent (petroleum ether:ethyl acetate=10:1) to give 43 mg pale yellow solid with a yield of 38.7%. LC-MS: 496.9 [M+H] detection value; $^1$H-NMR (400 MHz, DMSO-$d_6$) δ 9.82 (s, 1H), 9.67 (s, 1H), 8.58-8.54 (m, 3H), 8.16 (m, 1H), 7.96 (d, 1H, J=8.0 Hz), 7.80-7.72 (m, 3H), 7.20 (d, 1H, J=8.0 Hz), 7.13 (s, 1H), 6.64 (d, 1H, J=16.0 Hz), 6.55-6.48 (m, 1H), 3.99 (t, 2H, J=5.4 Hz), 3.88 (s, 2H), 3.36 (s, 3H), 2.20 (s, 3H).

Embodiment 15 mmol) was suspended in 1,1-dimethoxy-N,N-dimethylmethylamine (2 mL), the reaction solution was stirred at 90° C. for 1 hour, then evaporated to dryness under reduced pressure to give 1.2 g brown oil with a yield of 98%.

Step B: preparation of N-(4-([1,2,4]triazolo[4,3-c]pyrimidin-7-yloxy)-3-methylphenyl)-6-iodoquinazolin-4-amine: (E)-N'-(2-cyano-4-iodophenyl)-N,N-dimethylformamidine (306 mg, 1.02 mmol), 3-methyl-4-([1,2,4]triazolo[4,3-c]pyrimidin-7-yloxy)aniline (247 mg, 1.02 mmol) and glacial acetic acid (0.5 mL) were mixed in isopropyl acetate (3 mL), the mixture was stirred at room temperature overnight. A solid precipitated out and was filtered under reduced pressure to give 320 mg yellow solid with a yield of 63.2%.

Step C: preparation of 5-(4-((4-([1,2,4]triazolo[4,3-c]pyrimidin-7-yloxy)-3-methylphenyl)amino)quinazolin-6-yl)furan-2-carbaldehyde: N-(4-([1,2,4]triazolo[4,3-c]pyrimidin-7-yloxy)-3-methylphenyl)-6-iodoquinazolin-4-amine (200 mg, 0.40 mmol), 5-formyl-2-furanoboronic acid (60 mg, 0.43 mmol), triethylamine (122 mg, 1.21 mmol) and [1,1'-bis(diphenylphosphino)ferrocene]dichloropalladium dichloride dichloromethane complex (16 mg, 0.02 mmol) were suspended in 5 mL tetrahydrofuran, the mixture was stirred under reflux for 16 hours, then filtered and evaporated to dryness to give 187 mg brown solid with a yield of 99.9%.

Step D: preparation of N-(4-([1,2,4]triazolo[4,3-c]pyrimidin-7-yloxy)-3-methylphenyl)-6-(5-(((2-(methylsulfonyl)ethyl)amino)methyl)furan-2-yl)quinazolin-4-amine: 5-(4-((4-([1,2,4]triazolo[4,3-c]pyrimidin-7-yloxy)-3-methylphenyl)amino)quinazolin-6-yl)furan-2-carbaldehyde (187 mg, 0.40 mmol), 2-methylsulfonylethylamino hydrochloride (64 mg, 0.40 mmol) were mixed in a mixed solvent of 5 mL dichloromethane and 2 mL methanol, the mixture was stirred at 18° C. for 2.5 hours. Then sodium cyanoborohydride (76 mg, 1.21 mmol) was added, the resulting mixture was stirred for 16 hours, then evaporated to dryness under reduced pressure to give a crude product, which was purified by column chromatography to give 17 mg orange solid with a yield of 7.4%. LC-MS: 570.8 [M+H] detection value; $^1$H-NMR (400 MHz, CDCl$_3$) δ 9.82 (s, 1H), 9.67 (s, 1H), 8.58-8.54 (m, 3H), 8.16 (m, 1H), 7.96 (d, 1H, J=8.0 Hz), 7.80-7.72 (m, 3H), 7.20 (d, 1H, J=8.0 Hz), 7.13 (s, 1H), 6.64 (d, 1H, J=16.0 Hz), 6.55-6.48 (m, 1H), 3.99 (t, 2H, J=5.4 Hz), 3.88 (s, 2H), 3.36 (s, 3H), 2.20 (s, 3H).

Embodiment 16

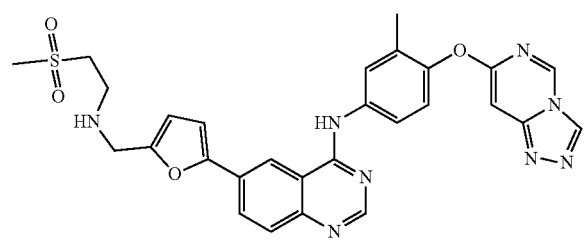 [SMILES: Cc1cc(Nc2ncnc3ccc(-c4ccc(CNCCS(C)(=O)=O)o4)cc23)ccc1Oc1cc2nncn2cn1]

Synthesis of N-(4-([1,2,4]triazolo[4,3-c]pyrimidin-7-yloxy)-3-methylphenyl)-6-(5-(((2-(methylsulfonyl)ethyl)amino)methyl)furan-2-yl)quinazolin-4-amine Step A: preparation of (E)-N'-(2-cyano-4-iodophenyl)-N,N-dimethylformamidine: 2-cyano-4-iodoaniline (1 g, 4.1

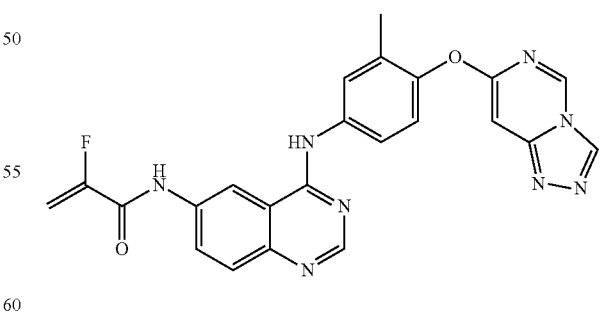

Synthesis of N-(4-((4-([1,2,4]triazolo[4,3-c]pyrimidin-7-yloxy)-3-methylphenyl)amino)quinazolin-6-yl)-2-fluoroacrylamide Step A: preparation of N-(4-([1,2,4]triazolo[4,3-c]pyrimidin-7-yloxy)-3-methylphenyl)-6-nitroquinazoline-4-amine:

4-([1,2,4]triazolo[4,3-c]pyrimidin-7-yloxy)-3-methylaniline (0.5 g, 2 mmol), 4-chloro-6-nitroquinazoline (0.522 g, 2.4 mmol) were suspended in isopropanol (40 mL), the mixture was stirred at room temperature overnight, then evaporated under reduced pressure to give a crude product, which was slurried in a saturated aqueous solution of sodium carbonate and stirred for 30 minutes, then filtered. The filter cake was washed with petroleum ether and dried to give 700 mg brown solid, which was used directly in the next step.

Step B: preparation of $N^4$-(4-([1,2,4]triazolo[4,3-c]pyrimidin-7-yloxy)-3-methylphenyl)quinazoline-4,6-diamine: N-(4-([1,2,4]triazolo[4,3-c]pyrimidin-7-yloxy)-3-methylphenyl)-6-nitroquinazoline-4-amine (700 mg, 1.69 mmol) was suspended in methanol (50 mL), Raney Nickel (70 mg) was added and the mixture was stirred under hydrogen atmosphere at room temperature overnight. The mixture was filtered, the filter cake was washed with methanol and the filtrate was evaporated to dryness to give a crude product, which was purified by column chromatography to give 400 mg yellow solid with a yield of 62%.

Step C: preparation of N-(4-((4-([1,2,4]triazolo[4,3-c]pyrimidin-7-yloxy)-3-methylphenyl)amino)quinazolin-6-yl)-2-fluoroacrylamide: $N^4$-(4-([1,2,4]triazolo[4,3-c]pyrimidin-7-yloxy)-3-methylphenyl)quinazoline-4,6-diamine (100 mg, 0.26 mmol), 2-fluoroacrylic acid (28 mg, 0.39 mmol) and 1-ethyl-(3-dimethylaminopropyl)carbodiimide hydrochloride (150 mg, 0.78 mmol) was dissolved in pyridine (10 mL) and the mixture was stirred at 50° C. for 2 hours. The reaction solution was evaporated to dryness under reduced pressure, then water was added, and the resulting mixture was extracted three times with dichloromethane. The organic phases were combined, washed with saturated brine, dried and concentrated under reduced pressure to give a crude product, which was purified by column chromatography to give 40 mg pale yellow solid with a yield of 35%. LC-MS: 457.9 [M+H] detection value; $^1$H-NMR (400 MHz, CDCl$_3$) δ 9.22 (s, 1H), 8.79 (s, 1H), 8.70 (s, 1H), 8.33 (s, 1H), 7.88 (d, 1H, J=8.0 Hz), 7.81-7.76 (m, 2H), 7.58 (d, 1H, J=8.0 Hz), 7.15 (d, 1H, J=8.0 Hz), 6.91 (s, 1H), 5.97-5.85 (m, 1H), 5.37 (d, 1H, J=12.0 Hz), 2.27 (s, 3H).

Embodiment 17

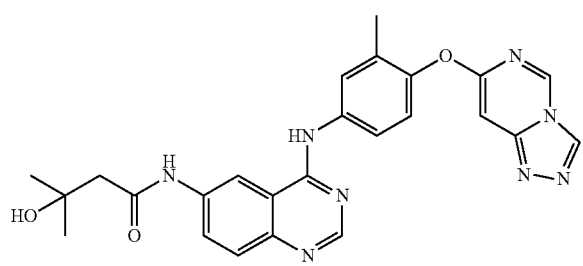 [SMILES: Cc1cc(Nc2ncnc3ccc(NC(=O)CC(C)(C)O)cc23)ccc1Oc1cc2nncn2cn1]

Synthesis of N-(4-((4-([1,2,4]triazolo[4,3-c]pyrimidin-7-yloxy)-3-methylphenyl)amino)quinoline-6-yl)-3-hydroxy-3-methylbutanamide Step A: preparation of N-(4-((4-([1,2,4]triazolo[4,3-c]pyrimidin-7-yloxy)-3-methylphenyl)amino)quinoline-6-yl)-3-hydroxy-3-methylbutanamide: according to the method of Embodiment 16, wherein 2-fluoroacrylic acid was replaced with 3-hydroxy-3-methylbutanoic acid, stirring was continued at room temperature for 36 hours. LC-MS: 484.9 [M+H] detection value; $^1$H-NMR (400 MHz, CD$_3$OD) δ 9.43 (s, 1H), 8.69 (m, 1H), 8.50 (s, 1H), 8.42 (s, 1H), 7.73-7.68 (m, 4H), 7.18-7.16 (d, 1H, J=8.0 Hz), 6.94 (s, 1H), 2.64 (s, 2H), 2.24 (s, 3H), 1.41 (s, 6H).

Embodiment 18

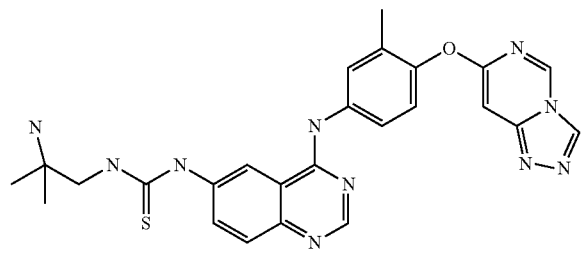 [SMILES: Cc1cc(Nc2ncnc3ccc(NC(=S)NCC(C)(C)N)cc23)ccc1Oc1cc2nncn2cn1]

Synthesis of 1-(4-((4-([1,2,4]triazolo[4,3-c]pyrimidin-7-yloxy)-3-methylphenyl)amino)quinazolin-6-yl)-3-(2-amino-2-methylpropyl)thiourea Step A: Preparation of 1-(4-((4-([1,2,4]triazolo[4,3-c]pyrimidin-7-yloxy)-3-methylphenyl)amino)quinazolin-6-yl)-3-(2-amino-2-methylpropyl)thiourea: thiocarbonyldiimidazole (165 mg, 0.93 mmol) was dissolved in N,N-dimethylformamide (2 mL), the mixture was cooled to −10° C., then a solution of $N^4$-(3-methyl-4-([1,2,4]triazolo[4,3-c]pyrimidin-7-yloxy)phenyl)quinazoline-4,6-diamine (225 mg, 0.59 mmol) in N,N-dimethylformamide (8 mL) and triethylamine (0.5 mL) were added dropwise, stirring was continued at 0° C. for 2 hours, a solution of 2-methylpropane-1,2-diamine (123 mg, 1.40 mmol) in N,N-dimethylformamide (2 mL) was added dropwise, and the mixture was warmed to room temperature and stirred for 16 hours. Saturated aqueous sodium chloride solution (40 mL) was added to the reaction solution, the mixture was extracted with dichloromethane (50 mL), the organic phase was washed once with saturated aqueous sodium chloride solution (50 mL), dried over anhydrous magnesium sulfate, filtered, and concentrated under reduced pressure to give a crude product, which was purified by acidic preparative HPLC to give 55 mg yellow solid with a yield of 18.3%. LC-MS: 515.9 [M+H] detection value; $^1$H-NMR (400 MHz, DMSO-d$_6$) δ 10.84 (s, 1H), 9.82 (s, 1H), 9.67 (s, 1H), 8.58 (m, 2H), 8.48 (s, 1H), 8.33 (s, 2H), 7.98 (d, 1H, J=8.0 Hz), 7.89-7.66 (m, 3H), 7.19 (d, 1H, J=8.0 Hz), 7.13 (s, 1H), 3.74 (s, 2H), 2.20 (s, 3H), 1.26 (s, 6H).

Embodiment 19

Synthesis of $N^4$-(4-([1,2,4]triazolo[4,3-c]pyrimidin-7-yloxy)-3-fluorophenyl)-$N^6$-(4,4-dimethyl-4,5-dihydrooxazol-2-yl)-quinazoline-4,6-diamine

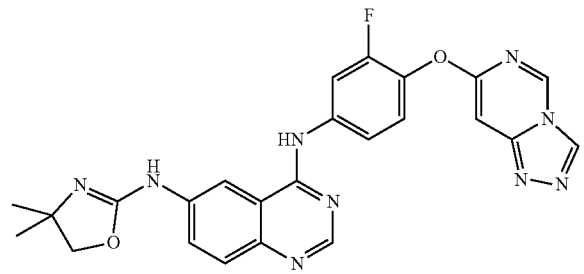 [SMILES: CC1(C)COC(Nc2ccc3ncnc(Nc4ccc(Oc5cc6nncn6cn5)c(F)c4)c3c2)=N1]

Step A: preparation of 7-(2-fluoro-4-nitro-phenoxy)-[1,2,4]triazolo[4,3-c]pyrimidine: 2-fluoro-4-nitro-phenol (1000 mg, 6.36 mmol), 7-chloro-[1,2,4]triazolo[4,3-c]pyrimidine (984 mg, 6.36 mmol) and sodium bicarbonate (700 mg, 8.33 mmol) were suspended in N,N-dimethylformamide (6 mL) and the mixture was stirred at 95° C. for 16 hours. After the reaction solution cooled to room temperature, ethyl acetate (100 mL) and water (100 mL) were added. The organic phase was separated, successively washed with saturated sodium bicarbonate solution (50 mL×3) and saturated aqueous sodium chloride solution (50 mL), dried over anhydrous magnesium sulfate for 2 hours, filtered, and evaporated to dryness under reduced pressure to give a crude product, which was purified by silica gel column to give 300 mg pale yellow solid with a yield of 17.1%.

Step B: preparation of 3-fluoro-4-([1,2,4]triazolo[4,3-c]pyrimidin-7-yloxy)aniline: 7-(2-fluoro-4-nitro-phenoxy)-[1,2,4]triazolo[4,3-c]pyrimidine (250 mg, 0.91 mmol) was dissolved in a mixed solvent of methanol (50 mL) and ethyl acetate (50 mL), Raney Nickel (50 mg) was added, the mixture was purged for three times with argon, then stirred under hydrogen atmosphere (balloon) at room temperature for 3 hours. The mixture was filtered through celite and concentrated under reduced pressure to give 240 mg viscous solid with a yield of 100%, which was used directly in the next step.

Step C: Preparation of 1-(4-((4-([1,2,4]triazolo[4,3-c]pyrimidin-7-yloxy)-3-methylphenyl)amino)quinazolin-6-yl)-3-(2-amino-2-methylpropyl)thiourea: 3-fluoro-4-([1,2,4]triazolo[4,3-c]pyrimidin-7-yloxy)aniline (260 mg, 1.06 mmol) and N'-(2-cyano-4-((4,4-dimethyl-4,5-dihydrooxazol-2-yl)amino)phenyl)-N,N-dimethylformamidine (302 mg, 1.06 mmol) was added to a reaction flask, then acetic acid (0.9 mL) and isopropyl acetate (2.7 mL) were successively added, the mixture was stirred at room temperature for 48 hours, then evaporated to dryness under reduced pressure to give a crude product, which was purified by thin layer chromatography to give 900 mg oil, which was purified by acidic preparative HPLC to give 120 mg pale yellow solid with a yield of 23.2%. LC-MS: 485.9 [M+H] detection value; $^1$H-NMR (400 MHz, DMSO-d$_6$) δ 9.70 (m, 2H), 8.61 (s, 1H), 8.54 (s, 1H), 8.1-8.15 (m, 2H), 8.02 (s, 1H), 7.80-7.64 (m, 3H), 7.45-7.37 (m, 2H), 4.08 (s, 2H), 1.28 (s, 6H).

Embodiment 20

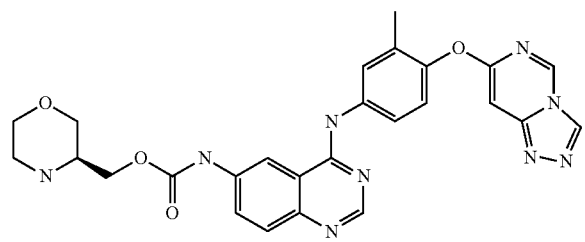 [SMILES: Cc1cc(Nc2ncnc3ccc(NC(=O)OC[C@@H]4COCCN4)cc23)ccc1Oc1cc2nncn2cn1]

Synthesis of morpholin-3-ylmethyl (S)-(4-((4-([1,2,4]triazolo[4,3-c]pyrimidin-7-yloxy)-3-methylphenyl)amino)quinazolin-6-yl)carbamate Step A: preparation of (E)-4-nitrophenyl-(3-cyano-4-(((dimethylamino)methylene)amino)phenyl)carbamate: 100 mL (E)-N'-(4-amino-2-cyanophenyl)-N,N-dimethylformamidine (540 mg, 2.87 mmol) and dichloromethane (30 mL) were mixed in a three-neck flask, the mixture was cooled to about 0° C. and a solution of 4-nitrophenyl chloroformate (630 mg, 3.13 mmol) in dichloromethane (10 mL) was added dropwise under stirring, the reaction was continued at 0° C. for 2 hours, then quenched by adding saturated sodium bicarbonate solution, the resulting mixture was extracted with dichloromethane. The organic phase was washed with saturated brine, dried over anhydrous sodium sulfate, filtered, concentrated to contain a small amount of dichloromethane, and a solid precipitated out. The solid was filtered to give 400 mg product with a yield of 39.45%, which was used directly in the next step.

Step B: preparation of tert-butyl (S,E)-3-((((3-cyano-4-(((dimethylamino)methylene)amino)phenyl)carbamoyl)oxy)methyl)morpholin-4-carboxylate: sodium hydrogen (108 mg, 4.50 mmol) and tetrahydrofuran (10 mL) were added to a 100 mL three-neck reaction flask, the reaction solution was cooled below 0° C., tert-butyl (R)-3-(hydroxymethyl)morpholine-4-carboxylate (420 mg, 1.94 mmol) was added under stirring, after stirring was continued at 0° C. for 1 hour, a solution of (E)-4-nitrophenyl-(3-cyano-4-(((dimethylamino)methylene)amino)phenyl)carbamate (400 mg, 1.13 mmol) in tetrahydrofuran (10 mL) was added. After the addition was completed, the reaction solution naturally warmed to room temperature and stirring was continued for 18 hours. After the reaction was completed, saturated aqueous sodium bicarbonate solution was added and the mixture was extracted with ethyl acetate. The organic phase was washed with saturated brine, dried over anhydrous sodium sulfate, filtered, and the filtrate was concentrated under reduced pressure. The residue was purified by silica gel column chromatography to give 380 mg product with a yield of 77.8%).

Step C: preparation of tert-butyl (S)-3-((((4-((4-([1,2,4]triazolo[4,3-c]pyrimidin-7-yloxy)-3-methylphenyl)amino)quinazolin-6-yl)carbamoyl)oxy)methyl)morpholine-4-carboxylate: tert-butyl (S,E)-3-(((3-cyano-4-(((dimethylamino)methylene)amino)phenyl)carbamoyl)oxy)methyl)morpholin-4-carboxylate (200 mg, 0.46 mmol) and 7-(2-methyl-4-aminophenoxy)-[1,2,4]triazolo[4,3-c]pyrimidine (200 mg, 0.83 mmol) were dissolved in acetic acid isopropyl ester (3 mL) in a 50 mL single-neck flask, then glacial acetic acid (0.5 mL) was added. The mixture was stirred at room temperature for 18 hours. After the reaction was completed, the mixture was concentrated and purified by silica gel column chromatography to give 220 mg product with a yield of 75.6%.

Step D: preparation of morpholin-3-ylmethyl (S)-(4-((4-([1,2,4]triazolo[4,3-c]pyrimidin-7-yloxy)-3-methylphenyl)amino)quinazolin-6-yl)carbamate: tert-butyl (S)-3-((((4-((4-([1,2,4]triazolo[4,3-c]pyrimidin-7-yloxy)-3-methylphenyl)amino)quinazolin-6-yl)carbamoyl)oxy)methyl)morpholine-4-carboxylate (220 mg, 0.42 mmol) and a solution of 10% trifluoroacetic acid in dichloromethane (2 mL) was added to a sealed vial, the mixture was stirred at room temperature for 4 hours. After the reaction was completed, the mixture was concentrated under reduced pressure and purified by silica gel column chromatography to give 83.71 mg product with a yield of 45.27%. LC-MS: 527.9 [M+H] detection value; $^1$H-NMR (400 MHz, CD$_3$OD) b 9.43 (s, 1H), 8.45 (s, 1H), 8.42-8.39 (m, 2H), 7.72-7.67 (m, 4H), 7.16 (d, 1H, J=8.0 Hz), 6.93 (s, 1H), 4.19 (d, 1H, J=4.0 Hz), 3.95-3.34 (m, 4H), 3.19-3.15 (m, 1H), 2.96-2.93 (m, 2H), 2.23 (s, 3H).

Embodiment 21

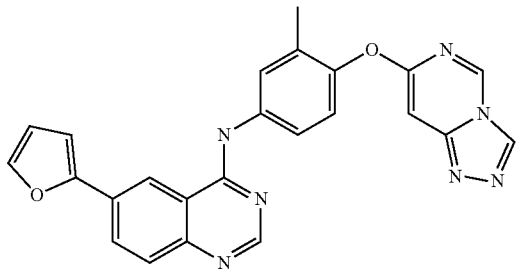 [SMILES: Cc1cc(Nc2ncnc3ccc(-c4ccco4)cc23)ccc1Oc1cc2nncn2cn1]

Synthesis of N-(4-([1,2,4]triazolo[4,3-c]pyrimidin-7-yloxy)-3-methylphenyl)-6-(furan-2-yl)-quinazolin-4-amine Step A: preparation of N-(4-([1,2,4]triazolo[4,3-c]pyrimidin-7-yloxy)-3-methylphenyl)-6-(furan-2-yl)-quinazolin-4-amine: N-(4-([1,2,4]triazolo[4,3-c]pyrimidin-7-yloxy)-3-methylphenyl)-6-iodoquinazolin-4-amine (100 mg, 0.20 mmol), furan-2-boronic acid (39 mg, 0.35 mmol), diisopropylethylamine (150 mg, 1.16 mmol) and [1,1' Bis(diphenylphosphino)ferrocene]dichloropalladium dichloride dichloromethane complex (50 mg) were mixed in tetrahydrofuran (3 mL) and the mixture was heated to 80° C. and stirred for 18 hours, then filtered, the filtrate was washed with saturated sodium bicarbonate solution and extracted with ethyl acetate. The organic phase was washed with saturated brine, dried over anhydrous sodium sulfate, filtered, evaporated under reduced pressure and the residue was purified by column chromatography to give 25.80 mg product with a yield of 29.4%. LC-MS: 435.9 [M+H] detection value; $^1$H-NMR (400 MHz, CD$_3$OD) δ 9.45 (s, 1H), 8.75 (d, 1H, J=4.0 Hz), 8.52 (s, 1H), 8.44 (s, 1H), 8.21 (d, 1H, J=8.0 Hz), 7.83-7.69 (m, 4H), 7.21 (d, 1H, J=8.0 Hz), 7.05 (s, 1H), 6.96 (s, 1H), 6.63 (dd, 1H, J=8.0, 4.0 Hz), 2.28 (s, 3H).

Embodiment 22

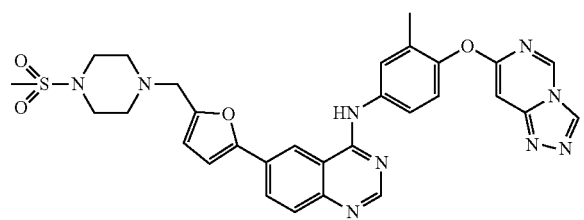 [SMILES: Cc1cc(Nc2ncnc3ccc(-c4ccc(CN5CCN(S(C)(=O)=O)CC5)o4)cc23)ccc1Oc1cc2nncn2cn1]

Synthesis of N-(4-([1,2,4]triazolo[4,3-c]pyrimidin-7-yloxy)-3-methylphenyl)-6-(5-((4-(methanesulfonyl)piperazin-1-yl)methyl)furan-2-yl)quinazolin-4-amine Step A: Preparation of N-(4-([1,2,4]triazolo[4,3-c]pyrimidin-7-yloxy)-3-methylphenyl)-6-(5-((4-(methanesulfonyl)piperazin-1-yl)methyl)furan-2-yl)quinazolin-4-amine: 5-(4-((4-([1,2,4]triazolo[4,3-]pyrimidin-7-yloxy)-3-methylphenyl)amino)quinazolin-6-yl)furan-2-carbaldehyde (105 mg, 0.23 mmol) and 1-(methylsulfonyl)piperazine (56 mg, 0.34 mmol) were added to methanol (5 mL) and dichloromethane (1.5 mL), then 4 drops of acetic acid and sodium triacetoxyborohydride (145 mg, 0.68 mmol) were added. The reaction mixture was stirred at room temperature for 24 hours, then concentrated, the residue was purified by column chromatography to give a crude product, which was purified by acidic preparative liquid chromatography to give a yellow solid (22 mg, 0.036 mmol) with a yield of 16%. LC-MS: 612.3 [M+H] detection value; $^1$H NMR (400 MHz, DMSO) δ 10.01 (s, 1H), 9.68 (d, J=1.2 Hz, 1H), 8.79 (s, 1H), 8.59 (s, 1H), 8.58 (s, 1H), 8.17 (dd, J=8.0, 4.0 Hz, 1H), 7.84-7.77 (m, 3H), 7.22 (d, J=8.0 Hz, 1H), 7.13 (d, J=4.0 Hz, 1H), 7.10 (d, J=4.0 Hz, 1H), 6.56 (d, J=4.0 Hz, 1H), 3.70 (s, 2H), 3.15 (t, J=4.0 Hz, 4H), 2.88 (s, 3H), 2.58 (t, J=4.0 Hz, 4H), 2.21 (s, 3H).

Embodiment 23

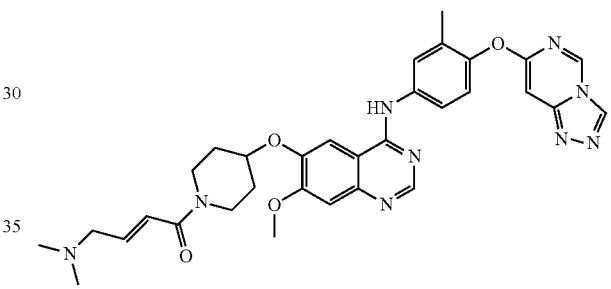

Synthesis of N-(4-([1,2,4]triazolo[4,3-c]pyrimidin-7-yloxy)-3-methylphenyl)-7-methoxy-6-(piperidin-4-yloxy)amine Step A: Preparation of N-(4-([1,2,4]triazolo[4,3-c]pyrimidin-7-yloxy)-3-methylphenyl)-7-methoxy-6-(piperidin-4-yloxy)amine: N-(4-([1,2,4]triazolo[4,3-c]pyrimidin-7-yloxy)-3-methylphenyl)-7-methoxy-6-(piperidin-4-yloxy)amine (97 mg, 0.18 mmol), (E)-4-(dimethylamino)but-2-ene hydrochloride (38 mg, 0.23 mmol), HATU (96 mg, 0.25 mmol) and N,N-diisopropylethylamine (126 mg, 0.97 mmol) were added to dichloromethane (5 mL). The reaction solution was stirred at room temperature for 48 hours, then concentrated to give a residue. The residue was purified by column chromatography to give a crude product, which was purified by acidic preparative liquid chromatography to give a yellow solid (15 mg, 0.025 mmol) with a yield of 14%. LC-MS: 610.3 [M+H] detection value; $^1$H NMR (400 MHz, DMSO) b 9.68 (s, 1H), 9.49 (s, 1H), 8.59 (s, 1H), 8.48 (s, 1H), 8.22 (s, 2H), 7.99 (s, 1H), 7.72 (s, 1H), 7.24 (s, 1H), 7.20 (d, J=9.2 Hz, 1H), 7.11 (s, 1H), 6.64-6.63 (m, 1H), 4.83-4.81 (m, 1H), 3.96 (s, 3H), 3.88-3.86 (m, 2H), 3.60-3.57 (m, 2H), 3.06 (d, J=4.8 Hz, 2H), 2.55 (s, 3H), 2.18 (d, J=12.0 Hz, 6H), 2.05-2.03 (m, 2H), 1.72-1.70 (m, 2H).

Embodiment 24

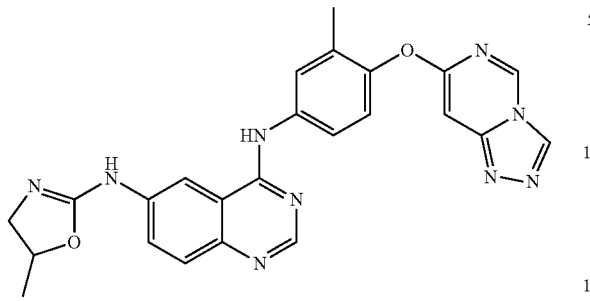

Synthesis of N⁴-(4-([1,2,4]triazolo[4,3-c]pyrimidin-7-yloxy)-3-methylphenyl)-N⁶-(5-methyl-4,5-dihydrooxazol-2-yl)quinazoline-4,6-diamine According to the method of Embodiment 7, wherein (R)-2-amino-1-propanol was replaced with 1-aminopropan-2-ol. LC-MS: 468.2 [M+H]⁺ detection value. ¹H NMR (400 MHz, DMSO) δ 9.67 (d, J=1.2 Hz, 1H), 9.57 (s, 1H), 8.58 (s, 1H), 8.48 (s, 1H), 8.15 (s, 1H), 7.83 (s, 1H), 7.79 (d, J=8.4 Hz, 1H), 7.67 (d, J=8.0 Hz, 1H), 7.17 (d, J=8.8 Hz, 1H), 7.11 (d, J=1.2 Hz, 1H), 4.80-4.78 (m, 1H), 3.77-3.75 (m, 1H), 3.23-3.21 (m, 1H), 2.19 (s, 3H), 1.37 (d, J=6.4 Hz, 3H)

Embodiment 25

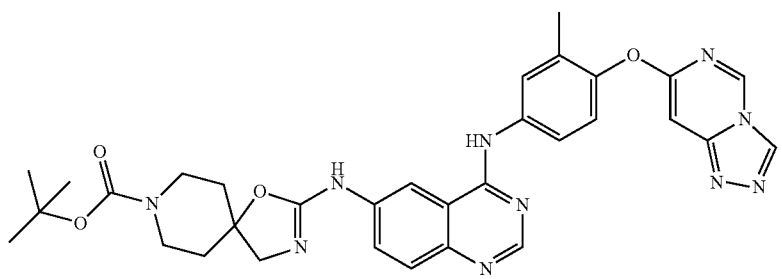 [SMILES: Cc1cc(Nc2ncnc3ccc(NC4=NCC5(CCN(C(=O)OC(C)(C)C)CC5)O4)cc23)ccc1Oc1cc2nncn2cn1]

Synthesis of tert-butyl 2-((4-((4-([1,2,4]triazolo[4,3-c]pyrimidin-7-yloxy)-3-methylphenyl)amino)quinazolin-6-yl)amino)-1-oxa-3,8-diazaspiro[4.5]dec-2-en-8-carboxylate Step A: preparation of tert-butyl 4-(aminomethyl)-4-hydroxypiperidine-1-carboxylate: aqueous ammonia (6 mL) was added to a solution of tert-butyl 1-oxa-6-azaspiro[2.5]octan-6-carboxylate (500 mg, 2 mmol) in methanol (4 mL) at 0° C. The reaction solution warmed to room temperature and was stirred for 16 hours, then concentrated under reduced pressure to give a colorless oil (530 mg, 2.3 mmol) with a yield of 100%, which was used directly in the next step without purification.

According to the method of Embodiment 7, wherein (R)-2-amino-1-propanol was replaced with tert-butyl 4-(aminomethyl)-4-hydroxypiperidine-1-carboxylate. LC-MS: 623.3 [M+H]⁺ detection value. ¹H NMR (400 MHz, CDCl₃) δ 9.22 (d, J=1.2 Hz, 1H), 8.71 (s, 1H), 8.35 (s, 2H), 7.84 (d, J=8.8 Hz, 1H), 7.80 (d, J=2.4 Hz, 1H), 7.74 (dd, J=8.4, 2.4 Hz, 1H), 7.43 (d, J=7.2 Hz, 1H), 7.13 (d, J=8.4 Hz, 1H), 6.90 (d, J=1.2 Hz, 1H), 3.84-3.82 (m, 2H), 3.70 (s, 2H), 3.34-3.31 (m, 2H), 2.26 (s, 3H), 1.97-1.94 (m, 2H), 1.79-1.74 (m, 2H), 1.50 (s, 9H).

Embodiment 26

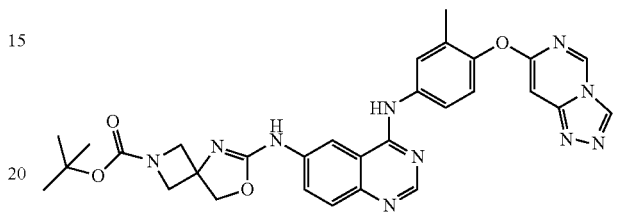
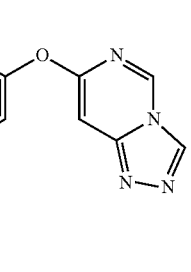

Synthesis of tert-butyl 6-((4-((4-([1,2,4]triazolo[4,3-c]pyrimidin-7-yloxy)-3-methylphenyl)amino)quinazolin-6-yl)-7-oxa-2,5-diazaspiro[3.4]oct-5-en-2-carboxylate Step A: preparation of tert-butyl 3-amino-3-(hydroxymethyl)azetidine-1-carboxylate: sodium borohydride (140 mg, 3.68 mmol) was added to a solution of 3-ethoxycarbonyl-3-amino-1-tert-butoxycarbonylazetidine (300 mg, 1.23 mmol) in ethanol (8 mL) at 0° C., after warming to room temperature, the mixture was heated to 80° C. and stirred under reflux for 16 hours. The reaction solution was concentrated under reduced pressure to give a residue, which was suspended in saturated brine. The resulting aqueous solution was extracted three times with ethyl acetate. The organic phases were combined, dried over anhydrous sodium sulfate, and concentrated under reduced pressure to give a colorless oil (290 mg, 1.4 mmol), which was used directly in the next step.

According to the method of Embodiment 7, wherein tert-butyl (R)-2-amino-1-propanol was replaced with 3-amino-3-(hydroxymethyl)azetidin-1-carboxylate. LC-MS: 595.3 [M+H] detection value. ¹H NMR (400 MHz, DMSO) δ 9.67 (d, J=1.2 Hz, 1H), 9.63 (s, 1H), 8.58 (s, 1H), 8.50 (s, 1H), 8.28 (s, 1H), 7.80-7.71 (m, 3H), 7.18 (d, J=8.8 Hz, 1H), 7.12 (d, J=1.2 Hz, 1H), 4.55 (s, 2H), 4.06-4.03 (m, 4H), 2.19 (s, 3H), 1.39 (s, 9H).

Embodiment 27

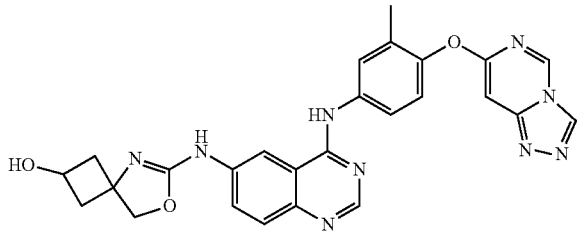 [SMILES: Cc1cc(Nc2ncnc3ccc(NC4=NC5(CO4)CC(O)C5)cc23)ccc1Oc1cc2nncn2cn1]

Synthesis of 6-((4-((4-([1,2,4]triazolo[4,3-c]pyrimidin-7-yloxy)-3-methylphenyl)amino)quinazolin-6-yl)amino)-7-oxa-5-azaspiro[3,4]oct-5-en-2-ol Step A: preparation of 3-amino-3-(hydroxymethyl)cyclobutan-1-ol: sodium borohydride (308 mg, 8.1 mmol) was added to a solution of ethyl 1-amino-3-hydroxylcyclobutan-1-carboxylate (430 mg, 2.7 mmol) in ethanol (10 mL) at 0° C., after warming to room temperature, the reaction solution was heated to 80° C. for 16 hours, then concentrated to dryness under reduced pressure and suspended in a mixed solvent (dichloromethane/methanol=10/1). The mixture was stirred for 30 minutes, then filtered, and concentrated under reduced pressure to give a crude product as a colorless oil (320 mg, 2.7 mmol), which was used directly in the next step.

According to the method of Embodiment 7, wherein (R)-2-amino-1-propanol was replaced with 3-amino-3-(hydroxymethyl)cyclobutan-1-ol. LC-MS: 510.2 [M+H] detection value. $^1$H NMR (400 MHz, CD$_3$OD) b 9.45 (d, J=1.2 Hz, 1H), 8.47 (d, J=2.0 Hz, 1H), 8.43 (s, 1H), 8.23-8.19 (m, 1H), 7.81-7.78 (m, 1H), 7.74 (dd, J=8.8, 4.4 Hz, 2H), 7.66-7.59 (m, 1H), 7.20 (d, J=8.8 Hz, 1H), 6.95 (d, J=1.2 Hz, 1H), 4.56-4.47 (m, 1H), 4.41 (d, J=7.6 Hz, 2H), 2.71-2.66 (m, 1H), 2.64-2.55 (m, 1H), 2.48-2.36 (m, 1H), 2.27 (s, 3H), 2.25-2.20 (m, 1H).

Embodiment 28

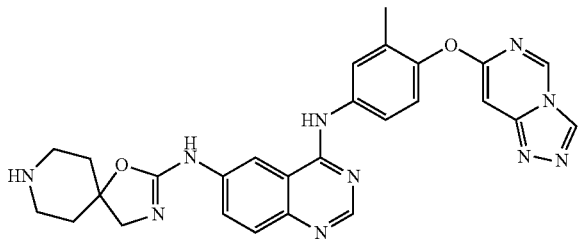 [SMILES: Cc1cc(Nc2ncnc3ccc(NC4=NCC5(CCNCC5)O4)cc23)ccc1Oc1cc2nncn2cn1]

Synthesis of N$^4$-(4-([1,2,4]triazolo[4,3-c]pyrimidin-7-yloxy)-3-methylphenyl)-N$^6$-(1-oxa-3,8-diazaspiro[4.5]dec-2-en-2-yl)quinazoline-4,6-diamine Step A: preparation of N$^4$-(4-([1,2,4]triazolo[4,3-c]pyrimidin-7-yloxy)-3-methylphenyl)-N$^6$-(1-oxa-3,8-diazaspiro[4.5]dec-2-en-2-yl)quinazoline-4,6-diamine:trifluoroacetic acid (0.3 mL) was added to a solution of tert-butyl 2-((4-((4-([1,2,4]triazolo[4,3-c]pyrimidin-7-yloxy)-3-methylphenyl)amino)quinazolin-6-yl)amino)-1-oxa-3,8-diazaspiro[4.5]dec-2-en-8-carboxylate (80 mg, 0.13 mmol) in dichloromethane (3 mL). The reaction solution was stirred at room temperature for 1.5 hours, diluted with dimethyl sulfoxide, concentrated under reduced pressure to remove trifluoroacetic acid, and the resulting residue was purified by preparative liquid chromatography to give a yellow solid (29 mg, 0.055 mmol) with a yield of 43%. LC-MS: 523.2 [M+H] detection value. $^1$H NMR (400 MHz, DMSO) δ 9.68 (d, J=1.2 Hz, 1H), 8.59 (s, 2H), 8.54 (s, 1H), 8.25 (s, 1H), 8.15 (s, 1H), 7.82 (s, 1H), 7.77 (d, J=9.2 Hz, 1H), 7.72 (s, 1H), 7.19 (d, J=8.8 Hz, 1H), 7.12 (d, J=1.2 Hz, 1H), 3.58 (s, 2H), 3.25 (s, 2H), 3.13-3.10 (m, 2H), 2.19 (s, 3H), 2.09-2.08 (m, 2H), 2.00-1.90 (m, 2H).

Embodiment 29

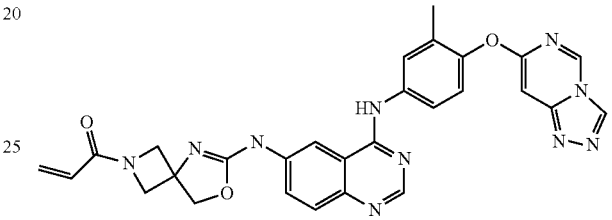

Synthesis of 1-(6-((4-((4-([1,2,4]triazolo[4,3-c]pyrimidin-7-yloxy)-3-methylphenyl)amino)quinazolin-6-yl)amino)-7-oxa-2,5-diazaspiro[3.4]oct-5-en-2-yl)prop-2-en-1-one According to the condensation method of Embodiment 23. LC-MS: 549.2 [M+H]$^+$ detection value. $^1$H NMR (400 MHz, CD$_3$OD) δ 9.45 (s, 1H), 8.49 (s, 1H), 8.44 (s, 1H), 8.34 (d, J=2.0 Hz, 1H), 7.81-7.66 (m, 4H), 7.20 (d, J=8.8 Hz, 1H), 6.95 (d, J=1.2 Hz, 1H), 6.42-6.35 (m, 1H), 6.29-6.25 (m, 1H), 5.77 (dd, J=10.0, 2.0 Hz, 1H), 4.63 (s, 2H), 4.54 (s, 2H), 4.36-4.28 (m, 2H), 2.26 (s, 3H).

Embodiment 30

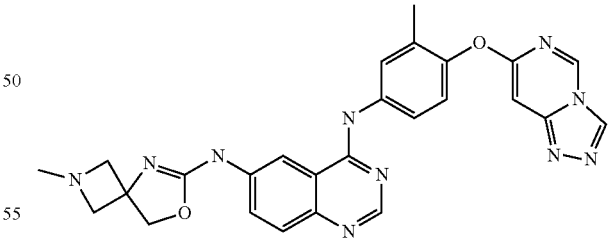

Synthesis of N$^4$-(4-([1,2,4]triazolo[4,3-c]pyrimidin-7-yloxy)-3-methylphenyl)-N$^6$-(2-methyl-7-oxa-2,5-diazaspiro[3.4]oct-5-en-6-yl)quinazoline-4,6-diamine Step A: preparation of N$^4$-(4-([1,2,4]triazolo[4,3-c]pyrimidin-7-yloxy)-3-methylphenyl)-N$^6$-(2-methyl-7-oxa-2,5-diazaspiro[3.4]oct-5-en-6-yl)quinazoline-4,6-diamine: N$^4$-(4-([1,2,4]triazolo[4,3-c]pyrimidin-7-yloxy)-3- methylphenyl)-N⁶-(7-oxa-2,5-diazaspiro[3.4]oct-5-en-6-yl)quinazoline-4,6-diamine (50 mg, 0.1 mmol) and 40% aqueous formaldehyde solution (15 mg, 0.2 mmol) were dissolved in ethanol (5 mL), sodium cyanoborohydride (19 mg, 0.29 mmol) was added and the reaction solution was stirred at room temperature for 16 hours, then quenched with aqueous sodium bicarbonate, concentrated under reduced pressure to give a residue. The residue was isolated by preparative TLC to give a crude product, which was purified by preparative HPLC to give a yellow solid (7.5 mg, 0.01 mmol) with a yield of 15%. LC-MS: 509.2 [M+H] detection value. ¹H NMR (400 MHz, CD₃OD) δ 9.47 (s, 1H), 8.50 (s, 1H), 8.45 (s, 1H), 8.41 (d, J=2.0 Hz, 1H), 7.98 (dd, J=9.2, 2.4 Hz, 1H), 7.79-7.76 (m, 2H), 7.71 (dd, J=8.8, 2.4 Hz, 1H), 7.23 (d, J=8.8 Hz, 1H), 6.95 (d, J=1.2 Hz, 1H), 4.62 (s, 2H), 4.38 (d, J=11.2 Hz, 2H), 4.29 (d, J=11.2 Hz, 2H), 2.99 (s, 3H), 2.28 (s, 3H).

Embodiment 31

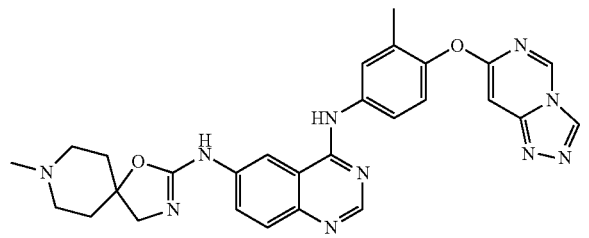 [SMILES: Cc1cc(Nc2ncnc3ccc(NC4=NCC5(CCN(C)CC5)O4)cc23)ccc1Oc1cc2nncn2cn1]

Preparation of N⁴-(4-([1,2,4]triazolo[4,3-c]pyrimidin-7-yloxy)-3-methylphenyl)-N⁶-(8-methyl-1-oxa-3,8-diazaspiro[4.5]dec-2-en-2-yl)quinazoline-4,6-diamine According to the method of Embodiment 30. LC-MS: 537.3 [M+H] detection value. ¹H NMR (400 MHz, CD₃OD) b 9.46 (s, 1H), 8.49 (s, 1H), 8.44 (s, 1H), 8.27 (s, 1H), 7.78-7.73 (m, 3H), 7.64 (d, J=7.2 Hz, 1H), 7.21 (d, J=8.4 Hz, 1H), 6.95 (s, 1H), 3.80 (s, 2H), 3.40-3.36 (m, 2H), 3.25-3.21 (m, 2H), 2.85 (s, 3H), 2.28 (s, 3H), 2.26-2.24 (m, 2H), 2.18-2.15 (m, 2H).

Embodiment 32

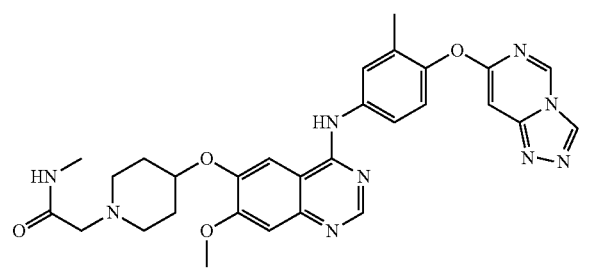 [SMILES: CNC(=O)CN1CCC(Oc2cc3c(Nc4ccc(Oc5cc6nncn6cn5)c(C)c4)ncnc3cc2OC)CC1]

Synthesis of 2-(4-(7-methoxy-4-(3-methyl-4-([1,2,4]triazolo[4,3-c]pyrimidin-7-yloxy)anilino)quinazolin-6-yl)oxy-1-piperidinyl)-N-methylacetamide Step A: preparation of 2-(4-(7-methoxy-4-(3-methyl-4-([1,2,4]triazolo[4,3-c]pyrimidin-7-yloxy)anilino)quinazolin-6-yl)oxy-1-piperidinyl)-N-methylacetamide:
7-methoxy-N-(3-methyl-4-([1,2,4]triazolo[4,3-c]pyrimidin-7-yloxy)phenyl)-6-(4-piperidinyloxy)quinazolin-4-amine (65 mg, 0.13 mmol) and potassium carbonate (60 mg, 0.43 mmol) were mixed in acetonitrile (3 mL) and stirred for 5 minutes, the pH of the reaction mixture acidic measured by a pH test paper. Therefore, triethylamine (20 mg, 0.20 mmol) was added to the reaction solution, and the pH became about 8-9. Then 2-chloro-N-methylacetamide (11 mg, 0.10 mmol) was added and the final reaction solution was heated at reflux under argon atmosphere for 16 hours. The reaction solution was filtered and the filtrate was evaporated to dryness under reduced pressure to give a crude product, which was purified by acidic preparative HPLC (gradient: 5-25% acetonitrile: water, containing 0.1% formic acid) to give 5.19 mg pale yellow solid with a yield of 7.0%. LC-MS: 569.9 [M+H] detection value. ¹H-NMR (400 MHz, CD₃OD) b 9.47 (s, 1H), 8.47-8.45 (m, 2H), 7.91 (s, 1H), 7.71 (s, 1H), 7.66 (d, 1H, J=8.0 Hz), 7.23-7.20 (m, 2H), 6.96 (s, 1H), 4.77 (m, 1H), 4.04 (s, 3H), 3.43 (m, 2H), 3.15 (m, 2H), 2.91-2.86 (m, 2H), 2.83 (s, 3H), 2.27 (s, 3H), 2.24-2.20 (m, 2H), 2.11 (m, 2H).

Embodiment 33

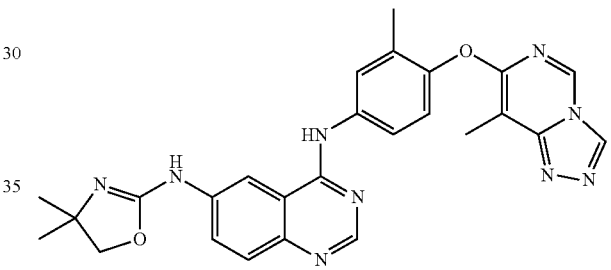

Synthesis of N⁶-(4,4-dimethyl-4,5-dihydrooxazol-2-yl)-N⁴-(3-methyl-4-((8-methyl-[1,2,4]triazolo[4,3-c]pyrimidin-7-yl)oxy)phenyl)quinazoline-4,6-diamine Step A: preparation of (Z)-4-chloro-6-hydrazono-5-methyl-1,6-dihydropyrimidine: 4,6-dichloro-5-methylpyrimidine (1 g, 6.14 mmol) was dissolved in isopropanol (13 mL), hydrazine hydrate (1.2 g, 15 mmol, 64%) was added dropwise. The reaction solution was stirred at 8° C. for 16 hours, then concentrated under reduced pressure to give a white solid. Then water (20 mL) was added to the white solid, and the mixture was stirred at 8° C. for 30 minutes and filtered to give 973 mg offwhite solid, which was used directly in the next step.

Step B: preparation of 7-chloro-8-methyl-[1,2,4]triazolo[4,3-c]pyrimidine: (Z)-4-chloro-6-hydrazono-5-methyl-1,6-dihydropyrimidine (973 mg, 6.14 mmol) was suspended in trimethylorthoformate (15 mL), the mixture was stirred at 100° C. for 2 hours and became clear. The reaction solution was then cooled to 60° C. and 4-methylbenzenesulfonyl chloride (21 mg, 0.11 mmol) was added. The resulting mixture was stirred at 60° C. for 2 hours, then concentrated under reduced pressure to give a yellow solid. Water (10 mL) was added to the yellow solid, and the mixture was stirred at 8° C. for 30 minutes, then filtered to give 1 g pale yellow solid, which was used directly directly in the next step.

Step C: preparation of 3-methyl-4-((8-methyl-[1,2,4]triazolo[4,3-c]pyrimidin-7-yl)oxy)aniline: 7-chloro-8-methyl-[1,2,4]triazolo[4,3-c]pyrimidine (308 mg, 1.83 mmol), 4-amino-2-methylphenol (224 mg, 1.82 mmol) and cesium carbonate (652 mg, 2.00 mmol) were suspended in dimethyl sulfoxide (8 mL), the mixture was stirred at 130° C. for 16 hours, then filtered. The filter cake was washed three times with ethyl acetate (5 mL) and the filtrate was washed once with water (30 mL) and saturated brine (30 mL), dried over anhydrous sodium sulfate, filtered, and concentrated under reduced pressure to give 366 mg dark brown oil, which was used directly in the next step.

Step D: preparation of $N^6$-(4,4-dimethyl-4,5-dihydrooxazol-2-yl)-$N^4$-(3-methyl-4-((8-methyl-[1,2,4]triazolo[4,3-c]pyrimidin-7-yl)oxy)phenyl)quinazoline-4,6-diamine: 3-methyl-4-((8-methyl-[1,2,4]triazolo[4,3-c]pyrimidin-7-yl)oxy)aniline (366 mg, 1.43 mmol), N'-(2-cyano-4-((4,4-dimethyl-5H-oxazol-2-yl)amino)phenyl)-N,N-dimethylformamidine (245 mg, 0.86 mmol) and glacial acetic acid (200 mg, 3.33 mmol) were mixed in isopropyl acetate (2 mL), the mixture was stirred at 28° C. for 40 hours, then evaporated to dryness under reduced pressure to give a crude product. The crude product was purified by column chromatography to give 100 mg yellow solid, which was then slurried with ethyl acetate (5 mL) and filtered to give 38.1 mg earthy yellow solid with a yield of 5.4%. LC-MS: 496.9 [M+H] detection value. $^1$H-NMR (400 MHz, DMSO) δ 9.54 (s, 1H), 9.47 (s, 1H), 8.57 (s, 1H), 8.46 (s, 1H), 8.02 (s, 1H), 7.77 (s, 1H), 7.72 (d, 1H, J=8.0 Hz), 7.66 (d, 1H, J=4.0 Hz), 7.10 (d, 1H, J=8.0 Hz), 4.08 (s, 2H), 2.54 (s, 3H), 2.17 (s, 3H), 1.29 (s, 6H).

Embodiment 34

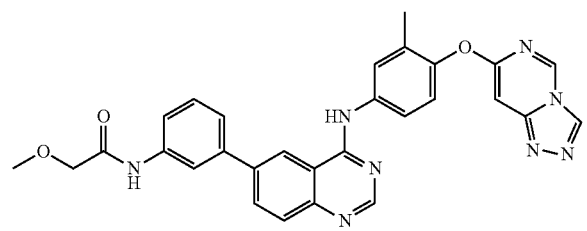

Synthesis of N-(3-(4-((4-([1,2,4]triazolo[4,3-c]pyrimidin-7-yloxy)-3-methylphenyl)amino)quinazoline-6-yl)phenyl)-2-methoxyacetamide Step A: preparation of (3-aminophenyl)boronic acid: 3-nitroboronic acid (1 g, 5.99 mmol) was dissolved in methanol (15 mL), Raney Nickel (0.2 g) was added and the mixture was stirred under 15 psi of hydrogen atmosphere (hydrogen balloon) at room temperature for 20 hours. The mixture was filtered and the filtrate was concentrated under reduced pressure to give 0.82 g crude product as a brown oil which was used directly in the next step.

Step B: preparation of (3-(2-methoxyacetylamino)phenyl)boronic acid: 3-(aminophenyl)boronic acid (200 mg, 1.46 mmol), 2-methoxyacetic acid (140 mg, 1.55 mmol)) and EDCI (400 mg, 2.09 mmol) were dissolved in pyridine (3 mL). The mixture was heated to 100° C. and stirred for 16 hours, then concentrated under reduced pressure to give a crude product, which was purified by silica gel column chromatography to give 240 mg light brown solid with a yield of 78.6%.

Step C: preparation of N-(3-(4-((4-([1,2,4]triazolo[4,3-c]pyrimidin-7-yloxy)-3-methylphenyl)amino)quinazoline-6-yl)phenyl)-2-methoxyacetamide: (3-(2-methoxyacetylamino)phenyl)boronic acid (30 mg, 0.14 mmol), 6-iodo-N-(3-methyl-4-([1,2,4]triazolo[4,3-c]pyrimidin-7-yloxy)phenyl)quinazolin-4-amine (72 mg, 0.15 mmol), [1,1'-bis(diphenylphosphino)ferrocene]dichloropalladium (6 mg, 0.0074 mmol) and DIEA (40 mg, 0.40 mmol) were mixed in 1,4-dioxane (2 mL), the mixture was stirred at reflux under argon atmosphere for 16 hours, then filtrated. The filtrate was evaporated under reduced pressure to give a crude product, which was purified by silica gel column and preparative liquid chromatography to give 10.09 mg yellow solid with a yield of 13.2%. LC-MS: 532.8 [M+H] detection value. $^1$H-NMR (400 MHz, CDCl$_3$) δ 9.23 (s, 1H), 8.73 (s, 1H), 8.50 (s, 1H), 8.36 (s, 1H), 8.32 (m, 1H), 8.13 (s, 1H), 8.01 (d, 1H, J=8.0 Hz), 7.96 (d, 1H, J=8.0 Hz), 7.82 (m, 1H), 7.77 (dd, 1H, J=8.0, 4.0 Hz), 7.45 (m, 3H), 7.15 (d, 1H, J=8.0 Hz), 6.93 (s, 1H), 4.08 (s, 2H), 3.56 (s, 3H), 2.27 (s, 3H).

Embodiment 35

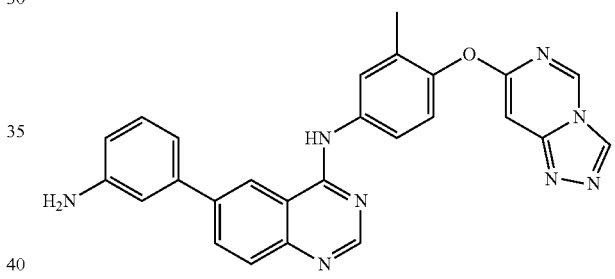

Synthesis of N-(4-([1,2,4]triazolo[4,3-c]pyrimidin-7-yloxy)-3-methylphenyl)-6-(3-aminophenyl)quinoline-4-amine Step A: preparation of N-(4-([1,2,4]triazolo[4,3-c]pyrimidin-7-yloxy)-3-methylphenyl)-6-(3-aminophenyl)quinoline-4-amine: 3-aminophenylboronic acid (28 mg, 0.20 mmol), 6-iodo-N-(3-methyl-4-([1,2,4]triazolo[4,3-c]pyrimidin-7-yloxy)phenyl]quinazolin-4-amine (100 mg, 0.20 mmol), [1,1'-bis(diphenylphosphino)ferrocene]dichloropalladium (10 mg, 0.012 mmol) and DIEA (78 mg, 0.60 mmol) were mixed in 1,4-dioxane (5 mL), the mixture was stirred at reflux under argon atmosphere for 16 hours, then filtrated, the filtrate was evaporated under reduced pressure to give a crude product, which was purified by silica gel column chromatography and preparative liquid chromatography to give 8.66 mg yellow solid with a yield of 9.3%. LC-MS: 461.8 [M+H] detection value. $^1$H-NMR (400 MHz, CD$_3$OD) δ 9.44 (s, 1H), 8.63 (d, 1H, J=4.0 Hz), 8.55 (s, 1H), 8.43 (s, 1H), 8.14 (d, 1H, J=8.0, 4.0 Hz), 7.84 (d, 1H, J=8.0 Hz), 7.78 (m, 1H), 7.73 (dd, 1H, J=8.0, 4.0 Hz), 7.26 (t, 1H, J=8.0 Hz), 7.20 (d, 1H, J=12.0 Hz), 7.16-7.14 (m, 2H), 6.96 (s, 1H), 6.81 (dd, 1H, J=8.0, 4.0 Hz), 2.27 (s, 3H).

Embodiment 36

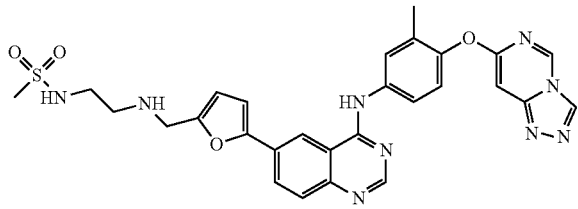 [SMILES: Cc1cc(Nc2ncnc3ccc(-c4ccc(CNCCNS(C)(=O)=O)o4)cc23)ccc1Oc1cc2nncn2cn1]

Synthesis of N-(2-(((5-(4-((4-([1,2,4]triazolo[4,3-c]pyrimidin-7-yloxy)-3-methylphenyl)amino)quinazolin-6-yl)furan-2-yl)methyl)amino)ethyl)methylsulfonamide Step A: preparation of tert-butyl (2-(methylsulfonamido)ethyl)carbamate: tert-butyl N-(2-aminoethyl)carbamate (1 g, 6.24 mmol) was dissolved in dry dichloromethane (10 mL), DIEA (0.947 g, 9.36 mmol) was added under an ice bath, followed by dropwise addition of methanesulfonyl chloride (1.07 g, 9.34 mmol). The mixture was warmed to 8° C. and stirred for 3 hours, then washed with water (10 mL) and saturated brine (10 mL), dried over anhydrous sodium sulfate, filtered, and the filtrate was concentrated under reduced pressure to give a crude product as an orange oil (1.5 g), which was used directly in the next step.

Step B: preparation of N-(2-aminoethyl)methylsulfonamide trifluoroacetate: tert-butyl (2-(methylsulfonamido)ethyl)carbamate (50 mg, 0.21 mmol) was dissolved in dichloromethane (1 mL), a solution of hydrochloric acid in dioxane (2 mL, 4M) was added. The mixture was stirred at 8° C. for 3 hours, then concentrated under reduced pressure to give 28 mg crude product as an orange oil, which was used directly in the next step.

Step C: preparation of N-(2-(((5-(4-((4-([1,2,4]triazolo[4,3-c]pyrimidin-7-yloxy)-3-methylphenyl)amino)quinazolin-6-yl)furan-2-yl)methyl)amino)ethyl)methylsulfonamide: according to the method of Embodiment 15, wherein 2-methylsulfonylethylamino hydrochloride was replaced with N-(2-aminoethyl)methylsulfonamide trifluoroacetate. LC-MS: 293.4 [M/2+H] detection value. $^1$H-NMR (400 MHz, DMSO) δ 9.97 (s, 1H), 9.69 (s, 1H), 8.83 (s, 1H), 8.60 (d, 1H, J=4.0 Hz), 7.22-8.16 (m, 2H), 7.83 (m, 2H), 7.23 (d, 1H, J=8.0 Hz), 7.14-7.06 (m, 2H), 6.57 (s, 1H), 3.96 (s, 2H), 3.13 (m, 2H), 2.94 (s, 3H), 2.52 (m, 2H), 2.22 (s, 3H).

Embodiment 37

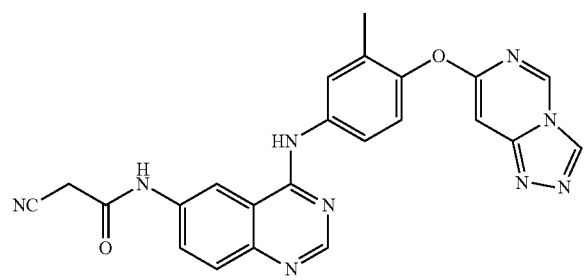 [SMILES: Cc1cc(Nc2ncnc3ccc(NC(=O)CC#N)cc23)ccc1Oc1cc2nncn2cn1]

Synthesis of N-(4-((4-([1,2,4]triazolo[4,3-c]pyrimidin-7-yloxy)-3-methylphenyl)amino)quinazoline-6-yl)-2-cyanoacetamide Step A: preparation of N-(4-((4-([1,2,4]triazolo[4,3-c]pyrimidin-7-yloxy)-3-methylphenyl)amino)quinazoline-6-yl)-2-cyanoacetamide: N-(3-methyl-4-([1,2,4]triazolo[4,3-c]pyrimidin-7-yloxo)phenyl)quinazoline-4,6-diamine (140 mg, 0.36 mmol), 2-cyanoacetic acid (42 mg, 0.49 mmol) and ethyl 2-ethoxy-2H-quinoline-1-carboxylate (140 mg, 0.57 mmol) were mixed in N,N-dimethylformamide (7 mL), the mixture was stirred at 100° C. for 16 hours, then evaporated under reduced pressure to give a crude product. The crude product was purified by preparative liquid chromatography to give 18.82 mg yellow solid with a yield of 11.5%. LC-MS: 451.9 [M+H] detection value. $^1$H-NMR (400 MHz, DMSO) δ 10.72 (s, 1H), 9.92 (s, 1H), 9.68 (s, 1H), 8.74 (s, 1H), 8.59 (s, 1H), 8.55 (s, 1H), 7.85-7.81 (m, 2H), 7.79 (d, 1H, J=4.0 Hz), 7.73 (dd, 1H, J=12.0, 4.0 Hz), 7.19 (d, 1H, J=8.0 Hz), 7.14 (s, 1H), 4.03 (s, 2H), 2.19 (s, 3H).

Embodiment 38

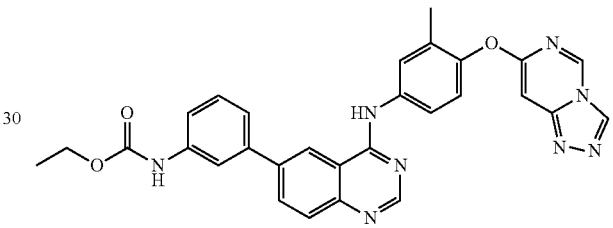

Synthesis of ethyl (3-(4-((4-([1,2,4]triazolo[4,3-c]pyrimidin-7-yloxy)-3-methylphenyl)amino)quinazoline-6-yl)phenyl)carbamate Step A: preparation of (3-((ethoxycarbonyl)amino)phenyl)boronic acid: 3-(aminophenyl)boronic acid (80 mg, 0.58 mmol), 2-fluoroacrylic acid (53 mg, 0.59 mmol) and ethyl 2-ethoxy-2H-quinoline-1-carboxylate (217 mg, 0.88 mmol) was dissolved in N,N-dimethylformamide (1 mL). The mixture was heated to 100° C. under argon atmosphere and stirred for 16 hours. Water (5 mL) was added to the reaction solution and the mixture was extracted with ethyl acetate (5 mL×3). The combined organic phases were washed with saturated brine (10 mL), dried over anhydrous sodium sulfate, filtered, and the filtrate was concentrated under reduced pressure to give a crude product, which was purified by silica gel column to give 100 mg orange oil which was a mixture of two compounds with similar molecular weight containing (3-((ethoxycarbonyl)amino)phenyl)boronic acid.

Step B: preparation of ethyl (3-(4-((4-([1,2,4]triazolo[4,3-c]pyrimidin-7-yloxy)-3-methylphenyl)amino)quinazoline-6-yl)phenyl)carbamate: the mixture containing (3-((ethoxycarbonyl)amino)phenyl)boronic acid (100 mg), 6-iodo-N-(3-methyl-4-([1,2,4]triazolo[4,3-c]pyrimidin-7-yloxy)phenyl)quinazolin-4-amine (178 mg, 0.36 mmol), [1,1'-bis(diphenylphosphino)ferrocene]dichloropalladium (2 mg, 0.0024 mmol) and DIEA (109 mg, 1.08 mmol) were mixed in 1,4-dioxane (5 mL). The mixture was stirred at reflux under an argon atmosphere for 16 hours, then filtrated, and the filtrate was evaporated under reduced pressure to give a crude product, which was purified by silica gel column and preparative liquid chromatography to give 4.85 mg yellow solid with a yield of 3.0%. LC-MS: 532.9 [M+H] detection value. $^1$H-NMR (400 MHz, CDCl$_3$) δ 10.01 (s, 1H), 9.78 (s, 1H), 9.68 (s, 1H), 8.82 (s, 1H), 8.63 (s, 1H), 8.59 (s, 1H), 8.09 (d, 1H, J=12.0 Hz), 7.94 (s, 1H), 7.90 (d, 1H, J=8.0 Hz), 7.83-7.81 (m, 2H), 7.52-7.46 (m, 3H), 7.22 (d, 1H, J=8.0 Hz), 7.14 (s, 1H), 4.17 (q, 2H, J=8.0 Hz), 2.21 (s, 3H), 1.26 (t, 3H, J=8.0 Hz).

Embodiment 39

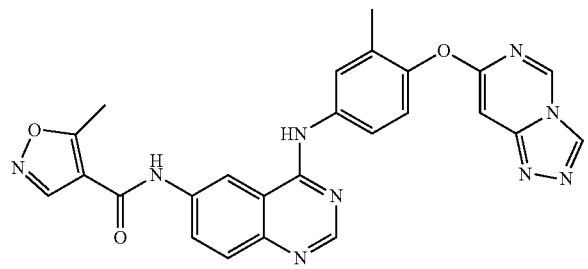 [SMILES: Cc1cc(Nc2ncnc3ccc(NC(=O)c4cnoc4C)cc23)ccc1Oc1cc2nncn2cn1]

Synthesis of N-(4-((4-([1,2,4]triazolo[4,3-c]pyrimidin-7-yloxy)-3-methylphenyl)amino)quinazoline-6-yl)-5-methylisoxazole-4-carboxamide According to the method of Embodiment 16, wherein 2-fluoroacrylic acid was replaced with 5-methylisoxazole-4-carboxylic acid and stirring was continued at 100° C. for 16 hours. LC-MS: 493.8 [M+H] detection value. $^1$H-NMR (400 MHz, DMSO) δ 12.728 (s, 1H), 11.35 (s, 1H), 9.69 (s, 1H), 8.84 (s, 1H), 8.61 (m, 3H), 7.78 (d, 1H, J=8.0 Hz), 7.69 (s, 1H), 7.62 (d, 1H, J=8.0 Hz), 7.29-7.25 (m, 2H), 2.23 (s, 3H), 2.09 (s, 3H).

Embodiment 40

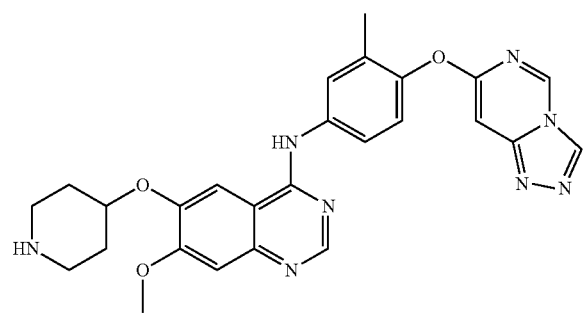 [SMILES: COc1cc2ncnc(Nc3ccc(Oc4cc5nncn5cn4)c(C)c3)c2cc1OC1CCNCC1]

Synthesis of N-(4-([1,2,4]triazolo[4,3-c]pyrimidin-7-yloxy)-3-methylphenyl)-7-methoxy-6-(piperidin-4-yloxy)quinazolin-4-amine Step A: preparation of 4-((4-([1,2,4]triazolo[4,3-c]pyrimidin-7-yloxy)-3-methylphenyl)amino)-7-methoxyquinazolin-6-yl acetate: 4-chloro-7-methoxyquinazolin-6-yl acetate (2000 mg, 7.92 mmol), 3-methyl-4-([1,2,4]triazolo[4,3-c]pyrimidin-7-yloxy)aniline (1668 mg, 15 mmol, 64%) and sodium carbonate (1470 mg, 13.87 mmol) were mixed in N,N-dimethylformamide (20 mL), the reaction solution was stirred at 80° C. for 16 hours, filtered, and the filtrate was concentrated under reduced pressure to give 3620 mg brownish black solid with a yield of 100%, which was used directly in the next step.

Step B: preparation of 4-((4-([1,2,4]triazolo[4,3-c]pyrimidin-7-yloxy)-3-methylphenyl)amino)-7-methoxyquinazoline-6-ol: 4-((4-([1,2,4]triazolo[4,3-c]pyrimidin-7-yloxy)-3-methylphenyl)amino)-7-methoxyquinazolin-6-yl acetate (3620 mg, 7.91 mmol) and potassium carbonate (2188 mg, 15.83 mmol) were suspended in methanol (80 mL) and the mixture was stirred at 8° C. for 3 hours, then filtered and the filtrate was concentrated under reduced pressure to give 1700 mg brownish black solid with a yield of 51.7%, which was used directly in the next step.

Step C: preparation of tert-butyl 4-((methylsulfonyl)oxy)piperidine-1-carboxylate: tert-butyl 4-hydroxypiperidine-1-carboxylate (1100 mg, 5.47 mmol) was dissolved in dichloromethane (13 mL), triethylamine (829 mg, 8.19 mmol) was added under an ice bath, then methanesulfonyl chloride (685 mg, 5.80 mmol) was added dropwise, and the mixture was slowly warmed to 8° C. and stirred for 1 hour. The reaction solution was washed once with water (10 mL), the organic phase was separated and washed once with saturated brine (10 mL), dried over anhydrous sodium sulfate, filtered, evaporated to dryness under reduced pressure to give 1138 mg pale yellow oil with a yield of 99.4%, which was used directly in the next step.

Step D: preparation of tert-butyl 4-(4-((4-([1,2,4]triazolo[4,3-c]pyrimidin-7-yloxy)-3-methylphenyl)amino)-7-methoxyquinazolin-6-yl)oxy)piperidine-1-carboxylate: tert-butyl 4-((methylsulfonyl)oxy)piperidine-1-carboxylate (1138 mg, 4.07 mmol), 4-((4-([1,2,4]triazolo[4,3-c]pyrimidin-7-yloxy)-3-methylphenyl)amino)-7-methoxyquinazoline-6-ol (700 mg, 1.69 mmol) and potassium carbonate (820 mg, 5.93 mmol) were mixed in N,N-dimethylformamide (10 mL), the mixture was stirred at 80° C. for 16 hours, then filtered, and the filtrate was concentrated under reduced pressure to give a crude product, which was purified by silica gel column to give 116 mg orange solid with a yield of 11.5%.

Step E: preparation of N-(4-([1,2,4]triazolo[4,3-c]pyrimidin-7-yloxy)-3-methylphenyl)-7-methoxy-6-(piperidin-4-yloxy)quinazolin-4-amine: tert-butyl 4-((4-((4-([1,2,4]triazolo[4,3-c]pyrimidin-7-yloxy)-3-methylphenyl)amino)-7-methoxyquinazolin-6-yl)oxy)piperidine-1-carboxylate (50 mg, 0.08 mmol) was dissolved in dichloromethane (2.7 mL), trifluoroacetic acid (0.3 mL) was added under an ice bath, and the reaction solution was stirred at 8° C. for 1.5 hours, then evaporated to dryness under reduced pressure to give a crude product, which was purified by acidic preparative HPLC (containing 0.1% formic acid) to give 13.34 mg yellow solid with a yield of 32.0%. LC-MS: 498.9 [M+H] detection value. $^1$H-NMR (400 MHz, CD$_3$OD) δ 9.46 (s, 1H), 8.52 (s, 1H), 8.45 (s, 1H), 8.00 (s, 1H), 7.72 (d, 1H, J=4.0 Hz), 7.67 (dd, 1H, J=8.0, 4.0 Hz), 7.24 (s, 1H), 7.21 (d, 1H, J=8.0 Hz), 6.95 (s, 1H), 4.05 (s, 3H), 3.54-3.48 (m, 2H), 3.29-3.28 (m, 2H), 2.30-2.18 (m, 8H).

Embodiment 41

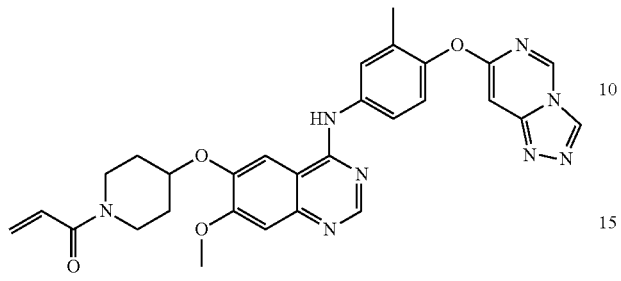

Synthesis of 1-(4-((4-((4-([1,2,4]triazolo[4,3-c]py-rimidin-7-yloxy)-3-methylphenyl)amino)-7-methoxyquinazolin-6-yl)oxy)piperidin-1-yl)pro-2-en-1-one According to the condensation method of Embodiment 23 and stirring was continued at 10° C. for 18 hours. LC-MS: 553.9 [M+H] detection value. $^1$H-NMR (400 MHz, DMSO) δ 9.68 (s, 1H), 9.49 (s, 1H), 8.59 (s, 1H), 8.48 (s, 1H), 8.14 (s, 1H), 7.99 (m, 1H), 7.72 (s, 1H), 7.24 (s, 1H), 7.20 (d, 1H, J=12.0 Hz), 7.11 (s, 1H), 6.86 (dd, 1H, J=16.0, 8.0 Hz), 6.13 (dd, 1H, J=20.0, 4.0 Hz), 5.70 (dd, 1H, J=12.0, 4.0 Hz), 4.83 (m, 1H), 3.96 (s, 3H), 3.87 (m, 2H), 3.50 (m, 2H), 2.20 (s, 3H), 2.05 (m, 2H), 1.72 (m, 2H).

Embodiment 42

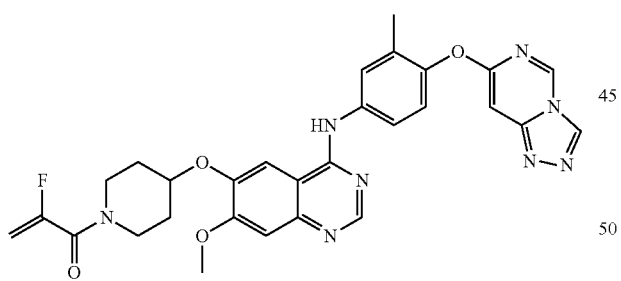

Synthesis of 1-(4-((4-((4-([1,2,4]triazolo[4,3-c]py-rimidin-7-yloxy)-3-methylphenyl)amino)-7-methoxyquinazolin-6-yl)oxy)piperidin-1-yl)-2-fluo-roprop-2-en-1-one According to the condensation method of Embodiment 23 and stirring was continued at 28° C. for 17 hours. LC-MS: 571.9 [M+H] detection value. $^1$H-NMR (400 MHz, DMSO) δ 10.68 (s, 1H), 9.69 (s, 1H), 8.80 (s, 1H), 8.61 (s, 1H), 8.12 (s, 1H), 7.64 (d, 1H, J=4.0 Hz), 7.59 (dd, 1H, J=8.0, 4.0 Hz), 7.30-7.27 (m, 2H), 7.21 (s, 1H), 5.29 (dd, 1H, J=8.0, 4.0 Hz), 5.24 (dd, 1H, J=64.0, 4.0 Hz), 4.88 (m, 1H), 4.02 (s, 3H), 3.79 (m, 2H), 3.56 (m, 2H), 2.23 (s, 3H), 2.11 (m, 2H), 1.82 (m, 2H).

Embodiment 43

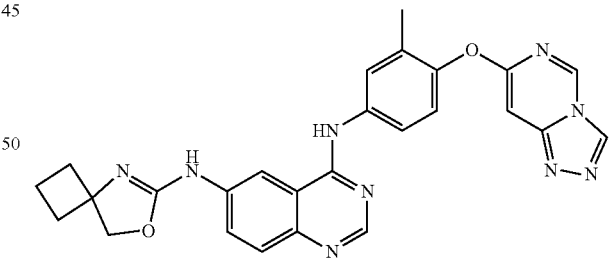

Preparation of $N^4$-(4-([1,2,4]triazolo[4,3-c]pyrimi-din-7-yloxy)-3-methylphenyl)-$N^6$-(5,5-difluoro-5,6-dihydro-4H-1,3-oxazin-2-yl)quinazoline-4,6-diamine According to the method of Embodiment 7, wherein (R)-2-amino-1-propanol was replaced with 3-amino-2,2-difluoropropyl-1-ol. LC-MS: 503.8 [M+H] detection value. $^1$H-NMR (400 MHz, CD$_3$OD) b 9.47 (s, 1H), 8.50-8.44 (m, 3H), 7.81-7.68 (m, 411), 7.22 (dd, 1H, J=8.0, 4.0 Hz), 6.96 (dd, 1H, J=8.0, 4.0 Hz), 4.42 (t, 2H, J=12.0 Hz), 3.84 (t, 2H, J=12.0 Hz), 2.28 (s, 3H).

Embodiment 44

$N^4$-(4-([1,2,4]triazolo[4,3-c]pyrimidin-7-yloxy)-3-meth-ylphenyl)-$N^6$-(7-oxa-5-azaspiro[3.4]oct-5-en-6-yl)quinazo-line-4,6-diamine According to the method of Embodiment 7, wherein (R)-2-amino-1-propanol was replaced with (1-aminocy-clobutyl)methanol hydrochloride. LC-MS: 494.2 [M+H] detection value. $^1$H-NMR (400 MHz, DMSO) δ 9.66 (s, 2H), 8.58 (s, 1H), 8.48 (s, 1H), 8.04 (br, s, 1H), 7.83 (s, 1H), 7.80 (d, 1H, J=12.0 Hz), 7.68 (d, 1H, J=8.0 Hz), 7.18 (d, 1H, J=8 Hz), 7.11 (s, 1H), 4.43 (s, 2H), 2.31-2.29 (m, 2H), 2.18-2.15 (m, 5H), 1.64 (m, 2H).

Embodiment 45

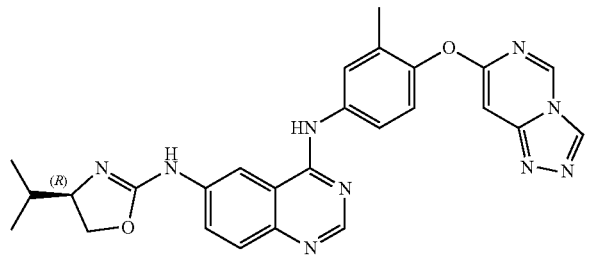

Synthesis of (R)—N$^4$-(4-([1,2,4]triazolo[4,3-c]pyrimidin-7-yloxy)-3-methylphenyl)-N$^6$-(4-isopropyl-4,5-dihydrooxazol-2-yl)quinazoline-4,6-diamine According to the method of Embodiment 7, wherein (R)-2-amino-1-propanol was replaced with (2R)-2-amino-3-methylbutyl-1-ol. LC-MS: 496.2 [M+H] detection value. $^1$H-NMR (400 MHz, DMSO) δ 9.67 (s, 1H), 9.57 (s, 1H), 8.59 (s, 1H), 8.48 (s, 1H), 8.05 (br, s, 1H), 7.84 (s, 1H), 7.80 (d, 1H, J=8.0 Hz), 7.67 (d, 1H, J=8.0 Hz), 7.18 (d, 1H, J=12.0 Hz), 7.12 (d, 1H, J=8.0 Hz), 4.43 (t, 1H, J=8.0 Hz), 4.13 (t, 1H, J=8.0 Hz), 2.19 (s, 3H), 1.75-1.67 (m, 1H), 0.95 (d, 3H, J=4.0 Hz), 0.89 (d, 3H, J=4.0 Hz).

Embodiment 46

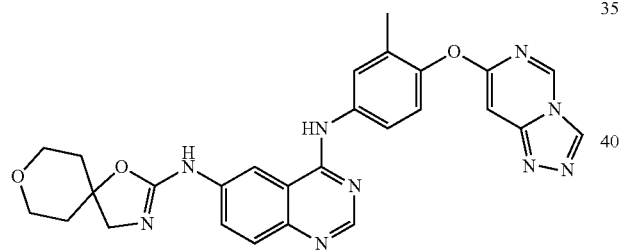

Synthesis of N$^4$-(4-([1,2,4]triazolo[4,3-c]pyrimidin-7-yloxy)-3-methylphenyl)-N$^6$-(1,8-dioxa-3-azaspiro[4.5]dec-2-en-2-yl)quinazoline-4,6-diamine Step A: preparation of 4-(aminomethyl)tetrahydropyran-4-ol: 2,6-dioxaspiro[2.5]octane (190 mg, 1.70 mmol) was dissolved in methanol (3.5 mL), the mixture was cooled to 0° C., concentrated aqueous ammonia (4.3 mL) was added dropwise, the reaction solution was warmed to 28° C. and stirred for 16 hours, then evaporated under reduced pressure to give 218 mg crude product as a yellow oil, which was used directly in the next step.

According to the method of Embodiment 7, wherein (R)-2-amino-1-propanol was replaced with 4-(aminomethyl)tetrahydropyran-4-ol. LC-MS: 524.2 [M+H] detection value. $^1$H-NMR (400 MHz, DMSO) δ 9.66-9.64 (m, 2H), 8.58 (s, 1H), 8.48 (s, 1H), 7.82 (s, 1H), 7.78 (d, 1H, J=8.0 Hz), 7.70-7.68 (m, 2H), 7.17 (d, 1H, J=8.0 Hz), 7.10 (s, 1H), 3.69 (t, 4H, J=12.0 Hz), 3.51 (s, 2H), 2.18 (s, 3H), 1.84 (t, 4H, J=4.0 Hz).

Embodiment 47

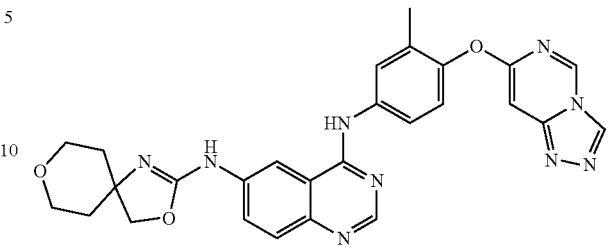

Synthesis of N$^4$-(4-([1,2,4]triazolo[4,3-c]pyrimidin-7-yloxy)-3-methylphenyl)-N$^6$-(3,8-dioxa-1-azaspiro[4.5]dec-1-en-2-yl)quinazoline-4,6-diamine Step A: preparation of (4-aminotetrahydropyran-4-yl)methanol: 4-aminotetrahydropyran-4-carboxylic acid (200 mg, 1.38 mmol) was suspended in tetrahydrofuran (2 mL), the mixture was cooled to 0° C., a borane-tetrahydrofuran solution (2.8 mL, 0.69 mmol) was added dropwise, and the reaction solution was warmed to 28° C. and stirred for 16 hours. Methanol (5 mL) was added to the reaction solution, and the solvent was evaporated under reduced pressure, the operation was repeated for 3 times. 187 mg crude brown oil was obtained and used directly in the next step.

According to the method of Embodiment 7, wherein (R)-2-amino-1-propanol was replaced with (4-aminotetrahydropyran-4-yl)methanol. LC-MS: 524.2 [M+H] detection value. $^1$H-NMR (400 MHz, DMSO) δ 9.67 (s, 1H), 9.57 (s, 1H), 8.59 (s, 1H), 8.49 (s, 1H), 8.17 (br, s, 1H), 7.83 (m, 2H), 7.78 (d, 1H, J=4.0 Hz), 7.69 (d, 1H, J=8.0 Hz), 7.18 (d, 1H, J=8.0 Hz), 7.12 (s, 1H), 4.20 (m, 2H), 3.83 (t, 2H, J=8.0 Hz), 3.52 (t, 2H, J=8.0 Hz), 2.19 (s, 3H), 1.71 (t, 4H, J=4.0 Hz).

Embodiment 48

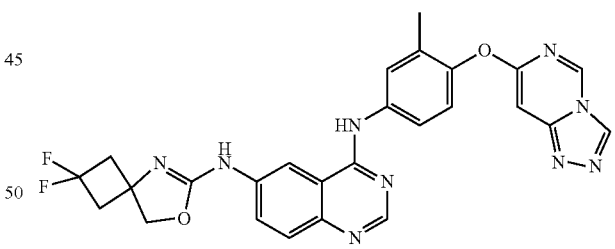

Synthesis of N$^4$-(4-([1,2,4]triazolo[4,3-c]pyrimidin-7-yloxy)-3-methylphenyl)-N$^6$-(2,2-difluoro-7-oxa-5-azaspiro[3.4]oct-5-en-6-yl)quinazoline-4,6-diamine Step A: preparation of ethyl 1-((tert-butoxycarbonyl)amino)-3,3-difluorocyclobutyl-1-carboxylate: ethyl 1-((tert-butoxycarbonyl)amino)-3-oxo-cyclobutylformate (500 mg, 1.94 mmol) was dissolved in dichloromethane (8 mL), DUST (1.6 g, 9.9 mmol) was added dropwise under a nitrogen atmosphere. The reaction solution was stirred at 28° C. for 16 hours, then cooled with an ice bath and neutralized to a pH of 8-9 with an aqueous sodium bicarbonate solution. The organic phase was separated and the aqueous phase was extracted with dichloromethane (10 mL). The organic phases were combined, dried over anhydrous sodium sulfate, filtered and the filtrate was evaporated to dryness under reduced pressure to give 560 mg crude product as a brown oil which was used directly in the next step.

Step B: preparation of tert-butyl (3,3-difluoro-1-(hydroxymethyl)cyclobutyl)carbamate: ethyl 1-((tert-butoxycarbonyl)amino)-3,3-difluorocyclobutyl-1-carboxylate (560 mg, 2.01 mmol) was suspended in ethanol (5 mL), sodium borohydride (379 mg, 10.02 mmol) was added. The reaction solution was stirred at reflux for 16 hours, then evaporated to dryness under reduced pressure to give a crude product. Water (10 mL) and ethyl acetate (10 mL) was added to the crude product. The organic phase was separated and the aqueous phase was further extracted with ethyl acetate (10 mL). The organic phases were combined, dried over anhydrous sodium sulfate, filtered and the filtrate was evaporated to dryness under reduced pressure to give 332 mg crude product as a yellow oil, which was used directly in the next step.

Step C: preparation of (1-amino-3,3-difluorocyclobutyl) methanol trifluoroacetate: tert-butyl (3,3-difluoro-1-(hydroxymethyl)cyclobutyl)carbamate (232 mg, 0.98 mmol) was dissolved in a mixed solvent of trifluoroacetic acid (0.3 mL) and dichloromethane (2.7 mL), the reaction solution was stirred at 28° C. for 4 hours, then evaporated to dryness under reduced pressure to give a crude product. Dichloromethane (10 mL) was added to the crude product, and the solvent was evaporated under reduced pressure to give 350 mg crude product as an orange oil which was a trifluoroacetate salt and used directly in the next step.

Step D: preparation of 1-(3-cyano-4-((E)-dimethylaminomethyleneamino)phenyl)-3-(3,3-difluoro-1-(hydroxymethyl)cyclobutyl)thiourea: thiocarbonyl diimidazole (171 mg, 0.96 mmol) was suspended in tetrahydrofuran (5 mL), the mixture was cooled to −5° C., and N'-(4-amino-2-cyanophenyl)-N,N-dimethylformamidine (156 mg, 0.83 mmol) was added, the reaction solution was stirred at −5 to 0° C. for 30 minutes. DIEA (180 mg, 1.39 mmol) was added to a solution of (4-aminotetrahydropyran-4-yl)methanol trifluoroacetate (190 mg, 1.39 mmol) in tetrahydrofuran (1 mL), the mixture was added to the above reaction solution. The final reaction solution was warmed to 28° C. and stirred for 16 hours, then evaporated under reduced pressure to give a crude product, which was purified by silica gel column to give 140 mg yellow solid with a yield of 46%.

Step E: preparation of (E)-N'-(2-cyano-4-((2,2-difluoro-7-oxa-5-azaspiro[3.4]oct-5-en-6-yl)aminophenyl)-N,N-dimethylformamidine: 1-(3-cyano-4-((E)-dimethylaminomethyleneamino)phenyl)-3-(3,3-difluoro-1-(hydroxymethyl)cyclobutyl)thiourea (115 mg, 0.31 mmol) was dissolved in tetrahydrofuran (3 mL), a solution of sodium hydroxide (31.2 mg, 0.78 mmol) in water (0.78 mL) and p-toluenesulfonyl chloride (67 mg, 0.35 mmol) were added. The mixture was stirred at 28° C. for 2 hours, then washed with saturated brine (10 mL), the organic phase was separated and washed with aqueous sodium hydroxide solution (10 mL, 1N). The aqueous phase was extracted with ethyl acetate (20 mL). The organic phases were combined, dried over anhydrous sodium sulfate, filtered, and evaporated to dryness under reduced pressure to give 127 mg crude product as a yellow oil which was used directly in the next step.

Step F: preparation of N⁴-(4-([1,2,4]triazolo[4,3-c]pyrimidin-7-yloxy)-3-methylphenyl)-N⁶-(2,2-difluoro-7-oxa-5-azaspiro[3.4]oct-5-en-6-yl)quinazolin-4,6-diamine: (E)-N'-(2-cyano-4-((2,2-difluoro-7-oxa-5-azaspiro[3.4]oct-5-en-6-yl)aminophenyl)-N,N-dimethylformamidine (127 mg, 0.38 mmol) was dissolved in isopropyl acetate (2 mL), 3-methyl-4-([1,2,4]triazolo[1,4,c]pyrimidin-7-oxy)aniline (91 mg, 0.38 mmol) and glacial acetic acid (0.2 mL) were added, the mixture was stirred at 28° C. for 32 hours, then evaporated to dryness under reduced pressure to give a crude product, which was purified by silica gel column to give 51.34 mg yellow solid with a yield of 25.5%. LC-MS: 530.2 [M+H] detection value. ¹H-NMR (400 MHz, DMSO) (59.67-9.66 (m, 1H), 8.58 (s, 1H), 8.50 (s, 1H), 8.27 (br, s, 1H), 7.91 (br, s, 1H), 7.81 (s, 1H), 7.76-7.72 (m, 2H), 7.19 (d, 1H, J=12.0 Hz), 7.12 (s, 1H), 4.48 (s, 2H), 3.03-2.88 (m, 4H), 2.19 (s, 3H).

Embodiment 49

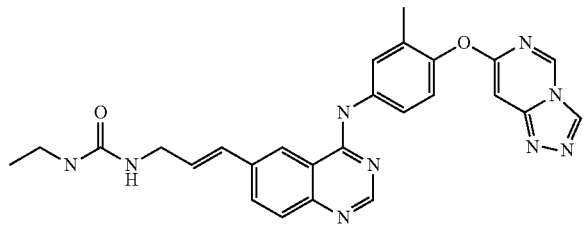 [SMILES: CCNC(=O)NC/C=C/c1ccc2ncnc(Nc3ccc(Oc4cc5nncn5cn4)c(C)c3)c2c1]

Synthesis of (E)-1-(3-(4-((4-([1,2,4]triazolo[4,3-c]pyrimidin-7-yloxy)-3-methylphenyl)amino)quinazolin-6-yl)allyl)-3-ethylurea Step A: preparation of (E)-1-(3-(4-((4-([1,2,4]triazolo[4,3-c]pyrimidin-7-yloxy)-3-methylphenyl)amino)quinazolin-6-yl)allyl)-3-ethylurea: the crude product of 6-((E)-3-aminopropyl-1-enyl)-N-(3-methyl-4-([1,2,4]triazolo[4,3-c]pyrimidin-(7-yloxy)phenyl)quinazolin-4-amine trifluoroacetate (180 mg, 0.42 mmol) was dissolved in a mixed solvent of dichloromethane (1.8 mL) and N,N-dimethylformamide (0.3 mL) ethylisocyanate (45 mg, 0.64 mmol) was added, and the mixture was stirred at 24° C. for 16 hours. Ethyl isocyanate (100 mg) was added to the reaction solution, the resulting mixture was stirred at 24° C. for another 5 hours. The reaction solution was evaporated to dryness under reduced pressure to give a crude product, which was purified by silica gel column and preparative liquid phase to give 12.24 mg white solid with a yield of 5.8%. LC-MS: 496.3 [M+H] detection value. ¹H-NMR (400 MHz, DMSO) δ 9.86 (s, 1H), 9.68 (s, 1H), 8.59 (s, 1H), 8.57 (s, 1H), 8.55 (s, 1H), 7.97 (d, 1H, J=8.0 Hz), 7.81-7.78 (m, 2H), 7.74 (d, 1H, J=8.0 Hz), 7.21 (d, 1H, J=8.0 Hz), 7.14 (s, 1H), 6.67-6.63 (m, 1H), 6.58-6.53 (m, 1H), 6.16 (d, 1H, J=4.0 Hz), 5.93 (d, 1H, J=4.0 Hz), 3.90 (t, 2H, J=8.0 Hz), 3.06 (m, 2H), 2.20 (s, 3H), 1.03 (t, 3H, J=4.0 Hz).

Embodiment 50

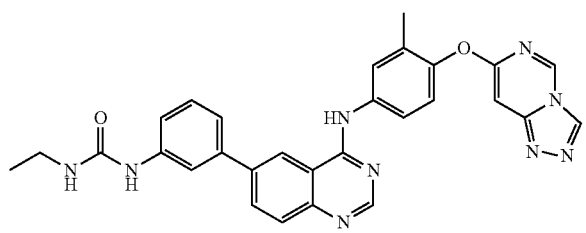 [SMILES: CCNC(=O)Nc1cccc(-c2ccc3ncnc(Nc4ccc(Oc5cc6nncn6cn5)c(C)c4)c3c2)c1]

Synthesis of 1-(3-(4-((4-([1,2,4]triazolo[4,3-c]pyrimidin-7-yloxy)-3-methylphenyl)amino)quinazolin-6-yl)phenyl)-3-ethylurea Step A: preparation of (3-(ethylcarbamoylamino)phenyl) boronic acid: 3-aminophenylboronic acid (100 mg, 0.73 mmol) was dissolved in tetrahydrofuran (1 mL), ethyl isocyanate (52 mg, 0.73 mmol) was slowly added, and the mixture was stirred at 14° C. for 16 hours to generate a precipitate, which was collected by filtration to give 81 mg white solid which was used directly in the next step.

Step B: preparation of 1-(3-(4-((4-([1,2,4]triazolo[4,3-c]pyrimidin-7-yloxy)-3-methylphenyl)amino)quinazolin-6-yl)phenyl)-3-ethylurea: according to the method of Embodiment 34, wherein (3-(2-methoxyacetylamino)phenyl) boronic acid was replaced with (3-(ethylcarbamoylamino)phenyl)boronic acid, which was dissolved in N,N-dimethyl formamide (2 mL) and stirred under argon atmosphere at 100° C. for 16 hours. LC-MS: 532.3 [M+H] detection value. $^1$H-NMR (400 MHz, DMSO) δ 10.01 (s, 1H), 9.68 (s, 1H), 8.81 (s, 1H), 8.62-8.59 (m, 3H), 8.10 (d, 1H, J=8.0 Hz), 7.89-7.88 (m, 2H), 7.83-7.81 (m, 2H), 7.57 (m, 1H), 7.42 (m, 2H), 7.22 (d, 1H, J=12.0 Hz), 7.13 (s, 1H), 6.21 (m, 1H), 3.16-3.13 (m, 2H), 2.21 (s, 3H), 1.08 (t, 3H, J=8.0 Hz).

Embodiment 51

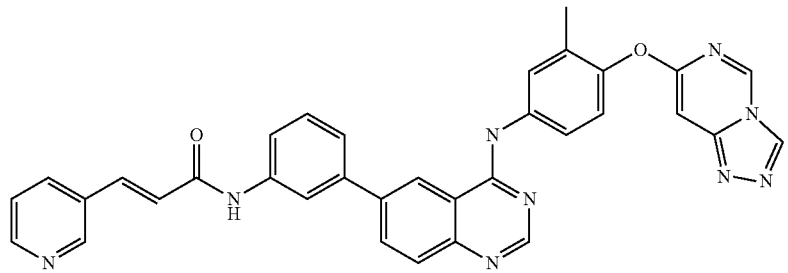 [SMILES: Cc1cc(Nc2ncnc3ccc(-c4cccc(NC(=O)/C=C/c5cccnc5)c4)cc23)ccc1Oc1cc2nncn2cn1]

Synthesis of (E)-N-(3-(4-((4-([1,2,4]triazolo[4,3-c]pyrimidin-7-yloxy)-3-methylphenyl)amino)quinazolin-6-yl)phenyl)-3-(pyridin-3-yl)acryiamide Step A: preparation of (E)-N-(3-(4-((4-([1,2,4]triazolo[4,3-c]pyrimidin-7-yloxy)-3-methylphenyl)amino)quinazolin-6-yl)phenyl)-3-(pyridin-3-yl)acrylamide: N-(4-([1,2,4]triazolo[4,3-c]pyrimidin-7-yloxy)-3-methylphenyl)-6-(3-aminophenyl)quinazolin-4-amine (80 mg, 0.21 mmol), (E)-3-(pyridin-3-yl)acrylic acid (52 mg, 0.35 mmol) and EDCI (83 mg, 0.43 mmol) were mixed in pyridine (1 mL), the mixture was heated to 50° C. and stirred for 16 hours. The reaction solution was concentrated under reduced pressure to give a crude product which was slurried with dichloromethane and methanol (1:1, 10 mL) and stirred for 3 hours. A precipitate generated, which was filtered, and the filter cake was washed with methanol to give 56.32 mg pale yellow solid with a yield of 52.5%. LC-MS: 592.3 [M+H] detection value. $^1$H-NMR (400 MHz, DMSO) δ 10.48 (s, 1H), 10.02 (s, 1H), 9.68 (s, 1H), 8.85 (s, 2H), 8.64 (s, 1H), 8.61 (d, 1H, J=4.0 Hz), 8.59 (s, 1H), 8.17 (s, 1H), 8.14 (d, 1H, J=8.0 Hz), 8.08 (dd, 1H, J=8.0, 4.0 Hz), 7.92 (d, 1H, J=8.0 Hz), 7.83 (s, 1H), 7.81 (m, 1H), 7.78 (s, 1H), 7.68 (d, 1H, J=16.0 Hz), 7.62 (d, 1H, J=8.0 Hz), 7.57 (d, 1H, J=8.0 Hz), 7.51 (dd, 1H, J=8.0, 4.0 Hz), 7.22 (d, 1H, J=8.0 Hz), 7.01 (s, 1H), 6.99 (d, 1H, J=16.0 Hz), 2.21 (s, 3H).

Embodiment 52

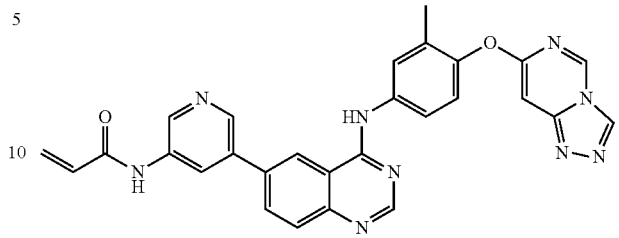

Synthesis of N-(5-(4-((4-([1,2,4]triazolo[4,3-c]pyrimidin-7-yloxy)-3-methylphenyl)amino)quinazolin-6-yl)pyridin-3-yl)acrylamide Step A: preparation of 2-amino-5-(4,4,5,5-tetramethyl-1,3,2-dioxaborol-2-yl)benzonitrile: 2-amino-5-bromobenzonitrile (1000 mg, 5.08 mmol), 4,4,4',4',5,5,5',5'-octamethyl-2,2'-bis(1,3,2-dioxaborolane) (1930 mg, 7.60 mmol), potassium acetate (1490 mg, 15.18 mmol) and [1,1'-bis(diphenylphosphino)ferrocene]dichloropalladium (21 mg) were mixed in 1,4-dioxane (15 mL), the reaction solution was stirred at 80° C. under argon atmosphere for 16 hours, then filtered, and the filtrate was evaporated under reduced pressure to give a crude product. Ethyl acetate (10 mL) and saturated brine (10 mL) were added to the crude product. The organic phase was separated, dried over anhydrous sodium sulfate, filtered, and the filtrate was concentrated under reduced pressure to give a crude product which was purified by silica gel column to give 1400 mg white solid with a yield of 100%.

Step B: preparation of (E)-N-(2-cyano-4-(4,4,5,5-tetramethyl-1,3,2-dioxaborol-2-yl)phenyl)-N,N-dimethylformamidine: 2-amino-5-(4,4,5,5-tetramethyl-1,3,2-dioxaborolin-2-yl)benzonitrile (1400 mg, 5.74 mmol) was mixed in DMF-DMA (14 mL), the reaction solution was heated to 80° C. and stirred for 3 hours. The reaction solution was evaporated under reduced pressure to give a crude product which was purified by silica gel column to give 1220 mg yellow oil with a yield of 71.1%. $^1$H-NMR (CDCl$_3$) δ 8.02 (d, 1H, J=4.0 Hz), 7.84 (dd, 1H, J=8.0, 4.0 Hz), 7.64 (s, 1H), 6.95 (d, 1H, J=8.0 Hz), 3.12 (d, 6H, J=12.0 Hz), 1.36-1.26 (m, 12H).

Step C: preparation of (E)-N'-(4-(5-aminopyridin-3-yl)-2-cyanophenyl)-N,N-dimethylformamidine: (E)-N-(2-cyano-4-(4,4,5,5-tetramethyl-1,3,2-dioxaborol-2-yl)phenyl)-N,N-dimethylformamidine (260 mg, 0.87 mmol), 5-bromopyridin-3-amine (130 mg, 0.75 mmol), sodium carbonate (260 mg, 2.45 mmol) and [1,1'-bis(diphenylphosphino)ferrocene]dichloropalladium (26 mg) were mixed in a mixed solvent of 1,4-dioxane (2.4 mL) and water (0.8 mL), and the reaction solution was stirred at 90° C. under argon atmosphere for 16 hours, then filtered, and the filtrate was evaporated under reduced pressure to give a crude product, which was purified by silica gel column to give 140 mg yellow solid with a yield of 75.9%.

Step D: preparation of (E)-N-(5-(3-cyano-4-(((dimethylamino)methylene)amino)phenyl)pyridin-3-yl)acrylamide: (E)-N-(4-(5-aminopyridin-3-yl)-2-cyanophenyl)-N,N-dimethylformamidine (100 mg, 0.38 mmol), acrylic acid (135 mg, 1.87 mmol) and EDCI (180 mg, 0.94 mmol) were dissolved in pyridine (1 mL) and the reaction solution was stirred at 60° C. for 16 hours, then evaporated under reduced pressure to give a crude product, which was purified by silica gel column to give 91 mg yellow oil with a yield of 75.6%.

Step E: preparation of N-(5-(4-((4-([1,2,4]triazolo[4,3-c]pyrimidin-7-yloxy)-3-methylphenyl)amino)quinazolin-6-yl)pyridin-3-yl)acrylamide: (E)-N-(5-(3-cyano-4-(((dimethylamino)methylene)amino)phenyl)pyridin-3-yl)acrylamide (91 mg, 0.28 mmol), 3-methyl-4([1,2,4]triazolo[1,4,c]pyrimidin-7-oxy)aniline (69 mg, 0.27 mmol) and glacial acetic acid (0.5 mL) were mixed in isopropyl acetate (2 mL), the mixture was stirred at 30° C. for 24 hours. A precipitate generated, which was filtered and collected. The precipitate was dissolved in DMSO, filtered, and the filtrate was purified by preparative liquid chromatography to give 4.76 mg pale brown solid with a yield of 3.2%. LC-MS: 516.2 [M+H] detection value. $^1$H-NMR (400 MHz, DMSO) δ 10.64 (s, 1H), 10.05 (s, 1H), 9.67 (s, 1H), 8.93 (s, 1H), 8.87-8.85 (m, 2H), 8.64 (s, 1H), 8.58 (m, 2H), 8.18 (d, 1H, J=8.0 Hz), 7.93 (d, 1H, J=8.0 Hz), 7.82 (m, 2H), 7.22 (d, 1H, J=8.0 Hz), 7.13 (s, 1H), 6.51 (dd, 1H, J=16.0, 8.0 Hz), 6.35 (d, 1H, J=16.0 Hz), 5.86 (d, 1H, J=8.0 Hz), 2.21 (s, 3H).

Embodiment 53

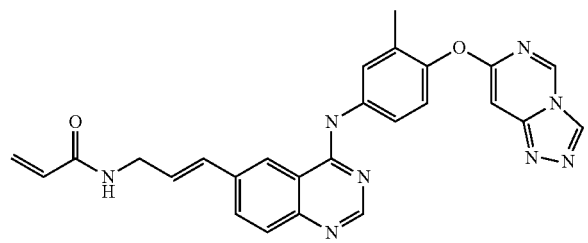 [SMILES: C=CC(=O)NC/C=C/c1ccc2ncnc(Nc3ccc(Oc4cc5nncn5cn4)c(C)c3)c2c1]

Preparation of (E)-N-(3-(4-((4-([1,2,4]triazolo[4,3-c]pyrimidin-7-yloxy)-3-methylphenyl)amino)quinazolin-6-yl)allyl)acrylamide According to the condensation method of Embodiment 23, stirred at 12° C. for 16 hours. LC-MS: 479.3 [M+H] detection value. $^1$H-NMR (400 MHz, DMSO) δ 9.84 (s, 1H), 9.66 (s, 1H), 8.58-8.55 (m, 3H), 8.49 (s, 1H), 7.99 (d, 1H, J=4.0 Hz), 7.80-7.78 (m, 2H), 7.74 (d, 1H, J=4.0 Hz), 7.20 (d, 1H, J=8.0 Hz), 7.12 (s, 1H), 6.88 (d, 1H, J=12.0 Hz), 6.57-6.54 (m, 1H), 6.32 (dd, 1H, J=12.0, 8.0 Hz), 6.17 (d, 1H, J=16.0 Hz), 5.65 (d, 1H, J=8.0 Hz), 4.05 (s, 2H), 2.19 (s, 3H).

Embodiment 54

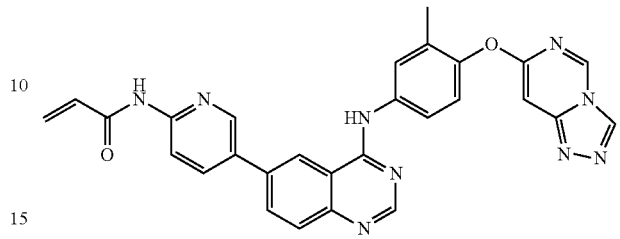

Synthesis of N-(5-(4-((4-([1,2,4]triazolo[4,3-c]pyrimidin-7-yloxy)-3-methylphenyl)amino)quinazolin-6-yl)pyridin-2-yl)acrylamide Step A: preparation of N-(5-bromopyridin-2-yl)acrylamide: 5-bromopyridin-2-amine (200 mg, 1.16 mmol), acrylic acid (208 mg, 2.89 mmol), and EDCI (554 mg, 2.89 mmol) were mixed in pyridine (2 mL), the reaction solution was heated to 50° C. and stirred for 16 hours, then evaporated under reduced pressure to give a crude product, which was purified by silica gel column to give 118 mg white solid with a yield of 45%.

Step B: preparation of (E)-N-(5-(3-cyano-4-(((dimethylamino)methylene)amino)phenyl)pyridin-2-yl)acrylamide: (E)-N'-(2-cyano-4-(4,4,5,5-tetramethyl-1,3,2-dioxaborol-2-yl)phenyl)-N,N-dimethylformamidine (200 mg, 0.67 mmol), N-(5-bromopyridin-2-yl)acrylamide (138 mg, 0.61 mmol), sodium carbonate (193 mg, 1.82 mmol) and [1,1'-bis(diphenylphosphino)ferrocene]dichloropalladium (25 mg) were mixed in a mixed solvent of 1,4-dioxane (3 mL) and water (1 mL). The reaction solution was stirred at 90° C. under argon atmosphere for 20 hours, then filtered through celite and the filtrate was evaporated to dryness under reduced pressure to give a crude product, which was purified by silica gel column to give 54 mg yellow solid with a yield of 27.8%.

Step C: Preparation of N-(5-(4-((4-([1,2,4]triazolo[4,3-c]pyrimidin-7-yloxy)-3-methylphenyl)amino)quinazolin-6-yl)pyridin-2-yl)acrylamide: (E)-N-(5-(3-cyano-4-(((dimethylamino)methylene)amino)phenyl)pyridin-2-yl)acrylamide (54 mg, 0.17 mmol), 3-methyl-4-([1,2,4]triazolo[1,4,c]pyrimidin-7-oxy)aniline (41 mg, 0.17 mmol) and glacial acetic acid (0.3 mL) were mixed in isopropyl acetate (1 mL), the mixture was stirred at 25° C. for 16 hours. A precipitate generated, which was filtered, and collected. The precipitate was dissolved in DMSO, filtered, the filtrate was purified by preparative liquid chromatography and silica gel column to give 15.07 mg yellow solid with a yield of 17.3%. LC-MS: 516.2 [M+H] detection value. $^1$H NMR (400 MHz, DMSO) δ 10.93 (s, 1H), 9.97 (s, 1H), 9.68 (s, 1H), 8.94 (s, 1H), 8.92 (s, 1H), 8.63 (s, 1H), 8.59 (s, 1H), 8.38 (m, 2H), 8.28 (d, J=8.8 Hz, 1H), 7.90 (d, J=8.4 Hz, 1H), 7.83-7.81 (m, 2H), 7.24 (d, J=9.2 Hz, 1H), 7.14 (s, 1H), 6.71-6.65 (dd, J=17.2, 10.4 Hz, 1H), 6.37 (dd, J=17.2, 1.6 Hz, 1H), 5.84 (dd, J=10.0, 1.6 Hz, 1H), 2.22 (s, 3H).

Embodiment 55

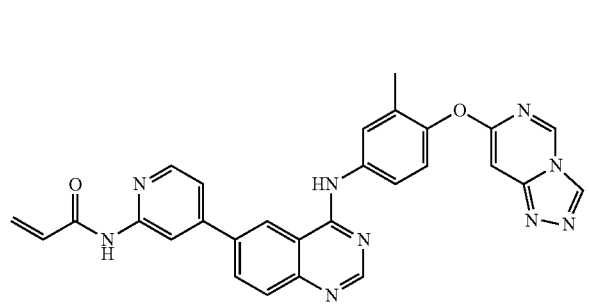

Synthesis of N-(4-(4-((4-([1,2,4]triazolo[4,3-c]pyrimidin-7-yloxy)-3-methylphenyl)amino)quinazolin-6-yl)pyridin-2-yl)acrylamide According to the method of Embodiment 54, wherein 5-bromopyridin-2-amine was replaced with 4-bromopyridin-2-amine. LC-MS: 516.2 [M+H] detection value. $^1$H NMR (400 MHz, DMSO) δ 10.90 (s, 1H), 10.13 (s, 1H), 9.68 (s, 1H), 8.97 (s, 1H), 8.68 (s, 1H), 8.66 (s, 1H), 8.59 (s, 1H), 8.53 (d, J=5.2 Hz, 1H), 8.22 (d, J=8.2 Hz, 1H), 7.96 (d, J=8.4 Hz, 1H), 7.80-7.79 (m, 2H), 7.67 (dd, J=5.2, 1.2 Hz, 1H), 7.24 (d, J=8.4 Hz, 1H), 7.15 (s, 1H), 6.68 (dd, J=17.2, 10.4 Hz, 1H), 6.38 (dd, J=16.8, 1.2 Hz, 1H), 5.85 (dd, J=10.4, 1.6 Hz, 1H), 2.22 (s, 3H).

Embodiment 56

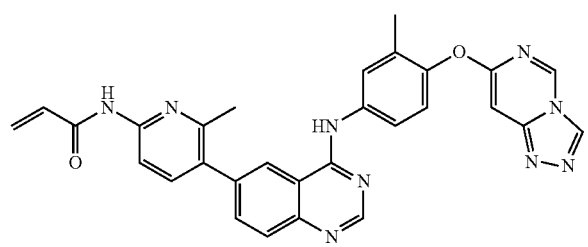 [SMILES: C=CC(=O)Nc1ccc(-c2ccc3ncnc(Nc4ccc(Oc5cc6nncn6cn5)c(C)c4)c3c2)c(C)n1]

Synthesis of N-(5-(4-((4-([1,2,4]triazolo[4,3-c]pyrimidin-7-yloxy)-3-methylphenyl)amino)quinazolin-6-yl)-6-methylpyridin-2-yl)acrylamide According to the method of Embodiment 54, wherein 5-bromopyridin-2-amine was replaced with 5-bromo-6-methylpyridin-2-amine. LC-MS: 530.3 [M+H] detection value. $^1$H NMR (400 MHz, DMSO) δ 10.85 (s, 1H), 9.87 (s, 1H), 9.67 (s, 1H), 8.66 (s, 1H), 8.63 (s, 1H), 8.59 (s, 1H), 8.22 (d, J=8.0 Hz, 1H), 7.95 (d, J=8.0 Hz, 1H), 7.89 (d, J=8.8 Hz, 1H), 7.86-7.83 (m, 3H), 7.22 (d, J=8.4 Hz, 1H), 7.13 (s, 1H), 6.68 (dd, J=16.8, 10.4 Hz, 1H), 6.36 (d, J=17.2 Hz, 1H), 5.82 (d, J=10.0 Hz, 1H), 2.53 (s, 3H), 2.21 (s, 3H).

Embodiment 57

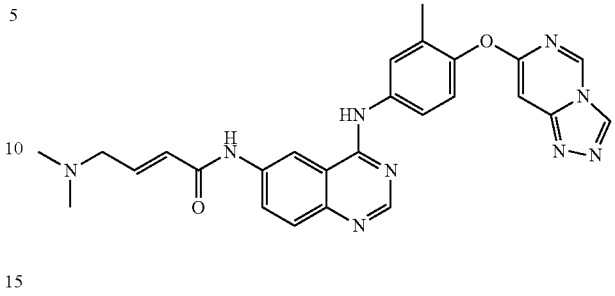

Synthesis of (E)-N-(4-((4-([1,2,4]triazolo[4,3-c]pyrimidin-7-yloxy)-3-methylphenyl)amino)quinazolin-6-yl)-4-(dimethylamino)-2-butenamide According to the method of Embodiment 16, wherein 2-fluoroacrylic acid was replaced with N,N-dimethyl-2-butenoic acid, stirred under argon atmosphere at room temperature for 38 hours. LC-MS: 495.9 [M+H] detection value. $^1$H-NMR (400 MHz, CD$_3$OD) δ 9.42 (s, 1H), 8.79 (s, 1H), 8.53 (s, 1H), 8.40 (s, 1H), 7.81-7.71 (m, 4H), 7.19 (d, 1H, J=8.0 Hz), 6.99-6.94 (m, 2H), 6.53 (d, 1H, J=16.0 Hz), 3.70 (d, 2H, J=8.0 Hz), 2.70 (s, 6H), 2.28 (s, 3H).

Embodiment 58

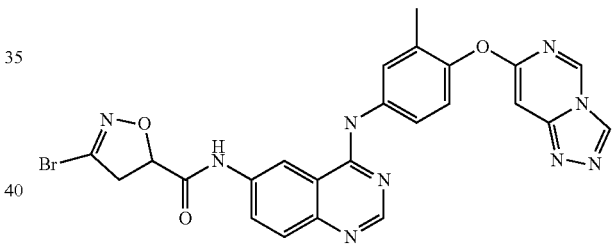

Synthesis of N-(4-((4-([1,2,4]triazolo[4,3-c]pyrimidin-7-yloxy)-3-methylphenyl)amino)quinazolin-6-yl)-3-bromo-4,5-dihydroisoxazol-5-carboxamide Step A: preparation of N-(3-cyano-4-((E)-dimethylaminomethyleneamino)phenyl)propyl-2-enamide: N'-(4-amino-2-cyano)phenyl)-N,N-dimethylformamidine (300 mg, 1.59 mmol), acrylic acid (114 mg, 1.58 mmol), HATU (909 mg, 2.39 mmol) and DIEA (0.78 mL) were mixed in N,N-dimethylformamide (5 mL), the mixture was stirred at 28° C. for 16 hours. Water (5 mL) was added to the reaction solution and the mixture was extracted with ethyl acetate (5 mL×3). The organic phases were combined, dried over anhydrous sodium sulfate, filtered, and the filtrate was concentrated under reduced pressure to give a crude product which was purified by silica gel column to give 213 mg yellow oil with a yield of 55.16%.

Step B: preparation of 3-bromo-N-(3-cyano-4-((E)-dimethylaminomethyleneamino)phenyl)-4,5-dihydroisoxazol-5-carboxamide: N-(3-cyano-4-((E)-dimethylaminomethyleneamino)phenyl)propyl-2-enamide (200 mg, 0.83 mmol) and N-(2,2-dibromovinyl)hydroxylamine (149 mg, 0.69 mmol) were mixed in N,N-dimethylformamide (1.8 mL).

The mixture was cooled to −5 to 0° C., the temperature was maintained while a solution of potassium bicarbonate (172 mg, 1.72 mmol) in water (1.8 mL) was added dropwise over 30 minutes. The final reaction solution was warmed to 10° C. and stirred for 16 hours. Water (10 mL) was added to the reaction solution, and the reaction solution was extracted with ethyl acetate (10 mL), the organic phase was washed with saturated brine (10 mL), dried over anhydrous sodium sulfate, filtered, and the filtrate was concentrated under reduced pressure to give a crude product which was purified by silica gel column to give 100 mg yellow oil with a yield of 33.26%.

Step C: Preparation of N-(4-((4-([1,2,4]triazolo[4,3-c]pyrimidin-7-yloxy)-3-methylphenyl)amino)quinazolin-6-yl)-3-bromo-4,5-dihydroisoxazol-5-carboxamide: 3-bromo-N-(3-cyano-4-((E)-dimethylaminomethyleneamino)phenyl)-4,5-dihydroisoxazol-5-carboxamide (70 mg, 0.19 mmol) and 7-(2-methyl-4-aminophenoxy)-[1,2,4]triazolo[4,3-c]pyrimidine (46 mg, 0.19 mmol) were mixed in 2 mL isopropyl acetate, 0.6 mL glacial acetic acid was added. The reaction solution was stirred at room temperature for 16 hours. Upon the completion of the reaction, the mixture was concentrated directly and the residue was purified by silica gel column and preparative liquid chromatography to give 5.0 mg light brown solid with a yield of 4.7%. LCMS: 560.7 [M+H] detection value. $^1$H-NMR (CDCl$_3$) δ 10.52 (s, 1H), 9.86 (s, 1H), 9.68 (s, 1H), 9.22 (s, 1H), 8.78-8.76 (m, 2H), 8.71 (d, 1H, J=4.0 Hz), 8.36 (s, 1H), 7.94 (d, 1H, J=8.0 Hz), 7.77-7.73 (m, 3H), 7.65 (dd, 1H, J=8.0, 4.0 Hz), 7.17 (d, 1H, J=8.0 Hz), 6.94 (s, 1H), 5.28 (dd, 1H, J=12.0, 4.0 Hz), 3.76-3.70 (m, 2H), 2.29 (s, 3H).

Embodiment 59

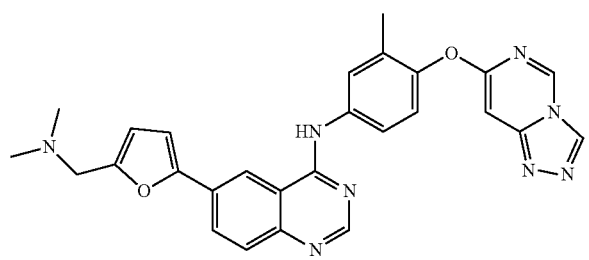 [SMILES: Cc1cc(Nc2ncnc3ccc(-c4ccc(CN(C)C)o4)cc23)ccc1Oc1cc2nncn2cn1]

Synthesis of N-(4-([1,2,4]triazolo[4,3-c]pyrimidin-7-yloxy)-3-methylphenyl)-6-(5-((dimethylamino)methyl)furan-2-yl)-4-aminoquinazoline According to the method of Embodiment 15, wherein 2-methylsulfonylethylamino hydrochloride was replaced with dimethylamine hydrochloride. LC-MS: 492.9 [M+H] detection value. $^1$H-NMR (400 MHz, CD$_3$OD) δ 9.46 (s, 1H), 8.75 (s, 1H), 8.52 (s, 1H), 8.44 (s, 1H), 8.21 (d, 1H, J=8 Hz), 7.82-7.80 (m, 2H), 7.75 (d, 1H, J=8 Hz), 7.21 (d, 1H, J=8 Hz), 7.02 (s, 1H), 6.96 (s, 1H), 6.60 (s, 1H), 3.82 (s, 2H), 2.49 (s, 6H), 2.28 (s, 3H).

Embodiment 60

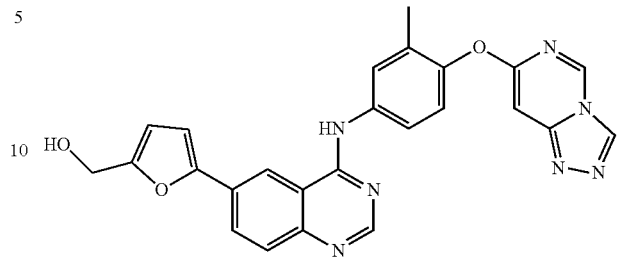

Synthesis of (5-(4-((4-([1,2,4]triazolo[4,3-c]pyrimidin-7-yloxy)-3-methylphenyl)amino)quinazolin-6-yl)furan-2-yl)methanol Step A: preparation of (5-(4-((4-([1,2,4]triazolo[4,3-c]pyrimidin-7-yloxy)-3-methylphenyl)amino)quinazolin-6-yl)furan-2-yl)methanol: 5-(4-((4-([1,2,4]triazolo[4,3-c]pyrimidin-7-yloxy)-3-methylphenyl)amino)quinazolin-6-yl) furan-2-carbaldehyde (80 mg, 0.17 mmol) and sodium cyanoborohydride (100 mg, 1.59 mmol) were added into 3 mL dichloromethane in a 50 mL single-neck flask. The reaction solution was stirred at room temperature for 18 hours, then concentrated directly, washed with saturated sodium bicarbonate and extracted with ethyl acetate. The organic phase was washed with saturated brine, dried over anhydrous sodium sulfate, filtered, and concentrated under reduced pressure. The residue was purified by column chromatography to give 18.5 mg product with a yield of 23.1%. LC-MS: 466.9 [M+H] detection value. $^1$H-NMR (400 MHz, DMSO-d$_6$) δ 10.01 (s, 1H), 9.69 (s, 1H), 8.81 (s, 1H), 8.59-8.58 (m, 2H), 8.19 (d, 1H, J=8.0 Hz), 7.81 (m, 3H), 7.23-7.08 (m, 3H), 6.53 (d, 1H, J=4.0 Hz), 5.34 (s, 1H), 4.55 (s, 2H), 2.22 (s, 3H).

Embodiment 61

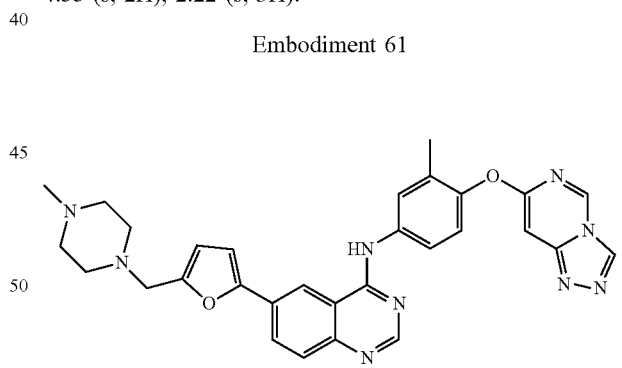

Synthesis of N-(4-([1,2,4]triazolo[4,3-c]pyrimidin-7-yloxy)-3-methylphenyl)-6-(5-(4-methylpiperidin-1-yl)methyl)furan-2-yl)-4-aminoquinazoline According to the method of Embodiment 15, wherein 2-methylsulfonylethylamino hydrochloride was replaced with N-methylpiperidine. LC-MS: 547.9 [M+H] detection value. $^1$H-NMR (400 MHz, CD$_3$OD) δ 9.46 (s, 1H), 8.75 (s, 1H), 8.52 (s, 1H), 8.44 (s, 1H), 8.21 (d, 1H, J=8 Hz), 7.84-7.74 (m, 3H), 7.23 (d, 1H, J=8 Hz), 7.02-3.97 (m, 2H), 6.53 (s, 1H), 3.77 (s, 2H), 2.84-2.50 (m, 8H), 2.45 (s, 3H), 2.29 (s, 3H).

Embodiment 62

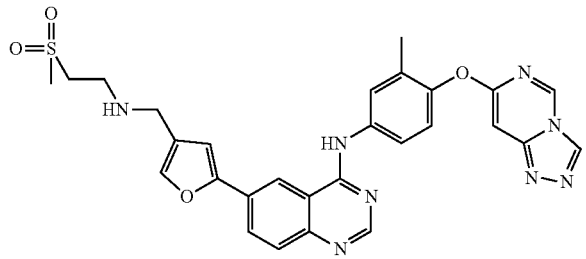 [SMILES: Cc1cc(Nc2ncnc3ccc(-c4cc(CNCCS(C)(=O)=O)co4)cc23)ccc1Oc1cc2nncn2cn1]

Synthesis of N-(4-([1,2,4]triazolo[4,3-c]pyrimidin-7-yloxy)-3-methylphenyl)-6-(4-(((2-methylsulfonyl)ethyl)amino)methyl)furan-2-yl)-4-aminoquinazoline Step A: preparation of 5-(4-((4-([1,2,4]triazolo[4,3-c]pyrimidin-7-yloxy)-3-methylphenyl)amino)quinazolin-6-yl)furan-3-carboxaldehyde: according to the method of Embodiment 15, wherein 5-formyl-2-furanboronic acid was replaced with 4-formylfuran-2-boronic acid.

Step B: preparation of N-(4-([1,2,4]triazolo[4,3-c]pyrimidin-7-yloxy)-3-methylphenyl)-6-(4-(((2-methylsulfonyl)ethyl)amino)methyl)furan-2-yl)-4-aminoquinazoline: according to the method of Embodiment 15, wherein 2-methylsulfonylethylamino hydrochloride was replaced with 2-(methylsulfonyl)ethylamine hydrochloride. LC-MS: 570.8 [M+H] detection value. $^1$H-NMR (400 MHz, DMSO-$d_6$) δ 9.99 (s, 1H), 9.68 (s, 1H), 8.86 (s, 1H), 8.59 (s, 2H), 8.17 (d, 1H, J=8 Hz), 7.83-7.80 (m, 4H), 7.22 (d, 1H, J=8 Hz), 7.14 (s, 1H), 3.70 (s, 2H), 3.49 (s, 2H), 3.06-3.02 (m, 5H), 2.21 (s, 3H).

Embodiment 63

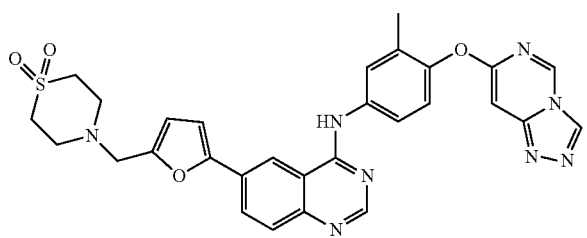 [SMILES: Cc1cc(Nc2ncnc3ccc(-c4ccc(CN5CCS(=O)(=O)CC5)o4)cc23)ccc1Oc1cc2nncn2cn1]

Synthesis of 4-((5-(4-((4-[1,2,4]triazolo[4,3-c]pyrimidin-7-yloxy)-3-methylphenyl)amino)quinazolin-6-yl)furan-2-yl)methyl)thiomorpholine-1,1-dioxide According to the method of Embodiment 15, wherein 2-methylsulfonylethylamino hydrochloride was replaced with thiomorpholine-1,1-dioxide. LC-MS: 583.8 [M+H] detection value. $^1$H-NMR (400 MHz, CD$_3$OD) δ 9.46 (s, 1H), 8.73 (s, 1H), 8.52 (s, 1H), 8.44 (s, 1H), 8.21 (d, 1H, J=8 Hz), 7.84-7.72 (m, 3H), 7.22 (d, 1H, 18 Hz), 7.01 (s, 1H), 6.97 (s, 1H), 6.54 (s, 1H), 3.90 (s, 2H), 3.17-3.14 (m, 8H), 2.28 (s, 3H).

Embodiment 64

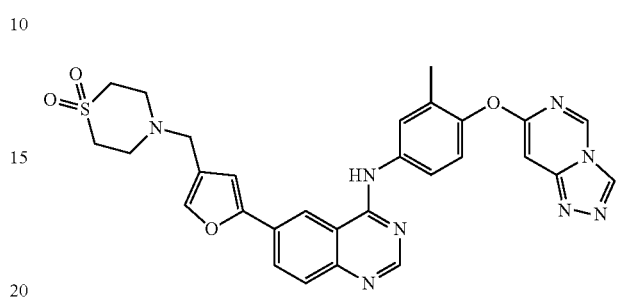

4-((5-(4-((4-[1,2,4]triazolo[4,3-c]pyrimidin-7-yloxy)-3-methylphenyl)amino)quinazolin-6-yl)furan-2-yl)methyl)thiomorpholine-1,1-dioxide According to the method of Embodiment 15, wherein 2-methylsulfonylethylamino hydrochloride was replaced with thiomorpholine-1,1-dioxide. LC-MS: 583.8 [M+H] detection value. $^1$H-NMR (400 MHz, DMSO-$d_6$) δ 9.98 (s, 1H), 9.68 (s, 1H), 8.87 (s, 1H), 8.59 (s, 2H), 8.19 (d, 1H, J=8 Hz), 7.83-7.81 (m, 4H), 7.22 (d, 1H, J=8 Hz), 7.15 (d, 2H, J=8 Hz), 3.63 (s, 2H), 3.14 (m, 4H), 2.96 (m, 4H), 2.22 (s, 3H).

Embodiment 65

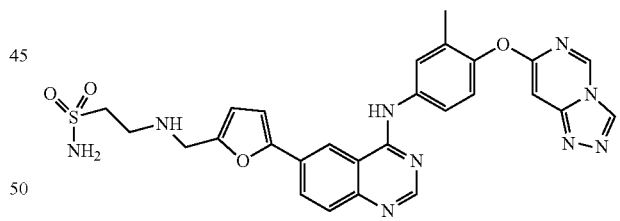

Synthesis of 2-(((5-(4-((4-[1,2,4]triazolo[4,3-c]pyrimidin-7-yloxy)-3-methylphenyl)amino)quinazolin-6-yl)furan-2-yl)methyl)amino)ethylsulfonamide-1,1-dioxide According to the method of Embodiment 15, wherein 2-methylsulfonylethylamino hydrochloride was replaced with 2-aminoethylsulfonamide. LC-MS: 571.8 [M+H] detection value. $^1$H-NMR (400 MHz, CD$_3$OD) δ 9.95 (s, 1H), 9.68 (s, 1H), 8.80 (s, 1H), 8.58 (s, 1H), 8.19 (d, 1H, J=8 Hz), 7.83-7.79 (m, 4H), 7.22 (d, 1H, J=8 Hz), 7.13 (s, 1H), 7.09 (s, 1H), 3.87 (s, 2H), 3.22-3.19 (m, 2H), 3.05-3.01 (m, 2H), 2.28 (s, 3H).

Embodiment 66

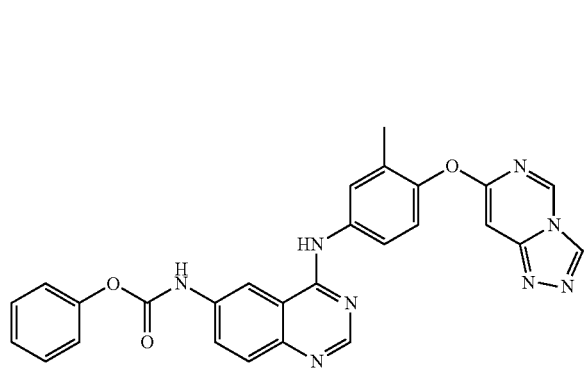 [SMILES: Cc1cc(Nc2ncnc3ccc(NC(=O)Oc4ccccc4)cc23)ccc1Oc1cc2nncn2cn1]

Synthesis of phenyl (4-((4-([1,2,4]triazolo[4,3-c]pyrimidin-7-yloxy)-3-methylphenyl)amino)quinazolin-6-carbamate Step A: preparation of phenyl (E)-(3-cyano-4-(((dimethylamino)methylene)amino)phenyl)carbamate: a mixture of (E)-N-(4-amino-2-cyanophenyl)-N,N-dimethylformamidine (1.0 g, 5.32 mmol) and sodium bicarbonate (500 mg, 5.95 mmol) was added to 30 mL tetrahydrofuran, and the reaction solution was cooled to 0° C. Phenyl chloroformate (780 mg, 5 mmol) was dissolved in 10 mL tetrahydrofuran, which was added dropwise to the above reaction solution, the mixture was stirred for 30 minutes under an ice bath. After another 10 minutes for reaction at room temperature, water was added to the reaction solution and the mixture was extracted with ethyl acetate. The organic phase was dried over anhydrous magnesium sulfate, then filtered. The filtrate was concentrated and purified by column chromatography to give 1.2 g product with a yield of 73.26%.

Step B: preparation of phenyl (4-((4-([1,2,4]triazolo[4,3-c]pyrimidin-7-yloxy)-3-methylphenyl)amino)quinazolin-6-carbamate: according to the method of Embodiment 7, wherein (R,E)-N'-(2-cyano-4-((4-methyl-4,5-dihydrooxazol-2-yl)amino)phenyl)-N,N-dimethylformamidine was replaced with phenyl (E)-(3-cyano-4-(((dimethylamino)methylene)amino)phenyl)carbamate. LC-MS: 504.9 [M+H] detection value. $^1$H-NMR (400 MHZ, CD$_3$OD) δ 9.45 (s, 1H), 8.52-8.50 (d, 2H, J=8 Hz), 8.44 (s, 1H), 7.83-7.80 (d, 1H, J=8 Hz), 7.75 (s, 1H), 7.71-7.69 (d, 2H, J=8 Hz), 7.48-7.44 (t, 2H, J=8 Hz), 7.30-7.26 (m, 3H), 7.22-7.20 (d, 1H, J=8 Hz), 6.97 (s, 1H), 2.27 (s, 3H).

Embodiment 67

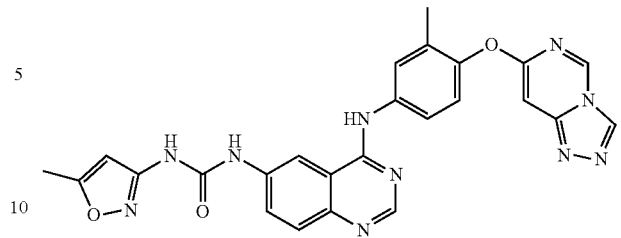

Synthesis of 1-(4-((4-([1,2,4]triazolo[4,3-c]pyrimidin-7-yloxy)-3-methylphenyl)amino)quinazolin-6-yl)-3-(5-methylisoxazol-3-yl)urea Step A: preparation of (E)-N'-(2-cyano-4-(3-(5-methylisoxazol-3-)urea)phenyl)-N,N-dimethylformamidine: phenyl (E)-(3-cyano-4-(((dimethylamino)methylene)amino)phenyl)carbamate (250 mg, 0.708 mmol) was dissolved in 5 mL tetrahydrofuran, 5-methyl-3-aminoisoxazole (150 mg, 1.529 mmol) was added. The reaction solution was heated to 65° C. and stirred for 18 hours. After completion of the reaction, the reaction solution was evaporated under reduced pressure and the residue was purified by column chromatography to give 150 mg solid with a yield of 67.9%.

Step B: preparation of 1-(4-((4-([1,2,4]triazolo[4,3-c]pyrimidin-7-yloxy)-3-methylphenyl)amino)quinazolin-6-yl)-3-(5-methylisoxazol-3-yl)urea: according to the method of Embodiment 7, wherein (R,E)-N'-(2-cyano-4-((4-methyl-4,5-dihydrooxazol-2-yl)amino)phenyl)-N,N-dimethylformamidine was replaced with (E)-N'-(2-cyano-4-(3-(5-methylisoxazol-3-yl)ureido)phenyl)-N,N-dimethylformamidine. LC-MS: 509.8 [M+H] detection value. $^1$H-NMR (400 MHz, DMSO-d$_6$) δ 9.81 (s, 1H), 9.74 (s, 1H), 9.68 (s, 1H), 9.09 (s, 1H), 8.59 (s, 1H), 8.54 (s, 1H), 8.45 (s, 1H), 8.00 (d, 1H, J=12 Hz), 7.79-7.75 (m, 3H), 7.19 (d, 1H, J=8 Hz), 7.13 (s, 1H), 6.57 (s, 1H), 2.40 (s, 3H), 2.20 (s, 3H).

Embodiment 68

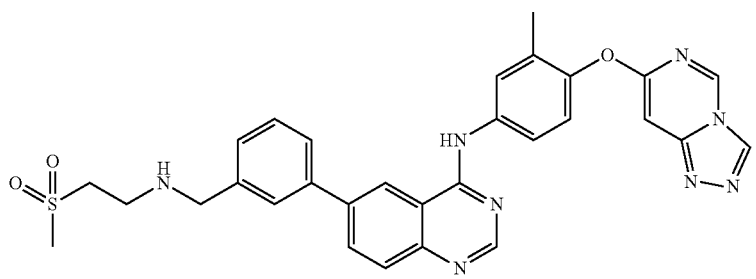 [SMILES: Cc1cc(Nc2ncnc3ccc(-c4cccc(CNCCS(C)(=O)=O)c4)cc23)ccc1Oc1cc2nncn2cn1]

Synthesis of N-(4-([1,2,4]triazolo[4,3-c]pyrimidin-7-yloxy)-3-methylphenyl)-6-(3-(((methylsulfonyl)ethyl)amino)phenyl)-4-aminoquinazoline Step A: preparation of 3-(4-((4-([1,2,4]triazolo[4,3-c]pyrimidin-7-yloxy)-3-methylphenyl)amino)quinazolin-6-yl)benzaldehyde: according to the method of Embodiment 15, wherein 5-formyl-2-furanoboronic acid was replaced with 3-formylphenylboronic acid.

Step B: preparation of N-(4-([1,2,4]triazolo[4,3-c]pyrimidin-7-yloxy)-3-methylphenyl)-6-(3-(((methylsulfonyl)ethyl)amino)phenyl)-4-aminoquinazoline: according to the method of Embodiment 15, wherein 5-(4-((4-([1,2,4]triazolo[4,3-c]pyrimidin-7-yloxy)$_3$-methylphenyl)amino)quinazolin-6-yl)furan-2-carbaldehyde was replaced with 3-(4-((4 ([1,2,4]triazolo[4,3-c]pyrimidin-7-yloxy)-3-methylphenyl)amino)quinazolin-6-yl)benzaldehyde.
LC-MS: 581.8 [M+H] detection value. ¹H-NMR (400 MHz, DMSO-d₆) δ 9.99 (s, 1H), 9.69 (s, 1H), 8.85 (s, 1H), 8.63 (s, 1H), 8.60 (s, 1H), 8.21 (d, 1H, J=8 Hz), 8.17 (s, 1H), 7.88-7.79 (m, 5H), 7.54-7.51 (m, 1H), 7.41 (d, 1H, J=8 Hz), 7.23 (d, 1H, J=12 Hz), 7.15 (s, 1H), 3.87 (s, 2H), 3.31 (t, 2H, J=8 Hz), 3.05 (s, 3H), 2.98 (t, 2H, J=8 Hz), 2.21 (s, 3H).

Embodiment 69

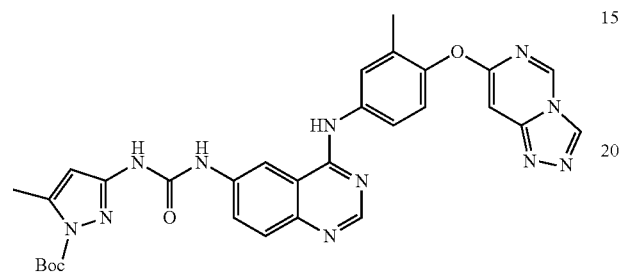

Synthesis of tert-butyl 3-(3-(4-((4-([1,2,4]triazolo[4,3-c]pyrimidin-7-yloxy)-3-methylphenyl)amino)quinazolin-6-yl)ureido)-5-methyl-1H-pyrazol-1-carbamate Step A: preparation of tert-butyl 3-amino-5-methyl-1H-pyrazol-1-carbamate: 5-methyl-3-amino-1H-pyrazole (1.0 g, 10.3 mmol), triethylamine (2.7 g, 26.7 mmol), N,N-dimethylaminopyridine (50 mg) and dioxane (20 mL) were mixed in a 100 mL three-neck flask, and the mixture was cooled to about 0° C. under an ice bath. Di-tert-butyl dicarbonate (3.1 g, 14.2 mmol) was added under stirring. The reaction solution was warmed to room temperature and stirred for 18 hours. Upon completion of the reaction, the reaction solution was directly concentrated and purified by column chromatography to give 810 mg product with a yield of 39.9%.

Step B: preparation of tert-butyl 3-(3-(3-cyano-4-(((dimethylamino)methylene)amino)phenyl)ureido)-4-methyl-1H-pyrazol-1-carbamate: triphosgene (708 mg, 2.39 mmol) and dichloromethane (10 mL) were added into a 100 mL three-neck flask, the reaction solution was cooled to 0° C. under argon atmosphere, then tert-butyl 3-amino-5-methyl-1H-pyrazol-1-carbamate (470 mg, 2.39 mmol) added under stirring, after the mixture was stirred at 0° C. for 1 hour, a solution of (E)-N'-(4-amino-2-cyanophenyl)-N,N-dimethylformamidine (470 mg, 2.50 mmol) in dichloromethane (10 mL) was added dropwise. After the addition, the reaction solution was naturally warmed to room temperature and stirred for 18 hours. Upon completion of the reaction, saturated aqueous sodium bicarbonate solution was added and the mixture was extracted with ethyl acetate. The organic phase was washed with saturated brine, dried over anhydrous sodium sulfate and filtered. The filtrate was concentrated under reduced pressure. The residue was purified by silica gel column chromatography to give 250 mg product with a yield of 25.5%.

Step C: preparation of tert-butyl 3-(3-(4-((4-([1,2,4]triazolo[4,3-c]pyrimidin-7-yloxy)-3-methylphenyl)amino)quinazolin-6-yl)ureido)-5-methyl-1H-pyrazol-1-carbamate:

according to the method of Embodiment 7, wherein (R,E)-N'-(2-cyano-4-((4-methyl-4,5-dihydrooxazol-2-yl)amino)phenyl)-N,N-dimethylformamidine was replaced with tert-butyl 3-(3-(3-cyano-4-(((dimethylamino)methylene)amino)phenyl)ureido)-4-methyl-1H-pyrazol-1-carbamate. LC-MS: 607.8 [M+H] detection value. ¹H-NMR (400 MHz, CD₃OD) δ 9.47 (s, 1H), 8.68 (s, 1H), 8.55 (s, 1H), 8.45 (s, 1H), 7.79-7.73 (m, 4H), 7.23 (d, 1H, J=8.0 Hz), 6.98 (s, 1H), 6.64 (s, 1H), 2.29 (s, 3H), 1.70 (s, 3H), 1.29 (s, 9H).

Embodiment 70

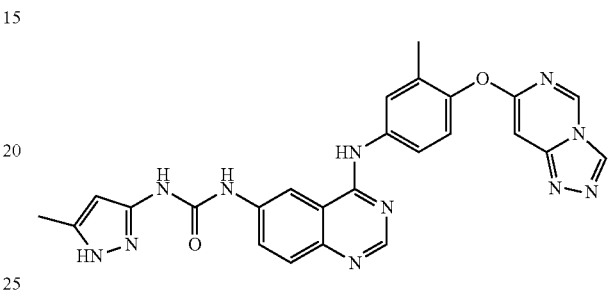

Synthesis of 1-(4-((4-([1,2,4]triazolo[4,3-c]pyrimidin-7-yloxy)-3-methylphenyl)amino)quinazolin-6-yl)-3-(5-methyl-1H-pyrazol-3-yl)urea Step A: preparation of 1-(4-((4-([1,2,4]triazolo[4,3-c]pyrimidin-7-yloxy)-3-methylphenyl)amino)quinazolin-6-yl)-3-(5-methyl-1H-pyrazol-3-yl)urea: tert-butyl 3-(3-(4 ((4-([1,2,4]triazolo[4,3-c]pyrimidin-7-yloxy)-3-methylphenyl)amino)quinazolin-6-yl)ureido)-5-methyl-1H-pyrazol-1-carbamate (80 mg, 0.13 mmol) and a solution of 10% trifluoroacetic acid in 2 mL methyl chloride were added into a sealed tube, the mixture was stirred at room temperature for 4 hours. After completion of the reaction, the mixture was concentrated under reduced pressure and the residue was purified by column chromatography to give 26.74 mg pale yellow solid with a yield of 40.0%. LC-MS: 507.9 [M+H] detection value. ¹H-NMR (400 MHz, DMSO-d₆) δ 11.99 (s, 1H), 9.80 (s, 1H), 9.68 (s, 1H), 9.60 (br, s, 1H), 9.21 (s, 1H), 8.59 (s, 1H), 8.52 (s, 1H), 8.43 (s, 1H), 8.04-8.02 (m, 1H), 7.79-7.75 (m, 3H), 7.19 (d, 1H, J=8.0 Hz), 7.13 (s, 1H), 6.02 (s, 1H), 2.22 (s, 3H), 2.20 (s, 3H).

Embodiment 71

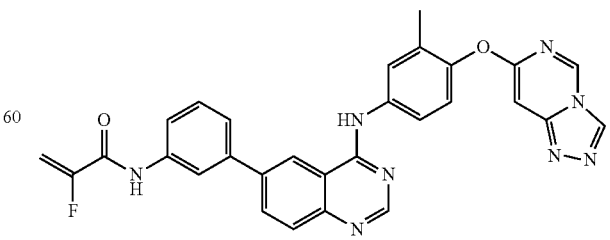

Synthesis of N-(3-(4-((4-([1,2,4]triazolo[4,3-c]pyrimidin-7-yloxy)-3-methylphenyl)amino)quinazolin-6-yl)phenyl)-2-fluoroacrylamide According to the method of Embodiment 16, wherein N⁴-(4-([1,2,4]triazolo[4,3-c]pyrimidin-7-yloxy)-3-methylphenyl)quinazolin-4,6-diamine was replaced with N-(4-([1,2,4]triazolo[4,3-c]pyrimidin-7-yloxy)-3-methylphenyl)-6-(3-aminophenyl)quinazolin-4-amine, the reaction was conducted at 100° C. under stirring for 18 hours. LC-MS: 532.8 [M+H] detection value. ¹H-NMR (400 MHz, DMSO-d₆) δ 10.48 (s, 1H), 10.04 (s, 1H), 9.68 (s, 1H), 8.86 (s, 1H), 8.61-8.59 (m, 2H), 8.20 (s, 1H), 8.14 (d, 1H, J=8.0 Hz), 7.81 (d, 1H, J=8.0 Hz), 7.68-7.65 (m, 3H), 7.59-7.57 (m, 1H), 7.55-7.53 (m, 1H), 7.22 (d, 1H, J=8.0 Hz), 7.15 (s, 1H), 5.84-5.71 (dd, 1H, J=48.0, 4.0 Hz), 5.51-5.46 (dd, 1H, J=16.0, 4.0 Hz), 2.21 (s, 3H).

Embodiment 72

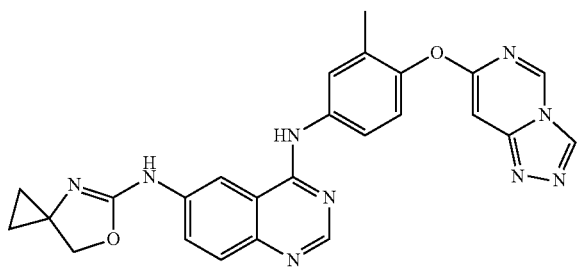 [SMILES: Cc1cc(Nc2ncnc3ccc(NC4=NC5(CC5)CO4)cc23)ccc1Oc1cc2nncn2cn1]

Synthesis of N'-(4-([1,2,4]triazolo[4,3-c]pyrimidin-7-yloxy)-3-methylphenyl)-N⁶-(6-oxa-4-azaspiro[2.4]hept-4-en-5-yl)quinazolin-4,6-diamine Step A: preparation of (1-amino-cyclopropyl)methanol: 1-aminocyclopropylcarboxylic acid (2.0 g, 19.8 mmol) and 20 mL tetrahydrofuran were added into a 100 mL single-neck flask, and the reaction solution was cooled to 0° C., then (1.4 g, 36.8 mmol) was added in portions, followed by dropwise addition of a solution of iodine (5.0 g 19.7 mmol) in tetrahydrofuran. After completion of the addition, the reaction solution was heated to reflux and stirred for 18 hours. Upon completion of the reaction, methanol was added dropwise until the reaction solution became clear, the mixture was concentrated to dryness, washed with 20 mL 20% sodium hydroxide solution, and extracted with dichloromethane. The organic phase was dried over anhydrous sodium sulfate, filtered and concentrated to give a crude product which was used directly in the next step.

According to the method of Embodiment 7, wherein (R)-2-amino-1-propanol was replaced with (I-amino-cyclopropyl)methanol. LC-MS: 479.8 [M+H] detection value. ¹H-NMR (400 MHz, DMSO-d₆) δ 9.67 (s, 1H), 9.65 (s, 1H), 8.59 (s, 1H), 8.49 (s, 1H), 8.28 (s, 1H), 7.96 (s, 1H), 7.77-7.71 (m, 3H), 7.18 (d, 1H, J=8.0 Hz), 7.12 (s, 1H), 4.31 (s, 2H), 2.18 (s, 3H), 0.97-0.95 (m, 2H), 0.74-0.71 (m, 2H).

Embodiment 73

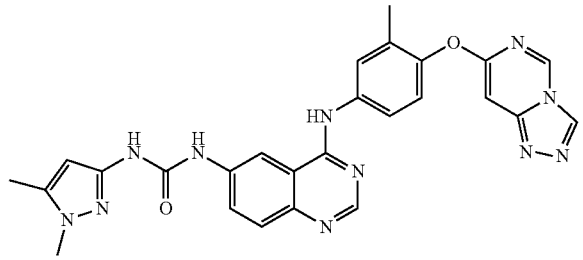 [SMILES: Cc1cc(Nc2ncnc3ccc(NC(=O)Nc4cc(C)n(C)n4)cc23)ccc1Oc1cc2nncn2cn1]

Synthesis of 1-(4-((4-([1,2,4]triazolo[4,3-c]pyrimidin-7-yloxy)-3-methylphenyl)amino)quinazolin-6-yl)-3-(1,5-dimethyl-1H-pyrazol-3-yl)urea Step A: preparation of (E)-N-(2-cyano-4-(3-(1,5-dimethyl-1H-pyrazol-3-yl)ureido)phenyl)-N,N-dimethylformamidine: triphosgene (320 mg, 1.08 mmol) was dissolved in 5 mL tetrahydrofuran and 1,5-dimethyl-1H-pyrazol-3-amine (110 mg, 0.99 mmol) was added, the reaction solution was heated to 65° C. under argon atmosphere and stirred for 18 hours. Additional (E)-N-(4-amino-2-cyanophenyl)-N,N-dimethylformamidine (250 mg, 1.33 mmol) and N,N-diisopropylethylamine (400 mg, 3.10 mmol) were added, the reaction solution was heated to 65° C. and stirred for 18 hours. Upon completion of the reaction, the reaction solution was washed with sodium bicarbonate solution, extracted with ethyl acetate, and dried over anhydrous sodium sulfate, filtered, and evaporated under reduced pressure. The residue was purified by column chromatography to give 39 mg solid with a yield of 12.1%.

Step B: preparation of 1-(4-((4-([1,2,4]triazolo[4,3-c]pyrimidin-7-yloxy)-3-methylphenyl)amino)quinazolin-6-yl)-3-(1,5-dimethyl-1H-pyrazol-3-yl)urea: according to the method of Embodiment 7, wherein (R,E)-N-(2-cyano-4-(3-(1-hydroxypropyl-2-yl)thioureido)phenyl)-N,N-dimethylformamidine was replaced with (L)-N'-(2-cyano-4-(3-(1,5-dimethyl-1H-pyrazol-3-)ureido)phenyl)-N,N-dimethylformamidine. LC-MS: 522.2 [M+H] detection value. ¹H-NMR (400 MHz, DMSO-d₆) δ 9.78 (s, 1H), 9.68 (s, 1H), 9.35 (br, 1H), 9.12 (s, 1H), 8.59 (s, 1H), 8.52 (s, 1H), 8.43 (s, 1H), 8.02 (d, 1H, J=12.0 Hz), 7.81-7.75 (m, 3H), 7.19 (d, 1H, J=8.0 Hz), 7.13 (s, 1H), 6.06 (s, 1H), 3.66 (s, 3H), 2.23 (s, 3H), 2.20 (s, 3H).

Embodiment 74

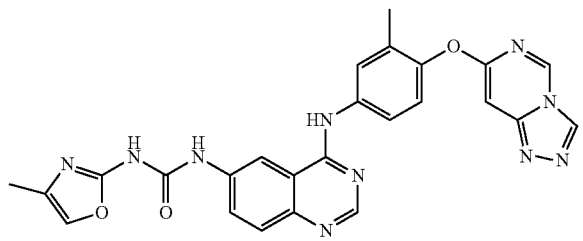 [SMILES: Cc1coc(NC(=O)Nc2ccc3ncnc(Nc4ccc(Oc5cc6nncn6cn5)c(C)c4)c3c2)n1]

Synthesis of 1-(4-((4-([1,2,4]triazolo[4,3-c]pyrimidin-7-yloxy)-3-methylphenyl)amino)quinazolin-6-yl)-3-(4-methyloxazol-2-yl)urea Step A: preparation of (L)-N'-(2-cyano-4-(3-(4-methyloxazol-2-yl)ureido)phenyl)-N,N-dimethylformamidine: triphosgene (900 mg, 3.03 mmol) was dissolved in 5 mL dichloromethane, 4-methyl-2-aminooxazole (310 mg, 3.16 mmol) was added, and the reaction solution was heated to 65° C. under argon atmosphere and stirred for 18 hours. Additional (E)-N'-(4-amino-2-cyanophenyl)-N,N-dimethylformamidine (540 mg, 2.87 mmol) and N,N-diisopropylethylamine (520 mg, 4.03 mmol), the reaction solution was heated to 65° C. and stirred for 18 hours. After completion of the reaction, the reaction solution was washed with sodium bicarbonate solution, extracted with ethyl acetate, dried over anhydrous sodium sulfate, filtered and evaporated under reduced pressure. The residue was purified by column chromatography to give 114 mg solid with a yield of 12.7%.

Step B: preparation of 1-(4-((4-([1,2,4]triazolo[4,3-c]pyrimidin-7-yloxy)-3-methylphenyl)amino)quinazolin-6-yl)-3-(4-methyloxazol-2-yl)urea: according to the method of Embodiment 7, wherein (R,E)-N'-(2-cyano-4-(3-(1-hydroxypropyl-2-yl)thioureido)phenyl)-N,N-dimethylformamidine was replaced with (E)-N'-(2-cyano-4-(3-(4-methyloxazol-2-yl)ureido)phenyl)-N,N-dimethylformamidine. LC-MS: 509.2 [M+H] detection value. $^1$H-NMR (400 MHz, MeOD) δ 9.35 (s, 1H), 8.58 (s, 1H), 8.54 (br, 1H), 8.36 (s, 1H), 7.81-7.77 (m, 3H), 7.71 (d, 1H, J=8.0 Hz), 7.18-7.16 (m, 2H), 6.93 (s, 1H), 2.27 (s, 3H), 2.20 (s, 3H).

Embodiment 75

Synthesis of N-(3-(4-((4-([1,2,4]triazolo[4,3-c]pyrimidin-7-yloxy)-3-methylphenyl)amino)quinazolin-6-yl)phenyl)acrylamide According to the method of Embodiment 51, wherein (E)-3-(pyridin-3-yl)acrylic acid was replaced with acrylic acid (230 mg, 3.20 mmol), the reaction was conducted at 60° C. under argon atmosphere for 18 hours. LC-MS: 515.2 [M+H] detection value. $^1$H-NMR (400 MHz, DMSO-d$_6$) δ 10.36 (s, 1H), 10.03 (s, 1H), 9.68 (s, 1H), 8.85 (s, 1H), 8.63-8.59 (d, 2H, J=16.0 Hz), 8.13 (m, 2H), 7.89-7.75 (m, 4H), 7.60-7.54 (m, 2H), 7.22 (d, 1H, J=8.0 Hz), 7.14 (s, 1H), 6.51-6.47 (m, 1H), 6.34-6.30 (m, 1H), 5.82 (d, 1H, J=12.0 Hz), 2.21 (s, 3H).

Embodiment 76

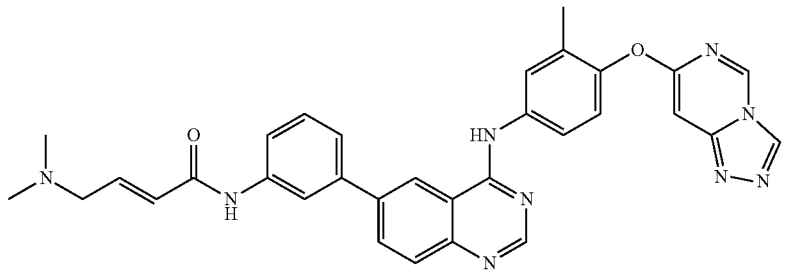 [SMILES: Cc1cc(Nc2ncnc3ccc(-c4cccc(NC(=O)/C=C/CN(C)C)c4)cc23)ccc1Oc1cc2nncn2cn1]

Synthesis of (E)-N-(3-(4-((4-([1,2,4]triazolo[4,3-c]pyrimidin-7-yloxy)-3-methylphenyl)amino)quinazolin-6-yl)phenyl)-4-(dimethylamino)but-2-enamide According to the method of Embodiment 51, wherein (E)-3-(pyridin-3-yl)acrylic acid was replaced with (E)-4-(dimethylamino)-2-butenoic acid, the reaction was conducted at 60° C. under argon atmosphere for 18 hours. LC-MS: 572.3 [M+H] detection value. $^1$H-NMR (400 MHz, DMSO-d$_6$) δ 10.31 (s, 1H), 10.02 (s, 1H), 9.68 (s, 1H), 8.84 (s, 1H), 8.63 (s, 1H), 8.59 (s, 1H), 8.15-8.10 (m, 2H), 7.91 (d, 1H, J=8.0 Hz), 7.83-7.81 (m, 2H), 7.73 (d, 1H, J=8.0 Hz), 7.60 (d, 1H, J=8.0 Hz), 7.54-7.50 (m, 1H), 7.22 (d, 1H, J=12.0 Hz), 7.14 (s, 1H), 6.83-6.76 (m, 1H), 6.35 (d, 1H, J=16.0 Hz), 3.19-3.18 (m, 2H), 2.26 (s, 6H), 2.21 (s, 3H).

Embodiment 77

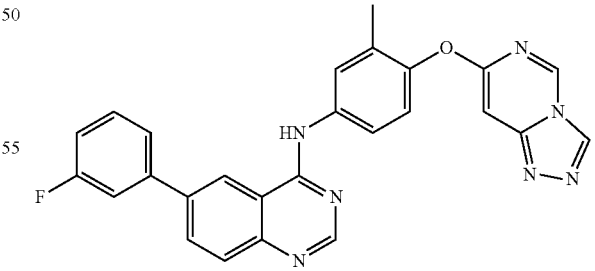

Synthesis of N-(4-([1,2,4]triazolo[4,3-c]pyrimidin-7-yloxy)-3-methylphenyl)-6-(3-fluorophenyl)-4-aminoquinazoline According to the method of Embodiment 15, wherein 5-formyl-2-furan boronic acid was replaced with 3-fluoro-

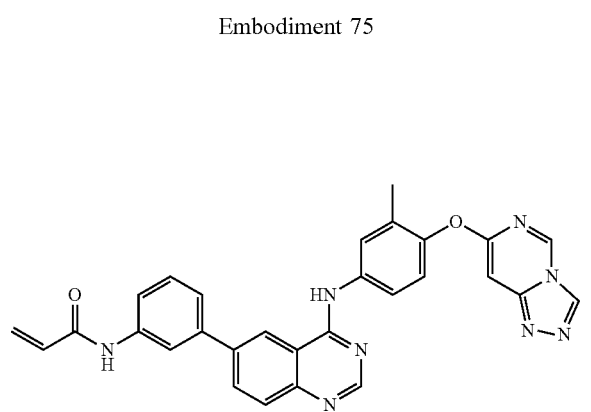

phenylboronic acid. LC-MS: 464.2 [M+H] detection value. $^{1}$H-NMR (400 MHz, DMSO-$d_6$) δ 10.01 (s, 1H), 9.69 (s, 1H), 8.90 (s, 1H), 8.63 (s, 1H), 8.59 (s, 1H), 8.26 (d, 1H, J=8.0 Hz), 7.90-7.78 (m, 5H), 7.65-7.62 (m, 1H), 7.32-7.22 (m, 2H), 7.15 (s, 1H), 2.22 (s, 3H).

Embodiment 78

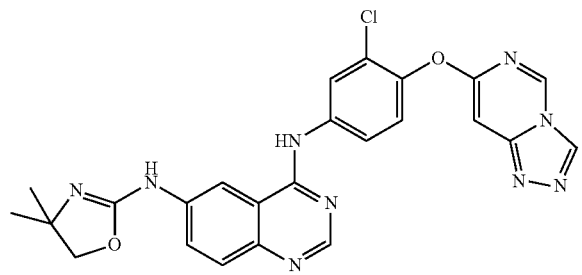 [SMILES: CC1(C)COC(Nc2ccc3ncnc(Nc4ccc(Oc5cc6nncn6cn5)c(Cl)c4)c3c2)=N1]

Synthesis of N'-[3-chloro-4-([1,2,4]triazolo[4,3-c]pyrimidin-7-yloxy)phenyl)-$N^6$-(4,4-dimethyl-4,5-dihydrooxazol-2-yl)quinazolin-4,6-diamine Step A: preparation of 7-(2-chloro-4-nitrophenoxy)-[1,2,4]triazolo[4,3-c]pyrimidine: 2-chloro-4-nitro-phenol (1000 mg, 5.76 mmol), 7-chloro-[1,2,4]triazolo[4,3-c]pyrimidine (900 mg, 5.82 mmol) and sodium bicarbonate (630 mg, 8.33 mmol) were suspended in N,N-dimethylformamide (6 mL), the mixture was stirred at 95° C. for 16 hours. The reaction solution was cooled to room temperature, then ethyl acetate (100 mL) and water (100 mL) were added. The organic phase was separated, washed with saturated sodium bicarbonate solution (50 mL×3) and saturated aqueous sodium chloride solution (50 mL) successively, dried over anhydrous magnesium sulfate for 2 hours. The mixture was filtered, evaporated to dryness under reduced pressure to give a crude product, which was purified by silica gel column chromatography to give 300 mg pale yellow solid with a yield of 18.9%.

Step B: preparation of 3-chloro-4-([1,2,4]triazolo[4,3-c]pyrimidin-7-yloxy)aniline: 7-(2-chloro-4-nitro-phenoxy)-[1,2,4]triazolo[4,3-c]pyrimidine (100 mg, 0.34 mmol) was dissolved in methanol (8 mL), saturated aqueous ammonium chloride solution (2 mL) was added, then the mixture was cooled to 0° C., zinc powder (448 mg, 6.85 mmol) was added, the reaction solution was purged with argon, then warmed to room temperature and stirred for 16 hours. The mixture was filtered through celite and evaporated to dryness under reduced pressure to give 68 mg yellow solid with a yield of 75.8%, which was used directly in the next step.

Step C: preparation of $N^4$-[3-chloro-4-([1,2,4]triazolo[4,3-c]pyrimidin-7-yloxy)phenyl)-$N^6$-(4,4-dimethyl-4,5-dihydrooxazol-2-yl)quinazolin-4,6-diamine: according to the method of Embodiment 19, wherein 3-fluoro-4-([1,2,4]triazolo[4,3-c]pyrimidin-7-yloxy)aniline was replaced with 3-chloro-4-([1,2,4]triazolo[4,3-c]pyrimidin-7-yloxy)aniline. LC-MS: 501.8 [M+H] detection value. $^{1}$H NMR (400 MHz, DMSO) δ 9.72 (s, 1-), 9.69 (s, 1H), 8.61 (s, 1H), 8.54 (s, 1H), 8.29 (s, 1H), 8.16 (s, 1H), 8.03 (s, 1H), 7.95 (d, J=8.8 Hz, 1H), 7.70-7.68 (m, 2H), 7.41 (d, J=8.8 Hz, 1H), 7.36 (s, 1H), 4.08 (s, 2H), 1.28 (s, 6H).

Embodiment 79

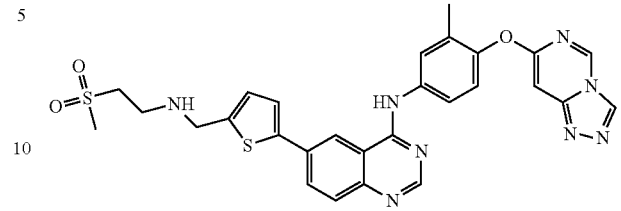

Synthesis of N-(4-([1,2,4]triazolo[4,3-c]pyrimidin-7-yloxy)-3-methylphenyl)-6-(5-(((2-methylsulfonyl)ethyl)amino)methyl)thiophen-2-yl)quinazolin-4-amine According to the method of Embodiment 15, wherein 5-formyl-2-furan boronic acid was replaced with 5-formyl-2-thiophene boronic acid. LC-MS: 586.8 [M+H] detection value. II-1 NMR (400 MHz, DMSO) δ 10.02 (s, 1H), 9.68 (s, 1H), 8.81 (s, 1H), 8.60 (d, J=5.6 Hz, 2H), 8.15-8.13 (m, 2H), 7.95-7.65 (m, 3H), 7.68 (d, J=3.6 Hz, 1H), 7.30 (s, 1H), 7.23 (d, J=8.4 Hz, 1H), 7.14 (s, 1H), 4.34 (s, 2H), 3.60-3.20 (m, 4H), 3.12 (s, 3H), 2.21 (s, 3H).

Embodiment 80

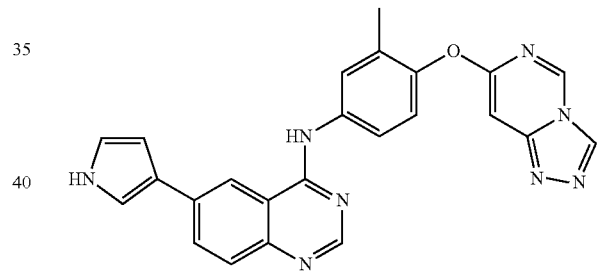

Synthesis of N-(4-([1,2,4]triazolo[4,3-c]pyrimidin-7-yloxy)-3-methylphenyl)-6-(1H-pyrrol-3-yl)quinazolin-4-amine Step A: preparation of N-(4-([1,2,4]triazolo[4,3-c]pyrimidin-7-yloxy)-3-methylphenyl)-6-(1H-pyrrol-3-yl)quinazolin-4-amine: N-(4-([1,2,4]triazolo[4,3-c]pyrimidin-7-yloxy)-3-methylphenyl)-6-iodoquinazolin-4-amine (150 mg, 0.30 mmol), (1-(triisopropylsilyl)-1H-pyrrol-3-yl)boronic acid (81 mg, 0.30 mmol), triethylamine (60 mg, 0.59 mmol) and [1,1'-bis(diphenylphosphino)ferrocene]dichloropalladium dichloromethane complex (10 mg) were suspended in tetrahydrofuran (10 mL) and the reaction solution was heated to 80° C. for 48 hours. The mixture was filtered, evaporated to dryness under reduced pressure to give a crude product, which was purified by acidic preparative HPLC to give 15 mg solid with a yield of 11.4%. LC-MS: 435.9 [M+H] detection value. $^{1}$H NMR (400 MHz, MeOD) δ 9.46 (s, 1H), 8.58 (s, 1H), 8.50 (s, 1H), 8.44 (s, 1H), 8.30-8.09 (m, 1H), 7.85-7.68 (m, 3H), 7.40 (s, 1H), 7.23 (d, J=8.4 Hz, 1H), 6.97 (s, 1H), 6.88 (s, 1H), 6.75 (s, 1H), 2.29 (s, 3H).

Embodiment 81

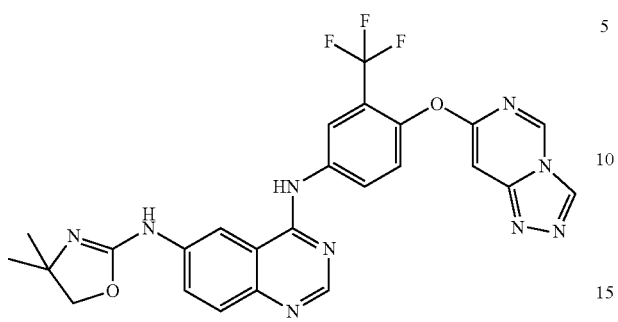

Synthesis of N⁴-(3-trifluoromethyl-4-([1,2,4]triazolo[4,3-c]pyrimidin-7-yloxy)phenyl)-N⁶-(4,4-dimethyl-4,5-dihydrooxazol-2-yl)quinazolin-4,6-diamine According to the method of Embodiment 19, wherein 2-fluoro-4-nitro-phenol was replaced with 2-trifluoromethyl-4-nitro-phenol, sodium bicarbonate was replaced with sodium carbonate. LC-MS: 535.8 [M+H] detection value. $^1$H NMR (400 MHz, DMSO) δ 9.84 (s, 1H), 9.70 (s, 1H), 8.63 (s, 1H), 8.54 (s, 1H), 8.42 (s, 1H), 8.31 (d, J=8.4 Hz, 1H), 8.03 (s, 1H), 7.71-7.69 (m, 2H), 7.46-7.44 (m, 2H), 7.19 (s, 1H), 4.08 (s, 2H), 1.28 (s, 6H).

Embodiment 82

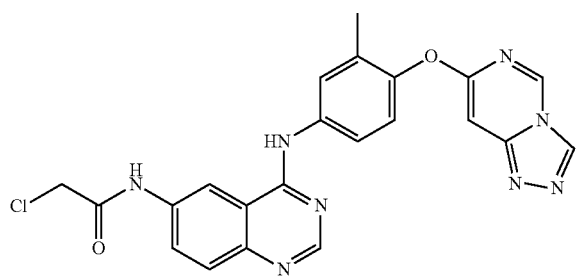 [SMILES: Cc1cc(Nc2ncnc3ccc(NC(=O)CCl)cc23)ccc1Oc1cc2nncn2cn1]

Synthesis of N-(4-((4-([1,2,4]triazolo[4,3-c]pyrimidin-7-yloxy)-3-methylphenyl)amino)quinazolin-6-yl)-2-chloroacetamide Step A: preparation of N-(4-((4-([1,2,4]triazolo[4,3-c]pyrimidin-7-yloxy)-3-methylphenyl)amino)quinazolin-6-yl)-2-chloroacetamide: N-(4-([1,2,4]triazolo[4,3-c]pyrimidin-7-yloxy)-3-methylphenyl)quinazolin-4,6-diamine (150 mg, 0.39 mmol), chloroacetyl chloride (222 mg, 1.96 mmol) and triethylamine (198 mg, 1.96 mmol) were dissolved in dichloromethane (5 mL) and N,N-dimethylformamide (5 mL), the reaction solution was stirred at room temperature for 16 hours. Dichloromethane (50 mL) was added to the reaction solution, and the mixture was successively washed with saturated aqueous sodium bicarbonate (50 mL), water (50 mL), and saturated aqueous sodium chloride (50 mL), then dried over anhydrous sodium sulfate for 2 hours, filtered, and concentrated under reduced pressure. The residue was purified by preparative chromatography to give 60 mg pale yellow solid with a yield of 33.4%. LC-MS: 461.8 [M+H] detection value. $^1$H NMR (400 MHz, DMSO) 10.61 (s, 1H), 9.87 (s, 1H), 9.64 (d, J=1.2 Hz, 1H), 8.70 (d, J=2.0 Hz, 1H), 8.55 (s, 1H), 8.50 (s, 1H), 7.91-7.58 (m, 4H), 7.14 (d, J=8.8 Hz, 1H), 7.09 (d, J=1.2 Hz, 1H), 4.33 (s, 2H), 2.14 (s, 3H).

Embodiment 83

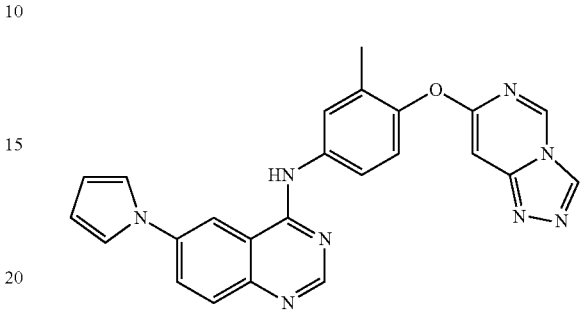

Synthesis of N-(4-([1,2,4]triazolo[4,3-c]pyrimidin-7-yloxy)-3-methylphenyl)-6-(1H-pyrrol-1-yl)-quinazolin-4-amine Step A: preparation of (E)-N-(2-cyano-4-(1H-pyrrol-1-yl)phenyl)-N,N-dimethylformamidine: (E)-N-(2-cyano-4-iodophenyl)-N,N-dimethylformamidine (300 mg, 1.00 mmol), 1H-pyrrole (140 mg, 2.08 mmol), potassium phosphate (530 mg, 2.50 mmol), copper iodide (230 mg, 1.21 mmol) and N,N-dimethylethane-1,2-diamine (110 mg, 1.25 mmol) were suspended in toluene (10 mL) and the reaction solution was heated to 80° C. for 16 hours, then filtered, and purified by silica gel column to give 220 mg solid with a yield of 92.05%.

Step B: preparation of N-(4-([1,2,4]triazolo[4,3-c]pyrimidin-7-yloxy)-3-methylphenyl)-6-(1H-pyrrol-1-yl)-quinazolin-4-amine: according to the method of Embodiment 7, (R,E)-N-(2-cyano-4-((4-methyl-4,5-dihydrooxazol-2-yl)amino)phenyl)-N, N-dimethylformamidine was replaced with (E)-N'-(2-cyano-4-(1H-pyrrol-1-yl)phenyl)-N,N-dimethylformamidine, reaction was conducted at room temperature under stirring for 48 hours. LC-MS: 435.9 [M+H] detection value. $^1$H NMR (400 MHz, DMSO) δ 9.83 (s, 1H), 9.68 (d, J=1.2 Hz, 1H), 8.66 (d, J=2.4 Hz, 1H), 8.59 (d, J=2.8 Hz, 2H), 8.20-8.14 (m, 1H), 7.88 (d, J=9.2 Hz, 1H), 7.84-7.76 (m, 2H), 7.63-7.57 (m, 2H), 7.25-7.19 (m, 1H), 7.14 (d, J=1.2 Hz, 1H), 6.47-6.30 (m, 2H), 2.21 (s, 3H).

Embodiment 84

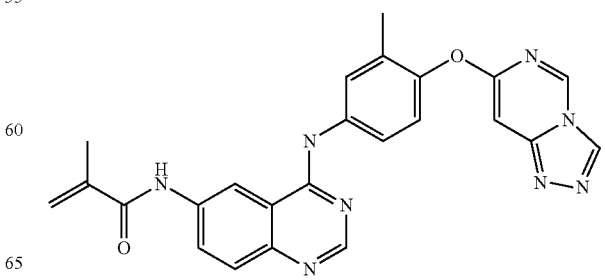

Synthesis of N-(4-((4-([1,2,4]triazolo[4,3-c]pyrimidin-7-yloxy)-3-methylphenyl)amino)quinazolin-6-yl)-methacrylamide According to the method of Embodiment 16, wherein 2-fluoroacrylic acid was replaced with methacrylic acid, reaction was conducted at 80° C. under stirring for 16 hours. LC-MS: 453.9 [M+H] detection value. ¹H NMR (400 MHz, DMSO) δ 10.14 (s, 1H), 9.83 (s, 1H), 9.67 (d, J=1.2 Hz, 1H), 8.78 (d, J=2.0 Hz, 1H), 8.58 (s, 1H), 8.54 (s, 1H), 7.96-7.88 (m, 1H), 7.86-7.67 (m, 3H), 7.17 (d, J=8.8 Hz, 1H), 7.12 (d, J=1.2 Hz, 1H), 5.93 (s, 1H), 5.61 (s, 1H), 2.18 (s, 3H), 2.01 (s, 3H).

Embodiment 85

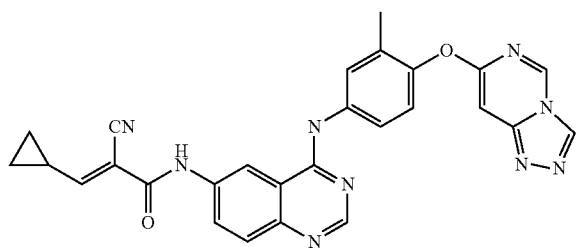 [SMILES: Cc1cc(Nc2ncnc3ccc(NC(=O)/C(C#N)=C/C4CC4)cc23)ccc1Oc1cc2nncn2cn1]

Synthesis of (E)-N-(4-((4-([1,2,4]triazolo[4,3-c]pyrimidin-7-yloxy)-3-methylphenyl)amino)quinazolin-6-yl)-2-cyano-3-cyclopropylacrylamide Step A: preparation of (E)-N-(4-((4-([1,2,4]triazolo[4,3-c]pyrimidin-7-yloxy)-3-methylphenyl)amino)quinazolin-6-yl)-2-cyano-3-cyclopropylacrylamide: N-(4-((4-([1,2,4]triazolo[4,3-c]pyrimidin-7-yloxy)-3-methylphenyl)amino)quinazolin-6-yl)-2-cyanoacetamide (200 mg, 0.83 mmol) and cyclopropylcarbaldehyde (200 mg, 0.83 mmol) were dissolved in ethanol (35 mL), then piperidine acetate (200 mg, 0.83 mmol) was added, the mixture was stirred at room temperature for 4 hours, filtered, the filter cake was washed with a small amount of ethanol, dried in vacuum to give 100 mg yellow solid with a yield of 25.6%. LC-MS: 504.00 [M+H] detection value. 1H NMR (400 MHz, DMSO) δ 10.38 (s, 1H), 9.87 (s, 1H), 9.69 (s, 1H), 8.73 (s, 1H), 8.59 (d, J=8.4 Hz, 2H), 7.93 (d, J=8.8 Hz, 1H), 7.88-7.73 (m, 3H), 7.30-7.16 (m, 2H), 7.14 (s, 1H), 2.21 (s, 3H), 2.10-1.98 (m, 1H), 1.48-1.24 (m, 2H), 1.14-1.00 (m, 2H).

Embodiment 86

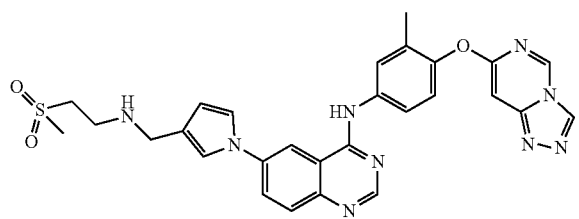 [SMILES: Cc1cc(Nc2ncnc3ccc(-n4ccc(CNCCS(C)(=O)=O)c4)cc23)ccc1Oc1cc2nncn2cn1]

Synthesis of N-(4-([1,2,4]triazolo[4,3-c]pyrimidin-7-yloxy)-3-methylphenyl)-6-(3-(((2-(methylsulfonyl)ethyl)amino)methyl)-1H-pyrrol-1-yl)quinazolin-4-amine Step A: preparation of (E)-N-(2-cyano-4-(3-formyl-1H-pyrrol-1-yl)phenyl)-N,N-dimethylformamidine: according to the method of Embodiment 83, wherein 1H-pyrrole was replaced with 1H-pyrrol-3-carboxaldehyde, the reaction was conducted at 110° C. under stirring for 16 hours.

Step B: preparation of 1-(4-((4-([1,2,4]triazolo[4,3-c]pyrimidin-7-yloxy)-3-methylphenyl)amino)quinazolin-6-yl)-1H-pyrrol-3-carbaldehyde: according to the method of Embodiment 7, wherein (R,E)-N-(2-cyano-4-((4-methyl-4,5-dihydrooxazol-2-yl)amino)phenyl)-N,N-dimethylformamidine was replaced with (E)-N-(2-cyano-4-(3-formyl-1H-pyrrol-1-yl)phenyl)-N,N-dimethylformamidine.

Step C: preparation of N-(4-([1,2,4]triazolo[4,3-c]pyrimidin-7-yloxy)-3-methylphenyl)-6-(3-(((2-(methylsulfonyl)ethyl)amino)methyl)-1H-pyrrol-1-yl)quinazolin-4-amine: according to the method of Embodiment 15, wherein 5-(4-((4-([1,2,4]triazolo[4,3-c]pyrimidine-7-yloxy)-3-methylphenyl)amino)quinazolin-6-yl)furan-2-carbaldehyde was replaced with 1-(4-((4-[1,2,4]triazolo[4,3-c]pyrimidin-7-yloxy)-3-methylphenyl)amino)quinazolin-6-yl)-1H-pyrrol-3-carbaldehyde. LC-MS: 569.8 [M+H] detection value. ¹H NMR (400 MHz, MeOD) δ 9.45 (d, J=1.2 Hz, 1H), 8.61-8.52 (m, 2H), 8.43 (s, 1H), 8.09 (dd, J=9.2, 2.4 Hz, 1H), 7.92 (d, J=9.2 Hz, 1H), 7.80 (d, J=2.4 Hz, 1H), 7.74 (dd, J=8.8, 2.4 Hz, 1H), 7.59 (s, 1H), 7.56-7.49 (m, 1H), 7.21 (d, J=8.8 Hz, 1H), 6.94 (d, J=1.2 Hz, 1H), 6.55-5.50 (m, 1H), 4.15 (s, 2H), 3.64-3.50 (m, 2H), 3.48-3.46 (m, 2H), 3.09 (s, 3H), 2.27 (s, 3H).

Embodiment 87

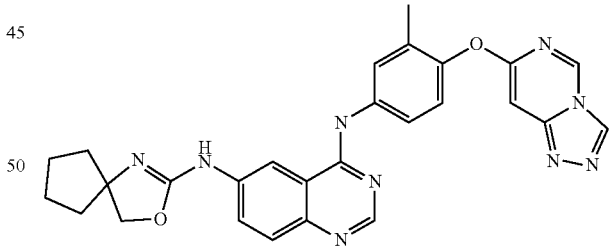

Synthesis of N⁴-(4-([1,2,4]triazolo[4,3-c]pyrimidin-7-yloxy)-3-methylphenyl)-N⁶-(3-oxo-1-azaspiro[4.4]non-1-en-2-yl)quinazolin-4,6-diamine According to the method of Embodiment 7, wherein (R)-2-amino-1-propanol was replaced with (1-aminocyclopentyl)methanol. LC-MS: 507.9 [M+H] detection value. ¹H NMR (400 MHz, MeOD) δ 9.44 (s, 1H), 8.50 (s, 1H), 8.43 (s, 1H), 8.20 (d, J=1.7 Hz, 1H), 7.84-7.64 (m, 4H), 7.19 (d, J=8.6 Hz, 1H), 6.94 (s, 1H), 4.40 (s, 2H), 2.26 (s, 3H), 2.00-1.92 (m, 2H), 1.92-1.76 (m, 4H), 1.77-1.57 (m, 2H).

Embodiment 88

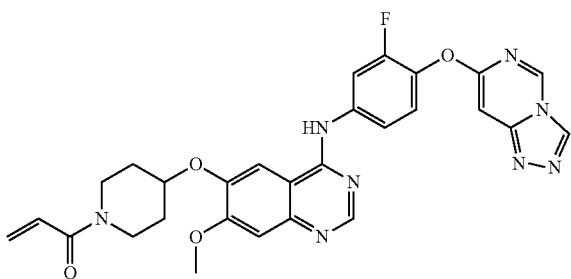 [SMILES: C=CC(=O)N1CCC(Oc2cc3c(Nc4ccc(Oc5cc6nncn6cn5)c(F)c4)ncnc3cc2OC)CC1]

Synthesis of 1-(4-((4-((4-([1,2,4]triazolo[4,3-c]pyrimidin-7-yloxy)-3-fluorophenyl)amino)-7-methoxyquinazolin-6-yl)oxy)piperidin-1-yl)prop-2-en-1-one Step A: preparation of 4-((4-([1,2,4]triazolo[4,3-c]pyrimidin-7-yloxy)-3-fluorophenyl)amino)-7-methoxyquinazolin-6-yl acetate: 4-chloro-7-methoxyquinazolin-6-yl acetate (421 mg, 1.67 mmol), 4-([1,2,4]triazolo[4,3-c]pyrimidin-7-yloxy)-3-fluoroaniline (250 mg, 1.02 mmol), potassium carbonate (400 mg, 2.89 mmol) were suspended in N,N-dimethylformamide (20 mL), the mixture was stirred at room temperature for 4 hours, then filtered and concentrated under reduced pressure, the residue was purified by column chromatography to give 300 mg white solid with a yield of 63.77%.

Step B: preparation of 4-((4-([1,2,4]triazolo[4,3-c]pyrimidin-7-yloxy)-3-fluorophenyl)amino)-7-methoxyquinazolin-6-ol: 4-((4-([1,2,4]triazolo[4,3-c]pyrimidin-7-yloxy)-3-fluorophenyl)amino)-7-methoxyquinazolin-6-yl acetate (260 mg, 0.56 mmol) was dissolved in methanol (15 mL), aqueous ammonia (1 mL) was added dropwise, the mixture was stirred at room temperature for 2 hours, then concentrated under reduced pressure to give 260 mg white solid, which was used directly in the next step.

Step C: preparation of tert-butyl 4-((4-((4-([1,2,4]triazolo[4,3-c]pyrimidin-7-yloxy)-3-fluorophenyl)amino)-7-methoxyquinazolin-6-yl)oxy)piperidin-1-carboxylate: 4-((4-([1,2,4]triazolo[4,3-c]pyrimidin-7-yloxy)-3-fluorophenyl)amino)-7-methoxyquinazolin-6-ol (250 mg, 0.60 mmol), tert-butyl 4-((methylsulfonyl)oxy)piperidin-1-carboxylate (363 mg, 1.30 mmol), potassium carbonate (121 mg, 0.88 mmol) were suspended in N,N-dimethylformamide (10 mL), the mixture was heated to 80° C. and stirred for 16 h, then filtered and concentrated under reduced pressure. The residue was purified by column chromatography to give 120 mg solid with a yield of 33.41%.

Step D: preparation of N-(4-([1,2,4]triazolo[4,3-c]pyrimidin-7-yloxy)-3-fluorophenyl)-7-methoxy-6-(piperidin-4-yloxy)quinazolin-4-amine: tert-butyl 4-((4-((4 ([1,2,4]triazolo[4,3-c]pyrimidin-7-yloxy)-3-fluorophenyl)amino)-7-methoxyquinazolin-6-yl)oxy)piperidin-1-carboxylate (100 mg, 0.16 mmol) was dissolved in a solution of 8% trifluoroacetic acid in dichloromethane (5 mL). The mixture was stirred at room temperature for 4 hours, concentrated under reduced pressure to give 100 mg of crude product which was used directly in the next step.

Step E: preparation of 1-(4-((4-((4-([1,2,4]triazolo[4,3-c]pyrimidin-7-yloxy)-3-fluorophenyl)amino)-7-methoxyquinazolin-6-yl)oxy)piperidin-1-yl)prop-2-en-1-one: N-(4-([1,2,4]triazolo[4,3-c]pyrimidin-7-yloxy)-3-fluorophenyl)-7-methoxy-6-(piperidin-4-yloxy)quinazolin-4-amine (100 mg, 0.20 mmol) obtained in the above step, HATU (143 mg, 0.38 mmol), acrylic acid (18 mg, 0.25 mmol), N,N-diisopropylethylamine (162 mg, 1.25 mmol) were dissolved in dichloromethane (5 mL), the mixture was stirred at room temperature for 16 hours. Water (20 mL) and ethyl acetate (40 mL) were added to the reaction solution, the resulting was shaken and allowed to stand was layered. The organic phase was taken, successively washed with water (20 mL) and saturated aqueous sodium chloride (20 mL), dried over anhydrous sodium sulfate, filtered, concentrated under reduced pressure and purified by preparative chromatography to give 30 mg pale yellow solid with a yield of 27.08%. LC-MS: 557.2 [M+H] detection value. $^1$H NMR (400 MHz, MeOD) δ 9.45 (s, 1H), 8.54 (s, 1H), 8.47 (s, 1H), 7.98 (dd, J=12.8, 2.4 Hz, 1H), 7.93 (s, 1H), 7.68-7.58 (m, 1H), 7.38 (t, J=8.8 Hz, 1H), 7.25 (s, 1H), 7.19 (s, 1H), 6.84 (dd, J=16.8, 10.8 Hz, 1H), 6.24 (dd, J=16.8, 2.0 Hz, 1H), 5.78 (dd, J=10.8, 2.0 Hz, 1H), 4.04 (s, 3H), 4.00-3.87 (m, 2H), 3.82-3.62 (m, 2H), 2.16-2.02 (m, 2H), 2.01-1.87 (m, 2H).

Embodiment 89

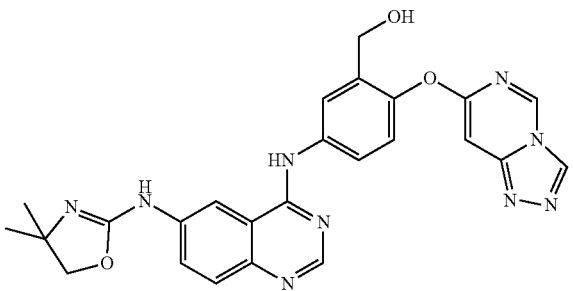 [SMILES: CC1(C)COC(Nc2ccc3ncnc(Nc4ccc(Oc5cc6nncn6cn5)c(CO)c4)c3c2)=N1]

Synthesis of $N^4$-(3-hydroxymethyl-4-([1,2,4]triazolo[4,3-c]pyrimidin-7-yloxy)phenyl)-$N^6$-(4,4-dimethyl-4,5-dihydrooxazol-2-yl)quinazolin-4,6-diamine According to the method of Embodiment 19, wherein 2-fluoro-4-nitro-phenol was replaced with 2-hydroxymethyl-4-nitro-phenol, the reaction was conducted at 100° C. under stirring for 16 hours. LC-MS: 498.2 [M+H] detection value. $^1$H NMR (400 MHz, DMSO) δ 9.64 (s, 2H), 8.56 (s, 1H), 8.45 (s, 1H), 8.01 (s, 2H), 7.89 (s, 2H), 7.64 (s, 2H), 7.15 (d, J=8.8 Hz, 1H), 7.09 (s, 1H), 5.23 (t, J=5.2 Hz, 1H), 4.48 (d, J=5.6 Hz, 2H), 4.06 (s, 2H), 1.27 (s, 6H).

Embodiment 90

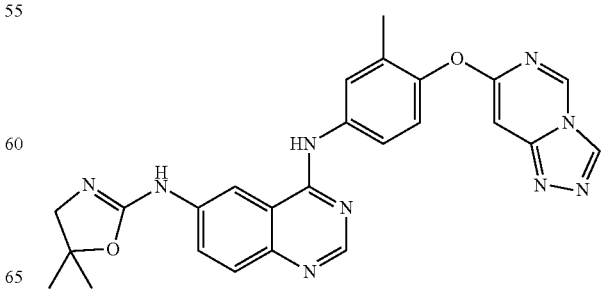

Synthesis of N⁴-(4-([1,2,4]triazolo[4,3-c]pyrimidin-7-yloxy)-3-methylphenyl)-N⁶-(5,5-dimethyl-4,5-dihydrooxazol-2-yl)quinazolin-4,6-diamine According to the method of Embodiment 7, wherein (R)-2-amino-1-propanol was replaced with 1-amino-2-methylpropan-2-ol. LC-MS: 482.2 [M+H] detection value. ¹H NMR (400 MHz, MeOD) δ 9.44 (d, J=1.2 Hz, 1H), 8.45 (s, 1H), 8.42 (s, 1H), 8.19 (s, 1H), 7.86-7.65 (m, 3H), 7.59 (dd, J=8.8, 2.4 Hz, 1H), 7.19 (d, J=8.8 Hz, 1H), 6.94 (d, J=1.2 Hz, 1H), 3.65 (s, 2H), 2.26 (s, 3H), 1.52 (s, 6H).

Embodiment 91

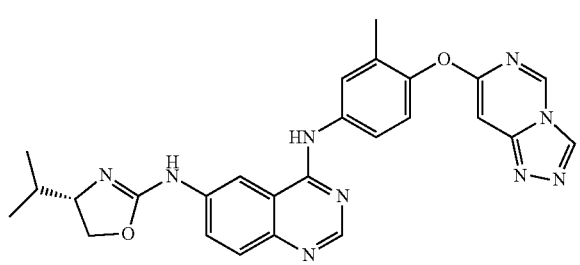 [SMILES: Cc1cc(Nc2ncnc3ccc(NC4=N[C@@H](C(C)C)CO4)cc23)ccc1Oc1cc2nncn2cn1]

Synthesis of (S)—N⁴-(4-([1,2,4]triazolo[4,3-c]pyrimidin-7-yloxy)-3-methylphenyl)-N⁶-(4-isopropyl-4,5-dihydrooxazol-2-yl)quinazolin-4,6-diamine According to the method of Embodiment 7, wherein (R)-2-amino-1-propanol was replaced with (S)-2-amino-3-methylbutan-1-ol. LC-MS: 496.3 [M+H] detection value. ¹H NMR (400 MHz, MeOD) δ 9.46 (d, J=1.2 Hz, 1H), 8.48 (s, 1H), 8.44 (s, 1H), 8.18 (s, 1H), 7.85-7.69 (m, 3H), 7.65 (dd, J=8.8, 2.4 Hz, 1H), 7.21 (d, J=8.8 Hz, 1H), 6.96 (d, J=1.2 Hz, 1H), 4.47 (t, J=8.8 Hz, 1H), 4.34-4.22 (m, 1H), 4.06-3.90 (m, 1H), 2.28 (s, 3H), 1.96-1.80 (m, 1H), 1.14-0.83 (m, 6H).

Embodiment 92

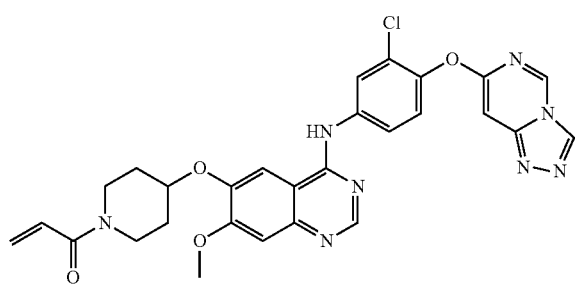 [SMILES: C=CC(=O)N1CCC(Oc2cc3c(Nc4ccc(Oc5cc6nncn6cn5)c(Cl)c4)ncnc3cc2OC)CC1]

Synthesis of 1-(4-((4-((4-([1,2,4]triazolo[4,3-c]pyrimidin-7-yloxy)-3-chlorophenyl)amino)-7-methoxyquinazolin-6-yl)oxy)piperidin-1-yl)prop-2-en-1-one According to the method of Embodiment 88, wherein 4-([1,2,4]triazolo[4,3-c]pyrimidin-7-yloxy)-3-fluoroaniline was replaced with 4-([1,2,4]triazolo[4,3-c]pyrimidin-7-yloxy)-3-chloroaniline. LC-MS: 574.2 [M+H] detection value. ¹H NMR (400 MHz, MeOD) 9.45 (d, J=1.2 Hz, 1H), 8.51 (s, 1H), 8.47 (s, 1H), 8.14 (d, J=2.4 Hz, 1H), 7.90 (s, 1H), 7.82 (dd, J=8.8, 2.4 Hz, 1H), 7.39 (d, J=8.8 Hz, 1H), 7.24 (s, 1H), 7.11 (d, J=1.2 Hz, 1H), 6.84 (dd, J=16.8, 10.8 Hz, 1H), 6.24 (dd, J=16.8, 2.0 Hz, 1H), 5.78 (dd, J=10.8, 2.0 Hz, 1H), 4.03 (s, 3H), 4.00-3.83 (m, 2H), 3.83-3.57 (m, 3H), 2.16-2.02 (s, 2H), 2.02-1.86 (s, 2H), 1.74-1.52 (m, 1H).

Embodiment 93

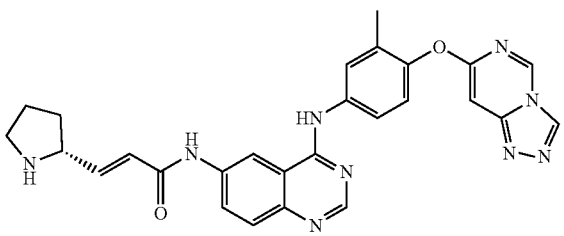 [SMILES: Cc1cc(Nc2ncnc3ccc(NC(=O)/C=C/[C@H]4CCCN4)cc23)ccc1Oc1cc2nncn2cn1]

Synthesis of (R,E)-N-(4-((4-([1,2,4]triazolo[4,3-c]pyrimidin-7-yloxy)-3-methylphenyl)amino)quinazolin-6-yl)-3-(1-methylpyrrolidin-2-yl)acrylamide Step A: preparation of diethyl (2-((4-((4-([1,2,4]triazolo[4,3-c]pyrimidin-7-yloxy)-3-methylphenyl)amino)quinazoline-6-yl)amino)-2-oxoethyl) phosphate: N-(4-([1,2,4]triazolo[4,3-c]pyrimidin-7-yloxy)-3-methylphenyl) quinazolin-4,6-diamine (270 mg, 0.70 mmol), 2-(diethoxyphosphoryl)acetic acid (276 mg, 1.41 mmol), 1-ethyl-(3-dimethylaminopropyl)carbodiimide hydrochloride (472 mg, 3.04 mmol), N,N-diisopropylethylamine (545 mg, 4.22 mmol) were dissolved in N,N-dimethylacetamide (5 mL), the mixture was heated to 50° C. and stirred for 16 hours, then cooled to room temperature, water (100 mL) and ethyl acetate (100 mL) were added. The mixture was shaken and allowed to stand to portion. The organic phase was taken, washed with saturated aqueous sodium chloride, dried over anhydrous sodium sulfate for 2 hours, filtered, and concentrated under reduced pressure. The residue was purified by column chromatography to give 350 mg viscous solid with a yield of 88.6%.

Step B: preparation of tert-butyl (R,E)-2-(3-((4-((4-([1,2,4]triazolo[4,3-c]pyrimidin-7-yloxy)-3-methylphenyl)amino)quinazolin-6-yl)amino)-3-oxoprop-1-en-1-yl)pyrrolidin-1-carboxylate:diethyl (2-((4-((4-([1,2,4]triazolo[4,3-c]pyrimidin-7-yloxy)-3-methylphenyl)amino)quinazoline-6-yl)amino)-2-oxoethyl) phosphate (123 mg, 0.69 mmol) was dissolved in tetrahydrofuran (5 mL), the solution was cooled to 0° C. under an ice bath, and sodium hydride (30 mg, 1.25 mmol) was added in portions under stirring. The reaction solution was stirred for 30 min. A solution of tert-butyl (R)-2-formylpyrrolidin-1-carboxylate (132 mg, 0.66 mmol) in tetrahydrofuran (5 mL) was added dropwise. After completion of the addition, the reaction solution was slowly warmed to room temperature and stirred for another 2 hours. Then 5% aqueous ammonium chloride solution (50 mL) and ethyl acetate (100 mL) were added to the reaction solution, the mixture was shaken and allowed to stand to portion. The organic phase was taken, successively washed water (50 mL) and saturated aqueous sodium chloride solution (50 mL), dried over anhydrous sodium sulfate, filtered and concentrated. The residue was purified by column chromatography to give 225 mg pale yellow solid with a yield of 69.4%.

Step C: preparation of (R,E)-N-(4-((4-([1,2,4]triazolo[4,3-c]pyrimidin-7-yloxy)-3-methylphenyl)amino)quinazolin-6-yl)-3-(1-methylpyrrolidin-2-yl)acrylamide: tert-butyl (R,E)-2-(3-((4-((4-([1,2,4]triazolo[4,3-c]pyrimidin-7-yloxy)-3-methylphenyl)amino)quinazolin-6-yl)amino)-3-oxoprop-1-en-1-yl)pyrrolidin-1-carboxylate (100 mg, 0.16 mmol) was dissolved in a solution of 8% trifluoroacetic acid in dichloromethane (10 mL). The reaction solution was stirred at room temperature for 4 hours, and concentrated under reduced pressure to give a crude product, which was purified by preparative HPLC to give 60 mg pale yellow solid with a yield of 71.8%. LC-MS: 508.3 [M+H] detection value.

$^1$H NMR (400 MHz, MeOD) δ 9.43 (s, 1H), 8.75 (s, 1H), 8.49 (s, 1H), 8.41 (s, 1H), 7.96-7.59 (m, 4H), 7.17 (d, J=8.8 Hz, 1H), 7.02 (dd, J=15.2, 7.6 Hz, 1H), 6.93 (s, 1H), 6.56 (d, J=15.2 Hz, 1H), 4.50-4.22 (m, 1H), 3.50-3.34 (m, 2H), 2.43-2.30 (m, 1H), 2.24 (s, 3H), 2.26-2.06 (m, 2H), 2.06-1.88 (m, 1H).

Embodiment 94

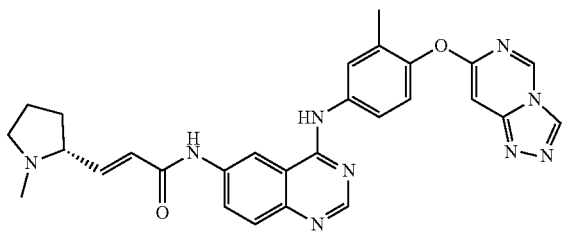 [SMILES: Cc1cc(Nc2ncnc3ccc(NC(=O)/C=C/[C@H]4CCCN4C)cc23)ccc1Oc1cc2nncn2cn1]

Synthesis of (R,E)-N-(4-((4-([1,2,4]triazolo[4,3-c]pyrimidin-7-yloxy)-3-methylphenyl)amino)quinazolin-6-yl)-3-(1-methylpyrrolidin-2-yl)acrylamide Step A: preparation of (R,E)-N-(4-((4-([1,2,4]triazolo[4,3-c]pyrimidin-7-yloxy)-3-methylphenyl)amino)quinazolin-6-yl)-3-(1-methylpyrrolidin-2-yl)acrylamide: (R,E)-N-(4-((4-([1,2,4]triazolo[4,3-c]pyrimidin-7-yloxy)-3-methylphenyl)amino)quinazolin-6-yl)-3-(pyrrolidin-2-yl)acrylamide (90 mg, 0.18 mmol) and 37% aqueous formaldehyde solution (216 mg) were dissolved in methanol (5 mL), the mixture was stirred at room temperature for 1 hour. Then sodium triacetoborohydride (266 mg, 1.25 mmol) was added to the reaction solution in portions. The resulting mixture was stirred at room temperature for 16 hours, then concentrated under reduced pressure and purified by preparative HPLC to give 80 mg pale yellow solid with a yield of 86.68%. LC-MS: 522.3 [M+H] detection value. $^1$H NMR (400 MHz, MeOD) δ 9.46 (s, 1H), 8.81 (s, 1H), 8.53 (s, 1H), 8.44 (s, 1H), 8.30 (s, 1H), 7.97-7.62 (m, 4H), 7.21 (d, J=8.8 Hz, 1H), 7.08-6.86 (m, 2H), 6.62 (d, J=14.8 Hz, 1H), 4.05-3.88 (m, 1H), 3.76-3.60 (m, 1H), 3.25-3.05 (m, 1H), 2.86 (d, J=3.6 Hz, 3H), 2.50-2.35 (m, 1H), 2.27 (s, 3H), 2.32-2.12 (m, 2H), 2.12-1.96 (m, 1H).

Embodiment 95

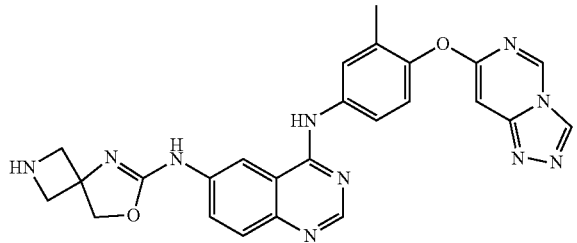 [SMILES: Cc1cc(Nc2ncnc3ccc(NC4=NC5(CNC5)CO4)cc23)ccc1Oc1cc2nncn2cn1]

Synthesis of N$^4$-(4-([1,2,4]triazolo[4,3-c]pyrimidin-7-yloxy)-3-methylphenyl)-N$^6$-(7-oxo-2,5-diazaspiro[3.4]dec-5-en-6-yl)quinazolin-4,6-diamine Step A: preparation of N$^4$-(4-([1,2,4]triazolo[4,3-c]pyrimidin-7-yloxy)-3-methylphenyl)-N6-(7-oxo-2,5-diazaspiro[3.4]dec-5-en-6-yl)quinazolin-4,6-diamine: tert-butyl 6-((4-((4-([1,2,4]triazolo[4,3-c]pyrimidin-7-yloxy)-3-methylphenyl)amino)quinazolin-6-yl)amino)-7-oxa-2,5-diazaspiro[3.4]dec-5-en-2-carboxylate (100 mg, 0.17 mmol) was dissolved in a solution of 8% trifluoroacetic acid in dichloromethane (5 mL), the mixture was stirred at room temperature for 4 hours, then concentrated under reduced pressure to give a crude product, which was purified by column chromatography to give 30 mg pale yellow solid with a yield of 36.07%. LC-MS: 495.2 [M+H] detection value. $^1$H NMR (400 MHz, MeOD) δ 9.46 (s, 1H), 8.71 (s, 1H), 8.57 (s, 1H), 8.46 (s, 1H), 8.29-8.05 (m, 1H), 7.96-7.60 (m, 3H), 7.38-7.18 (m, 1H), 7.01 (s, 1H), 4.70 (s, 2H), 4.40-4.35 (m, 4H), 2.31 (s, 3H).

Embodiment 96

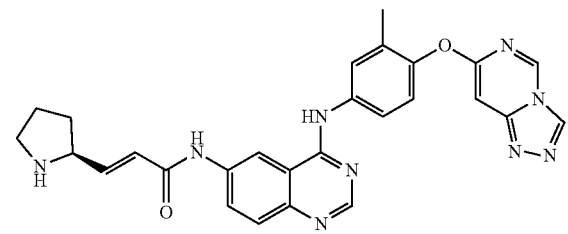 [SMILES: Cc1cc(Nc2ncnc3ccc(NC(=O)/C=C/[C@@H]4CCCN4)cc23)ccc1Oc1cc2nncn2cn1]

Synthesis of (S,E)-N-(4-((4-([1,2,4]triazolo[4,3-c]pyrimidin-7-yloxy)-3-methylphenyl)amino)quinazolin-6-yl)-3-(pyrrolidin-2-yl)acrylamide According to the method of Embodiment 93, wherein tert-butyl (R)-2-formylpyrrolidin-1-carboxylate was replaced with tert-butyl (S)-2-formylpyrrolidin-1-carboxylate. LC-MS: 508.25 [M+H] detection value. $^1$H NMR (400 MHz, MeOD) δ 9.47 (s, 1H), 8.81 (s, 1H), 8.54 (s, 1H), 8.45 (s, 1H), 8.42 (s, 1H), 8.06-7.66 (m, 4H), 7.23 (d, J=8.8 Hz, 1H), 7.07 (dd, J=15.2, 7.6 Hz, 1H), 6.97 (s, 1H), 6.59 (d, J=15.2 Hz, 1H), 4.38 (q, J=7.6 Hz, 1H), 3.56-3.38 (m, 2H), 2.49-2.34 (m, 1H), 2.29 (s, 3H), 2.35-2.10 (m, 2H), 2.09-1.90 (m, 1H).

Embodiment 97

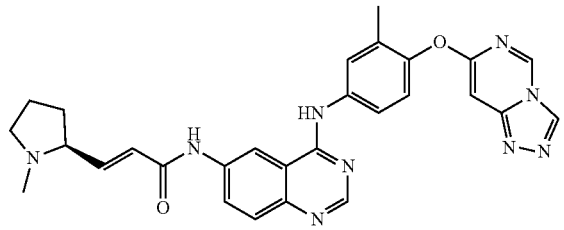 [SMILES: Cc1cc(Nc2ncnc3ccc(NC(=O)/C=C/[C@@H]4CCCN4C)cc23)ccc1Oc1cc2nncn2cn1]

(S,E)-N-(4-((4-([1,2,4]triazolo[4,3-c]pyrimidin-7-yloxy)-3-methylphenyl)amino)quinazolin-6-yl)-3-(1-methylpyrrolidin-2-yl)acrylamide According to the method of Embodiment 94. LC-MS: 522.3 [M+H] detection value. $^1$H NMR (400 MHz, DMSO) δ 10.44 (s, 1H), 9.83 (s, 1H), 9.67 (s, 1H), 8.81 (s, 1H), 8.56 (s, 1H), 8.53 (s, 1H), 7.99-7.64 (m, 4H), 7.18 (d, J=8.8 Hz, 1H), 7.12 (s, 1H), 6.75 (dd, J=15.2, 8.0 Hz, 1H), 6.39 (d, J=15.2 Hz, 1H), 2.60-2.22 (m, 4H), 2.16 (s, 3H), 2.07-2.04 (m, 2H), 1.88-1.71 (m, 2H), 1.72-1.51 (m, 2H).

Embodiment 98

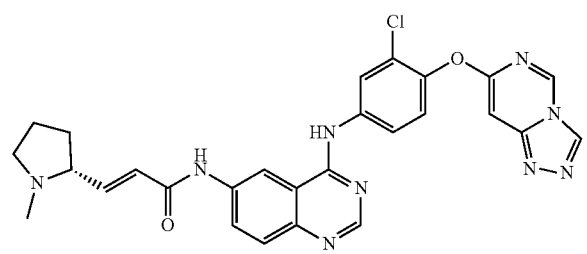 [SMILES: CN1CCC[C@@H]1/C=C/C(=O)Nc1ccc2ncnc(Nc3ccc(Oc4cc5nncn5cn4)c(Cl)c3)c2c1]

Synthesis of (R,E)-N-(4-((4-([1,2,4]triazolo[4,3-c]pyrimidin-7-yloxy)-3-chlorophenyl)amino)quinazolin-6-yl)-3-(1-methylpyrrolidin-2-yl)acrylamide Step A: preparation of N-(4-([1,2,4]triazolo[4,3-c]pyrimidin-7-yloxy)-3-chlorophenyl)-6-nitroquinazolin-4-amine: 4-([1,2,4]triazolo[4,3-c]pyrimidin-7-yloxy)-3-chloroaniline (200 mg, 0.76 mmol) and (E)-N'-(2-cyano-4-nitrophenyl)-N,N-dimethylformamidine (220 mg, 1.01 mmol) were dissolved in a mixed solvent of acetic acid (1.2 mL) and isopropyl acetate (3.6 mL). The reaction solution was stirred at room temperature for 48 hours. A large amount of solid precipitated, which were directly filtered. The filter cake was washed with a small amount of isopropyl acetate to give 290 mg more pure product with a yield of 91.6%.

Step B: Preparation of N-(4-([1,2,4]triazolo[4,3-c]pyrimidin-7-yloxy)-3-chlorophenyl)quinazolin-4,6-diamine: N-(4-([1,2,4]triazolo[4,3-c]pyrimidin-7-yloxy)-3-chlorophenyl)-6-nitroquinazolin-4-amine (240 mg, 0.55 mmol) was dissolved in methanol (20 mL), a small amount of Raney Nickel was added, the reaction system was purged for three times with argon. The reaction solution was stirred under 15 psi hydrogen atmosphere (hydrogen balloon) for 4 hours, filtered through celite and the filtrate was concentrated under reduced pressure to give 240 mg pale yellow solid, which was used directly in the next step.

According to the method of Embodiment 93, wherein N-(4-([1,2,4]triazolo[4,3-c]pyrimidin-7-yloxy)-3-methylphenyl)quinazolin-4,6-diamine was replaced with N-(4-([1,2,4]triazolo[4,3-c]pyrimidin-7-yloxy)-3-chlorophenyl)quinazolin-4,6-diamine.

The final product was prepared according to the method of Embodiment 94. LC-MS: 543.2 [M+H] detection value. $^1$H NMR (400 MHz, MeOD) δ 9.43 (s, 1H), 8.78 (s, 1H), 8.56 (s, 1H), 8.45 (s, 1H), 8.18 (s, 1H), 7.98-7.70 (m, 3H), 7.36 (d, J=8.8 Hz, 1H), 7.10 (s, 1H), 6.96-6.92 (m, 1H), 6.60 (d, J=15.2 Hz, 1H), 4.00-3.85 (m, 1H), 3.72-3.58 (m, 1H), 3.20-3.00 (m, 1H), 2.83 (s, 3H), 2.50-2.30 (m, 1H), 2.30-2.10 (m, 2H), 2.07-1.96 (m, 1H).

Embodiment 99

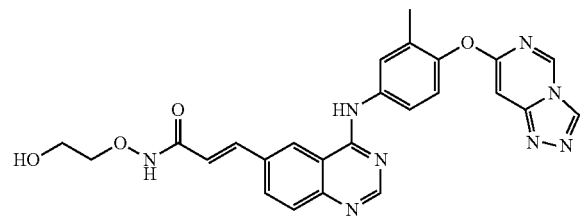 [SMILES: Cc1cc(Nc2ncnc3ccc(/C=C/C(=O)NOCCO)cc23)ccc1Oc1cc2nncn2cn1]

Synthesis of N-(4-((4-([1,2,4]triazolo[4,3-c]pyrimidin-7-yloxy)-3-methylphenyl)amino)quinazolin-6-yl)methacrylamide Step A: preparation of (E)-3-(4-((4-([1,2,4]triazolo[4,3-c]pyrimidin-7-yloxy)-3-methylphenyl)amino)quinazolin-6-yl)acrylic acid: N-(4-([1,2,4]triazolo[4,3-c]pyrimidin-7-yloxy)-3-methylphenyl)-6-iodoquinazolin-4-amine (500 mg, 1.01 mmol), acrylic acid (110 mg, 1.53 mmol), tris(dibenzylideneacetone)dipalladium (20 mg, 0.19 mmol), triethylamine (510 mg, 5.04 mmol) were dissolved in N,N-dimethylformamide (5 mL), the mixture was heated to 80° C. and stirred for 16 h, then filtered through celite and concentrated to dryness under reduced pressure. The residue was dissolved in N,N-dimethylformamide (5 mL) and the aqueous solution (10 mL) was slowly added dropwise under stirring. A large amount of solid precipitated, which was filtered. The filter cake was washed with a small amount of water and dried in vacuum to give 440 mg off-white solid, which was used directly in the next step.

Step B: preparation of N-(4-((4-([1,2,4]triazolo[4,3-c]pyrimidin-7-yloxy)-3-methylphenyl)amino)quinazolin-6-yl)methacrylamide: (E)-3-(4-((4-([1,2,4]triazolo[4,3-c]pyrimidin-7-yloxy)-3-methylphenyl)amino)quinazolin-6-yl)acrylic acid (150 mg, 0.34 mmol), 2-(aminooxy)ethanol (30 mg, 0.39 mmol), benzotriazole-1-yl-oxytripyrrolidinophosphonium hexafluorophosphate (250 mg, 0.48 mmol), triethylamine (90 mg, 0.89 mmol) were dissolved in N,N-dimethylformamide (5 mL) and the reaction solution was stirred at room temperature for 16 hours. Water (100 mL) and dichloromethane (100 mL) were added to the reaction solution, the resulting mixture was shaken and allowed to stand to portion. The organic phase was taken, washed with saturated aqueous sodium chloride solution, dried over anhydrous sodium sulfate for 2 hours, filtered, and concentrated under reduced pressure. The residue was purified by preparative HPLC to give 40 mg pale yellow solid with a yield of 23.51%. LC-MS: 500.2 [M+H] detection value. $^1$H NMR (400 MHz, CD$_3$OD) δ 9.44 (s, 1H), 8.55 (s, 2H), 8.42 (s, 1H), 8.14 (d, J=8.8 Hz, 1H), 7.88-7.68 (m, 4H), 7.20 (d, J=8.8 Hz, 1H), 6.94 (s, 1H), 6.63 (d, J=15.2 Hz, 1H), 4.11-3.94 (m, 2H), 3.82-3.73 (m, 2H), 2.25 (s, 3H).

Embodiment 100

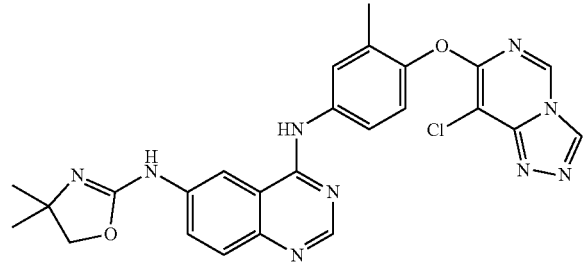 [SMILES: Cc1cc(Nc2ncnc3ccc(NC4=NC(C)(C)CO4)cc23)ccc1Oc1ncn2cnnc2c1Cl]

Synthesis of N$^4$-(4-((8-chloro-[1,2,4]triazolo[4,3-c]pyrimidin-7-yl)oxy)-3-methylphenyl)-N$^6$-(4,4-dimethyl-4,5-dihydrooxazol-2-yl)quinazolin-4,6-diamine Step A and B: according to the method of Embodiment 33, wherein 4,6-dichloro-5-methylpyrimidine was replaced with 4,5,6-trichloropyrimidine, the reaction was conducted at 8° C. under stirring for 2 hours.

Step C: preparation of 8-chloro-7-(2-methyl-4-nitrophenyloxy)-[1,2,4]triazolo[4,3-c]pyrimidine: according to the method of Embodiment 33, wherein cesium carbonate was replaced with potassium carbonate, the reaction was conducted under argon atmosphere for 5 hours.

Step D: preparation of 4-((8-chloro-[1,2,4]triazolo[4,3-c]pyrimidin-7-yl)oxy)-3-methy aniline: 8-chloro-7-(2-methyl-4-nitrophenyloxy)-[1,2,4]triazolo[4,3-c]pyrimidine (200 mg, 0.65 mmol) was dissolved in methanol (5 mL), Raney Nickel (30 mg) was added. The mixture was stirred at 10° C. for 1 hour under 15 psi hydrogen atmosphere (hydrogen balloon), then filtered and the filtrate was concentrated under reduced pressure to give 110 mg yellow oil which was used directly in the next step.

Step E: preparation of N$^4$-(4-((8-chloro-[1,2,4]triazolo[4,3-c]pyrimidin-7-yl)oxy)-3-methylphenyl)-N$^6$-(4,4-dimethyl-4,5-dihydrooxazol-2-yl)quinazolin-4,6-diamine: according to the method of Embodiment 33. LC-MS: 515.8 [M] detection value. $^1$H-NMR (400 MHz, CD$_3$OD) δ 9.33 (s, 1H), 8.52-8.51 (m, 2H), 8.28 (s, 1H), 8.23 (d, 1H, J=4.0 Hz), 7.78-7.67 (m, 3H), 7.20 (d, 1H, J=12.0 Hz), 4.29 (s, 2H), 2.23 (s, 3H), 1.46 (s, 6H).

Embodiment 101

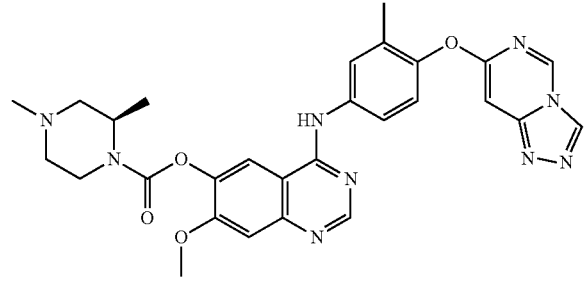 [SMILES: COc1cc2ncnc(Nc3ccc(Oc4cc5nncn5cn4)c(C)c3)c2cc1OC(=O)N1CCN(C)C[C@H]1C]

Synthesis of 4-((4-([1,2,4]triazolo[4,3-c]pyrimidin-7-yloxy)-3-methylphenyl)amino)-7-methoxyquinazolin-6-yl-(R)-2,4-dimethylpiperazin-1-carboxylate Step A: preparation of tert-butyl (R)-4-(chloroformyl)-3-methylpiperazin-1-carboxylate: triphosgene (148 mg, 0.50 mmol) was dissolved in dry dichloromethane (1.5 mL), the solution was cooled to 0° C., pyridine (118 mg, 1.49 mmol) and tert-butyl (3R)-3-methylpiperazin-1-carboxylate (100 mg, 0.50 mmol) were added dropwise, the reaction solution was slowly warmed to 11° C. and stirred for 3 hours, then concentrated under reduced pressure to give 131 mg yellow solid, which was used directly in the next step.

Step B: preparation of 1-(4-((4-([1,2,4]triazolo[4,3-c]pyrimidin-7-yloxy)-3-methylphenyl)amino)-7-methoxyquinazolin-6-yl)-4-tert-butyl-(R)-2-methylpiperazin-1,4-dicarboxylate: tert-butyl (R)-4-(chloroformyl)-3-methylpiperazin-1-carboxylate (138 mg, 0.53 mmol), 4-((4-([1,2,4]triazolo[4,3-c]pyrimidin-7-yloxy)-3-methylphenyl)amino)-7-methoxyquinazolin-6-ol (200 mg, 0.48 mmol) and potassium carbonate (140 mg, 1.01 mmol) were mixed in N,N-dimethylformamide (2 mL), the mixture was stirred at 80° C. for 20 hours, then filtered, the filtrate was concentrated under reduced pressure to give a crude product, which was purified by silica gel column chromatography to give 42 mg brown oil with yield of 13.6%.

Step C: preparation of 4-((4-([1,2,4]triazolo[4,3-c]pyrimidin-7-yloxy)-3-methylphenyl)amino)-7-methoxyquinazolin-6-yl-(R)-2-methylpiperazin-1-carboxylate: 1-(4-((4-[[1,2,4]triazolo[4,3-c]pyrimidin-7-yloxy)-3-methylphenyl)amino)-7-methoxyquinazolin-6-yl)-4-tert-butyl-(R)-2-methylpiperazin-1,4-dicarboxylate (42 mg, 0.07 mmol) was dissolved in dichloromethane (2 mL), trifluoroacetic acid (0.22 mL) was added under an ice bath, the reaction solution was stirred at 8° C. for 2.5 hours. Diisopropylethylamine (60 mg) was added to the reaction solution, and the reaction solution was evaporated to dryness under reduced pressure to give 35 mg orange oil which was used directly in the next step.

Step D: preparation of 4-((4-([1,2,4]triazolo[4,3-c]pyrimidin-7-yloxy)-3-methylphenyl)amino)-7-methoxyquinazolin-6-yl-(R)-2,4-dimethylpiperazin-1-carboxylate: 4 ((4-([1,2,4]triazolo[4,3-c]pyrimidin-7-yloxy)-3-methylphenyl)amino)-7-methoxyquinazolin-6-yl-(R)-2-methylpiperazin-1-carboxylate (35 mg, 0.06 mmol) was dissolved in dichloromethane (3 mL), aqueous formaldehyde (26 mg, 0.32 mmol, 37%) was added, the reaction solution was stirred at 8° C. for 30 minutes, then sodium cyanoborohydride (6 mg, 0.10 mmol) and methanol (0.1 mL) were added. The final reaction solution was stirred at 8° C. for 16 hours, then evaporated to dryness under reduced pressure to give a crude product, which was purified by silica gel column chromatography and preparative HPLC (containing 0.1% formic acid) to give 4.35 mg yellow solid with a yield of 12.1%. LC-MS: 555.9 [M+H] detection value. $^1$H-NMR (400 MHz, CD$_3$OD) δ 9.45 (s, 1H), 8.52 (s, 1H), 8.44 (s, 1H), 8.16 (s, 1H), 7.74 (m, 1H), 7.69 (dd, 1H, J=8.0, 4.0 Hz), 7.27 (s, 1H), 7.19 (d, 1H, J=8.0 Hz), 6.95 (s, 1H), 4.52 (m, 1H), 4.18-4.13 (m, 1H), 4.00 (s, 3H), 3.50-3.45 (m, 1H), 3.02 (d, 1H, J=12.0 Hz), 2.94 (d, 1H, J=12.0 Hz), 2.48-2.45 (m, 4H), 2.31-2.24 (m, 4H), 1.48-1.47 (d, 3H, J=4.0 Hz).

Embodiment 102

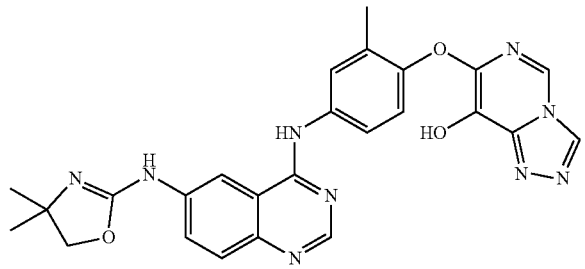 [SMILES: Cc1cc(Nc2ncnc3ccc(NC4=NC(C)(C)CO4)cc23)ccc1Oc1ncn2cnnc2c1O]

Synthesis of 7-(4-((6-((4,4-dimethyl-4,5-dihydrooxazol-2-yl)amino)quinazolin-4-yl)amino)-2-methylphenoxy)-[1,2,4]triazolo[4,3-c]pyrimidin-8-ol Step A: preparation of 7-(2-methyl-4-nitrophenyloxy)-[1,2,4]triazolo[4,3-c]pyrimidin-8-ol: this compound is the byproduct obtained in Step C of Embodiment 100.

According to the method of Embodiment 33. LC-MS: 497.9 [M+H] detection value. $^1$H-NMR (400 MHz, DMSO) δ 8.51 (s, 1H), 8.18 (s, 1H), 8.14 (s, 1H), 8.08 (s, 1H), 7.87 (s, 1H), 7.84 (d, 1H, J=12.0 Hz), 7.68-7.64 (m, 2H), 7.25 (d, 1H, J=8.0 Hz), 4.11 (s, 2H), 2.22 (s, 3H), 1.30 (s, 6H).

Embodiment 103

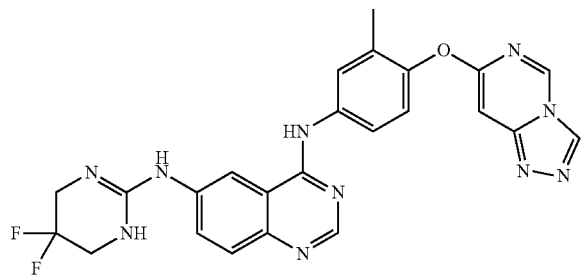 [SMILES: Cc1cc(Nc2ncnc3ccc(NC4=NCC(F)(F)CN4)cc23)ccc1Oc1cc2nncn2cn1]

Synthesis of $N^4$-(4-([1,2,4]triazolo[4,3-c]pyrimidin-7-yloxy)-3-methylphenyl)-$N^6$-(5,5-difluoro-1,4,5,6-tetrahydropyrimidin-2-yl)quinazolin-4,6-diamine Step A: preparation of 2,2-difluoromalonamide: ethyl 2,2-difluoromalonate (0.5 g, 2.55 mmol) was dissolved in methanol (5 mL), a solution of ammonia in ethanol (5.1 mL, 2 mmol/L) was added under an ice bath, the mixture was warmed to 15° C. and stirred for 16 hours. A precipitate generated. The reaction solution was concentrated under reduced pressure to give 345 mg white solid, which was used directly in the next step.

Step B: preparation of 2,2-difluoropropyl-1,3-diamine: 2,2-difluoromalonamide (460 mg, 3.33 mmol) was suspended in tetrahydrofuran (5 mL), the solution was cooled to 0° C., a solution of boron trifluoride-tetrahydrofuran (17 mL, 1 mmol/L) was added, the mixture became clear after warming to room temperature, then stirred at reflux under nitrogen atmosphere for 16 hours. The reaction solution was cooled to room temperature, methanol (17 mL) was added, and the mixture was stirred at room temperature for another 1 hour, then concentrated under reduced pressure to give a crude product, which was redissolved in methanol (17 mL) and concentrated under reduced pressure to 366.8 mg colorless oil, which was used directly in the next step.

Step C: preparation of 1-(3-amino-2,2-difluoro-propyl)-3-(3-cyano-4-((E)-dimethylaminomethyleneamino)phenyl)thiourea: thiocarbonyldiimidazole (498 mg, 2.79 mmol) was suspended in tetrahydrofuran (10 mL), the solution was cooled to 0° C., N-(4-amino-2-cyano-phenyl)-N,N-dimethylformamidine (478 mg, 2.54 mmol) was added. The mixture was stirred at 0° C. for 0.5 hour, then a solution of 2,2-difluoropropyl-1,3-diamine (366.8 mg, 2.00 mmol) in tetrahydrofuran (2 mL) was added. The mixture was warmed to 20° C. and stirred for 16 hours, then concentrated under reduced pressure to give a crude product, which was purified by silica gel column chromatography to give 280 mg yellow solid with a yield of 32.4%.

Step D: preparation of (E)-N-(2-cyano-4-((5,5-difluoro-1,4,5,6-tetrahydropyrimidin-2-yl)amino)phenyl)-N,N-dimethylformamidine: 1-(3-amino-2,2-difluoro-propyl)-3-(3-cyano-4-((E)-dimethylaminomethyleneamino)phenyl)thiourea (280 mg, 0.82 mmol) was suspended in acetonitrile (2 mL), the solution was cooled to 0° C., a solution of 2-chloro-3-ethylbenzothiazole tetrafluoroborate (332 mg, 1.23 mmol) in acetonitrile (2 mL) was added dropwise. The mixture was stirred at 0 to 10° C. for 1 hour, triethylamine (200 mg, 1.98 mmol) was added and the mixture became clear. The reaction solution was concentrated under reduced pressure to give a crude product, which was purified by silica gel column to give 100 mg orange oil with a yield of 39.7%.

Step E: preparation of $N^4$-(4-([1,2,4]triazolo[4,3-c]pyrimidin-7-yloxy)-3-methylphenyl)-$N^6$-(5,5-difluoro-1,4,5,6-tetrahydropyrimidin-2-yl)quinazolin-4,6-diamine: according to the method of Embodiment 7, wherein (R,E)-N-(2-cyano-4-((4-methyl-4,5-dihydrooxazol-2-yl)amino)phenyl)-N,N-dimethylformamidine was replaced with (E)-N'-(2-cyano-4-((5,5-difluoro-1,4,5,6-tetrahydropyrimidin-2-yl)amino)phenyl)-N, N-dimethylformamidine. LC-MS: 502.8 [M+H] detection value. $^1$H-NMR (400 MHz, CDCl$_3$) δ 9.68 (s, 1H), 9.64 (s, 1H), 8.59 (s, 1H), 8.51 (s, 1H), 8.24 (s, 2H), 7.83 (d, 1H, J=4.0 Hz), 7.78 (dd, 1H, J=12.0, 4.0 Hz), 7.73-7.71 (m, 1H), 7.68-7.66 (m, 1H), 7.19 (d, 1H, J=8.0 Hz), 7.12 (s, 1H), 3.64-3.57 (m, 2H), 2.55 (s, 2H), 2.19 (s, 3H).

Embodiment 104

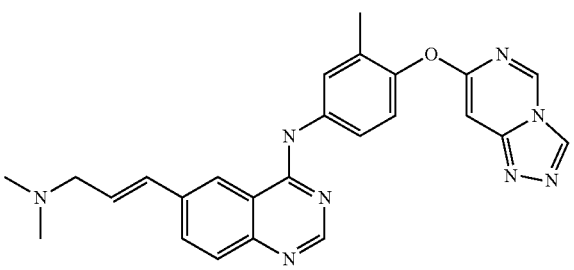 [SMILES: Cc1cc(Nc2ncnc3ccc(/C=C/CN(C)C)cc23)ccc1Oc1cc2nncn2cn1]

Synthesis of (E)-N-(4-([1,2,4]triazolo[4,3-c]pyrimidin-7-yloxy)-3-methylphenyl)-6-(3-(dimethylamino)propyl-1-en-1-yl)quinazolin-4-amine Step A: preparation of (E)-N-(4-([1,2,4]triazolo[4,3-c]pyrimidin-7-yloxy)-3-methylphenyl)-6-(3-(dimethylamino)

propyl-1-en-1-yl)quinazolin-4-amine: 6-((E)-3-aminopropyl-1-enyl)-N-(3-methyl-4-([1,2,4]triazolo[4,3-c]pyrimidin-7-yloxy)phenyl)quinazolin-4-amine trifluoroacetate (200 mg, 0.47 mmol) and aqueous formaldehyde (192 mg, 37%, 2.37 mmol) were mixed in ethanol (2 mL), the mixture was stirred at 25° C. for 10 minutes, then sodium borohydride (302 mg, 1.41 mmol) was added. The final reaction solution was stirred at 25° C. for 16 hours, then evaporated to dryness under reduced pressure to give a crude product, which was purified by silica gel column and preparative liquid phase to give 12.22 mg yellow solid with a yield of 5.7%. LC-MS: 453.2 [M+H] detection value. $^1$H-NMR (400 MHz, CD$_3$OD) δ 9.43 (s, 1H), 8.53 (s, 1H), 8.48 (s, 1H), 8.42 (s, 1H), 8.04 (d, 1H, J=8.0 Hz), 7.77-7.72 (m, 3H), 7.18 (d, 1H, J=8.0 Hz), 7.08 (d, 1H, J=12.0 Hz), 6.94 (s, 1H), 6.62-6.55 (m, 1H), 3.97 (d, 2H, J=8.0 Hz), 2.94-2.81 (m, 6H), 2.25 (s, 3H).

Embodiment 105

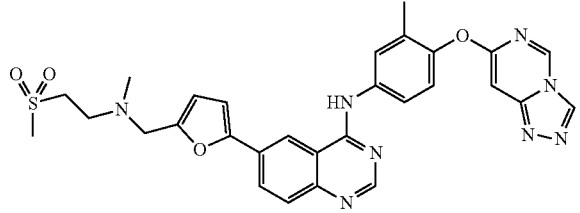 [SMILES: Cc1cc(Nc2ncnc3ccc(-c4ccc(CN(C)CCS(C)(=O)=O)o4)cc23)ccc1Oc1cc2nncn2cn1]

Synthesis of N-(4-([1,2,4]triazolo[4,3-c]pyrimidin-7-yloxy)-3-methylphenyl)-6-(5-((methyl(2-methylsulfonyl)ethyl)amino)methyl)furan-2-yl)quinazolin-4-amine According to the method of Embodiment 15, wherein 2-methylsulfonylethylamino hydrochloride was replaced with N-methyl-2-methylsulfonylethylamine. LC-MS: 584.8 [M+H] detection value. $^1$H-NMR (400 MHz, DMSO-d$_6$) δ 9.97 (s, 1H), 9.69 (s, 1H), 8.79 (s, 1H), 8.59 (d, 2H, J=8 Hz), 8.17 (d, 1H, J=8 Hz), 7.84-7.79 (m, 3H), 7.22 (d, 1H, J=8 Hz), 7.15 (s, 1H), 7.10 (s, 1H), 6.58 (s, 1H), 3.72 (s, 2H), 3.35-3.33 (m, 2H), 3.07 (s, 3H), 2.86-2.84 (m, 2H), 2.30 (s, 3H), 2.21 (s, 3H).

Embodiment 106

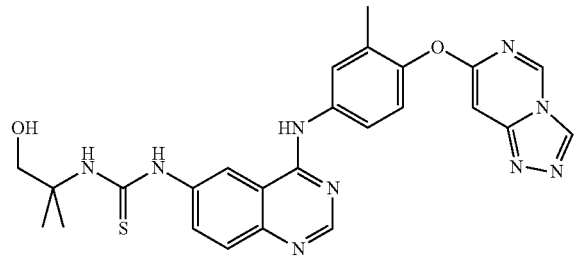 [SMILES: Cc1cc(Nc2ncnc3ccc(NC(=S)NC(C)(C)CO)cc23)ccc1Oc1cc2nncn2cn1]

Synthesis of 1-(4-((4-([1,2,4]triazolo[4,3-c]pyrimidin-7-yloxy)-3-methylphenyl)amino)quinazolin-6-yl)-3-(1-hydroxy-2-methylpropan-2-yl)thiourea Step A: preparation of 1-(4-((4-((4-([1,2,4]triazolo[4,3-c]pyrimidin-7-yloxy)-3-methylphenyl)amino)quinazolin-6-yl)-3-(1-hydroxy-2-methylpropan-2-yl)thiourea: according to the method of Embodiment 7, wherein (R,E)-N'-(2-cyano-4-((4-methyl-4,5-dihydrooxazol-2-yl)amino)phenyl)-N,N-dimethylformamidine was replaced with (Z)—N'-(2-cyano-4-(3-(1-hydroxy-2-methylpropan-2-yl)thioureido)phenyl)-N,N-dimethylformimidamide. LC-MS: 515.9 [M+H] detection value. $^1$H-NMR (400 MHz, DMSO-d$_6$) δ 9.74 (s, 1H), 9.66 (s, 1H), 8.58-8.57 (d, 1H, J=4 Hz), 8.39 (s, 1H), 7.87-7.73 (m, 3H), 7.49 (s, 1H), 7.20-7.13 (m, 3H), 6.66 (s, 1H), 3.25 (m, 2H), 1.92 (s, 3H), 1.48 (s, 6H).

Embodiment 107

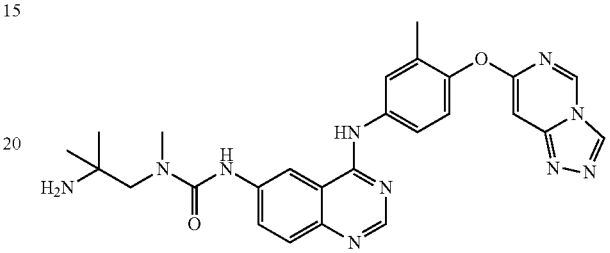

Synthesis of 3-(4-((4-([1,2,4]triazolo[4,3-c]pyrimidin-7-oxy)-3-methylphenyl)amino)quinazolin-6-yl)-1-(2-amino-2-methylpropan)-1-carbamoylamide Step A: preparation of tert-butyl (1-hydroxy-2-methylpropan-2-)carbamate: 2-amino-2-methyl-1-propanol (4.5 g, 50.56 mmol), sodium bicarbonate (8.4 g, 100 mmol) and sodium carbonate (10.6 g, 100 mmol) were mixed in a 250 mL reaction flask, a mixture of dioxane and water (160 mL, 3:1) was added, the reaction solution was cooled below 0° C. under an ice bath, a solution of di-tert-butyl dicarbonate (13.1 g, 59.82 mmol) in dioxane (5 mL) was added dropwise under stirring. After completion of the addition, the reaction solution was stirred for 6 hours. After completion of the reaction, dioxane was evaporated under reduced pressure, the residue was extracted with ethyl acetate. The organic phase was washed with saturated brine, dried over anhydrous sodium sulfate and concentrated. The residue was purified by silica gel column chromatography to give 8.2 g product with a yield of 85.77%.

Step B: preparation of tert-butyl (2-methyl-1-carbonylpropan-2-)carbamate: tert-butyl (1-hydroxy-2-methylpropan-2-)carbamate (1.0 g, 5.29 mmol) was dissolved in 20 mL dichloromethane in a reaction flask, the solution was cooled to about 0° C. under an ice bath, Dess-Martin reagent (4.49 g, 10.58 mmol) was added in portions, and the mixture was stirred at room temperature for 18 hours. After completion of the reaction, a saturated solution of sodium bicarbonate and sodium sulfite was added, the mixture was extracted with dichloromethane. The organic phase was dried over anhydrous sodium sulfate and filtered. The filtrate was evaporated to dryness under reduced pressure to give 0.8 g product with a yield of 80.81%.

Step C: preparation of tert-butyl (2-methyl-1-methylaminopropan-2-)carbamate: tert-butyl (2-methyl-1-carbonylpropan-2-)carbamate (1.3 g, 6.95 mmol) and methylamine hydrochloride (1.8 g, 26.87 mmol) were dissolved in 15 mL methanol in a 100 mL single-neck flask. The reaction solution was stirred under an ice bath, diisopropylethylamine (3.6 g, 27.91 mmol) was added and the reaction solution was stirred at room temperature for 4 hours. After completion of the reaction, the reaction solution was concentrated to give a solid, which was added to 20 mL dichloromethane, sodium cyanoborohydride (1.0 g, 15.87 mmol) was added in portions under an ice bath while stirring. The reaction solution was stirred at room temperature for 18 hours. Upon completion of the reaction, the reaction was quenched with saturated sodium bicarbonate solution and extracted with dichloromethane. The organic phase was dried over anhydrous sodium sulfate, filtered, concentrated to give 1.35 g oil as crude product.

Step D: preparation of tert-butyl (E)-(1-(3-(3-cyano-4-(((dimethylamino)methylene)amino)phenyl)-1-carbamoyl)-2-methylpropan-2-carbamate: phenyl (E)-(3-cyano-4-(((dimethylamino)methylene)amino)phenyl)carbamate (400 mg, 1.30 mmol) and tert-butyl (2-methyl-1-methylaminopropan-2-)carbamate (1.05 g, 5.17 mmol) were dissolved in 2 mL tetrahydrofuran in a sealed tube. The reaction solution was heated to 65° C. and stirred for 18 hours, then evaporated under reduced pressure. The residue was purified by column chromatography to give 300 mg of product with a yield of 55.50%.

Step E: preparation of tert-butyl (1-(3-(4-((-([1,2,4]triazolo[4,3-c]pyrimidin-7-yloxy)-3-methylphenyl)amino)quinazolin-6-yl)-1-carbamoyl)-2-methylpropan-2-carbamate: according to the method of Embodiment 7, wherein (R,E)-N-(2-cyano-4-((4-methyl-4,5-dihydrooxazol-2-yl)amino)phenyl)-N,N-dimethylformamidine was replaced with tert-butyl (E)-(1-(3-(3-cyano-4-(((dimethylamino)methylene)amino)phenyl)-1-carbamoyl)-2-methylpropan-2-carbamate. $^{1}$H-NMR (400 MHz, DMSO-$d_6$) δ 9.78 (s, 1H), 9.58 (s, 1H), 8.71 (s, 1H), 8.53 (s, 1H), 8.47 (s, 1H), 8.37 (s, 1H), 7.85 (d, 1H, J=4 Hz), 7.71 (d, 1H, J=4 Hz), 7.17 (d, 1H, J=4 Hz), 7.03 (s, 1H), 6.66 (s, 1H), 3.55 (s, 2H), 3.08 (s, 3H), 2.16 (s, 3H), 1.34 (s, 9H), 1.21 (s, 6H).

Step F: preparation of 3-(4-((4-([1,2,4]triazolo[4,3-c]pyrimidin-7-oxy)-3-methylphenyl)amino)quinazolin-6-yl)-1-(2-amino-2-methylpropan)-1-carbamoylamide: tert-butyl (1-(3-(4-((-([1,2,4]triazolo[4,3-c]pyrimidin-7-yloxy)-3-methylphenyl)amino)quinazolin-6-yl)-1-carbamoyl)-2-methylpropan-2-carbamate (80 mg, 0.13 mmol) and a solution of 10% trifluoroacetic acid in dichloromethane (2 mL) were added to a sealed tube, the reaction solution was stirred at room temperature for 2 hours. After completion of the reaction, the reaction solution was evaporated under reduced pressure and the residue was purified by column chromatography to give 1.68 mg yellow solid. LC-MS: 512.9 [M+H] detection value.

mmol) and triethyl orthoacetate (20 mL) were added to a reaction flask, a small amount of p-toluenesulfonic acid (5 mg) was added, the reaction solution was warmed to 130° C. and stirred for 18 hours. Additional p-toluenesulfonic acid (10 mg) was added and the reaction solution was warmed to 140° C. and stirred for another 18 hours. After completion of the reaction, the reaction solution was evaporated under reduced pressure and the residue was purified by silica gel column chromatography to give 1.0 g product with a yield of 57.18%.

Step B: preparation of 3-methyl-7-(2-methyl-4-nitrophenoxy)-[1,2,4]triazolo[4,3-c]pyrimidine: 7-chloro-3-methyl-[1,2,4]triazolo[4,3-c]pyrimidine (1.0 g, 5.93 mmol) and 2-methyl-4-nitrophenol (1.25 g, 8.16 mmol) were added to a reaction flask, anhydrous sodium carbonate (1.4 g, 13.21 mmol) and 30 mL N,N-dimethylformamide were added. The reaction solution was warmed to 80° C. and stirred for 36 hours. After completion of the reaction, ethyl acetate was added and the mixture was filtered. The filtrate was evaporated to dryness under reduced pressure and the residue was purified by silica gel column chromatography to give 1.1 g product with a yield of 65.09%.

Step C: preparation of 3-methyl-7-(2-methyl-4-aminophenoxy)-[1,2,4]triazolo[4,3-c]pyrimidine: 3-methyl-7-(2-methyl-4-nitrophenoxy)-[1,2,4]triazolo[4,3-c]pyrimidine (1.1 g, 3.86 mmol) was dissolved in a mixed solvent of methanol:ethyl acetate (2:1,150 mL). A small amount of Raney nickel was added, the reaction solution was stirred under hydrogen atmosphere (hydrogen balloon) at room temperature for 4 hours. After completion of the reaction, the reaction solution was filtered. The filtrate was evaporated to dryness under reduced pressure and the residue was purified by silica gel column chromatography to give 700 mg product with a yield of 71.12%.

Step D: preparation of $N^6$-(4,4-dimethyl-4,5-dihydrooxazol-2-yl)-$N^4$-(3-methyl-4-((3-methyl-[1,2,4]triazolo[4,3-c]pyrimidin-7-yl)oxy)phenyl)quinazolin-4,6-diamine: according to the method of Embodiment 7, wherein 3-methyl-4([1,2,4]triazolo[1,4,c]pyrimidin-7-oxy)aniline was replaced with 3-methyl-7-(2-methyl-4-aminophenoxy)-[1,2,4]triazolo[4,3-c]pyrimidine. LC-MS: 495.9 [M+H] detection value. $^{1}$H-NMR (400 MHz, DMSO-$d_6$) δ 9.58 (s, 1H), 9.52 (s, 1H), 8.48 (s, 1H), 8.04 (s, 1H), 7.83-7.78 (m, 2H), 7.69-7.66 (m, 2H), 7.17-7.15 (d, 1H, J=8 Hz), 6.96 (s, 1H), 4.28 (s, 2H), 2.47 (s, 3H), 2.18 (s, 3H), 1.30 (s, 6H).

Embodiment 108

Embodiment 109

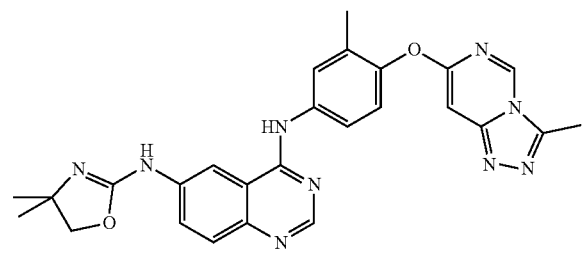

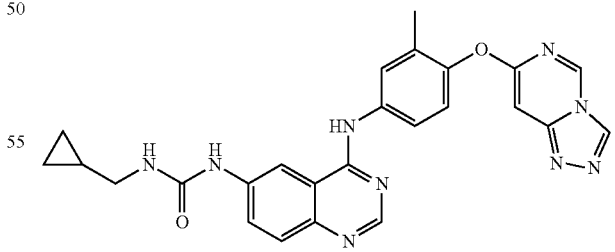

Synthesis of $N^6$-(4,4-dimethyl-4,5-dihydrooxazol-2-)—$N^4$-(3-methyl-4-((3-methyl-[1,2,4]triazolo[4,3-c]pyrimidin-7-)oxy)phenyl)-4,6-diaminoquinazoline Synthesis of 1-(4-((4-([1,2,4]triazolo[4,3-c]pyrimidin-7-yloxy)-3-methylphenyl)amino)quinazolin-6-yl)-3-(cyclopropylmethyl)urea Step A: preparation of 7-chloro-3-methyl-[1,2,4]triazolo[4,3-c]pyrimidine: 4-chloro-6-pyrimidine (1.5 g, 3.47

Step A: preparation of (E)-N-(2-cyano-4-(3-(cyclopropylmethyl)ureido)phenyl)-N,N-dimethylformamidine: phenyl (E)-(3-cyano-4-(((dimethylamino)methylene)amino)phenyl)carbamate (530 mg, 1.50 mmol) was dissolved in 5 mL tetrahydrofuran, cyclopropylmethylamine (400 mg, 5.63 mmol) was added. The reaction solution was heated to 65° C. and stirred for 18 hours. After completion of the reaction, the reaction solution was evaporated under reduced pressure and the residue was purified by column chromatography to give 260 mg solid with a yield of 60.7%.

Step B: preparation of I-(4-((4-([1,2,4]triazolo[4,3-c]pyrimidin-7-yloxy)-3-methylphenyl)amino)quinazolin-6-yl)-3-(cyclopropylmethyl)urea: according to the method of Embodiment 7, wherein (R,E)-N-(2-cyano-4-((4-methyl-4,5-dihydrooxazol-2-yl)amino)phenyl)-N,N-dimethylformamidine was replaced with (E)-N-(2-cyano-4-(3-(cyclopropylmethyl)ureido)phenyl)-N,N-dimethylformamidine. LC-MS: 482.9 [M+H] detection value. $^1$H-NMR (400 MHz, DMSO-$d_6$) δ 9.75 (s, 1H), 9.30 (s, 1H), 8.62 (s, 1H), 8.51 (s, 1H), 8.19 (s, 1H), 7.92 (d, 1H, J=8 Hz), 7.66-7.73 (m, 2H), 7.59 (d, 1H, J=8 Hz), 7.45 (d, 1H, J=8 Hz), 7.28 (s, 1H), 6.71 (s, 1H), 3.04 (t, 2H, J=8 Hz), 2.27 (s, 3H), 1.01-0.98 (m, 1H), 0.46-0.44 (m, 2H), 0.22-0.21 (m, 2H).

Embodiment 110

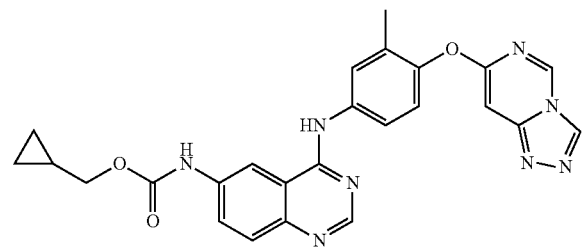 [SMILES: Cc1cc(Nc2ncnc3ccc(NC(=O)OCC4CC4)cc23)ccc1Oc1cc2nncn2cn1]

Synthesis of cyclopropylmethyl (4-((4-([1,2,4]triazolo[4,3-c]pyrimidin-7-oxy)-3-methylphenyl)amino)quinazolin-6-)carbamate Step A: preparation of cyclopropylmethyl (E)-3-(cyano-4-(((dimethylamino)methylene)amino)phenyl)carbamate: sodium hydride (57 mg, 2.38 mmol) was added to 3 mL anhydrous tetrahydrofuran, a solution of cyclopropyl methanol (240 mg, 3.33 mmol) in tetrahydrofuran was added dropwise under argon atmosphere and the mixture was stirred under an ice bath for 30 minutes. Then phenyl (E)-(3-cyano-4-(((dimethylamino)methylene)amino)phenyl)carbamate (150 mg, 0.43 mmol) was added and the reaction solution was stirred at room temperature for 18 hours. The reaction solution was quenched with saturated sodium bicarbonate solution, extracted with ethyl acetate, dried, concentrated and the residue was purified by column chromatography to give 120 mg solid with a yield of 98.8%.

Step B: Preparation of cyclopropylmethyl (4-((4-([1,2,4]triazolo[4,3-c]pyrimidin-7-oxy)-3-methylphenyl)amino)quinazolin-6-)carbamate: according to the method of Embodiment 7, wherein (R,E)-N'-(2-cyano-4-((4-methyl-4,5-dihydrooxazol-2-yl)amino)phenyl)-N,N-dimethylformamidine was replaced with cyclopropylmethyl (E)-(3-cyano-4-(((dimethylamino)methylene)amino)phenyl)carbamate. LC-MS: 483.9 [M+H] detection value. $^1$H-NMR (DMSO-$d_6$) δ 9.94 (s, 1H), 9.51 (s, 1H), 9.17 (s, 1H), 8.48 (s, 1H), 8.39 (s, 1H), 7.71-7.67 (m, 2H), 7.36 (s, 1H), 7.32 (d, 1H, J=8 Hz), 6.78 (d, 1H, J=8 Hz), 3.99 (d, 2H, J=8 Hz), 2.15 (s, 3H), 1.24-1.20 (m, 1H), 0.58-0.56 (m, 2H), 0.35-0.34 (m, 2H).

Embodiment 111

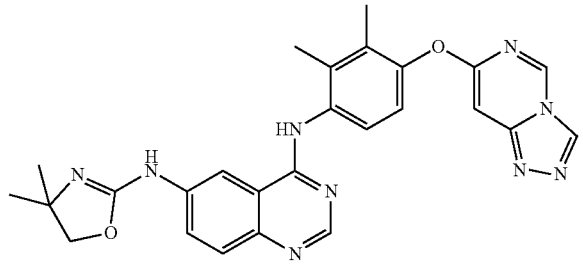 [SMILES: Cc1c(Nc2ncnc3ccc(NC4=NC(C)(C)CO4)cc23)ccc(Oc2cc3nncn3cn2)c1C]

Synthesis of $N^4$-(2,3-dimethyl-4-([1,2,4]triazolo[4,3-c]pyrimidin-7-yloxy)phenyl)-$N^6$-(4,4-dimethyl-4,5-dihydrooxazol-2-yl)quinazolin-4,6-diamine According to the method of Embodiment 19, wherein 2-fluoro-4-nitro-phenol was replaced with 2,3-dimethyl-4-nitro-phenol, sodium bicarbonate was replaced with sodium carbonate, the reaction was conducted at 80° C. under stirring for 16 hours. LC-MS: 495.9 [M+H] detection value. $^1$H NMR (400 MHz, DMSO) δ 9.67 (s, 1H), 9.40 (s, 1H), 8.58 (s, 1H), 8.29 (s, 1H), 8.18 (s, 1H), 7.99 (s, 1H), 7.63 (s, 2H), 7.26 (d, J=8.4 Hz, 1H), 7.14 (s, 1H), 7.06 (d, J=8.4 Hz, 1H), 4.06 (s, 2H), 2.14 (s, 6H), 1.28 (s, 6H).

Embodiment 112

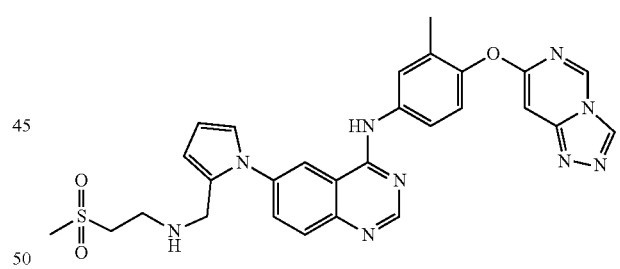

Synthesis of N-(4-([1,2,4]triazolo[4,3-c]pyrimidin-7-yloxy)-3-methylphenyl)-6-(2-(((2-(methylsulfonyl)ethyl)amino)methyl)-1H-pyrrol-1-yl)quinazolin-4-amine According to the method of Embodiment 86, wherein 1H-pyrrol-3-carbaldehyde was replaced with 1H-pyrrol-2-carbaldehyde. LC-MS: 570.8 [M+H] detection value. $^1$H NMR (400 MHz, MeOD) δ 9.46 (s, 1H), 8.65 (s, 1H), 8.52 (s, 1H), 8.45 (s, 1H), 8.05-7.94 (m, 2H), 7.82 (d, J=2.4 Hz, 1H), 7.79-7.73 (m, 1H), 7.23 (d, J=8.8 Hz, 1H), 7.10-7.18 (m, 1H), 6.97 (d, J=1.2 Hz, 1H), 6.58-6.48 (m, 1H), 6.44-6.32 (m, 1H), 4.13 (s, 2H), 3.33-3.26 (m, 2H), 3.24-3.17 (m, 2H), 2.94 (s, 3H), 2.29 (s, 3H).

Embodiment 113

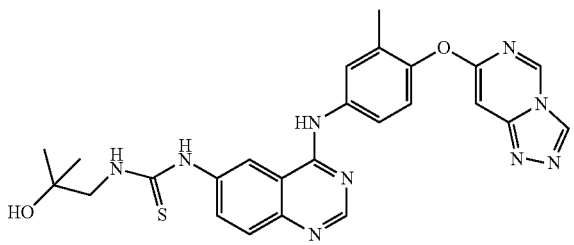 [SMILES: Cc1cc(Nc2ncnc3ccc(NC(=S)NCC(C)(C)O)cc23)ccc1Oc1cc2nncn2cn1]

Synthesis of 1-(4-((4-([1,2,4]triazolo[4,3-c]pyrimidin-7-yloxy)-3-methylphenyl)amino)quinazolin-6-yl)-3-(2-hydroxy-2-methylpropyl)thiourea According to the method of Embodiment 7, wherein (R)-2-amino-1-propanol was replaced with 1-amino-2-methylpropan-2-ol. LC-MS: 515.8 [M+H] detection value. $^1$H NMR (400 MHz, MeOD) δ 9.44 (d, J=1.2 Hz, 1H), 8.52 (s, 1H), 8.42 (s, 1H), 7.89 (d, J=8.8 Hz, 1H), 7.85-7.73 (m, 2H), 7.71 (d, J=8.4 Hz, 1H), 7.19 (d, J=8.8 Hz, 1H), 6.94 (d, J=1.2 Hz, 1H), 3.71 (s, 2H), 2.26 (s, 3H), 1.27 (s, 6H).

Embodiment 114

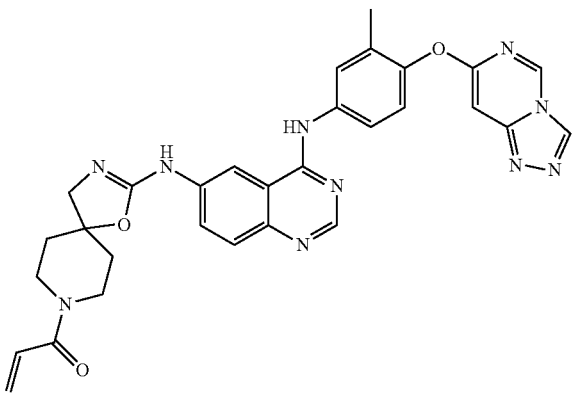 [SMILES: C=CC(=O)N1CCC2(CC1)CN=C(Nc1ccc3ncnc(Nc4ccc(Oc5cc6nncn6cn5)c(C)c4)c3c1)O2]

Synthesis of 1-(2-((4-((4-([1,2,4]triazolo[4,3-c]pyrimidin-7-yloxy)-3-methylphenyl)amino)quinazolin-6-yl)amino)-1-oxa-3,8-diazaspiro[4,5]dec-2-en-8-yl)-2-acrylamide Step A: Preparation of N$^4$-(4-([1,2,4]triazolo[4,3-c]pyrimidin-7-yloxy)-3-methylphenyl)-N$^6$-(1-oxa-3,8-diazaspiro[4.5]dec-2-en-2-yl)quinazolin-4,6-diamine: tert-butyl 1-(2-((4-((4-([1,2,4]triazolo[4,3-c]pyrimidin-7-yloxy)-3-methylphenyl)amino)quinazolin-6-yl)amino)-1-oxa-3,8-diazaspiro[4.5]decyl-2-ene-8-yl)prop-2-en-1-one (300 mg, 0.22 mmol) was dissolved in 10 mL anhydrous dichloromethane, 1 mL trifluoroacetic acid was added, the reaction solution was stirred at room temperature for 18 hours in a sealed tube. Upon completion of the reaction monitored by TLC, 4% ammonia-ethanol solution was added until the mixture was basic, then the mixture was concentrated to dryness, and purified by column chromatography to give 230 mg crude product, which was used directly in the next step.

Step B: preparation of 1-(2-((4-((4-([1,2,4]triazolo[4,3-c]pyrimidin-7-yloxy)-3-methylphenyl)amino)quinazolin-6-yl)amino)-1-oxa-3,8-diazaspiro[4,5]dec-2-en-8-yl)-2-acrylamide: according to the method of Embodiment 16, wherein 2-fluoroacrylic acid was replaced with acrylic acid, the reaction was conducted under argon atmosphere at 60° C. for 18 hours. LC-MS: 577.3 [M+H] detection value.

Embodiment 115

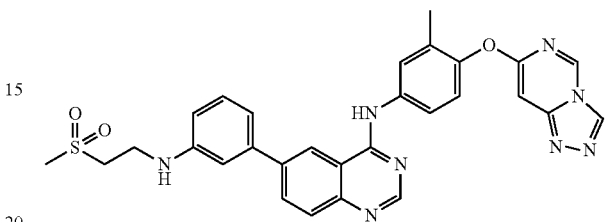

Synthesis of N-(4-([1,2,4]triazolo[4,3-c]pyrimidin-7-yloxy)-3-methylphenyl)-6-(3-((2-(methylsulfonyl)ethyl)phenyl)quinazolin-4-amine Step A: preparation of 2-(methylsulfonyl)acetaldehyde: 2-(methylsulfonyl)ethanol (500 mg, 4.03 mmol) was dissolved in 10 mL anhydrous dichloromethane in a 50 mL single-neck flask, Dess-Martin reagent (2.5 g, 5.90 mmol) was added in portions under an ice bath. The reaction solution was stirred at room temperature under argon atmosphere for 18 hours. After completion of the reaction, the reaction solution was filtered. The filter cake was washed with a small amount of anhydrous dichloromethane, dried over anhydrous sodium sulfate and filtered, evaporated under reduced pressure to give a crude product, which was used directly in the next step.

Step B: preparation of N-(4-([1,2,4]triazolo[4,3-c]pyrimidin-7-yloxy)-3-methylphenyl)-6-(3-((2-(methylsulfonyl)ethyl)phenyl)quinazolin-4-amine: N-(4-([1,2,4-c]pyrimidin-7-yloxy)-3-methylphenyl)-6-(3-aminophenyl)quinazolin-4-amine (130 mg, 0.28 mmol) and 2-(methylsulfonyl)acetaldehyde (100 mg) were dissolved in 5 mL dichloromethane. Sodium triacetoxyborohydride (500 mg, 2.36 mmol) was added under argon atmosphere and stirred for 18 hours. Upon completion of the reaction, the reaction solution was evaporated under reduced pressure, washed with sodium bicarbonate and extracted with ethyl acetate. The organic phase was dried over anhydrous sodium sulfate, filtered and concentrated, the residue was isolated as 2.1 mg pale yellow solid. LC-MS: 567.2 [M+H] detection value.

Embodiment 116

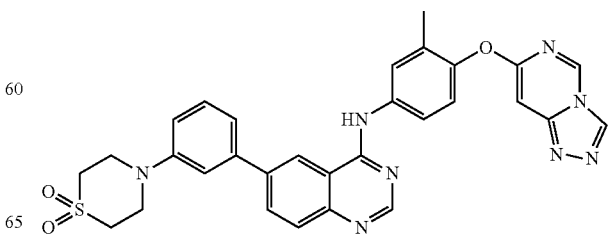

Synthesis of 4-(3-(4-((4-([1,2,4]triazolo[4,3-c]pyrimidin-7-yloxy)-3-methylphenyl)amino)quinazolin-6-yl)phenyl)thiomorpholin-1,1-dioxide Step A: Preparation of 4-(3-bromophenyl)thiomorpholin-1,1-dioxide: 1,3-dibromobenzene (1.6 g, 6.81 mmol), thiomorpholine dioxide (300 mg, 2.22 mmol) BINAP (300 mg, 0.48 mmol), cesium carbonate (2.5 g, 23.67 mmol) and palladium acetate (150 mg) were dissolved in 10 mL dry toluene in a 50 mL single-neck flask. The reaction solution was heated to 90° C. under argon atmosphere and stirred for 18 hours. After completion of the reaction, the reaction solution was filtered, the filtrate was evaporated to dryness under reduced pressure, and the residue was purified by column chromatography to give 90 mg product, which was directly used in the next step.

Step B: preparation of 4-(3-(4-((4-([1,2,4]triazolo[4,3-c]pyrimidin-7-yloxy)-3-methylphenyl)amino)quinazolin-6-yl)phenyl)thiomorpholin-1,1-dioxide: The above product (90 mg, 0.31 mmol), N-(4-([1,2,4]triazolo[4,3-c]pyrimidin-7-yloxy)-3-methylphenyl)-6-(4,4,5,5-tetramethyl-1,3,2-dioxaborolan-2-yl)-4-aminoquinazoline (145 mg, 0.29 mmol), sodium bicarbonate (180 mg, 2.14 mmol) and [1,1'-bis(diphenylphosphino)ferrocene]dichloropalladium (50 mg) were added to 5 mL N,N-dimethylformamide. The reaction solution was heated to 90° C. under argon atmosphere and stirred for 18 hours. After completion of the reaction, the reaction solution was evaporated under reduced pressure, washed with sodium bicarbonate and extracted with ethyl acetate. The organic phase was dried over anhydrous sodium sulfate, filtered and concentrated. The residue was isolated to give 38 mg pale yellow solid with a yield of 22.4%. LC-MS: 579.2 [M+H] detection value. $^1$H-NMR (400 MHz, DMSO-$d_6$) δ 9.96 (s, 1H), 9.68 (s, 1H), 8.82 (s, 1H), 8.62 (s, 1H), 8.59 (m, 2H), 8.24 (d, 1H, J=8 Hz), 7.89-7.80 (m, 3H), 7.48-7.44 (m, 2H), 7.35-7.33 (m, 1H), 7.23 (d, 1H, J=8 Hz), 7.14 (m, 2H), 3.93 (m, 4H), 3.20 (m, 4H), 2.22 (s, 3H).

Embodiment 117

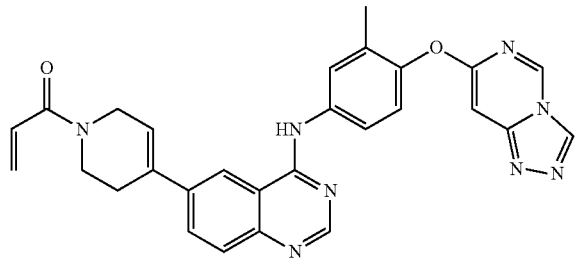 [SMILES: C=CC(=O)N1CC=C(c2ccc3ncnc(Nc4ccc(Oc5cc6nncn6cn5)c(C)c4)c3c2)CC1]

Synthesis of 1-(4-(4-((4-([1,2,4]triazolo[4,3-c]pyrimidin-7-yloxy)-3-methylphenyl)amino)quinazolin-6-yl)-5,6-dihydropyridin-1(2H)-yl)prop-2-en-1-one Step A: preparation of N-(4-([1,2,4]triazolo[4,3-c]pyrimidin-7-yloxy)-3-methylphenyl)-6-(4,4,5,5-tetramethyl-1,3,2-dioxyborolan-2-yl)quinazolin-4-amine: N4-(4-([1,2,4]triazolo[4,3-c]pyrimidin-7-yloxy)-3-methylphenyl)-6-iodoquinazolin-4-amine (1.0 g, 4.04 mmol), 4,4,5,5-tetramethyl-1,3,2-dioxaborolane (2.0 g, 7.88 mmol), potassium acetate (600 mg, 6.12 mmol) and [1,1'-bis(diphenylphosphino)ferrocene] dichloropalladium (300 mg) were added to 25 mL N,N-dimethylformamide. The reaction solution was heated to 90° C. under argon atmosphere and stirred for 18 hours. After the completion of reaction, the reaction solution was evaporated under reduced pressure, washed with sodium bicarbonate and extracted with ethyl acetate. The organic phase was dried over anhydrous sodium sulfate, filtered and concentrated. The residue was purified by column chromatography to give 1.5 g gray solid with a yield of 75.0%.

Step B: preparation of tert-butyl 4-(4-((4-([1,2,4]triazolo[4,3-c]pyrimidin-7-yloxy)-3-methylphenyl)amino)quinazolin-6-yl)-5,6-dihydropyridin-1(2H)-carbamate: tert-butyl 4-bromo-5,6-dihydropyridin-1(2l)-carbamate (200 mg, 0.76 mmol), N-(4-([1,2,4]triazolo[4,3-c]pyrimidin-7-yloxy)-3-methylphenyl)-6-(4,4,5,5-tetramethyl-1,3,2-dioxyborolan-2-yl)quinazolin-4-amine (300 mg, 0.61 mmol), sodium bicarbonate (150 mg, 1.79 mmol) and [1,1'-bis(diphenylphosphino)ferrocene]dichloropalladium (50 mg) were added to 10 mL N,N-dimethylformamide. The reaction solution was heated to 90° C. under argon atmosphere and stirred for 18 hours. After completion of the reaction, the reaction solution was evaporated under reduced pressure, washed with sodium bicarbonate and extracted with ethyl acetate. The organic phase was dried over anhydrous sodium sulfate, filtered and concentrated. The residue was purified by column chromatography to give 200 mg pale yellow solid with a yield of 59.9%.

Step C: preparation of N-(4-([1,2,4]triazolo[4,3-c]pyrimidin-7-yloxy)-3-methylphenyl)-6-(1,2,3,6-tetrahydropyridin-4-yl)quinazolin-4-amine: tert-butyl 4-(4-((4 ([1,2,4]triazolo[4,3-c]pyrimidin-7-yloxy)-3-methylphenyl)amino) quinazolin-6-yl)-5,6-dihydropyridin-1(2H)-carbamate (200 mg, 0.40 mmol) and 5 mL of a solution of 10% trifluoroacetic acid in dichloromethane were added into a sealed tube. The reaction solution was stirred at room temperature for 4 hours. Upon completion of the reaction, the reaction solution was concentrated under reduced pressure and the residue was purified by column chromatography to give 170 mg solid.

Step D: preparation of 1-(4-(4-((4-([1,2,4]triazolo[4,3-c]pyrimidin-7-yloxy)-3-methylphenyl)amino)quinazolin-6-yl)-5,6-dihydropyridin-1(2H)-yl)prop-2-en-1-one: according to the method of Embodiment 16, wherein 2-fluoroacrylic acid was replaced with acrylic acid, the reaction was conducted under argon atmosphere at 60° C. for 18 hours. LC-MS: 505.3 [M+H] detection value. $^1$H-NMR (400 MHz, DMSO-$d_6$) δ 9.89 (s, 1H), 9.68 (s, 1H), 8.59-8.52 (m, 2H), 8.06-8.02 (m, 1H), 7.79-7.77 (m, 2H), 7.23 (d, 1H, J=8 Hz), 7.14 (s, 1H), 7.00-6.95 (m, 1H), 6.47-6.45 (m, 1H), 6.19 (d, 1H, J=16 Hz), 5.76 (d, 1H, J=8 Hz), 5.35-5.32 (m, 1H), 4.39-4.30 (m, 2H), 3.89-3.86 (m, 2H), 2.76-2.73 (m, 2H), 2.22 (s, 3H), 2.03-1.99 (m, 2H).

Embodiment 118

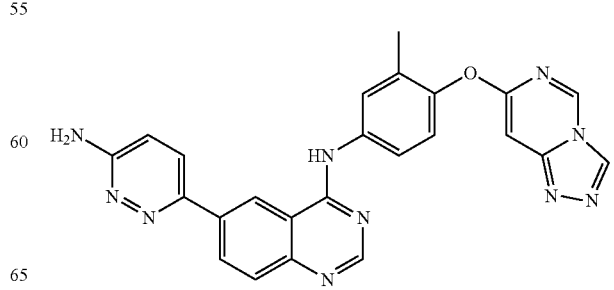

173

Synthesis of N-(4-([1,2,4]triazolo[4,3-c]pyrimidin-7-yloxy)-3-methylphenyl)-6-(6-aminopyridazin-3-yl)quinazolin-4-amine Step A: preparation of (E)-N-(4-(6-aminopyridazin-3-yl)-2-cyanophenyl)-N,N-dimethylformamidine: 6-bromo-3-pyridazinamine (77 mg, 0.44 mmol), (E)-N-(2-cyano-4-(4,4,5,5-tetramethyl-1,3,2-dioxaborolan-2-yl)phenyl)-N,N-dimethylformamidine (120 mg, 0.40 mmol), [1,1'-bis(diphenylphosphino)ferrocene]dichloropalladium dichloromethane complex (32 mg, 0.04 mmol) and cesium carbonate (391 mg, 1.2 mmol) were dissolved in N,N-dimethylformamide (8 mL) and water (0.8 mL), the mixture was stirred at 85° C. under argon atmosphere for 4 hours, then filtered and concentrated to give a residue which was purified by column chromatography to give 90 mg yellow solid with a yield of 84%.

Step B: preparation of N-(4-([1,2,4]triazolo[4,3-c]pyrimidin-7-yloxy)-3-methylphenyl)-6-(6-aminopyridazin-3-yl)quinazolin-4-amine: (E)-N-(4-(6-aminopyridazin-3-yl)-2-cyanophenyl)-N,N-dimethylformamidine (80 mg, 0.3 mmol) and 4-([1,2,4]triazolo[4,3-c]pyrimidin-7-yloxy)-3-methylaniline (73 mg, 0.3 mmol) were dissolved in isopropyl acetate (4 mL) and acetic acid (1 mL), the mixture was stirred at room temperature for 48 hours, then concentrated under reduced pressure. The residue was purified by column chromatography to give 68 mg yellow solid with a yield of 49%. LC-MS: 463.2 [M+H] detection value. $^1$H NMR (400 MHz, DMSO) δ 10.04 (s, 1H), 9.68 (d, 1H, J=1.2 Hz), 9.06 (d, 1H, J=1.6 Hz), 8.62 (s, 1H), 8.59 (s, 1H), 8.56 (dd, 1H, J=8.8, 1.6 Hz), 8.07 (d, 1H, J=9.2 Hz), 7.88 (d, 1H, J=8.8 Hz), 7.83-7.80 (m, 2H), 7.23 (d, 1H, J=8.4 Hz), 7.14 (d, 1H, J=1.2 Hz), 6.98 (d, 1H, J=9.2 Hz), 6.63 (s, 2H), 2.22 (s, 3H).

Embodiment 119

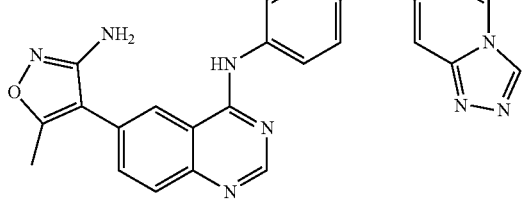

Synthesis of 4-(4-((4-([1,2,4]triazolo[4,3-c]pyrimidin-7-yloxy)-3-methylphenyl)amino)quinazolin-6-yl)-5-methylisoxazol-3-amine According to the method of Embodiment 118, wherein 6-bromo-3-pyridazinamine was replaced with 4-bromo-5-methylisoxazol-3-amine. LC-MS: 466.2 [M+H] detection value. 1H NMR (400 MHz, DMSO) δ 10.07 (s, 1H), 9.67 (s, 1H), 8.67 (s, 1H), 8.59 (s, 1H), 8.51 (s, 1H), 7.87 (s, 2H), 7.77-7.75 (m, 2H), 7.22 (d, 1H, J=8.4 Hz), 7.15 (s, 1H), 5.59 (s, 2H), 2.37 (s, 3H), 2.19 (s, 3H).

174

Embodiment 120

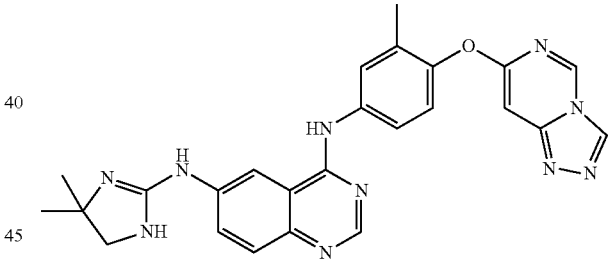

Synthesis of 1-(5-(4-((4-([1,2,4]triazolo[4,3-c]pyrimidin-7-yloxy)-3-methylphenyl)amino)quinazolin-6-yl)-3,6-dihydropyridin-1(2H)-yl)prop-2-en-1-one According to the method of Embodiment 117, wherein tert-butyl 4-bromo-5,6-dihydropyridin-1(2H)-carbamate was replaced with tert-butyl 3-bromo-5,6-dihydropyridin-1(2H)-carbamate. LC-MS: 503.3 [M+H] detection value. $^1$H NMR (400 MHz, DMSO) δ 9.68 (s, 1H), 8.66 (s, 1H), 8.60 (s, 1H), 8.56 (s, 1H), 8.09 (d, 1H, J=8.4 Hz), 7.81 (d, 1H, J=8.8 Hz), 7.75-7.73 (m, 2H), 7.25 (d, 1H, J=8.8 Hz), 7.16 (s, 1H), 7.09-6.91 (m, 1H), 6.64 (d, 1H, J=13.6 Hz), 6.21 (t, 1H, J=16.0 Hz), 5.76 (d, 1H, J=9.2 Hz), 4.64 (s, 2H), 3.79-3.77 (m, 2H), 2.45-2.40 (m, 2H), 2.22 (s, 3H).

Embodiment 121

Synthesis of N$^6$-(4,4-dimethyl-1,5-dihydroimidazol-2-yl)-N$^4$-(3-methyl-4-([1,2,4]triazolo[4,3-c]pyrimidin-7-yloxy)phenyl)quinazolin-4,6-diamine Step A: preparation of N$^6$-(4,4-dimethyl-1,5-dihydroimidazol-2-yl)-N$^4$-(3-methyl-4-([1,2,4]triazolo[4,3-c]pyrimidin-7-yloxy)phenyl)quinazolin-4,6-diamine: 2-chloro-3-ethyl-1,3-benzoxazole tetrafluoroborate (177 mg, 0.66 mmol) was added to a solution of 1-(2-amino-2-methylpropyl)-3-(4-(3-methyl-4-([1,2,4]triazolo[4,3-c]pyrimidin-7-yloxy)anilino)quinazolin-6-yl)thiourea (140 mg, 0.27 mL) in acetonitrile (12 mL). The reaction solution was warmed to room temperature and stirred for 16 hours. Triethylamine (2 mL) was added to the reaction solution and the resulting mixture was stirred at room temperature for another 1 hour, then concentrated under reduced pressure to give a crude product, which was purified by acidic preparative HPLC to give 25 mg pale yellow solid with a yield of 19.1%. LC-MS: 480.9 [M+H] detection value. $^1$H NMR (400 MHz, DMSO)

9.66 (s, 2H), 8.58 (s, 1H), 8.53 (s, 1H), 8.25 (s, 1H), 8.15 (s, 1H), 7.91-7.77 (m, 2H), 7.74 (d, 1H, J=8.0 Hz), 7.56 (d, 1H, J=8.0 Hz), 7.18 (d, 1H, J: 8.0 Hz), 7.11 (s, 1H), 3.30 (s, 2H), 2.19 (s, 3H), 1.30 (s, 6H).

Embodiment 122

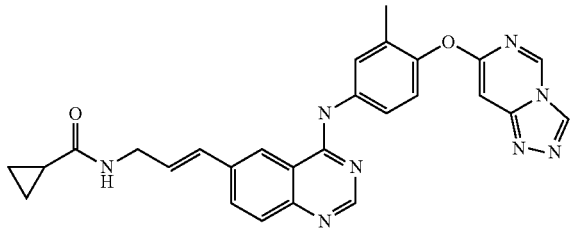 [SMILES: Cc1cc(Nc2ncnc3ccc(/C=C/CNC(=O)C4CC4)cc23)ccc1Oc1cc2nncn2cn1]

Synthesis of (E)-N-(3-(4-((4-([1,2,4]triazolo[4,3-c]pyrimidin-7-yloxy)-3-methylphenyl)amino)quinazolin-6-yl)allyl)cyclopropylcarboxamide According to the condensation method of Embodiment 23, the reaction was conducted at 25° C. under stirring for 16 hours. LC-MS: 493.2 [M+H] detection value. $^1$H-NMR (400 MHz, DMSO) δ 9.92 (s, 1H), 9.66 (s, 1H), 8.58-8.57 (m, 2H), 8.44 (d, 1H, J=4.0 Hz), 8.00 (d, 1H, J=12.0 Hz), 7.79 (s, 1H), 7.75 (d, 1H, J=8.0 Hz), 7.21 (d, 1H, J=8.0 Hz), 7.12 (s, 1H), 6.68 (d, 1H, J=16.0 Hz), 6.53 (dd, 1H, J=16.0, 8.0 Hz), 3.99 (d, 2H, J=8.0 Hz), 2.20 (s, 3H), 1.65-1.60 (m, 1H), 1.26-1.23 (m, 2H), 0.74-0.71 (m, 2H).

Embodiment 123

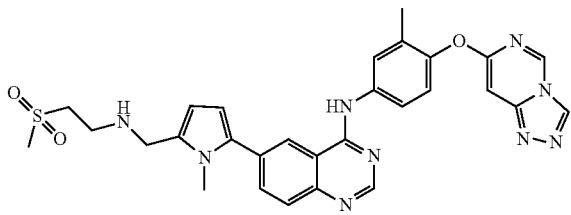 [SMILES: Cc1cc(Nc2ncnc3ccc(-c4ccc(CNCCS(C)(=O)=O)n4C)cc23)ccc1Oc1cc2nncn2cn1]

Synthesis of N-(4-([1,2,4]triazolo[4,3-c]pyrimidin-7-yloxy)-3-methylphenyl)-6-(1-methyl-5-(((2-(methylsulfonyl)ethyl)amino)methyl)-1H-pyrrol-2-yl)quinazolin-4-amine Step A: preparation of (E)-N-(2-cyano-4-(5-formyl-1-methyl-1H-pyrrol-2-yl)phenyl)-N,N-dimethylformamidine: (E)-N-(2-cyano-4-iodophenyl)-N,N-dimethylformamidine (330 mg, 1.10 mmol), 1-methyl-1H-pyrrol-2-formaldehyde (242 mg, 2.22 mmol), potassium carbonate (310 mg, 2.24 mmol), palladium acetate (30 mg, 0.13 mmol) were suspended in N,N-dimethylacetamide (15 mL), the reaction solution was heated to 135° C. and stirred for 16 hours, then filtered and purified by silica gel column to give 100 mg solid with a yield of 32.3%.

Step B: preparation of 5-(4-((4-([1,2,4]triazolo[4,3-c]pyrimidin-7-yloxy)-3-methylphenyl)amino)quinazolin-6-yl)-1-methyl-1H-pyrrol-2-carbaldehyde: 7-(2-methyl-4-aminophenoxy)-[1,2,4]triazolo[4,3-c]pyrimidine (90 mg, 0.37 mmol) and (E)-N'-(2-cyano-4-(5-formyl-1-methyl-1H-pyrrol-2-yl)phenyl)-N,N-dimethylformamidine (100 mg, 0.36 mmol) were dissolved in acetic acid (0.5 mL) and isopropyl acetate (1 mL), the reaction solution was stirred at room temperature for 48 hours, then concentrated under reduced pressure and purified by silica gel column to give 105 mg solid with a yield of 61.8%.

Step C: preparation of N-(4-([1,2,4]triazolo[4,3-c]pyrimidin-7-yloxy)-3-methylphenyl)-6-(1-methyl-5-(((2-(methylsulfonyl)ethyl)amino)methyl)-1H-pyrrol-2-yl)quinazolin-4-amine: according to the method of Embodiment 15, wherein 5-(4-((4 ([1,2,4]triazolo[4,3-c]pyrimidin-7-yloxy)-3-methylphenyl)amino)quinazolin-6-yl)furan-2-carbaldehyde was replaced with 5-(4-((4-([1,2,4]triazolo[4,3-c]pyrimidin-7-yloxy)-3-methylphenyl)amino)quinazolin-6-yl)-1-methyl-1H-pyrrol-2-carbaldehyde. LC-MS: 583.8 [M+H] detection value. $^1$H NMR (400 MHz, CDCl$_3$) δ 9.20 (d, 1H, J=1.1 Hz), 8.79 (s, 1H), 8.33 (s, 1H), 8.02-7.91 (m, 2H), 7.88-7.82 (m, 1H), 7.82-7.69 (m, 2H), 7.15 (d, 1H, J=8.6 Hz), 6.91 (d, 1H, J=1.1 Hz), 6.26 (d, 1H, J=3.5 Hz), 6.19 (d, J=3.5 Hz, 1H), 3.93 (s, 2H), 3.68 (s, 3H), 3.28-3.19 (m, 2H), 3.19-3.08 (m, 2H), 2.98 (s, 3H), 2.27 (s, 3H).

Embodiment 124

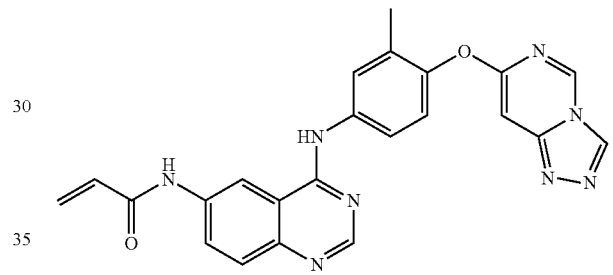

Synthesis of N-(4-((4-([1,2,4]triazolo[4,3-c]pyrimidin-7-yloxy)-3-methylphenyl)amino)quinazolin-6-yl) acrylamide According to the method of Embodiment 16, wherein 2-fluoroacrylic acid was replaced with acrylic acid. LCMS: 438.9 [M+H] detection value. $^1$H-NMR (DMSO-d$_6$): δ 10.52 (s, 1H), 9.86 (s, 1H), 9.68 (s, 1H), 8.83 (s, 1H), 8.59 (s, 1H), 8.55 (s, 1H), 8.20 (s, 1H), 7.92 (d, 1H, J=9.6 Hz), 7.81 (s, 1H), 7.75 (dd, 1H, J=8.0, 2.2 Hz), 7.19 (d, 1H, J=8.0 Hz), 7.13 (s, 1H), 6.55 (dd, 1H, J=16.0, 8.0 Hz), 6.36 (d, 1H, J=16.0 Hz), 5.85 (dd, 1H, J=8.0, 4.0 Hz), 2.16 (s, 3H).

Embodiment 125

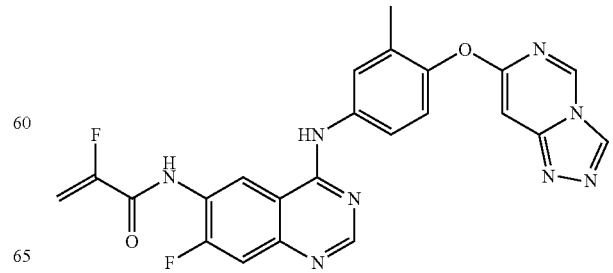

Synthesis of N-(4-((4-([1,2,4]triazolo[4,3-c]pyrimidin-7-yloxy)-3-methylphenyl)amino)-7-fluoroquinolin-6-yl)-2-fluoroacryamide Step A: preparation of N⁴-(4-([1,2,4]triazolo[4,3-c]pyrimidin-7-yloxy)-3-methylphenyl)-7-fluoroquinazolin-4,6-diamine: N-(4-([1,2,4]triazolo[4,3-c]pyrimidin-7-yloxy)-3-methylphenyl)-7-fluoro-6-nitroquinazolin-4-amine (150 mg, 0.35 mmol) was dissolved in methanol (10 mL), Raney Nickel (50 mg) was added, the reaction system was purged with argon for three times, the reaction solution was stirred under a hydrogen balloon at room temperature for 16 hours, then filtered through celite and concentrated under reduced pressure to give 100 mg brown solid, which was used directly in the next step.

Step B: preparation of N-(4-((4-([1,2,4]triazolo[4,3-c]pyrimidin-7-yloxy)-3-methylphenyl)amino)-7-fluoroquinolin-6-yl)-2-fluoroacrylamide: according to the method of Embodiment 16, the reaction was conducted at 50° C. for 16 hours. LCMS: 474.8 [M+H] detection value. ¹H-NMR (DMSO): δ 10.6 (s, 1H), 9.95 (s, 1H), 9.68 (s, 1H), 8.75 (d, 1H, J=8.0 Hz), 8.62 (s, 1H), 8.60 (s, 1H), 7.79 (s, 1H), 7.76 (dd, 1H, J=12.0, 4.0 Hz), 7.69 (d, 1H, J=12.0 Hz), 7.20 (d, 1H, J=12.0 Hz), 7.16 (s, 1H), 5.81 (dd, 1H, J=48.0, 4.0 Hz), 5.56 (dd, 1H, J=16.0, 4.0 Hz), 2.19 (s, 3H).

Embodiment 126

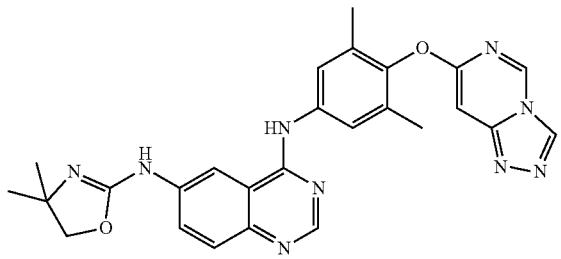 [SMILES: Cc1cc(Nc2ncnc3ccc(NC4=NC(C)(C)CO4)cc23)cc(C)c1Oc1cc2nncn2cn1]

Synthesis of N⁴-(4-([1,2,4]triazolo[4,3-c]pyrimidin-7-yloxy)-3,5-dimethylphenyl)-N⁶-(4,4-dimethyl-4,5-dihydrooxazol-2-yl)quinazolin-4,6-diamine According to the method of Embodiment 19, wherein 2-fluoro-4-nitro-phenol was replaced with 2,6-dimethyl-4-nitrophenol, sodium bicarbonate was replaced with sodium carbonate, the reaction was conducted at 80° C. for 16 hours. LCMS: 495.9 [M+H] detection value. ¹H-NMR (DMSO): δ 9.65 (s, 1H), 9.52 (s, 1H), 8.58 (s, 1H), 8.48 (s, 1H), 8.16 (s, 1H), 8.03 (s, 1H), 7.67-7.66 (m, 3H), 7.07 (s, 1H), 4.08 (s, 2H), 2.13 (s, 6H), 1.29 (s, 6H).

Embodiment 127

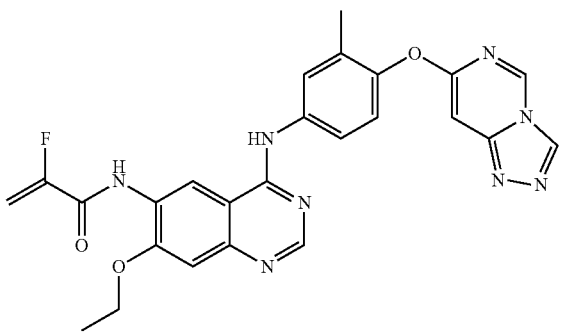 [SMILES: C=C(F)C(=O)Nc1cc2c(Nc3ccc(Oc4cc5nncn5cn4)c(C)c3)ncnc2cc1OCC]

Synthesis of N-(4-((4-([1,2,4]triazolo[4,3-c]pyrimidin-7-yloxy)-3-methylphenyl)amino)-7-ethoxyquinazolin-6-yl)-2-fluoroacrylamide Step A: preparation of N-(4-([1,2,4]triazolo[4,3-c]pyrimidin-7-yloxy)-3-methylphenyl)-7-ethoxy-6-nitroquinazolin-4-amine: N-(4-([1,2,4]triazolo[4,3-c]pyrimidin-7-yloxy)-3-methylphenyl)-7-fluoro-6-nitroquinazolin-4-amine (200 mg, 0.47 mmol) was suspended in tetrahydrofuran (2 mL), the solution was cooled to 0° C. Sodium ethoxide (120 mg, 1.76 mmol) was dissolved in ethanol (470 mg, 10.2 mmol) to prepare a solution. The prepared solution of sodium ethoxide was added dropwise to the above reaction mixture maintaining the temperature below 0° C. The final mixture was warmed to room temperature and stirred for 2 hours. A solution of the above crude product (800 mg) in tetrahydrofuran (10 mL) was added dropwise. The reaction solution was allowed to warm to room temperature and stirred for another 18 hours, then concentrated under reduced pressure to give a brown solid, which was used directly in the next step.

According to the method of Embodiment 16, wherein N-(4-([1,2,4]triazolo[4,3-c]pyrimidin-7-yloxy)-3-methylphenyl)-6-nitroquinazolin-4-amine was replaced with N-(4-([1,2,4]triazolo[4,3-c]pyrimidin-7-yloxy)-3-methylphenyl)-7-ethoxy-6-nitroquinazolin-4-amine. LCMS: 500.8 [M+H] detection value.

Embodiment 128

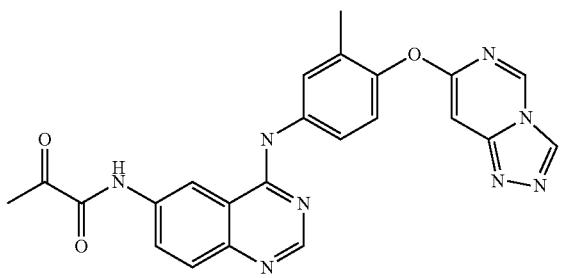 [SMILES: CC(=O)C(=O)Nc1ccc2ncnc(Nc3ccc(Oc4cc5nncn5cn4)c(C)c3)c2c1]

Synthesis of N-(4-((4-([1,2,4]triazolo[4,3-c]pyrimidin-7-yloxy)-3-methylphenyl)amino)quinazolin-6-yl)-2-oxopropionamide According to the method of Embodiment 16, wherein 2-fluoroacrylic acid was replaced with 2-oxopropionic acid, the reaction was conducted at 50° C. under stirring for 16 hours. LCMS: 455.8 [M+H] detection value. ¹H-NMR (CDCl₃): δ 9.83 (s, 1H), 9.16 (s, 1H), 8.65 (s, 1H), 8.59 (s, 1H), 8.24 (s, 1H), 8.02 (d, 1H, J=12.0 Hz), 7.99 (s, 1H), 7.78 (d, 1H, J=8.0 Hz), 7.74 (s, 1H), 7.68 (d, 1H, J=8.0 Hz), 7.04 (d, 1H, J=8.0 Hz), 6.80 (s, 1H), 2.51 (s, 3H), 2.17 (s, 3H).

Embodiment 129

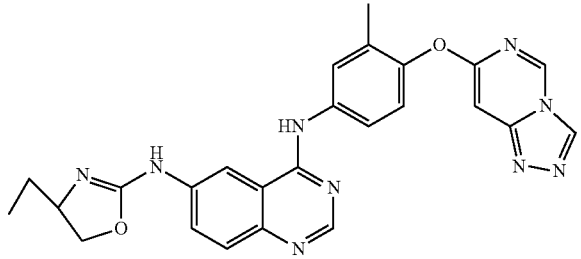 [SMILES: CCC1COC(Nc2ccc3ncnc(Nc4ccc(Oc5cc6nncn6cn5)c(C)c4)c3c2)=N1]

Synthesis of N⁴-(4-([1,2,4]triazolo[4,3-c]pyrimidin-7-yloxy)-3-methylphenyl)-N⁶-(4-ethyl-4,5-dihydrooxazol-2-yl)quinazolin-4,6-diamine Step A: preparation of 2-amino-1-butanol: methyl 1-aminocyclopropylcarboxylate (800 mg, 6.96 mmol) and 20 mL tetrahydrofuran were added into a 100 mL three-neck flask, the mixture was cooled to 0° C. under argon atmosphere, then a solution of lithium aluminum hydride in tetrahydrofuran (15 mL, 7.5 mmol) was added dropwise. After completion of the addition, the reaction solution was stirred at room temperature for 18 hours. After completion of the reaction, the reaction solution was quenched, filtered through celite, dried over anhydrous sodium sulfate and concentrated to give 800 mg crude product, which was used directly in the next step.

Step B: preparation of (E)-N-(2-cyano-4-(3-(1-hydroxybut-2-yl)thioureido)phenyl)-N,N-dimethylformamidine: thiocarbonyldiimidazole (650 mg, 3.65 mmol) and tetrahydrofuran (20 mL) were added into a 100 mL three-neck flask, the reaction solution was cooled to 0° C. under argon atmosphere, (E)-N'-(4-amino-2-cyanophenyl)-N,N-dimethylformamidine (530 mg, 2.82 mmol) was added under stirring. The reaction solution was stirred at 0° C. for 1 hour, then a solution of the above crude product (800 mg) in tetrahydrofuran (10 mL) was added dropwise. The reaction solution was warmed to room temperature and stirred for 18 hours. Then saturated aqueous sodium bicarbonate solution was added and the mixture was extracted with ethyl acetate. The organic phase was washed with saturated brine, dried over anhydrous sodium sulfate and filtered. The filtrate was concentrated under reduced pressure and the residue was purified by silica gel column chromatography to give 650 mg product with a yield of 72.3%.

According to the method of Embodiment 4, wherein (Z)—N'-(2-cyano-4-(3-(1-hydroxy-2-methylpropan-2-yl)thioureido)phenyl)-N,N-dimethylformimidamide was replaced with (E)-N-(2-cyano-4-(3-(1-hydroxybut-2-yl)thioureido)phenyl)-N,N-dimethylformamidine. LC-MS: 482.9 [M+H] detection value. ¹H-NMR (MeOD-d₄) δ 9.46 (s, 1H), 8.47 (s, 1H), 8.44 (s, 1H), 8.19 (s, 1H), 7.79 (s, 1H), 7.75-7.73 (m, 2H), 7.63 (d, 1H, J=8 Hz), 7.21 (d, 1H, J=8 Hz), 6.96 (s, 1H), 4.55-4.51 (m, 1H), 4.17-4.13 (m, 2H), 2.28 (s, 3H), 1.78-1.74 (m, 1H), 1.68-1.61 (m, 1H), 1.01 (t, 3H, J=8 Hz).

Effect Embodiment

Embodiment A

Enzymatic Experiment on EGFR/ErbB2

Firstly, preparing 1× reaction buffer required for the kinase, 5× Enzymatic buffer (HEPES 20 mM pH7.0, NaN₃ 0.1%, BSA 0.05%, sodium orthovanadate 0.5 mM) in the HTRF kinEASE-TK kit was diluted to 1 time with deionized water, 50 nM Supplement Enzymatic buffer (SEB reagent), 1 mM MnCl₂, 5 mM MgCl₂ and 1 mM DTT were added. Secondly, preparing 5× compound, 10 mM test compound stock solution was diluted in multiple steps with DMSO in a 96-well compound plate to prepare 100× compound as initial concentration, which was then used as the first concentration to perform a 3-fold gradient dilution with DMSO to obtain 10 concentrations. Afterwards, 1 µl gradient dilution was added to 19 µl 1× reaction buffer to prepare 5× compound for use. Then 2 µl 5× compound was transferred from the 96 well plate into a 384-well plate. To the compound-free control wells was added with 2 µl the following liquid: 19 µl 1× reaction buffer with addition of 1 µl DMSO. To the blank control wells was added 2 µl 250 mM EDTA. The third step was enzymatic reaction, the kinase, substrate (TK Substrate-biotin) and ATP were formulated into 2.5× enzyme/substrate mixture and 2.5×ATP solution using 1× reaction buffer respectively. The final concentration of ErbB2 kinase was 0.06 ng/µl, the final concentration of ATP was 4 µM; the final concentration of EGFR kinase was 0.06 units/µl, the final concentration of ATP was 1.65 µM; 4 µl 2.5× enzyme/substrate mixture was added to a 384-well plate, which was incubated at room temperature for 5 minutes; 4 µl 2.5×ATP solution was added to each well and the mixture was allowed to react for 30 minutes at room temperature. The fourth step was termination of the reaction, HTRF Detection buffer was used to prepare a mixture of 2×TK Antibody-Eu(K) and Sa-XL665, the amount of TK Antibody-Eu(K) was 5 µl per well. After the enzymatic reaction was performed for 30 minutes, 10 µl of the above liquid was added to the 384-well plate and the mixture was allowed to react at room temperature for 1 hour. The data was measured on EnVision™, the laser of 337 nM wavelength was selected as the excitation light, $RFU_{665\ nM}$ and $RFU_{620\ nM}$ were measured, and $RFU_{665\ nM}/RFU_{620\ nM} \times 10000$ was used as the final data for analysis.

Embodiment B

Proliferation Inhibition Assay In Vitro of Cell Lines

1. Cell culture and inoculation: on the first day of the experiment, normal cultured cells were taken in the exponential growth phase, the cells were dispersed by digesting, then the cell density was adjusted to 8.8×10⁴ cells/mL for BT-474 and 6.6×10⁴ cells/mL for N87, 90 µl of which were inoculated to each well in a 96-well cell culture plate; after inoculation, the microplate was placed at condition of 37° C., 5% CO₂ overnight. 2. Dosing to cells: on the second day of the experiment, the microplate was taken out from incubator, 104, of 10× compound was separately added to each well of the microplate, 2 duplicated wells were set for each concentration, 9 dosing concentrations were set for each compound. According to different cell lines, the initial concentration of each compound was different. Upon completion of addition, the microplate was placed at condition of 37° C., 5% CO₂ for 72 hours. 3. Data acquisition:

the microplate was taken out from the incubator and allowed to stand at room temperature to equilibrate for 30 minutes. 100 μl CellTiter-Glo® Luminescent Cell Viability Assay reaction solution which had been equilibrated at room temperature was added to each well and the microplate was shaken at 1300 rpm for 2 minutes at room temperature. The microplate was centrifuged at 2000 rpm for 1 minute in a HERAEUS Multifuge X1R and then allowed to equilibrate at room temperature for 10 minutes. The fluorescence signal was measured on EnVision™.

Biological Test Data

The following data are all determined according to the methods of the above effect embodiments, and the test data of the embodiment compounds are enumerated. "--" in the following table indicates that it has not been tested yet.

| Compound | Kinase IC$_{50}$ (nM) in vitro | | IC$_{50}$(nM) cell | |
|---|---|---|---|---|
| | ErbB2 | EGFR | N87 | BT-474 |
| End-product of Embodiment 2 | 16.7 | 230 | — | — |
| End-product of Embodiment 3 | 1.1 | 18.7 | 48.7 | 38.5 |
| End-product of Embodiment 4 (Compound I-4) | 2.4 | 44.3 | 23 | 19.7 |
| End-product of Embodiment 5 | 12.9 | 703 | 313 | 460 |
| End-product of Embodiment 6 | 24.8 | 1890 | — | — |
| End-product of Embodiment 7 | 8.1 | 164 | 71 | 45 |
| End-product of Embodiment 8 | 7.8 | 115 | 68.7 | 43.4 |
| End-product of Embodiment 9 | 7.4 | 35.9 | 39.5 | 33.4 |
| End-product of Embodiment 10 | 12.6 | 143 | 200 | 92.3 |
| End-product of Embodiment 11 | 58.1 | >3333 | — | — |
| End-product of Embodiment 12 | 4.3 | 231.3 | 482.5 | 136.3 |
| End-product of Embodiment 13 | 2.6 | 15.2 | 203.6 | 47.9 |
| End-product of Embodiment 14 | 1.7 | 114.6 | 94.1 | 35.2 |
| End-product of Embodiment 15 | 1.2 | 14.9 | 33.2 | 17.4 |
| End-product of Embodiment 16 | 3.4 | 32.3 | 5.6 | 7.7 |
| End-product of Embodiment 17 | 7.9 | 80.9 | 712 | 304 |
| End-product of Embodiment 18 | 13.2 | 79.5 | — | — |
| End-product of Embodiment 19 | 3.3 | 22.1 | 125 | 98.2 |
| End-product of Embodiment 20 | 4.3 | 40.6 | — | — |
| End-product of Embodiment 21 | 2.2 | 43.5 | 73.8 | 140 |
| End-product of Embodiment 22 | 4.1 | 18 | 35.6 | 40.7 |
| End-product of Embodiment 23 | 5.2 | 0.7 | 55.7 | 79.5 |
| End-product of Embodiment 24 | 4.1 | 126.7 | 177.4 | 127.7 |
| End-product of Embodiment 25 | 53.35 | 499.1 | 463.5 | 984 |
| End-product of Embodiment 26 | 3.8 | 96.85 | 130 | 122.2 |
| End-product of Embodiment 27 | 1.92 | 8.1 | 543 | 111.7 |
| End-product of Embodiment 28 | 4.79 | 17.7 | — | — |
| End-product of Embodiment 29 | 3.6 | 41.8 | — | — |
| End-product of Embodiment 30 | 4.9 | 17.3 | 771 | 141 |
| End-product of Embodiment 31 | 10.05 | 57.4 | 433 | 187.1 |
| End-product of Embodiment 32 | 4.3 | 2.0 | 440 | 92.6 |
| End-product of Embodiment 34 | 2.1 | 8.2 | 46.3 | 55.6 |

| Compound | Kinase IC$_{50}$ (nM) in vitro | | IC$_{50}$(nM) cell | |
| --- | --- | --- | --- | --- |
| | ErbB2 | EGFR | N87 | BT-474 |
| End-product of Embodiment 35 | 1.1 | 10.9 | 52.9 | 49.6 |
| End-product of Embodiment 36 | 1.5 | 1.9 | 47.5 | 21.5 |
| End-product of Embodiment 37 | 4.8 | 45.2 | — | — |
| End-product of Embodiment 38 | 5.0 | 28.1 | 86.6 | 186 |
| End-product of Embodiment 39 | 1.8 | 20.0 | — | — |
| End-product of Embodiment 40 | 6.9 | 12.7 | — | — |
| End-product of Embodiment 41 | 4.3 | 1.3 | 11.7 | 6.9 |
| End-product of Embodiment 42 | 5.2 | 8.3 | 39.2 | 36.7 |
| End-product of Embodiment 43 | 9.26 | 69.7 | — | — |
| End-product of Embodiment 44 | 1.43 | 11.6 | 46 | 41 |
| End-product of Embodiment 45 | 2.8 | 53.4 | 93.4 | 85.4 |
| End-product of Embodiment 46 | 12.01 | 51.6 | 316 | 172 |
| End-product of Embodiment 47 | 2.6 | 31.36 | 68.4 | 35 |
| End-product of Embodiment 48 | 1.3 | 9.4 | 64 | 42.2 |
| End-product of Embodiment 49 | 1.85 | 28.07 | 271 | 33.4 |
| End-product of Embodiment 50 | 3.6 | 27.79 | 116 | 104.2 |
| End-product of Embodiment 51 | 8.41 | 47.14 | 93.7 | 107.9 |
| End-product of Embodiment 52 | 2.35 | 21.57 | 116.9 | 30.4 |
| End-product of Embodiment 53 | 3.58 | 57.91 | 6.2 | 5.9 |
| End-product of Embodiment 54 | 6.4 | 370.3 | 150 | 32.8 |
| End-product of Embodiment 55 | 1.0 | 15.9 | 121.8 | 28.4 |
| End-product of Embodiment 56 | 34.0 | 2448 | 465.5 | 35.4 |
| End-product of Embodiment 57 | 1.7 | 2.7 | 12.8 | 5.6 |
| End-product of Embodiment 58 | 5.4 | 206 | 192 | 352 |
| End-product of Embodiment 59 | 5.7 | 40.2 | 61.1 | 281 |
| End-product of Embodiment 60 | 1.1 | 15.6 | 23.4 | 108 |
| End-product of Embodiment 61 | 6.0 | 44.7 | 35.4 | 48.9 |
| End-product of Embodiment 62 | 1.5 | 14.2 | 72.4 | 30 |
| End-product of Embodiment 63 | 1.8 | 29.5 | 13 | 12.7 |
| End-product of Embodiment 64 | 1.6 | 29.0 | 42.7 | 27.6 |
| End-product of Embodiment 65 | 1.0 | 3.8 | 63.2 | 19.8 |
| End-product of Embodiment 66 | 12.9 | 566.7 | 487 | 275 |
| End-product of Embodiment 67 | 3.2 | 157 | 264 | 177 |
| End-product of Embodiment 68 | 2.2 | 5.4 | 52 | 38.7 |
| End-product of Embodiment 69 | 7.0 | 92.7 | — | — |
| End-product of Embodiment 70 | 3.3 | 73.4 | 852 | 172 |
| End-product of Embodiment 71 | 3.5 | 20.7 | 66.4 | 42.7 |

-continued

| Compound | Kinase IC$_{50}$ (nM) in vitro | | IC$_{50}$(nM) cell | |
| --- | --- | --- | --- | --- |
| | ErbB2 | EGFR | N87 | BT-474 |
| End-product of Embodiment 72 | 0.9 | 4.3 | 34.2 | 30 |
| End-product of Embodiment 73 | 4.21 | 34.9 | 161.5 | 139.3 |
| End-product of Embodiment 74 | 2.4 | 43.3 | 106.3 | 85.8 |
| End-product of Embodiment 75 | 1.34 | 19.2 | 15 | 9 |
| End-product of Embodiment 76 | 4.9 | 82.2 | 42.8 | 27.9 |
| End-product of Embodiment 77 | 5.03 | 23.65 | 509.2 | 254 |
| End-product of Embodiment 78 | 1.8 | 3.3 | 22.34 | 13.16 |
| End-product of Embodiment 79 | 1.7 | 7.7 | 37.2 | 24.7 |
| End-product of Embodiment 80 | 1.0 | 12.6 | 36 | 120 |
| End-product of Embodiment 81 | 16.6 | 51.9 | 749 | 1269 |
| End-product of Embodiment 82 | 1.1 | 2.2 | 5 | 7.1 |
| End-product of Embodiment 83 | 2.3 | 36.4 | 104 | 72.7 |
| End-product of Embodiment 84 | 3.0 | 89.4 | 31.1 | 21.8 |
| End-product of Embodiment 85 | 2.2 | 14.9 | — | — |
| End-product of Embodiment 86 | 3.1 | 7.7 | 160 | 33.8 |
| End-product of Embodiment 87 | 1.9 | 6.5 | 25.3 | 15.3 |
| End-product of Embodiment 88 | 1.13 | 1.9 | 5.2 | 6.3 |
| End-product of Embodiment 89 | 8.5 | 167.2 | — | — |
| End-product of Embodiment 90 | 11.1 | 494.4 | 271 | 185.1 |
| End-product of Embodiment 91 | 2.76 | 26.9 | 76.8 | 38.8 |
| End-product of Embodiment 92 | 0.44 | 0.7 | 3.4 | 2.2 |
| End-product of Embodiment 93 | 2.4 | 0.75 | 101.4 | 69.5 |
| End-product of Embodiment 94 | 2.99 | 3.16 | 4.7 | 4.8 |
| End-product of Embodiment 96 | 3.43 | 3.79 | 93.5 | 55.9 |
| End-product of Embodiment 97 | 4.84 | 11.41 | 10 | 6.4 |
| End-product of Embodiment 98 | 1.78 | 1.6 | 2.5 | 3 |
| End-product of Embodiment 99 | 22.12 | 82.72 | — | — |
| End-product of Embodiment 102 | 4.5 | 11.4 | — | — |
| End-product of Embodiment 105 | 1.2 | 26.0 | 17.3 | 22.9 |
| End-product of Embodiment 106 | 21.5 | 445 | 933 | 264 |
| End-product of Embodiment 113 | 9.4 | 170 | — | — |
| End-product of Embodiment 114 | 24.47 | 622.7 | — | — |
| End-product of Embodiment 115 | 5.91 | 75.93 | 84 | 58.6 |
| End-product of Embodiment 116 | 1.3 | 11.7 | 18.3 | 12.6 |
| End-product of Embodiment 117 | 3.6 | 100.3 | 2.1 | 3.1 |
| End-product of Embodiment 118 | 8.59 | 28.4 | 388.9 | 73.43 |
| End-product of Embodiment 120 | 1.31 | 7.41 | 2.68 | 5.85 |

-continued

| Compound | Kinase IC$_{50}$ (nM) in vitro | | IC$_{50}$(nM) cell | |
|---|---|---|---|---|
| | ErbB2 | EGFR | N87 | BT-474 |
| End-product of Embodiment 122 | 2.7 | 87.2 | 92 | 37 |
| End-product of Embodiment 123 | 4.4 | 32.8 | 429 | 219 |
| End-product of Embodiment 124 | 2.8 | 2.3 | 11.4 | 9.5 |
| End-product of Embodiment 125 | 3.4 | 14.7 | 6.8 | 13.6 |
| End-product of Embodiment 126 | 6.7 | 53 | 82.9 | 143 |
| End-product of Embodiment 127 | 5.6 | 6.6 | 30.7 | 8 |
| End-product of Embodiment 128 | 14.8 | 28.7 | 868 | 484 |
| End-product of Embodiment 129 | 4.4 | 56.9 | 121 | 189 |

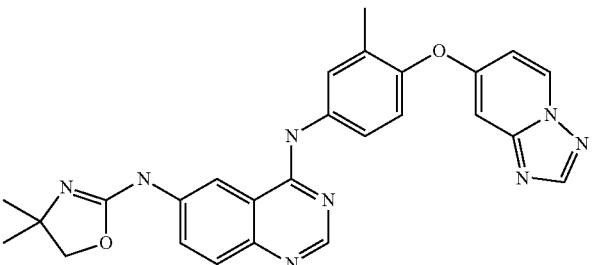

ARRAY-380

| | 2.0 | 57.6 | 13.2 | 14.2 |
|---|---|---|---|---|

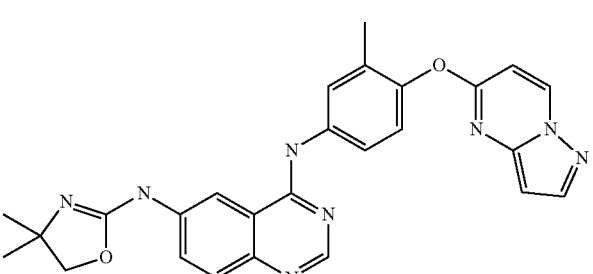

| | 49.4 | 82.7 | — | — |
|---|---|---|---|---|

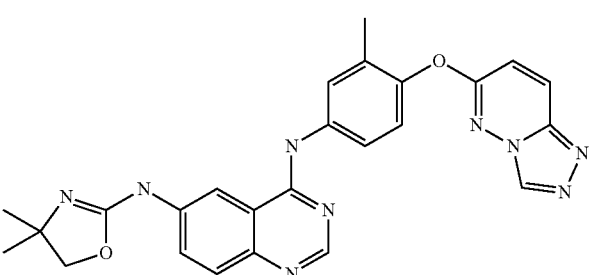

| | 935 | 557 | — | — |
|---|---|---|---|---|

Research on Direct Inhibition of CYP3A4, CYP2D6, CYP2C9, CYP2C19, CYP1A2

100 μL human liver microsome (with final concentration of 0.2 mg/mL) was used for direct inhibition under warm incubation, the positive control system contained NADPH (with final concentration of 1 mmol/L), a mixture of positive inhibitors (ketoconazole 0.01 to 10 μmol/L, quinidine 0.01 to 10 μmol/L, sulfaphenazole 0.1 to 100 μmol/L, tranylcypromine 1 to 1000 μmot/L, α-naphthoflavone 0.01 to 10 μmol/L), and a substrate mixture (with final concentration of midazolam 10 μmol/L, testosterone 100 μmol/L, dextromethorphan 10 μmol/L, diclofenac 20 μmol/L, S-mephenytoin 50 μmol/L, phenacetin 100 μmol/L), and the reaction was terminated after incubation for 20 min. The positive inhibitor was replaced with 0.1 to 100 μmol/L test compound in the test compound group. The reaction was terminated with acetonitrile containing 0.11 μg/mL internal standard tinidazole (1:3), vortexed for 10 min, centrifuged at 6000×g for 10 min, 50 μL supernatant was taken and put into a 96-well plate for injection. The relative activity of the enzyme was denoted by measuring the relative production of the substrate metabolite, and the inhibition rate of the test compound against the enzyme=(1−the relative enzyme activity of the test compound/the relative activity of the negative control enzyme)×100%, IC$_{50}$ was calculated according to the concentration and inhibitory rate.

Research on Direct Inhibition of CYP2B6 and CYP2C8

100 μL human liver microsome (with final concentration of 0.2 mg/mL) was used for direct inhibition under warm incubation. The positive control system contained NADPH (with final concentration of 1 mmol/L), a mixture of positive inhibitors (ketoconazole 0.05 to 50 μmol/L, montelukast sodium 0.001 to 1 μmol/L), and a substrate mixture (with final concentration of amfepramone 50 μmol/L and paclitaxel 5 μmol/L), and the reaction was terminated after incubation for 20 min. The positive inhibitor was replaced with 0.1 to 100 μmol/L test compound in the test compound group. The reaction was terminated with acetonitrile containing 0.114 mL internal standard tinidazole (1:3), vortexed for 10 min, centrifuged at 6000×g for 10 min, and 50 μL supernatant was taken and put into a 96-well plate for injection. The relative activity of the enzyme was denoted by measuring the relative production of the substrate metabolite, and the inhibition rate of the test compound against the enzyme=(1-the relative enzyme activity of the test compound/the relative activity of the negative control enzyme)×100%, IC$_{50}$ was calculated according to the concentration and inhibitory rate.

In this experiment, IC$_{50}$ of inhibition of the compound on the enzyme was calculated by measuring relative production of the probe metabolite. The activity of CYP3A4 was simultaneously characterized by two probes of midazolam and testosterone. According to literature, IC$_{50}$>10 μM means weak inhibition, 1 μM<IC$_{50<1004}$ means moderate inhibition, and IC$_{50}$<1 μM means strong inhibition. Compound I-4 and ARRY 380 were tested simultaneously, the results (see the table below) showed that Compound I-4 exhibited a weaker inhibitory activity on CYP450 than ARRY 380, indicating the possibility of drug-drug interactions in clinical application was lower than ARRY-380.

24 male ICR mices, with weight of 18 to 22 g. The mice were fasted for 12 to 16 hours before the experiment, without restricting drinking water. 24 mice were divided into 2 groups, 12 mice for each group. The first group was intravenously administrated with test compound (10 mL/kg, 0.3 mg/mL) at a dose of 3 mg/kg, 0.4 mL blood sample was taken from venous plexus of the fundus of the eye into a pre-heparinized centrifuge tube (sodium heparin solution 10 μL/tube) before administration and 2, 5, 15, 30, 60, 90, 120, 240, 360, 480, 720, 1440 min after administration, respectively. The second group was dosed with compound (20 mL/kg, 0.5 mg/mL) by intragastric administration at a dose of 10 mg/kg, 0.4 mL blood sample was taken from venous plexus of the fundus of the eye into a pre-heparinized centrifuge tube (sodium heparin solution 10 μL/tube) before administration and 5, 15, 30, 60, 90, 120, 240, 360, 480, 720, and 1440 min after administration, respectively. 2 to 3 time points were taken for each mouse. The blood sample was centrifuged at 8000 rpm for 5 min, the plasma was collected in a centrifuge tube and stored at −20° C. for use.

Taking 50 μL plasma sample of rat or mouse, adding 2004 acetonitrile containing internal standard (propranolol, 2.5 ng/ml) to precipitate protein. Vortexing for 10 min, centrifuging at 6000 g for 10 min, the supernatant was taken and diluted with mobile phase in a 96-well plate, the drug concentration in plasma was measured by UPLC/MS-MS.

The drug concentration of the plasma of rat or mouse was obtained, and the pharmacokinetic parameters were calculated by non-compartmental model, wherein Cmax is the peak concentration, Tmax is the time when reaching Cmax, they are both measured values under intragastric administration, AUC$_{0-t}$=$\int_0^t c(t)dt$, is the area under the drug concentration-time curve; AUC$_{0-\infty}$=AUC$_{0-t}$+Ct/ke, wherein Ct is the plasma concentration at the final time point, ke is elimination rate constant of the terminal phase of the drug concentration-time curve; T$_{1/2}$=0.693/ke, is half-life period.

| IC$_{50}$ of Compound I-4 and ARRY-380 for each subtype of CYP enzyme* | | | | | | | |
|---|---|---|---|---|---|---|---|
| IC$_{50}$(μM) | 3A4 (Midazolam) | 3A4 (testosterone) | 2D6 (Dextromethorphan) | 2C9 (Diclofenac) | 1A2 (Phenacetin) | 2C19 (Mephenytoin) | 2B6 (Bupropion) | 2C8 (Paclitaxel) |
| Compound I-4 | 25 | 21 | 12 | 53 | 34 | 53 | >100 | 15 |
| ARRY-380 | 11 | 11 | 3 | 13 | 94 | 35 | >100 | 3 |

*IC$_{50}$ > 10 μM means weak inhibition, 1 μM < IC$_{50}$ < 10 μM means moderate inhibition, and IC$_{50}$ < 1 μM means strong inhibition.

In Vivo Pharmacokinetics Study in Rats and Mice 5 male SD rats, with weight of 180 to 220 g. The rats were fasted for 12 to 16 hours before the experiment, without restricting drinking water. Two rats were intravenously administrated with dosing solution (3 mL/kg, 1 mg/mL) at a dose of 3 mg/kg, 0.4 mL blood sample was taken from venous plexus of the fundus of the eye into a pre-heparinized centrifuge tube (sodium heparin solution 10 μL/tube) before administration and 2, 5, 15, 30, 60, 90, 120, 240, 360, 480, 720, 1440 min after administration, respectively. Three rats were intragastricly administrated with dosing suspension (8 mL/kg, 0.75 mg/mL) at a dose of 6 mg/kg, 0.4 mL blood sample was taken from venous plexus of the fundus of the eye into a pre-heparinized centrifuge tube (sodium heparin solution 10 μL/tube) before administration and 5, 15, 30, 60, 90, 120, 240, 360, 480, 720, and 1440 min after administration, respectively. The blood sample was centrifuged at 8000 rpm for 5 min, the plasma was collected in a centrifuge tube and stored at −20° C. for use.

After intravenous administration, CL=Dose/AUC$_{0-\infty}$, is the plasma clearance rate, wherein Dose is the dose administered; Vss=CL×MRT, is steady-state volume of distribution, wherein MRT=$\int_0^t tc(t)dt$/AUC, is mean residence time. Absolute bioavailability F=(AUCpo×Doseiv)/(AUCiv×Dosepo)×100%, wherein po represents intragastric administration, and iv represents intravenous administration.

The pharmacokinetic study of Compound I-4 and ARRY 380 in rats and mice showed that F values of Compound I-4 and ARRY 380 were 15.4% and 9.5% in rats respectively and were 96.2% and 61.0% in mice respectively. Therefore, the absolute bioavailability of Compound I-4 is higher than that of ARRY-380 in both rats and mice at the same dose.

In Vivo Experiment on Nude Mice Xenograft Model of Human Cancer

We had established two HER2 overexpressing xenograft model in nude mice at the same time.

Pharmacodynamic evaluation of compound I-4 on HER2 overexpressing human gastric cancer NCI-N87 xenograft model in nude mice: male Balb/c nude mice were subcutaneously inoculated with NCI-N87 cell from ATCC at 5*10^6 cells per mouse, when the tumor volume reached about 210 mm³, the animals were divided into groups and administrated; the activity of Compound I-4 was denoted with the tumor volume inhibition rate (GI %), which was calculated by the formula: GI (%)=[1−(Ti−T0)/(Vi−V0)]×100 (wherein Ti was tumor volume of the administration group, T0 was tumor volume at D0 day of the administration group, Vi was tumor volume of the solvent control group, V0 was tumor volume of the solvent control group at D0 day). T test was used for the comparison between the two groups, p<0.05 meaned significant difference, p<0.01 meaned very significant difference. After continuous oral administration for 22 days, there was a very significant difference (**P<0.01) of the anti-tumor inhibitory activity between Compound I-4 100MPK group (GI % was 117.9%) and Lapatinib 50MPK group (BID) (GI % was 87.8%). There was a significant difference (*P<0.05) of the anti-tumor inhibitory activity between Compound I-4 50MPK group (GI % was 84.3%) and ARRY 380 50MPK group (GI % was 59.5%). There was no significant decrease in the weight of animals in each group by the day of the terminal of the experiment.

Pharmacodynamic evaluation on HER2 overexpressing human breast cancer BT-474 xenograft model in nude mice: female Balb/c nude mice were subcutaneously implanted with β-estradiol sustained-release tablet and inoculated with BT-474 cell from ATCC at 1*10^7 cells per mouse, when the tumor volume reached about 130 mm³, the animals were divided into groups and administrated; the pharmacodynamic activity of Compound I-4 was denoted with the tumor volume inhibition rate (GI %), which was calculated by the formula: GI (%)=[1−(Ti−T0)/(Vi−V0)]×100 (wherein Ti was tumor volume of the administration group, T0 was tumor volume at D0 day of the administration group, Vi was tumor volume of the solvent control group, V0 was tumor volume of the solvent control group at D0 day). T test was used for the comparison between the two groups, p<0.05 meaned significant difference, p<0.01 meaned very significant difference. After continuous oral administration of the candidate compound for 20 days, the GI % of 50 and 100MPK groups of Compound I-4 were 103.2% and 126.4% respectively, there was a very significant difference (**P<0.01) compared to the anti-tumor activity of the Lapatinib 50MPK (BID) group (GI % was 19.2%). There was a significant difference (*P<0.05) of the anti-tumor activity between Compound I-4 25MPK group (GI % was 70.3%) and Lapatinib 50MPK group (BID). There was a significant difference (*P<0.05) of the anti-tumor activity between Compound I-4 100MPK group (GI % was 126.4%) and ARRY 380 100MPK group (GI % was 108.8%). Compound I-4 exhibited more obvious dose-dependency and good tolerability in this experiment.

It is to be understood that the foregoing description of the preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. A nitrogenous heterocyclic compound represented by formula I, a pharmaceutically acceptable salt, an enantiomer, a diastereomer, a tautomer or a solvate thereof;

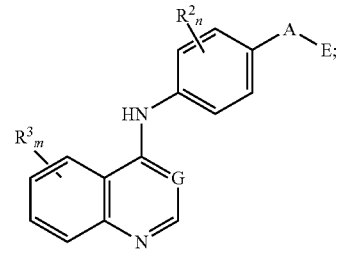

wherein, A is —O— or —S—;
G is N or C—CN;
E is

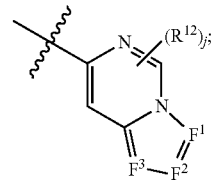

in the definition of E, $F^1$, $F^2$ and $F^3$ are independently N or $CR^{19}$;
in the definition of E, j is 0, 1 or 2;
in the definition of E, each $R^{12}$ is independently selected from the group consisting of halogen, cyano, nitro, haloalkyl, haloalkoxy, azido, —$SR^{18}$, —$OR^{15}$, —$C(=O)R^{15}$, —$C(=O)OR^{15}$, —$NR^{15}C(=O)OR^{18}$, —$OC(=O)R^{15}$, —$OC(=O)NR^{15}R^{13}$, —$NR^{15}SO_2R^{18}$, —$SO_2NR^{15}R^{14}$, —$NR^{14}C(=O)R^{15}$, $C(=O)NR^{15}R^{14}$, —$NR^{14}C(=O)NR^{15}R^{13}$, —$NR^{14}SO_2NR^{15}R^{13}$, —$NR^{14}C(=N—CN)NR^{15}R^{13}$, —$NR^{15}R^{14}$, alkyl, alkenyl, alkynyl, saturated or partially unsaturated cycloalkyl, cycloalkyl alkyl, —$S(=O)_p$(alkyl), —$S(=O)_p(CR^{13}R^{14})_q$-aryl, aryl, arylalkyl, heteroaryl, heteroarylalkyl, saturated or partially unsaturated heterocyclyl, heterocyclylalkyl, —$O(CR^{13}R^{14})_q$-aryl, —$NR^{15}(CR^{13}R^{14})_q$-aryl, —$O(CR^{13}R^{14})_q$-heteroaryl, —$NR^{15}(CR^{13}R^{14})_q$-heteroaryl, —$O(CR^{13}R^{14})_q$-heterocyclyl and —$NR^{15}(CR^{13}R^{14})_q$-heterocyclyl;
in the definition of $R^{12}$, the alkyl, alkenyl, alkynyl, cycloalkyl, aryl, arylalkyl, heteroaryl, heteroarylalkyl, heterocyclyl and heterocyclylalkyl are independently substituted with the substituent selected from the group consisting of oxo, halogen, cyano, nitro, haloalkyl, haloalkoxy, azido, —$NR^{15}SO_2R^{18}$, —$SO_2NR^{15}R^{13}$, —$C(=O)R^{15}$, —$C(=O)OR^{15}$, —$OC(=O)R^{15}$, —$OC(=O)NR^{15}R^{13}$, —$NR^{15}C(=O)OR^{18}$, —$NR^{13}C(=O)R^{15}$, —$C(=O)NR^{15}R^{13}$, —$NR^{15}R^{13}$, —$NR^{14}C(=O)NR^{15}R^{13}$, —$NR^{14}SO_2NR^{15}R^{13}$, —$NR^{14}C(=N—CN)NR^{15}R^{13}$, —$OR^{15}$, aryl, heteroaryl, arylalkyl, heteroarylalkyl, saturated or partially unsaturated heterocyclyl, and heterocyclylalkyl, when there are more than one substituents, the substituents are the same or different; wherein the aryl, heteroaryl, arylalkyl, heteroarylalkyl, heterocyclyl or heterocyclylalkyl is independently substituted with the substituent selected from the group consisting of halogen, hydroxy, cyano, nitro, azido, haloalkyl, alkyl, alkenyl, alkynyl, saturated or partially unsaturated cycloalkyl, saturated or partially unsaturated heterocyclyl, —$NR^{15}R^{13}$ and —$OR^{15}$, when there are more than one substituents, the substituents are the same or different;

in the definition of E, each $R^{19}$ is independently selected from the group consisting of H, halogen, cyano, nitro, haloalkyl, haloalkoxy, azido, —$SR^{18}$, —$OR^{15}$, —C(=O)$R^{15}$, —C(=O)O$R^{15}$, —$NR^{15}$C(=O)$OR^{18}$, —OC(=O)$R^{15}$, —OC(=O)$NR^{15}R^{13}$, —$NR^{15}SO_2R^{18}$, —$SO_2NR^{15}R^{14}$, —$NR^{14}$C(=O)$R^{15}$, —C(=O)$NR^{15}R^{14}$—$NR^{14}$C(=O)$NR^{15}R^{13}$, —$NR^{14}SO_2NR^{15}R^{13}$, —$NR^{14}$C(=N—CN)$NR^{15}R^{13}$, —$NR^{15}R^{14}$, alkyl, alkenyl, alkynyl, saturated or partially unsaturated cycloalkyl, cycloalkyl alkyl, —S(O)$_p$(alkyl), —S(O)$_p(CR^{13}R^{14})_q$-aryl, aryl, arylalkyl, heteroaryl, heteroarylalkyl, saturated or partially unsaturated heterocyclyl, heterocyclylalkyl, —O$(CR^{13}R^{14})_q$-aryl, —$NR^{15}(CR^{13}R^{14})_q$-aryl, —O$(CR^{13}R^{14})_q$-heteroaryl, —$NR^{15}(CR^{13}R^{14})_q$-heteroaryl, —O$(CR^{13}R^{14})_q$-heterocyclyl and —$NR^{15}(CR^{13}R^{14})_q$-heterocyclyl;

in the definition of $R^{19}$, the alkyl, alkenyl, alkynyl, cycloalkyl, aryl, arylalkyl, heteroaryl, heteroarylalkyl, heterocyclyl, and heterocyclylalkyl are independently substituted with the substituent selected from the group consisting of oxo, halogen, cyano, nitro, haloalkyl, haloalkoxy, azido, —$NR^{15}SO_2R^{18}$, —$SO_2NR^{15}R^{13}$, —C(=O)$R^{15}$, —C(=O)$OR^{15}$, —OC(=O)$R^{15}$, —OC(=O)$NR^{15}R^{13}$, —$NR^{15}$C(=O)$OR^{18}$, —$NR^{13}$C(=O)$R^{15}$, —C(=O)$NR^{15}R^{13}$, —$NR^{15}R^{13}$, —$NR^{14}$C(=O)$NR^{15}R^{13}$, —$NR^{14}SO_2NR^{15}R^{13}$, —$NR^{14}$C(=N—CN)$NR^{15}R^{13}$, —$OR^{15}$, aryl, heteroaryl, arylalkyl, heteroarylalkyl, saturated or partially unsaturated heterocyclyl, and heterocyclylalkyl, when there are more than one substituents, the substituents are the same or different; wherein the aryl, heteroaryl, arylalkyl, heteroarylalkyl, heterocyclyl or heterocyclylalkyl is further independently substituted with the substituent selected from the group consisting of halogen, hydroxy, cyano, nitro, azido, haloalkyl, alkyl, alkenyl, alkynyl, saturated or partially unsaturated cycloalkyl, saturated or partially unsaturated heterocyclyl, —$NR^{15}R^{13}$ and —$OR^{15}$, when there are more than one substituents, the substituents are the same or different;

each $R^2$ is independently selected from the group consisting of halogen, cyano, nitro, haloalkyl, haloalkoxy, azido, —$SR^{18}$, —$OR^{15}$, —C(=O)$R^{15}$, —C(=O)$OR^{15}$, —$NR^{15}$C(=O)$OR^{18}$, —OC(=O)$R^{15}$, —OC(=O)$NR^{15}R^{13}$, —$NR^{15}SO_2R^{18}$, —$SO_2NR^{15}R^{14}$, —$NR^{14}$C(=O)$R^{15}$, —C(=O)$NR^{15}R^{14}$, —$NR^{14}$C(=O)$NR^{15}R^{13}$, —$NR^{14}SO_2NR^{15}R^{13}$, —$NR^{14}$C(=N—CN)$NR^{15}R^{13}$, —$NR^{15}R^{14}$ alkyl, alkenyl, alkynyl, saturated or partially unsaturated cycloalkyl, cycloalkyl alkyl, —S(O)$_p$(alkyl), —S(O)$_p(CR^{13}R^{14})_q$-aryl, aryl, arylalkyl, heteroaryl, heteroarylalkyl, saturated or partially unsaturated heterocyclyl, heterocyclylalkyl, —O$(CR^{13}R^{14})_q$-aryl, —$NR^{15}(CR^{13}R^{14})_q$-aryl, —O$(CR^{13}R^{14})_q$-heteroaryl, —$NR^{15}(CR^{13}R^{14})_q$-heteroaryl, —O$(CR^{13}R^{14})_q$-heterocyclyl and —$NR^{15}(CR^{13}R^{14})_q$-heterocyclyl;

in the definition of $R^2$, the alkyl, alkenyl, alkynyl, cycloalkyl, aryl, arylalkyl, heteroaryl, heteroarylalkyl, heterocyclyl, and heterocyclylalkyl are independently substituted with the substituent selected from the group consisting of oxo, halogen, cyano, nitro, haloalkyl, haloalkoxy, azido, —$NR^{15}SO_2R^{18}$, —$SO_2NR^{15}R^{13}$, —C(=O)$R^{15}$, —C(=O)$OR^{15}$, —OC(=O)$R^{15}$, —OC(=O)$NR^{15}R^{13}$, —$NR^{15}$C(=O)$OR^{18}$, —$NR^{13}$C(=O)$R^{15}$, —C(=O)$NR^{15}R^{13}$, —$NR^{15}R^{13}$, —$NR^{14}$C(=O) $R^{15}R^{13}$, —$NR^{14}SO_2NR^{15}R^{16}$, —$NR^{14}$C(=N—CN)$NR^{15}R^{13}$, —$OR^{15}$, aryl, heteroaryl, arylalkyl, heteroarylalkyl, saturated and partially unsaturated heterocyclyl, and heterocyclylalkyl, when there are more than one substituents, the substituents are the same or different; wherein the aryl, heteroaryl, arylalkyl, heteroarylalkyl, heterocyclyl or heterocyclylalkyl are independently substituted with the substituent selected from the group consisting of halogen, hydroxy, cyano, nitro, azido, haloalkyl, alkyl, alkenyl, alkynyl, saturated and partially unsaturated cycloalkyl, saturated and partially unsaturated heterocyclyl, —$NR^{15}R^{13}$ and —$OR^{15}$; when there are more than one substituents, the substituents are the same or different;

each $R^3$ is independently selected from the group consisting of Z, "5 to 6 membered heterocycle having 1 to 4 heteroatom selected from the group consisting of N, O, S, SO and $SO_2$, substituted with -$M_1$-$M_2$-$M_3$-$M_4$ or -$M_1$-$M_5$" which is substituted with $C_1$-$C_4$ alkyl or unsubstituted, aryl substituted with -$M_1$-$M_2$-$M_3$-$M_4$ or -$M_1$-$M_5$, —$(CR^{13}R^{14})_s$—C≡C—$(CR^{13}R^{14})_t$—$R^4$, —$(CR^{13}R^{14})_s$—C=C—$(CR^{13}R^{14})_t$—$R^4$, —$(CR^{13}R^{14})_s$—C≡C—$(CR^{13}R^{14})_k$—$R^5$, —$(CR^{13}R^{14})_s$—C=C—$(CR^{13}R^{14})_k$—$R^5$, halogen, cyano, nitro, alkyl, alkenyl, alkynyl, heteroalkyl, heteroalkenyl, heteroalkynyl, saturated or partially unsaturated cycloalkyl, saturated or partially unsaturated heterocyclyl, cycloalkyl alkyl, heterocyclylalkyl, aryl, arylalkyl, heteroaryl, heteroarylalkyl, haloalkyl, haloalkoxy, —$OR^{15}$, —$NR^{15}R^{16}$, —$NR^{15}OR^{16}$, —$NR^{15}$C(=O)$OR^{18}$, —$NR^{15}$C(=O)$SR^{18}$, —$NR^{15}$C(=O)$R^{16}$, —$NR^{15}SO_2R^{18}$, —$SO_2NR^{15}R^{16}$, —$SR^{15}$, —$SOR^{15}$, —$SO_2R^{15}$, —C(=O)$R^{15}$, —C(=O)$OR^{15}$, —OC(=O)$R^{15}$, —OC(=O)$OR^{15}$, —$OSO_2R^{15}$, —$OSO_2NR^{15}R^{13}$, —OC(=O)$NR^{15}R^{13}$, —C(=O)$NR^{15}R^{16}$, —$NR^{15}$C(=O)$NR^{16}R^{17}$, —$NR^{15}SO_2NR^{16}R^{17}$, —$NR^{15}$C(=S)$NR^{16}R^{17}$, —$NR^{15}$C(=S)$R^{16}$, —$NR^{15}$C(=N—CN)$NR^{16}R^{17}$, —$NR^{15}$C(=N—CN)$R^{16}$, —S(O)$_p(CR^{13}R^{14})_q$-aryl, —O$(CR^{13}R^{14})_q$-aryl, —$NR^{15}(CR^{13}R^{14})_q$-aryl, —O$(CR^{13}R^{14})_q$-heteroaryl, —$NR^{13}(CR^{13}R^{14})_q$-heteroaryl, —O$(CR^{13}R^{14})_q$-heterocyclyl and —$NR^{15}(CR^{13}R^{14})_q$-heterocyclyl;

in the definition of $R^3$, the alkyl, alkenyl, alkynyl, heteroalkyl, heteroalkenyl, heteroalkynyl, cycloalkyl, heterocyclyl, aryl, arylalkyl, heteroaryl, heteroarylalkyl are independently substituted with the substituent selected from the group consisting of halogen, oxo, cyano, nitro, alkyl, alkenyl, alkynyl, aryl, arylalkyl, heteroaryl, heteroarylalkyl, haloalkyl, haloalkoxy, —$OR^{15}$, —$NR^{15}R^{16}$, —$NR^{15}OR^{16}$, —$NR^{15}$C(=O)$OR^{18}$, —$NR^{15}$C(=O)$R^{16}$, —$NR^{15}SO_2R^{18}$, —$SO_2NR^{15}R^{16}$, —$SR^{15}$, —$SOR^{15}$, —$SO_2R^{15}$, —C(=O)$R^{15}$, —C(=O)$OR^{15}$, —OC(=O)$R^{15}$, —OC(=O)$OR^{15}$, —$OSO_2R^{15}$, —$OSO_2NR^{15}R^{13}$, —OC(=O)$NR^{15}R^{13}$, —C(=O)$NR^{15}R^{16}$, —$NR^{15}$C(=O)$NR^{16}R^{17}$, —$NR^{15}SO_2NR^{16}R^{17}$, —$NR^{15}$C(=S)$NR^{16}R^{17}$, —$NR^{15}$C(=S)$R^{16}$, —$NR^{15}$C(=N—CN)$NR^{16}R^{17}$, —$NR^{15}$C(=N—CN)$R^{16}$, —($C_1$-$C_4$ alkyl)$NR^aR^b$ and —$NR^{15}$C(=O)$CH_2OR^a$, when there are more than one substituents, the substituents are the same or different;

in the definition of $R^3$, $M_1$ is $C_1$-$C_4$ alkylene, wherein, —$CH_2$— is optionally replaced with —C(=O)—; $M_2$ is —$NR^e$—, —O— or —$CR^eR^f$—; $M_3$ is $C_1$-$C_4$ alkylene; $M_4$ is —CN, —$NR^eS(=O)_{0-2}R^f$, —S(=O)$_{0-2}NR^gR^h$, —C(=O)$NR^gR^h$, —S(=O)$_{0-2}R^f$, —CO₂Rᶠ, —P(=O)RᵉRᶠ, —NRᵉP(=O)RᵉRᶠ or —P(=O)RᶠNRᵍRʰ; and M₅ is —OH or —NRᵍRʰ; wherein, each of Rᵉ, Rᶠ, Rᵍ and Rʰ is independently H, $C_1$-$C_6$ alkyl, $C_3$-$C_6$ cycloalkyl or aryl, or, Rᵍ and Rʰ together with the N atom attached form 5 to 6 membered heterocyclyl having 1 to 3 heteroatom selected from the group consisting of N, O, S, SO and SO₂, wherein any N atom on the ring is optionally substituted with $C_1$-$C_4$ alkyl or —S(=O)$_p$ alkyl, and the cycle optionally has one or two substituent selected from oxo or thioxo;

in the definition of R³, Z is selected from

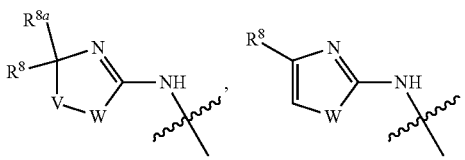

or a tautomer thereof;

in the definition of Z, W and V is independently —O—, —NR⁶—, —S—, —SO—, —SO₂—, —CR⁷R⁸—, —CR⁸R⁹— or —C(=O)—;

the requirement is that when W is —O—, —NR⁶—, —S—, —SO— or —SO₂—, V is —CR⁷R⁸— or —CR⁸R⁹—, and when V is —O—, —NR⁶—, —S—, —SO— or —SO₂—, W is —CR⁷R⁸— or —CR⁸R⁹—;

in the definition of Z, each of R⁸, R⁸ᵃ and R⁹ is independently hydrogen, haloalkyl, alkyl, saturated or partially unsaturated cycloalkyl, cycloalkyl alkyl, saturated or partially unsaturated heterocyclyl, aryl, arylalkyl, heteroaryl, heteroarylalkyl, or heterocyclylalkyl;

in the definition of R⁸, R⁸ᵃ and R⁹, the alkyl, cycloalkyl, cycloalkyl alkyl, heterocyclyl, aryl, arylalkyl, heteroaryl, heteroarylalkyl, and heterocyclylalkyl are independently substituted with the substituent selected from the group consisting of oxo, halogen, alkyl, alkenyl, alkynyl, saturated or partially unsaturated cycloalkyl, saturated or partially unsaturated heterocyclyl, cycloalkyl alkyl, cyano, nitro, —OR¹⁵, —NR¹⁵R¹⁶, —SR¹⁵, —SOR¹⁵, —SO₂R¹⁵, haloalkyl, haloalkoxy, azido, aryl, heteroaryl, arylalkyl, heteroarylalkyl, and heterocyclylalkyl, when there are more than one substituents, the substituents are the same or different;

in the definition of Z, R⁷ is selected from the group consisting of hydrogen, halogen, cyano, nitro, alkyl, alkenyl, alkynyl, saturated or partially unsaturated cycloalkyl, saturated or partially unsaturated heterocyclyl, cycloalkyl alkyl, aryl, arylalkyl, heteroaryl, heteroarylalkyl, heterocyclylalkyl, —NR¹⁵SO₂R¹⁶, —SO₂NR¹⁵R¹⁶, —C(=O)R¹⁵, —C(=O)OR¹⁵, —OC(=O)R¹⁵, —OC(=O)NR¹⁵R¹³, —NR¹⁵C(=O)OR¹⁸, —NR¹⁵C(=O)R¹⁶, —C(=O)NR¹⁵R¹⁶, —NR¹⁵R¹⁶, —NR¹⁵C(=O)NR¹⁶R¹⁷, —OR¹⁵, —S(=O)R¹⁵, —SO₂R¹⁵ and —SR¹⁵;

in the definition of R⁷, the alkyl, alkenyl, alkynyl, cycloalkyl, heterocyclyl, cycloalkyl alkyl, aryl, arylalkyl, heteroaryl, heteroarylalkyl, and heterocyclylalkyl are independently substituted with the substituent selected from the group consisting of oxo, halogen, alkyl, alkenyl, alkynyl, saturated or partially unsaturated cycloalkyl, saturated or partially unsaturated heterocyclyl, cycloalkyl alkyl, cyano, nitro, haloalkyl, haloalkoxy, azido, —NR¹⁵SO₂R¹⁶, —SO₂NR¹⁵R¹⁶, —C(=O)R¹⁵, —C(=O)OR¹⁵, —OC(=O)R¹⁵, —OC(=O)NR¹⁵R¹³, —NR¹⁵C(=O)OR¹⁸, —NR¹⁵C(=O)R¹⁶, —C(=O)NR¹⁵R¹⁶, —NR¹⁵R¹⁶, —NR¹⁵C(=O)NR¹⁶R¹⁷, —OR¹⁵, —S(=O)R¹⁵, —SO₂R¹⁵, —SR¹⁵aryl, heteroaryl, arylalkyl, heteroarylalkyl, and heterocyclylalkyl, when there are more than one substituents, the substituents are the same or different;

or, in the definition of Z, R⁸ and R⁸ᵃ together with the atom attached form a 3 to 6 membered carbocycle, or, a 3 to 10 membered saturated or partially unsaturated heterocyclyl; wherein the carbocycle and heterocyclyl are independently substituted with the substituent selected from the group consisting of oxo, halogen, alkyl, alkenyl, alkynyl, saturated or partially unsaturated cycloalkyl, saturated or partially unsaturated heterocyclyl, cycloalkyl alkyl, cyano, nitro, haloalkyl, haloalkoxy, azido, aryl, —C(=O)OR¹⁵, —C(=O)R¹⁵, —OR¹⁵, —NR¹⁵R¹⁶, —SR¹⁵, heteroaryl, arylalkyl, heteroarylalkyl, and heterocyclylalkyl, when there are more than one substituents, the substituents are the same or different;

or, in the definition of Z, R⁷ and R⁸ together with the atom attached form a 3 to 10 membered saturated or partially unsaturated cycloalkyl or heterocyclyl; the heterocyclyl has the heteroatom selected from the group consisting of N, O, S, SO, SO₂ and NR⁶, wherein the cycloalkyl and heterocyclyl are independently substituted with the substituent selected from the group consisting of oxo, halogen, alkyl, alkenyl, alkynyl, saturated or partially unsaturated cycloalkyl, saturated or partially unsaturated heterocyclyl, cycloalkyl alkyl, cyano, nitro, haloalkyl, haloalkoxy, azido, aryl, —OR¹⁵, —NR¹⁵R¹⁶, —SR¹⁵, heteroaryl, arylalkyl, heteroarylalkyl, and heterocyclylalkyl, when there are more than one substituents, the substituents are the same or different;

or, in the definition of Z, R⁸ and R⁹ together with the atom attached form a 3 to 10 membered saturated or partially unsaturated cycloalkyl or heterocyclyl; the heterocyclyl has the heteroatom selected from the group consisting of N, O, S, SO, SO₂ and NR⁶, wherein the cycloalkyl and heterocyclyl are independently substituted with the substituent selected from the group consisting of oxo, halogen, alkyl, alkenyl, alkynyl, saturated or partially unsaturated cycloalkyl, saturated or partially unsaturated heterocyclyl, cycloalkyl alkyl, cyano, nitro, haloalkyl, haloalkoxy, azido, aryl, —C(=O)OR¹⁵, —C(=O)R¹⁵, —OR¹⁵, —NR¹⁵R¹⁶, —SR¹⁵, heteroaryl, arylalkyl, heteroarylalkyl, and heterocyclylalkyl, when there are more than one substituents, the substituents are the same or different;

in the definition of R³, each R⁴ is independently H, alkyl, alkenyl, alkynyl, heteroalkyl, heteroalkenyl, heteroalkynyl, saturated or partially unsaturated cycloalkyl, saturated or partially unsaturated heterocyclyl, aryl, arylalkyl, heteroaryl or heteroarylalkyl; the heterocyclyl has the heteroatom selected from the group consisting of N, O, S, SO, SO₂ and NR⁶;

in the definition of R⁴, the alkyl, alkenyl, alkynyl, heteroalkyl, heteroalkenyl, heteroalkynyl, cycloalkyl, heterocyclyl, aryl, arylalkyl, heteroaryl, heteroarylalkyl are independently substituted with the substituent selected from the group consisting of alkyl, alkenyl, alkynyl, saturated or partially unsaturated cycloalkyl, saturated or partially unsaturated heterocyclyl, cycloalkyl alkyl, aryl, heteroaryl, arylalkyl, heteroarylalkyl, and heterocyclylalkyl, halogen, cyano, nitro, haloalkyl, haloalkoxy, azido, oxo, —$OR^{15}$, —$R^{15}R^{16}$, —$NR^{15}OR^{16}$, —$NR^{15}C(=O)OR^{18}$, —$NR^{15}C(=O)R^{16}$, —$SO_2NR^{15}R^{16}$, —$SR^{15}$, —$SOR^{15}$, —$SO_2R^{15}$, —$C(=O)R^{15}$, —$C(=O)OR^{15}$, —$OC(=O)R^{15}$, —$OC(=O)NR^{15}R^{13}$, —$OC(=O)OR^{15}$, —$OSO_2R^{15}$, —$OSO_2NR^{15}R^{13}$—$C(=O)NR^{15}R^{16}$, —$NR^{15}C(=O)NR^{16}R^{17}$—$NR^{15}SO_2R^{18}$, —$NR^{15}SO_2NR^{16}R^{17}$, —$NR^{15}C(=S)NR^{16}R^{17}$, —$NR^{15}C(=S)R^{16}$, —$NR^{15}C(=N—CN)NR^{16}R^{17}$, —$NR^{15}C(=N—CN)R^{16}$, —$(C_1$-$C_4$ alkyl)$NR^aR^b$ and —$NR^{15}C(=O)CH_2OR^a$, when there are more than one substituents, the substituents are the same or different;

in the definition of $R^3$, each $R^5$ is independently —$NR^{15}R^{13}$, —$NR^{15}OR^{16}$, —$NR^{15}C(=O)OR^{18}$, —$NR^{15}C(=O)R^{16}$, —$NR^{15}C(=O)NR^{16}R^{17}$, —$NR^{15}SO_2R^{18}$, —$NR^{15}SO_2NR^{16}R^{17}$, —$OR^{15}$, —$OC(=O)R^{15}$, —$OC(=O)OR^{15}$, —$OSO_2R^{15}$, —$OSO_2NR^{15}R^{13}$—$OC(=O)NR^{15}R^{13}$;

each of $R^{13}$ and $R^{14}$ is independently hydrogen or alkyl, or, $R^{13}$ and $R^{14}$ together with the atom attached form saturated or partially unsaturated cycloalkyl, or, saturated or partially unsaturated heterocyclyl; wherein, the alkyl, cycloalkyl and heterocyclyl are independently substituted with the substituent selected from the group consisting of halogen, cyano, nitro, haloalkyl, haloalkoxy, azido, oxo, —$OR^a$, —$NR^aR^b$, —$NR^aOR^b$, —$NR^aCO_2R^b$, —$NR^aCOR^b$, —$SO_2NR^aR^b$, —$SR^a$, —$SOR^a$, —$SO_2R^a$, —S—S—$R^a$, —$C(=O)R^a$, —$C(=O)OR^a$, —$OC(=O)R^a$, —$OC(=O)OR^a$, —$OSO_2R^a$, —$OSO_2NR^aR^b$, —$OC(=O)NR^aR^b$, —$C(=O)NR^aR^b$, —$NR^aC(=O)R^b$, —$NR^aSO_2R^b$, —$NR^aSO_2NR^bR^c$ and —$NR^aC(=O)NR^bR^c$, when there are more than one substituents, the substituents are the same or different;

each of $R^{15}$, $R^{16}$ and $R^{17}$ is independently selected from the group consisting of H, alkyl, alkenyl, alkynyl, heteroalkyl, heteroalkenyl, heteroalkynyl, saturated or partially unsaturated cycloalkyl, saturated or partially unsaturated heterocyclyl, cycloalkyl alkyl, aryl, arylalkyl, heteroaryl, heteroarylalkyl, —$C(=O)R^a$, $OR^a$, and heterocyclylalkyl;

in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with the substituent selected from the group consisting of alkyl, alkenyl, alkynyl, heteroalkyl, heteroalkenyl, heteroalkynyl, saturated or partially unsaturated cycloalkyl, saturated or partially unsaturated heterocyclyl substituted with $C_1$-$C_6$ alkyl or unsubstituted, aryl, heteroaryl, halogen, haloalkyl, haloalkoxy, oxo, cyano, —$OR^a$, —$NR^aR^b$, —$NR^aOR^b$, —$NR^aCO_2R^b$, —$NR^aCOR^b$, —$SO_2NR^aR^b$, —$SR^a$, —$SOR^a$, —$SO_2R^a$, —S—S—$R^a$, —$C(=O)R^a$, —$C(=O)OR^a$, —$OC(=O)R^a$, —$OC(=O)OR^a$, —$OSO_2R^a$, —$OSO_2NR^aR^b$, —$OC(=O)NR^aR^b$, —$C(=O)NR^aR^b$, $NR^aC(=O)R^b$, —$NR^aC(=O)NR^bR^c$, —$NR^aSO_2R^b$, —$NR^aSO_2NR^bR^c$, —$OC(=O)NR^aR^b$, —$C(=O)$—$CR^a=CR^aR^b$, —$C(=O)$—$C≡C$—$(CR^aR^b)_{1-3}NR^aR^b$, —$(CH_2)_{1-3}C(=O)NR^a$, —$C(=O)(CH_2)_{1-3}OR^a$ and —$(CR^aR^b)_{1-3}NR^aR^b$, when there are more than one substituents, the substituents are the same or different;

or, any two of $R^{15}$, $R^{16}$ and $R^{17}$ together with the atom attached form heterocycle; the heterocycle has the heteroatom selected from the group consisting of N, O, S, SO, $SO_2$ and $NR^6$, wherein the heterocycle is substituted with the substituent selected from the group consisting of oxo, halogen, alkyl, alkenyl, alkynyl, saturated or partially unsaturated cycloalkyl, saturated or partially unsaturated heterocyclyl, cycloalkyl alkyl, cyano, nitro, haloalkyl, haloalkoxy, azido, aryl, —$OR^a$, —$NR^aR^b$, —$SR^a$, heteroaryl, arylalkyl, heteroarylalkyl, and heterocyclylalkyl, when there are more than one substituents, the substituents are the same or different:

or, $R^{13}$ and $R^{15}$ together with the atom attached form saturated or partially unsaturated heterocyclyl; wherein, the heterocyclyl is substituted with the substituent selected from the group consisting of halogen, cyano, nitro, haloalkyl, haloalkoxy, azido, oxo, cyano, —$OR^a$, —$NR^aR^b$, —$NR^aOR^b$, —$NR^aCO_2R^b$, —$NR^aCOR^b$, —$SO_2NR^aR^b$, —$SR^a$, —$SOR^a$, —$SO_2R^a$, —S—S—$R^a$, —$C(=O)R^a$, —$C(=O)OR^a$, —$OC(=O)R^a$, —$C(=O)NR^aR^b$, —$OC(=O)OR^a$, —$OSO_2R^a$, —$OSO_2NR^aR^b$, —$OC(=O)NR^aR^b$, $NR^aC(=O)R^b$, —$NR^aSO_2R^b$, —$NR^aSO_2NR^bR^c$, —$C(=O)(CH_2)_{1-3}OR^a$ and —$(CR^aR^b)_{1-3}NR^aR^b$ and —$NR^aC(=O)NR^bR^c$, when there are more than one substituents, the substituents are the same or different;

each $R^{18}$ is independently H, —$CF_3$, alkyl, alkenyl, alkynyl, heteroalkyl, heteroalkenyl, heteroalkynyl, saturated or partially unsaturated cycloalkyl, saturated or partially unsaturated heterocyclyl, cycloalkyl alkyl, aryl, arylalkyl, heteroaryl, heteroarylalkyl, or heterocyclylalkyl;

in the definition of $R^{18}$, the alkyl, alkenyl, alkynyl, cycloalkyl, saturated or partially unsaturated heterocyclyl, cycloalkyl alkyl, aryl, arylalkyl, heteroaryl, heteroarylalkyl and heterocyclylalkyl are independently substituted with the substituent selected from the group consisting of alkyl, alkenyl, alkynyl, heteroalkyl, heteroalkenyl, heteroalkynyl, saturated or partially unsaturated cycloalkyl, saturated or partially unsaturated heterocyclyl, aryl, heteroaryl, halogen, oxo, —$OR^a$, —$NR^aR^b$, —$NR^aOR^b$, —$NR^aCO_2{}^b$, —$NR^aCOR^b$, —$SO_2NR^aR^b$, —$SR^a$, —$SOR^a$, —$SO_2R^a$, —S—S—$R^a$, —$C(=O)R^a$, —$C(=O)OR^a$, —$OC(=O)R^a$, —$OC(=O)OR^a$, —$OSO_2R^a$, —$OSO_2NR^aR^b$, —$OC(=O)NR^aR^b$, —$C(=O)NR^aR^b$, —$NR^aC(=O)R^b$, —$NR^aC(=O)NR^bR^c$, —$NR^aSO_2R^b$, and —$NR^aSO_2NR^bR^c$, when there are more than one substituents, the substituents are the same or different:

or, $R^{15}$ and $R^{18}$ together with the atom attached form saturated or partially unsaturated heterocyclyl; wherein, the heterocyclyl is substituted with the substituent selected from the group consisting of halogen, cyano, nitro, haloalkyl, haloalkoxy, azido, oxo, —$OR^a$, —$NR^aR^b$, —$NR^aOR^b$, —$NR^aCO_2R^b$, —$NR^aCOR^b$, —$SO_2NR^aR^b$, —$SR^a$, —$SOR^a$, —$SO_2R^a$, —S—S—$R^a$, —$C(=O)R^a$, —$C(=O)OR^a$, —$OC(=O)R^a$, —$OC(=O)OR^a$, —$OSO_2R^a$, —$OSO_2NR^aR^b$, —$OC(=O)NR^aR^b$, —$C(=O)NR^aR^b$, —$NR^aC(=O)R^b$, —$NR^aSO_2R^b$, —$NR^aSO_2NR^bR^c$ and —$NR^aC(=O)NR^bR^c$, when there are more than one substituents, the substituents are the same or different;

each $R^6$ is independently hydrogen, haloalkyl, alkyl, saturated or partially unsaturated cycloalkyl, saturated or partially unsaturated heterocyclyl, aryl, arylalkyl, heteroaryl, heteroarylalkyl, or heterocyclylalkyl;

in the definition of $R^6$, the alkyl, cycloalkyl, heterocyclyl, aryl, arylalkyl, heteroaryl, heteroarylalkyl, and heterocyclylalkyl are independently substituted with the substituent selected from the group consisting of oxo, halogen, alkyl, alkenyl, alkynyl, saturated or partially unsaturated cycloalkyl, saturated or partially unsaturated heterocyclyl, cycloalkyl alkyl, cyano, nitro, —OR$^{15}$, —SR$^{15}$, —SOR$^{15}$, —SO$_2$R$^{15}$, haloalkyl, haloalkoxy, azido, aryl, heteroaryl, arylalkyl, heteroarylalkyl, and heterocyclylalkyl, when there are more than one substituents, the substituents are the same or different;

each of R$^a$, R$^b$ and R$^c$ is independently H, halogen, alkyl, alkenyl, alkynyl, saturated or partially unsaturated cycloalkyl, saturated or partially unsaturated heterocyclyl, aryl or heteroaryl;

or, —NR$^b$R$^c$ forms a 5 to 6 membered heterocycle having 1 to 2 nitrogen atom(s) on the ring and optionally substituted with C$_1$-C$_3$ alkyl;

or, —NR$^b$R$^c$ forms a 5 to 6 membered heterocycle having 1 to 2 nitrogen atom(s) on the ring;

m is 1, 2, 3 or 4;
n is 0, 1, 2, 3 or 4;
g is 0, 1, 2, 3, 4 or 5;
p is 0, 1 or 2;
s is 0, 1, 2 or 3;
k is 1, 2 or 3; and
t is 0, 1, 2, 3, 4 or 5.

2. The nitrogenous heterocyclic compound as defined in claim 1, wherein when j is 1, E is

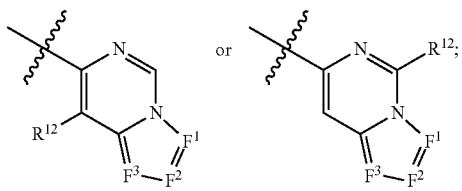

when R$^{12}$ is halogen, the halogen is fluorine, chlorine, bromine or iodine;

when each R$^{12}$ is independently haloalkyl, the halogen in the "haloalkyl" is fluorine, chlorine or bromine;

when each R$^{12}$ is independently haloalkyl, the alkyl in the "haloalkyl" is C$_1$-C$_6$ alkyl;

when each R$^{12}$ is independently haloalkoxy, the halogen in the "haloalkoxy" is fluorine, chlorine or bromine;

when each R$^{12}$ is independently haloalkoxy, the alkoxy in the "haloalkoxy" is C$_1$-C$_6$ alkoxy;

when R$^{12}$ is alkyl, the alkyl is C$_1$-C$_6$ alkyl;

when in the definition of R$^{12}$, the alkyl, alkenyl, alkynyl, cycloalkyl, aryl, arylalkyl, heteroaryl, heteroarylalkyl, heterocyclyl and heterocyclylalkyl are independently substituted with one or more haloalkyl, the halogen in the "haloalkyl" is fluorine, chlorine or bromine;

when in the definition of R$^{12}$, the alkyl, alkenyl, alkynyl, cycloalkyl, aryl, arylalkyl, heteroaryl, heteroarylalkyl, heterocyclyl and heterocyclylalkyl are independently substituted with one or more haloalkyl, the alkyl in the "haloalkyl" is C$_1$-C$_6$ alkyl;

when in the definition of R$^{12}$, the alkyl, alkenyl, alkynyl, cycloalkyl, aryl, arylalkyl, heteroaryl, heteroarylalkyl, heterocyclyl and heterocyclylalkyl are independently substituted with one or more haloalkoxy, the halogen in the "haloalkoxy" is fluorine, chlorine or bromine;

when in the definition of R$^{12}$, the alkyl, alkenyl, alkynyl, cycloalkyl, aryl, arylalkyl, heteroaryl, heteroarylalkyl, heterocyclyl and heterocyclylalkyl are independently substituted with one or more haloalkoxy, the alkoxy in the "haloalkoxy" is C alkoxy;

when in the definition of R$^{12}$, the alkyl, alkenyl, alkynyl, cycloalkyl, aryl, arylalkyl, heteroaryl, heteroarylalkyl, heterocyclyl and heterocyclylalkyl are independently substituted with the substituent selected from the group consisting of aryl, heteroaryl, arylalkyl, heteroarylalkyl, heterocyclyl and heterocyclylalkyl, wherein the aryl, heteroaryl, arylalkyl, heteroarylalkyl, heterocyclyl or heterocyclylalkyl are independently substituted with one or more haloalkyl, the halogen in the "haloalkyl" is fluorine, chlorine or bromine;

when in the definition of R$^{12}$, the alkyl, alkenyl, alkynyl, cycloalkyl, aryl, arylalkyl, heteroaryl, heteroarylalkyl, heterocyclyl and heterocyclylalkyl are independently substituted with the substituent selected from the group consisting of aryl, heteroaryl, arylalkyl, heteroarylalkyl, heterocyclyl and heterocyclylalkyl, wherein the aryl, heteroaryl, arylalkyl, heteroarylalkyl, heterocyclyl or heterocyclylalkyl are independently substituted with one or more haloalkyl, the alkyl in the "haloalkyl" is C$_1$-C$_6$ alkyl;

when each R$^{19}$ is independently haloalkyl, the halogen in the "haloalkyl" is fluorine, chlorine or bromine;

when each R$^{19}$ is independently haloalkyl, the alkyl in the "haloalkyl" is C$_1$-C$_6$ alkyl;

when each R$^{19}$ is independently haloalkoxy, the halogen in the "haloalkoxy" is fluorine, chlorine or bromine;

when each R$^{19}$ is independently haloalkoxy, the alkoxy in the "haloalkoxy" is C$_1$-C$_6$ alkoxy;

when in the definition of R$^{19}$, the alkyl, alkenyl, alkynyl, cycloalkyl, aryl, arylalkyl, heteroaryl, heteroarylalkyl, heterocyclyl and heterocyclylalkyl are independently substituted with one or more haloalkyl, the halogen in the "haloalkyl" is fluorine, chlorine or bromine;

when in the definition of R$^{19}$, the alkyl, alkenyl, alkynyl, cycloalkyl, aryl, arylalkyl, heteroaryl, heteroarylalkyl, heterocyclyl and heterocyclylalkyl are independently substituted with one or more haloalkyl, the alkyl in the "haloalkyl" is C$_1$-C$_6$ alkyl;

when in the definition of R$^{19}$, the alkyl, alkenyl, alkynyl, cycloalkyl, aryl, arylalkyl, heteroaryl, heteroarylalkyl, heterocyclyl and heterocyclylalkyl are independently substituted with one or more haloalkoxy, the halogen in the "haloalkoxy" is fluorine, chlorine or bromine;

when in the definition of R$^{19}$, the alkyl, alkenyl, alkynyl, cycloalkyl, aryl, arylalkyl, heteroaryl, heteroarylalkyl, heterocyclyl and heterocyclylalkyl are independently substituted with one or more haloalkoxy, the alkoxy in the "haloalkoxy" is C$_1$-C$_6$ alkoxy;

when in the definition of R$^{19}$, the alkyl, alkenyl, alkynyl, cycloalkyl, aryl, arylalkyl, heteroaryl, heteroarylalkyl, heterocyclyl and heterocyclylalkyl are independently substituted with the substituent selected from the group consisting of aryl, heteroaryl, arylalkyl, heteroarylalkyl, heterocyclyl and heterocyclylalkyl, wherein the aryl, heteroaryl, arylalkyl, heteroarylalkyl, heterocyclyl or heterocyclylalkyl is independently substituted with one or more haloalkyl, the halogen in the "haloalkyl" is fluorine, chlorine or bromine;

when in the definition of R$^{19}$, the alkyl, alkenyl, alkynyl, cycloalkyl, aryl, arylalkyl, heteroaryl, heteroarylalkyl, heterocyclyl and heterocyclylalkyl are independently substituted with the substituent selected from the group consisting of aryl, heteroaryl, arylalkyl, heteroarylalkyl, heterocyclyl and heterocyclylalkyl, wherein the aryl, heteroaryl, arylalkyl, heteroarylalkyl, heterocyclyl or heterocyclylalkyl is independently substituted with one or more haloalkyl, the alkyl in the "haloalkyl" is $C_1$-$C_6$ alkyl;

when in the definition of $R^{19}$, the alkyl, alkenyl, alkynyl, cycloalkyl, aryl, arylalkyl, heteroaryl, heteroarylalkyl, heterocyclyl and heterocyclylalkyl are independently substituted with the substituent selected from the group consisting of aryl, heteroaryl, arylalkyl, heteroarylalkyl, heterocyclyl and heterocyclylalkyl, wherein the aryl, heteroaryl, arylalkyl, heteroarylalkyl, heterocyclyl or heterocyclylalkyl is independently substituted with one or more haloalkoxy, the halogen in the "haloalkoxy" is fluorine, chlorine or bromine;

when in the definition of $R^{19}$, the alkyl, alkenyl, alkynyl, cycloalkyl, aryl, arylalkyl, heteroaryl, heteroarylalkyl, heterocyclyl and heterocyclylalkyl are independently substituted with the substituent selected from the group consisting of aryl, heteroaryl, arylalkyl, heteroarylalkyl, heterocyclyl and heterocyclylalkyl, wherein the aryl, heteroaryl, arylalkyl, heteroarylalkyl, heterocyclyl or heterocyclylalkyl is independently substituted with one or more haloalkoxy, the alkoxy in the "haloalkoxy" is $C_1$-$C_6$ alkoxy;

when $R^2$ is halogen, the halogen is fluorine, chlorine, bromine or iodine;

when $R^2$ is alkyl, the alkyl is $C_1$-$C_6$ alkyl;

when in the definition of $R^2$, the alkyl, alkenyl, alkynyl, cycloalkyl, aryl, arylalkyl, heteroaryl, heteroarylalkyl, heterocyclyl and heterocyclylalkyl are independently substituted with one or more haloalkyl, the halogen in the "haloalkyl" is fluorine, chlorine or bromine;

when in the definition of $R^2$, the alkyl, alkenyl, alkynyl, cycloalkyl, aryl, arylalkyl, heteroaryl, heteroarylalkyl, heterocyclyl and heterocyclylalkyl are independently substituted with one or more haloalkyl, the alkyl in the "haloalkyl" is $C_1$-$C_6$ alkyl;

when in the definition of $R^2$, the alkyl, alkenyl, alkynyl, cycloalkyl, aryl, arylalkyl, heteroaryl, heteroarylalkyl, heterocyclyl and heterocyclylalkyl are independently substituted with one or more haloalkoxy, the halogen in the "haloalkoxy" is fluorine, chlorine or bromine;

when in the definition of $R^2$, the alkyl, alkenyl, alkynyl, cycloalkyl, aryl, arylalkyl, heteroaryl, heteroarylalkyl, heterocyclyl and heterocyclylalkyl are independently substituted with one or more haloalkoxy, the alkoxy in the "haloalkoxy" is $C_1$-$C_6$ alkoxy;

when in the definition of $R^2$, the alkyl, alkenyl, alkynyl, cycloalkyl, aryl, arylalkyl, heteroaryl, heteroarylalkyl, heterocyclyl and heterocyclylalkyl are independently substituted with the substituent selected from the group consisting of aryl, heteroaryl, arylalkyl, heteroarylalkyl, heterocyclyl and heterocyclylalkyl, wherein the aryl, heteroaryl, arylalkyl, heteroarylalkyl, heterocyclyl or heterocyclylalkyl is independently substituted with one or more haloalkyl, the halogen in the "haloalkyl" is fluorine, chlorine or bromine;

when in the definition of $R^2$, the alkyl, alkenyl, alkynyl, cycloalkyl, aryl, arylalkyl, heteroaryl, heteroarylalkyl, heterocyclyl and heterocyclylalkyl are independently substituted with the substituent selected from the group consisting of aryl, heteroaryl, arylalkyl, heteroarylalkyl, heterocyclyl and heterocyclylalkyl, wherein the aryl, heteroaryl, arylalkyl, heteroarylalkyl, heterocyclyl or heterocyclylalkyl is independently substituted with one or more haloalkyl, the alkyl in the "haloalkyl" is $C_1$-$C_6$ alkyl;

when $R^3$ is "5 to 6 membered heterocycle having 1 to 4 heteroatom selected from the group consisting of N, O, S, SO and $SO_2$, substituted with -$M_1$-$M_2$-$M_3$-$M_4$ or -$M_1$-$M_5$" which is substituted with $C_1$-$C_4$ alkyl or unsubstituted, the 5 to 6 membered heterocycle is pyrrolyl, thienyl or furyl;

when $R^3$ is aryl substituted with -$M_1$-$M_2$-$M_3$-$M_4$ or -$M_1$-$M_5$, the "aryl" is $C_6$-$C_{10}$ aryl;

when $R^3$ is halogen, the halogen is fluorine, chlorine, bromine or iodine;

when $R^3$ is alkenyl, the alkenyl is $C_2$-$C_6$ alkenyl;

when $R^3$ is saturated or partially unsaturated heterocyclyl, the saturated or partially unsaturated heterocyclyl is a 5 to 6 membered heterocyclyl having 1 to 2 heteroatom selected from the group consisting of N and O;

when $R^3$ is aryl, the aryl is $C_6$-$C_{10}$ aryl;

when $R^3$ is heteroaryl, the heteroaryl is a 5 to 6 membered heteroaryl having 1 to 2 heteroatom selected from the group consisting of N and O;

when in the definition of $R^3$, the alkyl, alkenyl, alkynyl, heteroalkyl, heteroalkenyl, heteroalkynyl, cycloalkyl, heterocyclyl, aryl, arylalkyl, heteroaryl, heteroarylalkyl are independently substituted with one or more halogen, the halogen is fluorine, chlorine, bromine or iodine;

when in the definition of $R^3$, the alkyl, alkenyl, alkynyl, heteroalkyl, heteroalkenyl, heteroalkynyl, cycloalkyl, heterocyclyl, aryl, arylalkyl, heteroaryl, heteroarylalkyl are independently substituted with one or more alkyl, the alkyl is $C_1$-$C_6$ alkyl;

and/or, the $C_1$-$C_4$ alkylene in $M_1$ is —$CH_2$— or —$CH_2CH_2$—;

and/or, the $C_1$-$C_4$ alkylene in $M_3$ is methylene, ethylene or propylene;

when each of $R^e$, $R^f$, $R^g$ and $R^h$ is independently $C_1$-$C_6$ alkyl, the $C_1$-$C_6$ alkyl is $C_1$-$C_4$ alkyl;

when each of $R^e$, $R^f$, $R^g$ and $R^h$ is independently aryl, the aryl is $C_6$-$C_{10}$ aryl;

when $R^g$ and $R^h$ together with the N atom attached form a 5 to 6 membered heterocyclyl having 1 to 3 heteroatom(s) selected from the group consisting of N, O, S, SO and $SO_2$, the 5 to 6 membered heterocyclyl having 1 to 3 heteroatom(s) selected from the group consisting of N, O, S, SO and $SO_2$ is piperazinyl or

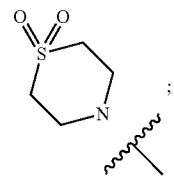

when $R^g$ and $R^h$ together with the N atom attached form a 5 to 6 membered heterocyclyl having 1 to 3 heteroatom(s) selected from the group consisting of N, O, S, SO and $SO_2$, wherein any N atom on the ring is substituted with $C_1$-$C_4$ alkyl, the $C_1$-$C_4$ alkyl is methyl or ethyl;

when $R^g$ and $R^h$ together with the N atom attached form a 5 to 6 membered heterocyclyl having 1 to 3 heteroatom(s) selected from the group consisting of N, O, S, SO and $SO_2$, wherein any N atom on the ring is substituted with —$S(=O)_p$ alkyl, the alkyl in the —$S(=O)_p$ alkyl $C_1$-$C_6$ alkyl;

when each of $R^8$, $R^{8a}$ and $R^9$ is independently haloalkyl, the halogen in the "haloalkyl" is fluorine, chlorine or bromine;

when each of $R^8$, $R^{8a}$ and $R^9$ is independently haloalkyl, the alkyl in the "haloalkyl" is $C_1$-$C_6$ alkyl;

when each of $R^8$, $R^{8a}$ and $R^9$ is independently alkyl, the alkyl is $C_1$-$C_6$ alkyl;

when in the definition of $R^8$, $R^{8a}$ and $R^9$, the alkyl, cycloalkyl, cycloalkyl alkyl, heterocyclyl, aryl, arylalkyl, heteroaryl, heteroarylalkyl, and heterocyclylalkyl are independently substituted with one or more haloalkyl, the halogen in the "haloalkyl" is fluorine, chlorine or bromine;

when in the definition of $R^8$, $R^{8a}$ and $R^9$, the alkyl, cycloalkyl, cycloalkyl alkyl, heterocyclyl, aryl, arylalkyl, heteroaryl, heteroarylalkyl, and heterocyclylalkyl are independently substituted with one or more haloalkyl, the alkyl in the "haloalkyl" is $C_1$-$C_6$ alkyl;

when in the definition of $R^8$, $R^{8a}$ and $R^9$, the alkyl, cycloalkyl, cycloalkyl alkyl, heterocyclyl, aryl, arylalkyl, heteroaryl, heteroarylalkyl, and heterocyclylalkyl are independently substituted with one or more haloalkoxy, the halogen in the "haloalkoxy" is fluorine, chlorine or bromine;

when in the definition of $R^8$, $R^{8a}$ and $R^9$, the alkyl, cycloalkyl, cycloalkyl alkyl, heterocyclyl, aryl, arylalkyl, heteroaryl, heteroarylalkyl, and heterocyclylalkyl are independently substituted with one or more haloalkoxy, the alkoxy in the "haloalkoxy" is $C_1$-$C_6$ alkoxy;

when in the definition of $R^7$, the alkyl, alkenyl, alkynyl, cycloalkyl, heterocyclyl, cycloalkyl alkyl, aryl, arylalkyl, heteroaryl, heteroarylalkyl, and heterocyclylalkyl are independently substituted with one or more haloalkyl, the halogen in the "haloalkyl" is fluorine, chlorine or bromine;

when in the definition of $R^7$, the alkyl, alkenyl, alkynyl, cycloalkyl, heterocyclyl, cycloalkyl alkyl, aryl, arylalkyl, heteroaryl, heteroarylalkyl, and heterocyclylalkyl are independently substituted with one or more haloalkyl, the alkyl in the "haloalkyl" is $C_1$-$C_6$ alkyl;

when in the definition of $R^7$, the alkyl, alkenyl, alkynyl, cycloalkyl, heterocyclyl, cycloalkyl alkyl, aryl, arylalkyl, heteroaryl, heteroarylalkyl, and heterocyclylalkyl are independently substituted with one or more haloalkoxy, the halogen in the "haloalkoxy" is fluorine, chlorine or bromine;

when in the definition of $R^7$, the alkyl, alkenyl, alkynyl, cycloalkyl, heterocyclyl, cycloalkyl alkyl, aryl, arylalkyl, heteroaryl, heteroarylalkyl, and heterocyclylalkyl are independently substituted with one or more haloalkoxy, the alkoxy in the "haloalkoxy" is $C_1$-$C_6$ alkoxy;

when $R^8$ and $R^{8a}$ together with the atom attached form a 3 to 6 membered carbocycle, the 3 to 6 membered carbocycle is cyclopentyl, cyclopropyl or cyclobutyl;

when $R^8$ and $R^{8a}$ together with the atom attached form a 3 to 10 membered saturated or partially unsaturated heterocyclyl, the 3 to 10 membered saturated or partially unsaturated heterocyclyl is a 4 to 6 membered heterocyclyl having 1 to 3 heteroatom selected from the group consisting of N, O, S, SO and $SO_2$;

when $R^8$ and $R^{8a}$ together with the atom attached form a 3 to 6 membered carbocycle or a 3 to 10 membered saturated or partially unsaturated heterocyclyl, wherein when the carbocycle and heterocyclyl are independently substituted with one or more halogen, the halogen is fluorine, chlorine, bromine or iodine;

when $R^8$ and $R^{8a}$ together with the atom attached form a 3 to 6 membered carbocycle or a 3 to 10 membered saturated or partially unsaturated heterocyclyl, wherein when the carbocycle and heterocyclyl are independently substituted with one or more alkyl, the alkyl is $C_1$-$C_6$ alkyl;

when $R^8$ and $R^{8a}$ together with the atom attached form a 3 to 6 membered carbocycle or a 3 to 10 membered saturated or partially unsaturated heterocyclyl, wherein when the carbocycle and heterocyclyl are independently substituted with one or more haloalkyl, the halogen in the "haloalkyl" is fluorine, chlorine or bromine;

when $R^8$ and $R^{8a}$ together with the atom attached form a 3 to 6 membered carbocycle or a 3 to 10 membered saturated or partially unsaturated heterocyclyl, wherein when the carbocycle and heterocyclyl are independently substituted with one or more haloalkyl, the alkyl in the "haloalkyl" is $C_1$-$C_6$ alkyl;

when $R^8$ and $R^{8a}$ together with the atom attached form a 3 to 6 membered carbocycle or a 3 to 10 membered saturated or partially unsaturated heterocyclyl, wherein when the carbocycle and heterocyclyl are independently substituted with one or more haloalkoxy, the halogen in the "haloalkoxy" is fluorine, chlorine or bromine;

when $R^8$ and $R^{8a}$ together with the atom attached form a 3 to 6 membered carbocycle or a 3 to 10 membered saturated or partially unsaturated heterocyclyl, wherein when the carbocycle and heterocyclyl are independently substituted with one or more haloalkoxy, the alkoxy in the "haloalkoxy" is $C_1$-$C_6$ alkoxy;

when $R^8$ and $R^{8a}$ together with the atom attached form a 3 to 10 membered saturated or partially unsaturated cycloalkyl or heterocyclyl, wherein when the cycloalkyl and heterocyclyl are independently substituted with one or more haloalkyl, the halogen in the "haloalkyl" is fluorine, chlorine or bromine;

when $R^8$ and $R^{8a}$ together with the atom attached form a 3 to 10 membered saturated or partially unsaturated cycloalkyl or heterocyclyl, wherein when the cycloalkyl and heterocyclyl are independently substituted with one or more haloalkyl, the alkyl in the "haloalkyl" is $C_1$-$C_6$ alkyl;

when $R^8$ and $R^{8a}$ together with the atom attached form a 3 to 10 membered saturated or partially unsaturated cycloalkyl or heterocyclyl, wherein when the cycloalkyl and heterocyclyl are independently substituted with one or more haloalkoxy, the halogen in the "haloalkoxy" is fluorine, chlorine or bromine;

when $R^8$ and $R^{8a}$ together with the atom attached form a 3 to 10 membered saturated or partially unsaturated cycloalkyl or heterocyclyl, wherein when the cycloalkyl and heterocyclyl are independently substituted with one or more haloalkoxy, the alkoxy in the "haloalkoxy" is $C_1$-$C_6$ alkoxy;

when $R^8$ and $R^9$ together with the atom attached form a 3 to 10 membered saturated or partially unsaturated cycloalkyl, the 3 to 10 membered saturated or partially unsaturated cycloalkyl is a 3 to 6 membered saturated or partially unsaturated cycloalkyl;

when $R^8$ and $R^9$ together with the atom attached form a 3 to 10 membered saturated or partially unsaturated heterocyclyl, the 3 to 10 membered saturated or partially unsaturated heterocyclyl is a 5 to 6 membered heterocyclyl having 1 to 3 heteroatom(s) selected from the group consisting of N, O, S, SO and $SO_2$;

when $R^8$ and $R^9$ together with the atom attached form a 3 to 10 membered saturated or partially unsaturated cycloalkyl or heterocyclyl, wherein when the cycloalkyl and heterocyclyl are independently substituted with one or more alkyl, the alkyl is $C_1$-$C_6$ alkyl;

when $R^8$ and $R^9$ together with the atom attached form a 3 to 10 membered saturated or partially unsaturated cycloalkyl or heterocyclyl, wherein when the cycloalkyl and heterocyclyl are independently substituted with one or more haloalkyl, the halogen in the "haloalkyl" is fluorine, chlorine or bromine;

when $R^8$ and $R^9$ together with the atom attached form a 3 to 10 membered saturated or partially unsaturated cycloalkyl or heterocyclyl, wherein when the cycloalkyl and heterocyclyl are independently substituted with one or more haloalkyl, the alkyl in the "haloalkyl" is $C_1$-$C_6$ alkyl;

when $R^8$ and $R^9$ together with the atom attached form a 3 to 10 membered saturated or partially unsaturated cycloalkyl or heterocyclyl, wherein when the cycloalkyl and heterocyclyl are independently substituted with one or more haloalkoxy, the halogen in the "haloalkoxy" is fluorine, chlorine or bromine;

when $R^8$ and $R^9$ together with the atom attached form a 3 to 10 membered saturated or partially unsaturated cycloalkyl or heterocyclyl, wherein when the cycloalkyl and heterocyclyl are independently substituted with one or more haloalkoxy, the alkoxy in the "haloalkoxy" is $C_1$-$C_6$ alkoxy;

when in $R^4$, the alkyl, alkenyl, alkynyl, heteroalkyl, heteroalkenyl, heteroalkynyl, cycloalkyl, heterocyclyl, aryl, arylalkyl, heteroaryl, heteroarylalkyl are independently substituted with one or more haloalkyl, the halogen in the "haloalkyl" is fluorine, chlorine or bromine;

when in the definition of $R^4$, the alkyl, alkenyl, alkynyl, heteroalkyl, heteroalkenyl, heteroalkynyl, cycloalkyl, heterocyclyl, aryl, arylalkyl, heteroaryl, heteroarylalkyl are independently substituted with one or more haloalkyl, the alkyl in the "haloalkyl" is $C_1$-$C_6$ alkyl;

when in the definition of $R^4$, the alkyl, alkenyl, alkynyl, heteroalkyl, heteroalkenyl, heteroalkynyl, cycloalkyl, heterocyclyl, aryl, arylalkyl, heteroaryl, heteroarylalkyl are independently substituted with one or more haloalkoxy, the halogen in the "haloalkoxy" is fluorine, chlorine or bromine;

when in the definition of $R^4$, the alkyl, alkenyl, alkynyl, heteroalkyl, heteroalkenyl, heteroalkynyl, cycloalkyl, heterocyclyl, aryl, arylalkyl, heteroaryl, heteroarylalkyl are independently substituted with one or more haloalkoxy, the alkoxy in the "haloalkoxy" is $C_1$-$C_6$ alkoxy;

and/or, the alkyl in the definition of $R^{13}$ and $R^{14}$ is $C_1$-$C_6$ alkyl;

when $R^{13}$ and $R^{14}$ together with the atom attached form saturated or partially unsaturated cycloalkyl, the saturated or partially unsaturated cycloalkyl is $C_3$-$C_6$ cycloalkyl;

when $R^{13}$ and $R^{14}$ are independently alkyl, or, $R^{13}$ and $R^{14}$ together with the atom attached form saturated or partially unsaturated cycloalkyl, wherein when the alkyl, cycloalkyl and heterocyclyl are independently substituted with one or more haloalkyl, the halogen in the "haloalkyl" is fluorine, chlorine or bromine;

when $R^{13}$ and $R^{14}$ are independently alkyl, or, $R^{13}$ and $R^{14}$ together with the atom attached form saturated or partially unsaturated cycloalkyl, wherein when the alkyl, cycloalkyl and heterocyclyl are independently substituted with one or more haloalkyl, the alkyl in the "haloalkyl" is $C_1$-$C_6$ alkyl;

when $R^{13}$ and $R^{14}$ are independently alkyl, or, $R^{13}$ and $R^{14}$ together with the atom attached form saturated or partially unsaturated cycloalkyl, wherein when the alkyl, cycloalkyl and heterocyclyl are independently substituted with one or more haloalkoxy, the halogen in the "haloalkoxy" is fluorine, chlorine or bromine;

when $R^{13}$ and $R^{14}$ are independently alkyl, or, $R^{13}$ and $R^{14}$ together with the atom attached form saturated or partially unsaturated cycloalkyl, wherein when the alkyl, cycloalkyl and heterocyclyl are independently substituted with one or more haloalkoxy, the alkoxy in the "haloalkoxy" is $C_1$-$C_6$ alkoxy;

when $R^{15}$, $R^{16}$ and $R^{17}$ are independently alkyl, the alkyl is $C_1$-$C_6$ alkyl;

when $R^{15}$, $R^{16}$ and $R^{17}$ are independently alkenyl, the alkenyl is $C_2$-$C_6$ alkenyl;

when $R^{15}$, $R^{16}$ and $R^{17}$ are independently heteroalkyl, the heteroalkyl is $C_1$-$C_6$ alkoxy,

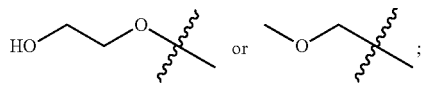

when $R^{15}$, $R^{16}$ and $R^{17}$ are independently saturated or partially unsaturated cycloalkyl, the saturated or partially unsaturated cycloalkyl is $C_3$-$C_6$ cycloalkyl;

when $R^{15}$, $R^{16}$ and $R^{17}$ are independently saturated or partially unsaturated heterocyclyl, the saturated or partially unsaturated heterocyclyl is a 5 to 6 membered heterocyclyl having 1 to 2 heteroatom(s) selected from the group consisting of N and O;

when $R^{15}$, $R^{16}$ and $R^{17}$ are independently heteroaryl, the heteroaryl is a 5 to 6 membered heteroaryl having 1 to 2 heteroatom(s) selected from the group consisting of N and O;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more alkyl, the alkyl is $C_1$-$C_6$ alkyl;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more saturated or partially unsaturated cycloalkyl, the saturated or partially unsaturated cycloalkyl is $C_3$-$C_6$ cycloalkyl;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more saturated or partially unsaturated heterocyclyl substituted with $C_1$-$C_6$ alkyl or unsubstituted, the saturated or partially unsaturated heterocyclyl contained in the term "saturated or partially unsaturated heterocyclyl substituted with $C_1$-$C_6$ alkyl or unsubstituted" is a 5 to 6 membered heterocyclyl having 1 to 2 heteroatom(s) selected from the group consisting of N and O;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more heteroaryl, the heteroaryl is a 5 to 6 membered heteroaryl having 1 to 2 heteroatom(s) selected from the group consisting of N and O;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more halogen, the halogen is fluorine, chlorine, bromine or iodine;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more haloalkyl, the halogen in the "haloalkyl" is fluorine, chlorine or bromine;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more haloalkyl, the alkyl in the "haloalkyl" is $C_1$-$C_6$ alkyl;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more haloalkoxy, the halogen in the "haloalkoxy" is fluorine, chlorine or bromine;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more haloalkoxy, the alkoxy in the "haloalkoxy" is $C_1$-$C_6$ alkoxy;

when any two of $R^{15}$, $R^{16}$ and $R^{17}$ together with the atom attached form heterocycle, the heterocycle is a 5 to 6 membered heterocyclyl having 1 to 2 heteroatom(s) selected from the group consisting of N and O, a 5 to 6 membered heterocycle having a second heteroatom selected from N and O, or

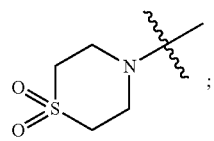 [SMILES: *N1CCS(=O)(=O)CC1]

when any two of $R^{15}$, $R^{16}$ and $R^{17}$ together with the atom attached form heterocycle, and the heterocycle is substituted with one or more alkyl, the alkyl is $C_1$-$C_6$ alkyl;

when any two of $R^{15}$, $R^{16}$ and $R^{17}$ together with the atom attached form heterocycle, and the heterocycle is substituted with one or more haloalkyl, the halogen in the "haloalkyl" is fluorine, chlorine or bromine;

when any two of $R^{15}$, $R^{16}$ and $R^{17}$ together with the atom attached form heterocycle, and the heterocycle is substituted with one or more haloalkyl, the alkyl in the "haloalkyl" is $C_1$-$C_6$ alkyl;

when any two of $R^{15}$, $R^{16}$ and $R^{17}$ together with the atom attached form heterocycle, and the heterocycle is substituted with one or more haloalkoxy, the halogen in the "haloalkoxy" is fluorine, chlorine or bromine;

when any two of $R^{15}$, $R^{16}$ and $R^{17}$ together with the atom attached form heterocycle, and the heterocycle is substituted with one or more haloalkoxy, the alkoxy in the "haloalkoxy" is $C_1$-$C_6$ alkoxy;

when $R^{13}$ and $R^{15}$ together with the atom attached form saturated or partially unsaturated heterocyclyl, and the heterocyclyl is substituted with one or more haloalkyl, the halogen in the "haloalkyl" is fluorine, chlorine or bromine;

when $R^{13}$ and $R^{15}$ together with the atom attached form saturated or partially unsaturated heterocyclyl, and the heterocycle is substituted with one or more haloalkyl, the alkyl in the "haloalkyl" is $C_1$-$C_6$ alkyl;

when $R^{13}$ and $R^{15}$ together with the atom attached form saturated or partially unsaturated heterocyclyl, and the heterocycle is substituted with one or more haloalkoxy, the halogen in the "haloalkoxy" is fluorine, chlorine or bromine;

when $R^{13}$ and $R^{15}$ together with the atom attached form saturated or partially unsaturated heterocyclyl, and the heterocycle is substituted with one or more haloalkoxy, the alkoxy in the "haloalkoxy" is $C_1$-$C_6$ alkoxy;

when each $R^{12}$ is independently alkyl, the alkyl is $C_1$-$C_6$ alkyl;

when each $R^{12}$ is independently aryl, the aryl is $C_6$-$C_{10}$aryl;

when each $R^{12}$ is independently heterocyclylalkyl, the heterocyclyl in the heterocyclylalkyl has 1 or 2 heteroatom(s) independently selected from the group consisting of N, O, and $SO_2$ on the ring;

when each $R^{12}$ is independently heterocyclylalkyl, the alkyl in the heterocyclylalkyl $C_1$-$C_4$ alkyl;

when in the definition of $R^{12}$, the alkyl, alkenyl, alkynyl, cycloalkyl, saturated or partially unsaturated heterocyclyl, cycloalkyl alkyl, aryl, arylalkyl, heteroaryl, heteroarylalkyl and heterocyclylalkyl are independently substituted with one or more saturated or partially unsaturated cycloalkyl, the saturated or partially unsaturated cycloalkyl is $C_3$-$C_6$ cycloalkyl;

when $R^{15}$ and $R^{18}$ together with the atom attached form saturated or partially unsaturated heterocyclyl, and the heterocyclyl is independently substituted with one or more haloalkyl, the halogen in the "haloalkyl" is fluorine, chlorine or bromine;

when $R^{15}$ and $R^{18}$ together with the atom attached form saturated or partially unsaturated heterocyclyl, and the heterocycle is independently substituted with one or more haloalkyl, the alkyl in the "haloalkyl" is $C_1$-$C_6$ alkyl;

when $R^{15}$ and $R^{18}$ together with the atom attached form saturated or partially unsaturated heterocyclyl, and the heterocycle is independently substituted with one or more haloalkoxy, the halogen in the "haloalkoxy" is fluorine, chlorine or bromine;

when $R^{15}$ and $R^{18}$ together with the atom attached form saturated or partially unsaturated heterocyclyl, and the heterocycle is independently substituted with one or more haloalkoxy, the alkoxy in the "haloalkoxy" is $C_1$-$C_6$ alkoxy;

when $R^6$ is haloalkyl, the halogen in the "haloalkyl" is fluorine, chlorine or bromine;

when $R^6$ is haloalkyl, the alkyl in the "haloalkyl" is $C_1$-$C_6$ alkyl;

when in the definition of $R^6$, the alkyl, cycloalkyl, heterocyclyl, aryl, arylalkyl, heteroaryl, heteroarylalkyl, and heterocyclylalkyl are independently substituted with one or more haloalkyl, the halogen in the "haloalkyl" is fluorine, chlorine or bromine;
when in the definition of $R^6$, the alkyl, cycloalkyl, heterocyclyl, aryl, arylalkyl, heteroaryl, heteroarylalkyl, and heterocyclylalkyl are independently substituted with one or more haloalkyl, the alkyl in the "haloalkyl" is $C_1$-$C_6$ alkyl;
when in the definition of $R^6$, the alkyl, cycloalkyl, heterocyclyl, aryl, arylalkyl, heteroaryl, heteroarylalkyl, and heterocyclylalkyl are independently substituted with one or more haloalkoxy, the halogen in the "haloalkoxy" is fluorine, chlorine or bromine;
when in the definition of $R^6$, the alkyl, cycloalkyl, heterocyclyl, aryl, arylalkyl, heteroaryl, heteroarylalkyl, and heterocyclylalkyl are independently substituted with one or more haloalkoxy, the alkoxy in the "haloalkoxy" is $C_1$-$C_6$ alkoxy;
when $R^a$, $R^b$ and $R^c$ are independently halogen, the halogen is fluorine, chlorine, bromine or iodine;
when $R^a$, $R^b$ and $R^c$ are independently alkyl, the alkyl is $C_1$-$C_6$ alkyl;
when $R^a$, $R^b$ and $R^c$ are independently alkenyl, the alkenyl is $C_2$-$C_6$ alkenyl;
when $R^a$, $R^b$ and $R^c$ are independently saturated or partially unsaturated cycloalkyl, the saturated or partially unsaturated cycloalkyl is $C_3$-$C_6$ cycloalkyl;
when —$NR^aR^b$ forms a 5 to 6 membered heterocycle having 1 to 2 nitrogen atom(s) on the ring and optionally substituted with $C_1$-$C_3$ alkyl, the 5 to 6 membered heterocycle having 1 to nitrogen atom(s) on the ring is

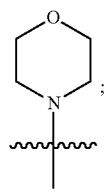

when m is 1, the compound I is

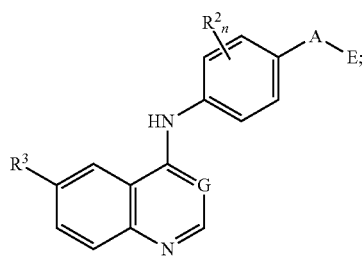

when m is 2, the compound I is

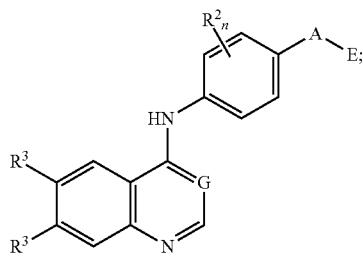

when n is 1, the compound I is

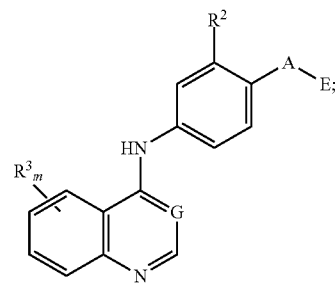

when n is 2, the compound I is

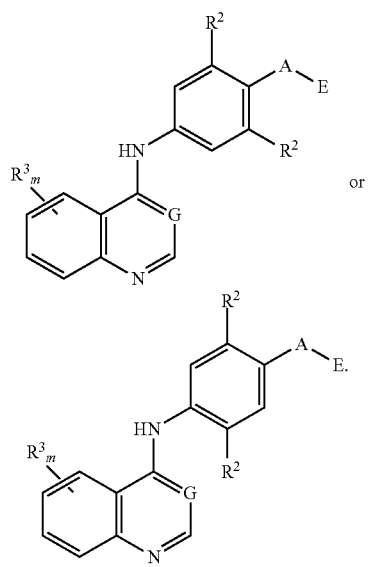

or

3. The nitrogenous heterocyclic compound as defined in claim 2, wherein, when each $R^{12}$ is independently haloalkyl, the "haloalkyl" is methoxy, ethoxy or propoxy;
when each $R^{12}$ is independently haloalkoxy, the "haloalkoxy" is trifluoromethoxy, difluoromethoxy or monofluoromethoxy;
when $R^{12}$ is alkyl, the alkyl is $C_1$-$C_4$ alkyl;
when in the definition of $R^{12}$, the alkyl, alkenyl, alkynyl, cycloalkyl, aryl, arylalkyl, heteroaryl, heteroarylalkyl, heterocyclyl and heterocyclylalkyl are independently substituted with one or more haloalkyl, the "haloalkyl" is trifluoromethyl, difluoromethyl or monofluoromethyl;
when in the definition of $R^{12}$, the alkyl, alkenyl, alkynyl, cycloalkyl, aryl, arylalkyl, heteroaryl, heteroarylalkyl, heterocyclyl and heterocyclylalkyl are independently substituted with one or more haloalkoxy, the "haloalkoxy" is trifluoromethoxy, difluoromethoxy or monofluoromethoxy;
when in the definition of $R^{12}$, the alkyl, alkenyl, alkynyl, cycloalkyl, aryl, arylalkyl, heteroaryl, heteroarylalkyl, heterocyclyl and heterocyclylalkyl are independently substituted with the substituent selected from the group consisting of aryl, heteroaryl, arylalkyl, heteroarylalkyl, heterocyclyl and heterocyclylalkyl, wherein the aryl, heteroaryl, arylalkyl, heteroarylalkyl, heterocyclyl or heterocyclylalkyl are independently substituted with one or more haloalkyl, the "haloalkyl" is trifluoromethyl, difluoromethyl or monofluoromethyl;

when each $R^{19}$ is independently haloalkyl, the "haloalkyl" is trifluoromethyl, difluoromethyl or monofluoromethyl;

when each $R^{19}$ is independently haloalkoxy, the "haloalkoxy" is trifluoromethoxy, difluoromethoxy or monofluoromethoxy;

when in the definition of $R^{19}$, the alkyl, alkenyl, alkynyl, cycloalkyl, aryl, arylalkyl, heteroaryl, heteroarylalkyl, heterocyclyl and heterocyclylalkyl are independently substituted with one or more haloalkyl, the "haloalkyl" is trifluoromethyl, difluoromethyl or monofluoromethyl;

when in the definition of $R^{19}$, the alkyl, alkenyl, alkynyl, cycloalkyl, aryl, arylalkyl, heteroaryl, heteroarylalkyl, heterocyclyl and heterocyclylalkyl are independently substituted with one or more haloalkoxy, the "haloalkoxy" is trifluoromethoxy, difluoromethoxy or monofluoromethoxy;

when in the definition of $R^{19}$, the alkyl, alkenyl, alkynyl, cycloalkyl, aryl, arylalkyl, heteroaryl, heteroarylalkyl, heterocyclyl and heterocyclylalkyl are independently substituted with the substituent selected from the group consisting of aryl, heteroaryl, arylalkyl, heteroarylalkyl, heterocyclyl and heterocyclylalkyl, wherein the aryl, heteroaryl, arylalkyl, heteroarylalkyl, heterocyclyl or heterocyclylalkyl are independently substituted with one or more haloalkyl, the "haloalkyl" is trifluoromethyl, difluoromethyl or monofluoromethyl;

when $R^2$ is alkyl, the alkyl is $C_1$-$C_4$ alkyl;

and/or, when in the definition of $R^2$, the alkyl, alkenyl, alkynyl, cycloalkyl, aryl, arylalkyl, heteroaryl, heteroarylalkyl, heterocyclyl and heterocyclylalkyl are independently substituted with one or more haloalkyl, the "haloalkyl" is trifluoromethyl, difluoromethyl or monofluoromethyl;

when in the definition of $R^2$, the alkyl, alkenyl, alkynyl, cycloalkyl, aryl, arylalkyl, heteroaryl, heteroarylalkyl, heterocyclyl and heterocyclylalkyl are independently substituted with one or more haloalkoxy, the "haloalkoxy" is trifluoromethoxy, difluoromethoxy or monofluoromethoxy;

when in the definition of $R^2$, the alkyl, alkenyl, alkynyl, cycloalkyl, aryl, arylalkyl, heteroaryl, heteroarylalkyl, heterocyclyl and heterocyclylalkyl are independently substituted with the substituent selected from the group consisting of aryl, heteroaryl, arylalkyl, heteroarylalkyl, heterocyclyl and heterocyclylalkyl, wherein the aryl, heteroaryl, arylalkyl, heteroarylalkyl, heterocyclyl or heterocyclylalkyl are independently substituted with one or more haloalkyl, the "haloalkyl" is trifluoromethyl, difluoromethyl or monofluoromethyl;

when $R^3$ is a "5 to 6 membered heterocycle having 1 to 4 heteroatom(s) selected from the group consisting of N, O, S, SO and $SO_2$, substituted with -$M_1$-$M_2$-$M_3$-$M_4$ or -$M_1$-$M_5$" which is substituted with $C_1$-$C_4$ alkyl or unsubstituted, the "5 to 6 membered heterocycle having 1 to 4 heteroatom(s) selected from the group consisting of N, O, S, SO and $SO_2$, substituted with -$M_1$-$M_2$-$M_3$-$M_4$ or -$M_1$-$M_5$" which is substituted with $C_1$-$C_4$ alkyl or unsubstituted, is 1-methyl-pyrrol-2-yl, pyrrol-2-yl, pyrrol-1-yl, thiophen-2-yl or furan-2-yl;

when $R^3$ is saturated or partially unsaturated heterocyclyl, the saturated or partially unsaturated heterocyclyl is a 5 to 6 membered heterocyclyl having 1 to 2 heteroatom(s) selected from the group consisting of N and O, the 5 to 6 membered heterocyclyl having 1 to 2 heteroatom(s) selected from the group consisting of N and O is dihydropyridinyl;

when $R^3$ is heteroaryl, the heteroaryl is isoxazolyl, pyridazinyl, pyrrolyl, furyl or pyridinyl;

when in the definition of $R^3$, the alkyl, alkenyl, alkynyl, heteroalkyl, heteroalkenyl, heteroalkynyl, cycloalkyl, heterocyclyl, aryl, arylalkyl, heteroaryl, heteroarylalkyl are independently substituted with one or more alkyl, the alkyl is $C_1$-$C_6$ alkyl, the $C_1$-$C_6$ alkyl is $C_1$-$C_4$ alkyl;

when each of $R^e$, $R^f$, $R^g$ and $R^h$ is independently $C_1$-$C_6$ alkyl, the $C_1$-$C_6$ alkyl is methyl or ethyl;

when $R^g$ and $R^h$ together with the N atom attached form a 5 to 6 membered heterocyclyl having 1 to 3 heteroatom(s) selected from the group consisting of N, O, S, SO and $SO_2$, the 5 to 6 membered heterocyclyl having 1 to 3 heteroatom(s) selected from the group consisting of N, O, S, SO and $SO_2$ is piperazin-1-yl;

when $R^g$ and $R^h$ together with the N atom attached form a 5 to 6 membered heterocyclyl having 1 to 3 heteroatom(s) selected from the group consisting of N, O, S, SO and $SO_2$, wherein any N atom on the ring is substituted with —S($\equiv$O)$_p$ alkyl, the alkyl in the —S($\equiv$O)$_p$ alkyl is methyl or ethyl;

when each $R^8$, $R^{8a}$ and $R^9$ is independently haloalkyl, the "haloalkyl" is trifluoromethyl, difluoromethyl or monofluoromethyl;

when each of $R^8$, $R^{8a}$ and $R^9$ is independently alkyl, the alkyl is isopropyl, methyl or ethyl;

when in the definition of $R^8$, $R^{8a}$ and $R^9$, the alkyl, cycloalkyl, cycloalkyl alkyl, heterocyclyl, aryl, arylalkyl, heteroaryl, heteroarylalkyl, and heterocyclylalkyl are independently substituted with one or more haloalkyl, the "haloalkyl" is trifluoromethyl, difluoromethyl or monofluoromethyl;

when in the definition of $R^8$, $R^{8a}$ and $R^9$, the alkyl, cycloalkyl, cycloalkyl alkyl, heterocyclyl, aryl, arylalkyl, heteroaryl, heteroarylalkyl, and heterocyclylalkyl are independently substituted with one or more haloalkoxy, the "haloalkoxy" is trifluoromethoxy, difluoromethoxy or monofluoromethoxy;

when in the definition of $R^7$, the alkyl, alkenyl, alkynyl, cycloalkyl, heterocyclyl, cycloalkyl alkyl, aryl, arylalkyl, heteroaryl, heteroarylalkyl, and heterocyclylalkyl are independently substituted with one or more haloalkyl, the "haloalkyl" is trifluoromethyl, difluoromethyl or monofluoromethyl;

when in the definition of $R^7$, the alkyl, alkenyl, alkynyl, cycloalkyl, heterocyclyl, cycloalkyl alkyl, aryl, arylalkyl, heteroaryl, heteroarylalkyl, and heterocyclylalkyl are independently substituted with one or more haloalkoxy, the "haloalkoxy" is trifluoromethoxy, difluoromethoxy or monofluoromethoxy;

when $R^8$ and $R^{8a}$ together with the atom attached form a 3 to 10 membered saturated or partially unsaturated heterocyclyl, the 3 to 10 membered saturated or partially unsaturated heterocyclyl is oxahex-4-yl, piperidin-4-yl or azetidin-3-yl;

when $R^8$ and $R^{8a}$ together with the atom attached form a 3 to 6 membered carbocycle or a 3 to 10 membered saturated or partially unsaturated heterocyclyl, wherein when the carboncycle and heterocyclyl are independently substituted with one or more alkyl, the alkyl is $C_1$-$C_4$ alkyl;

when $R^8$ and $R^{8a}$ together with the atom attached form a 3 to 6 membered carbocycle or a 3 to 10 membered saturated or partially unsaturated heterocyclyl, wherein when the carboncycle and heterocyclyl are independently substituted with one or more haloalkyl, the "haloalkyl" is trifluoromethyl, difluoromethyl or monofluoromethyl;

when $R^8$ and $R^{8a}$ together with the atom attached form a 3 to 6 membered carbocycle or a 3 to 10 membered saturated or partially unsaturated heterocyclyl, wherein when the carboncycle and heterocyclyl are independently substituted with one or more haloalkoxy, the "haloalkoxy" is trifluoromethoxy, difluoromethoxy or monofluoromethoxy;

when $R^8$ and $R^{8a}$ together with the atom attached form a 3 to 10 membered saturated or partially unsaturated cycloalkyl or heterocyclyl, wherein when the cycloalkyl and heterocyclyl are independently substituted with one or more haloalkyl, the "haloalkyl" is trifluoromethyl, difluoromethyl or monofluoromethyl;

when $R^8$ and $R^{8a}$ together with the atom attached form a 3 to 10 membered saturated or partially unsaturated cycloalkyl or heterocyclyl, wherein when the cycloalkyl and heterocyclyl are independently substituted with one or more haloalkoxy, the "haloalkoxy" is trifluoromethoxy, difluoromethoxy or monofluoromethoxy;

when $R^8$ and $R^9$ together with the atom attached form a 3 to 10 membered saturated or partially unsaturated cycloalkyl, the 3 to 10 membered saturated or partially unsaturated cycloalkyl is is cyclobutyl;

when $R^8$ and $R^9$ together with the atom attached form a 3 to 10 membered saturated or partially unsaturated heterocyclyl, the 3 to 10 membered saturated or partially unsaturated heterocyclyl is azahex-4-yl, oxahex-4-yl, piperidin-4-yl or azetidin-3-yl;

when $R^8$ and $R^9$ together with the atom attached form a 3 to 10 membered saturated or partially unsaturated cycloalkyl or heterocyclyl, wherein when the cycloalkyl and heterocyclyl are independently substituted with one or more alkyl, the alkyl is $C_1$-$C_4$ alkyl;

when $R^8$ and $R^9$ together with the atom attached form a 3 to 10 membered saturated or partially unsaturated cycloalkyl or heterocyclyl, wherein when the cycloalkyl and heterocyclyl are independently substituted with one or more haloalkyl, the "haloalkyl" is trifluoromethyl, difluoromethyl or monofluoromethyl;

when $R^8$ and $R^9$ together with the atom attached form a 3 to 10 membered saturated or partially unsaturated cycloalkyl or heterocyclyl, wherein when the cycloalkyl and heterocyclyl are independently substituted with one or more haloalkoxy, the "haloalkoxy" is trifluoromethoxy, difluoromethoxy or monofluoromethoxy;

when in the definition of $R^4$, the alkyl, alkenyl, alkynyl, heteroalkyl, heteroalkenyl, heteroalkynyl, cycloalkyl, heterocyclyl, aryl, arylalkyl, heteroaryl, heteroarylalkyl are independently substituted with one or more haloalkyl, the "haloalkyl" is trifluoromethyl, difluoromethyl or monofluoromethyl;

when in the definition of $R^4$, the alkyl, alkenyl, alkynyl, heteroalkyl, heteroalkenyl, heteroalkynyl, cycloalkyl, heterocyclyl, aryl, arylalkyl, heteroaryl, heteroarylalkyl are independently substituted with one or more haloalkoxy, the "haloalkoxy" is trifluoromethoxy, difluoromethoxy or monofluoromethoxy;

when the alkyl in the definition of $R^{13}$ and $R^{14}$ is $C_1$-$C_6$ alkyl, the $C_1$-$C_6$ alkyl is $C_1$-$C_4$ alkyl;

when $R^{13}$ and $R^{14}$ together with the atom attached form saturated or partially unsaturated cycloalkyl, the saturated or partially unsaturated cycloalkyl is cyclopropyl or cyclobutyl;

when $R^{13}$ and $R^{14}$ are independently alkyl, or, $R^{13}$ and $R^{14}$ together with the atom attached form saturated or partially unsaturated cycloalkyl, wherein when the alkyl, cycloalkyl and heterocyclyl are independently substituted with one or more haloalkyl, the "haloalkyl" is trifluoromethyl, difluoromethyl or monofluoromethyl;

when $R^{13}$ and $R^{14}$ are independently alkyl, or, $R^{13}$ and $R^{14}$ together with the atom attached form saturated or partially unsaturated cycloalkyl, wherein when the alkyl, cycloalkyl and heterocyclyl are independently substituted with one or more haloalkoxy, the "haloalkoxy" is trifluoromethoxy, difluoromethoxy or monofluoromethoxy;

when $R^{15}$, $R^{16}$ and $R^{17}$ are independently alkyl, the alkyl is $C_1$-$C_4$ alkyl;

when $R^{15}$, $R^{16}$ and $R^{17}$ are independently alkenyl, the alkenyl is vinyl or propenyl;

when $R^{15}$, $R^{16}$ and $R^{17}$ are independently heteroalkyl, the heteroalkyl is ethoxy;

when $R^{15}$, $R^{16}$ and $R^{17}$ are independently saturated or partially unsaturated heterocyclyl, and the saturated or partially unsaturated heterocyclyl is tetrahydropyrimidinyl, dihydroisoxazolyl, dihydrooxazinyl, pyrrolidinyl, piperazinyl, morpholinyl or piperidinyl;

when $R^{15}$, $R^{16}$ and $R^{17}$ are independently heteroaryl, the heteroaryl is oxazolyl, pyrazolyl or isoxazolyl;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more alkyl, the alkyl is methyl or ethyl;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more saturated or partially unsaturated heterocyclyl substituted with $C_1$-$C_6$ alkyl or unsubstituted, the "saturated or partially unsaturated heterocyclyl" contained in the term "saturated or partially unsaturated heterocyclyl substituted with $C_1$-$C_6$ alkyl or unsubstituted" is tetrahydropyrrolyl;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more heteroaryl, the heteroaryl is pyridinyl;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more haloalkyl, the "haloalkyl" is trifluoromethyl, difluoromethyl or monofluoromethyl;

when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more haloalkoxy, the "haloalkoxy" is trifluoromethoxy, difluoromethoxy or monofluoromethoxy;

when any two of $R^{15}$, $R^{16}$ and $R^{17}$ together with the atom attached form heterocycle, the heterocycle is morpholinyl or piperazinyl;
when any two of $R^{15}$, $R^{16}$ and $R^{17}$ together with the atom attached form heterocycle, and the heterocycle is substituted with one or more haloalkyl, the "haloalkyl" is trifluoromethyl, difluoromethyl or monofluoromethyl;
when any two of $R^{15}$, $R^{16}$ and $R^{17}$ together with the atom attached form heterocycle, and the heterocycle is substituted with one or more haloalkoxy, the "haloalkoxy" is trifluoromethoxy, difluoromethoxy or monofluoromethoxy;
when $R^{13}$ and $R^{15}$ together with the atom attached form saturated or partially unsaturated heterocyclyl, and the heterocycle is substituted with one or more haloalkyl, the "haloalkyl" is trifluoromethyl, difluoromethyl or monofluoromethyl;
when $R^{13}$ and $R^{15}$ together with the atom attached form saturated or partially unsaturated heterocyclyl, and the heterocycle is substituted with one or more haloalkoxy, the "haloalkoxy" is trifluoromethoxy, difluoromethoxy or monofluoromethoxy;
when each $R^{12}$ is independently alkyl, the alkyl is $C_1$-$C_4$ alkyl;
when each $R^{12}$ is independently heterocyclylalkyl, the heterocyclylalkyl is

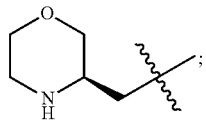 [SMILES: *C[C@@H]1COCCN1]
;

when $R^{15}$ and $R^{18}$ together with the atom attached form saturated or partially unsaturated heterocyclyl, and the heterocycle is substituted with one or more haloalkyl, the "haloalkyl" is trifluoromethyl, difluoromethyl or monofluoromethyl;
when $R^{15}$ and $R^{18}$ together with the atom attached form saturated or partially unsaturated heterocyclyl, and the heterocycle is substituted with one or more haloalkoxy, the "haloalkoxy" is trifluoromethoxy, difluoromethoxy or monofluoromethoxy;
when $R^6$ is haloalkyl, the "haloalkyl" is trifluoromethyl, difluoromethyl or monofluoromethyl;
when in the definition of $R^6$, the alkyl, cycloalkyl, heterocyclyl, aryl, arylalkyl, heteroaryl, heteroarylalkyl, and heterocyclylalkyl are independently substituted with one or more haloalkyl, the "haloalkyl" is trifluoromethyl, difluoromethyl or monofluoromethyl;
when in the definition of $R^6$, the alkyl, cycloalkyl, heterocyclyl, aryl, arylalkyl, heteroaryl, heteroarylalkyl, and heterocyclylalkyl are independently substituted with one or more haloalkoxy, the "haloalkoxy" is trifluoromethoxy, difluoromethoxy or monofluoromethoxy;
when $R^a$, $R^b$ and $R^c$ are independently alkyl, the alkyl is methyl or tert-butyl.

4. The nitrogenous heterocyclic compound as defined in claim 3,
wherein, when $R^{12}$ is alkyl, the alkyl is methyl or ethyl;
when $R^2$ is alkyl, the alkyl is methyl or ethyl;
when $R^3$ is saturated or partially unsaturated heterocyclyl, the saturated or partially unsaturated heterocyclyl is 3,6-dihydropyridin-4(2H)-yl or 5,6-dihydropyridin-4(2H)-yl);

when $R^3$ is heteroaryl, the heteroaryl is isoxazol-5-yl, pyridazin-3-yl, pyrrol-1-yl, pyrrol-3-yl, furan-2-yl, furan-3-yl, pyridin-4-yl or pyridin-3-yl;
when in the definition of $R^3$, the alkyl, alkenyl, alkynyl, heteroalkyl, heteroalkenyl, heteroalkynyl, cycloalkyl, heterocyclyl, aryl, arylalkyl, heteroaryl, heteroarylalkyl are independently substituted with one or more alkyl, the alkyl is methyl or ethyl;
when $R^8$ and $R^{8a}$ together with the atom attached form a 3 to 6 membered carbocycle or a 3 to 10 membered saturated or partially unsaturated heterocyclyl, wherein when the carbocycle and heterocyclyl are independently substituted with one or more alkyl, the alkyl is methyl or ethyl;
when $R^8$ and $R^9$ together with the atom attached form a 3 to 10 membered saturated or partially unsaturated cycloalkyl or heterocyclyl, wherein when the cycloalkyl and heterocyclyl are independently substituted with one or more alkyl, the alkyl is methyl or ethyl;
when the alkyl in the definition of $R^{13}$ and $R^{14}$ is methyl or ethyl;
when $R^{15}$, $R^{16}$ and $R^{17}$ are independently alkyl, the alkyl is methyl, ethyl,

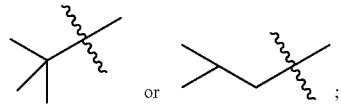

when $R^{15}$, $R^{16}$ and $R^{17}$ are independently alkenyl, the alkenyl is propenyl, the propenyl is propen-1-yl or propen-2-yl;
when $R^{15}$, $R^{16}$ and $R^{17}$ are independently saturated or partially unsaturated heterocyclyl, the saturated or partially unsaturated heterocyclyl is 1,4,5,6-tetrahydropyrimidin-2-yl, piperazin-1-yl, 4,5-dihydroisoxazol-5-yl, 5,6-dihydro-4H-1,3-oxazin-2-yl, morpholin-1-yl or piperidin-4-yl;
when $R^{15}$, $R^{16}$ and $R^{17}$ are independently heteroaryl, the heteroaryl is oxazol-2-yl, pyrazol-3-yl, isoxazol-3-yl or isoxazol-4-yl;
when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more saturated or partially unsaturated heterocyclyl substituted with $C_1$-$C_6$ alkyl or unsubstituted, the "saturated or partially unsaturated heterocyclyl" contained in the term saturated or partially unsaturated heterocyclyl substituted with $C_1$-$C_6$ alkyl or unsubstituted is tetrahydropyrrol-2-yl;
when in the definition of $R^{15}$, $R^{16}$ and $R^{17}$, the alkyl, alkenyl, alkynyl, heteroalkyl, cycloalkyl, heterocyclyl, cycloalkyl alkyl, aryl, arylalkyl, heteroaryl, heteroarylalkyl, and heterocyclylalkyl are independently substituted with one or more heteroaryl, the heteroaryl is pyridin-3-yl;
when any two of $R^{15}$, $R^{16}$ and $R^{17}$ together with the atom attached form heterocycle, the heterocycle is morpholin-4-yl or piperazin-1-yl;
when each $R^{12}$ is independently alkyl, the alkyl is methyl or ethyl.

5. The nitrogenous heterocyclic compound as defined in claim 1, wherein, A is —O—;

and/or, G is N;
and/or, E is

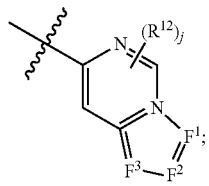

and/or, in the definition of E, $F^1$, $F^2$ and $F^3$ are independently N or $CR^{19}$;
and/or, in the definition of E, j is 0 or 1;
and/or, in the definition of E, each $R^{12}$ is independently halogen, —$OR^{15}$, alkyl;
and/or, in the definition of E, each $R^{19}$ is independently H;
and/or, each $R^2$ is independently halogen, haloalkyl or alkyl;
and/or, in the definition of $R^2$, the haloalkyl and alkyl are independently substituted with one or more —$OR^{15}$, when there are more than one substituents, the substituents are the same or different;
and/or, each $R^3$ is independently selected from the group consisting of Z, "5 to 6 membered heterocycle having 1 to 4 heteroatom(s) selected from the group consisting of N, O, S, SO and $SO_2$, substituted with -$M_1$-$M_2$-$M_3$-$M_4$ or -$M_1$-$M_5$", aryl substituted with -$M_1$-$M_2$-$M_3$-$M_4$ or -$M_1$-$M_5$, —$(CR^{13}R^{14})_s$—C=C—$(CR^{13}R^{14})_k$—$R^5$, halogen, alkenyl, saturated or partially unsaturated heterocyclyl, aryl, heteroaryl, —$OR^{15}$, —$NR^{15}C(=O)$ $OR^{16}$, —$NR^{15}C(=O)R^{16}$, —$OC(=O)R^{15}$, —$NR^{15}C(=O)NR^{16}R^{17}$ and —$NR^{15}C(=S)NR^{16}R^{17}$;
and/or, in the definition of $R^3$, the alkenyl, heterocyclyl, aryl and heteroaryl are independently substituted with the substituent selected from the group consisting of halogen, alkyl, —$NR^{15}R^{16}$, —$NR^{15}C(=O)OR^{18}$, —$NR^{15}C(=O)R^{16}$, —$C(=O)R^{15}$, —$C(=O)NR^{15}R^{16}$, —$NR^{15}C(=O)NR^{16}R^{17}$, —$(C_1$-$C_4$ alkyl)$NR^aR^b$ and —$NR^{15}C(=O)CH_2OR^a$, when there are more than one substituents, the substituents are the same or different;
and/or, in the definition of $R^3$, $M_1$ is $C_1$-$C_4$ alkylene; $M_2$ is —$NR^e$—; $M_3$ is $C_1$-$C_4$ alkylene; $M_4$ is —$NR^e$ $S(=O)_{0-2}R^f$, —$S(=O)_{0-2}NR^gR^h$ or —$S(=O)_{0-2}R^f$; and $M_5$ is —OH or —$NR^gR^h$; wherein, each of $R^e$, $R^f$, $R^g$ and $R^h$ is independently H or $C_1$-$C_6$ alkyl, or, $R^g$ and $R^h$ together with the N atom attached form a 5 to 6 membered heterocyclyl having 1 to 3 heteroatom(s) selected from the group consisting of N, O, S, SO and $SO_2$, wherein any N atom on the ring is optionally substituted with $C_1$-$C_4$ alkyl or —$S(=O)_p$alkyl;
and/or, in the definition of $R^3$, Z is

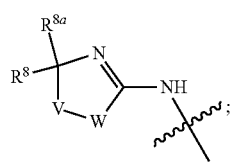

and/or, in the definition of Z, W and V are independently —O—, —$NR^6$—, —S— or —$CR^8R^9$;
the requirement is that when W is —O—, —$NR^6$—, —S—, V is —$CR^7R^8$— or —$CR^8R^9$—, and when V is —O—, —$NR^6$—, —S—, W is —$CR^7R^8$— or —$CR^8R^9$—;
and/or, in the definition of Z, each of $R^8$, $R^{8a}$ and $R^9$ is independently hydrogen or alkyl;
and/or, in the definition of $R^8$, $R^{8a}$ and $R^9$, the alkyl is substituted with one or more —$OR^{15}$ when there are more than one substituents, the substituents are the same or different;
and/or, in the definition of Z, $R^8$ and $R^{8a}$ together with the atom attached form a 3 to 6 membered carbocycle, or, a 3 to 10 membered saturated or partially unsaturated heterocyclyl; wherein the carbocycle and heterocyclyl are independently substituted with the substituent selected from the group consisting of halogen, alkyl, —$C(=O)OR^{15}$ and —$C(=O)R^{15}$, when there are more than one substituents, the substituents are the same or different;
and/or, in the definition of Z, $R^8$ and $R^9$ together with the atom attached form a 3 to 10 membered saturated or partially unsaturated cycloalkyl or heterocyclyl; the cycloalkyl and heterocyclyl are independently substituted with the substituent selected from the group consisting of alkyl, —$C(=O)OR^{15}$ and —$C(=O)R^{15}$, when there are more than one substituents, the substituents are the same or different;
and/or, in the definition of $R^3$, each $R^5$ is independently —$NR^{15}R^{13}$, —$NR^{15}C(=O)R^{16}$ or —$NR^{15}C(=O)NR^{16}R^{17}$;
and/or, each $R^{13}$ and $R^{14}$ is independently hydrogen or alkyl;
and/or, each of $R^{15}$, $R^{16}$ and $R^{17}$ is independently selected from the group consisting of H, alkyl, alkenyl, heteroalkyl, saturated or partially unsaturated cycloalkyl, saturated or partially unsaturated heterocyclyl, heteroaryl, $OR^a$ and —$C(=O)R^a$;
and/or, in the definition of $R^{15}$, $R^{16}$ and $R^{17}$, the alkyl, alkenyl, heteroalkyl, cycloalkyl, heterocyclyl, heteroaryl are independently substituted with the substituent selected from the group consisting of alkyl, saturated or partially unsaturated cycloalkyl, saturated or partially unsaturated heterocyclyl substituted with $C_1$-$C_6$ alkyl or unsubstituted, heteroaryl, halogen, cyano, —$OR^a$, —$NR^aR^b$, —$NR^aCO_2R^b$, —$SO_2R^a$, —$C(=O)R^a$, —$C(=O)OR^a$, —$C(=O)$— $CR^a=CR^aR^b$, —$C(=O)$—C≡C—$(CR^aR^b)_{1-3}NR^aR^b$ and —$(CH_2)_{13}C(=O)NR^a$, when there are more than one substituents, the substituents are the same or different:
and/or, any two of $R^{15}$, $R^{16}$ and $R^{17}$ together with the atom attached form heterocycle;
and/or, each $R^{18}$ is independently alkyl, aryl or heterocyclylalkyl;
and/or, in the definition of $R^{18}$, the alkyl, aryl and heterocyclylalkyl are independently substituted with one or more saturated or partially unsaturated cycloalkyl, when there are more than one substituents, the substituents are the same or different;
and/or, each $R^6$ is independently hydrogen;
and/or, each of $R^a$, $R^b$ and $R^c$ is independently H, halogen, alkyl or alkenyl;
and/or, m is 1 or 2;
and/or, n is 1 or 2;
and/or, p is 2;
and/or, s is 0;
and/or, k is 1.

6. The nitrogenous heterocyclic compound as defined in claim 1, wherein, s and t are not 0 at the same time;

and/or, A is —O—;
and/or, G is N;
and/or, $F^1$, $F^2$ and $F^3$ are independently N or CH;
and/or, j is 0;
and/or, n is 1 or 2;
and/or, each $R^2$ is independently halogen, —CN, trifluoromethyl, difluoromethyl, monofluoromethyl, $C_1$-$C_4$-alkyl, $C_1$-$C_4$-alkoxy, or cycloalkyl;
and/or, m is =1 or 2;
and/or, each $R^3$ is independently —$NR^{15}C(=O)NR^{16}R^{17}$, —$NR^{15}C(=O)OR^{16}$, —$NR^{15}C(=O)R^{16}$, halogen, —$NR^{15}C(=S)NR^{16}R^{17}$, Z, —$(CR^{13}R^{14})_s$—C≡C—$(CR^{13}R^{14})_kR^5$, $OR^{15}$ or —$OC(=O)R^{15}$.

7. The nitrogenous heterocyclic compound as defined in claim 6, wherein, the E is any one of the following groups:

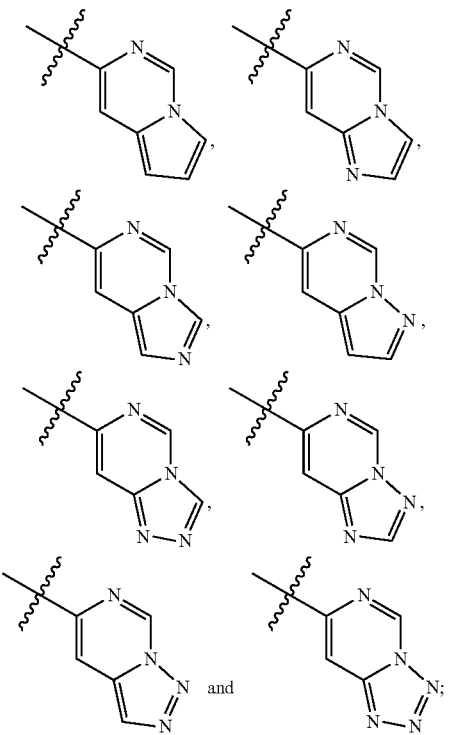

and/or, each $R^3$ is independently any one of the following groups:

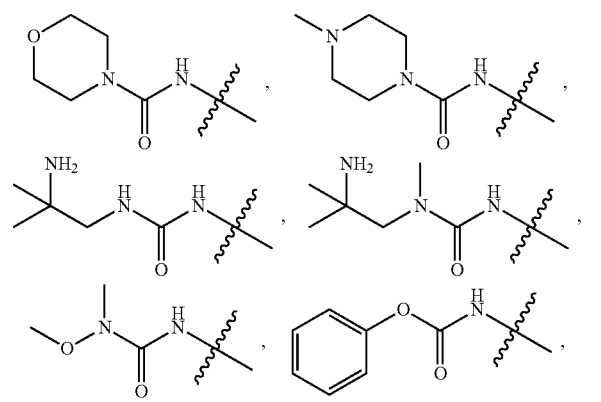

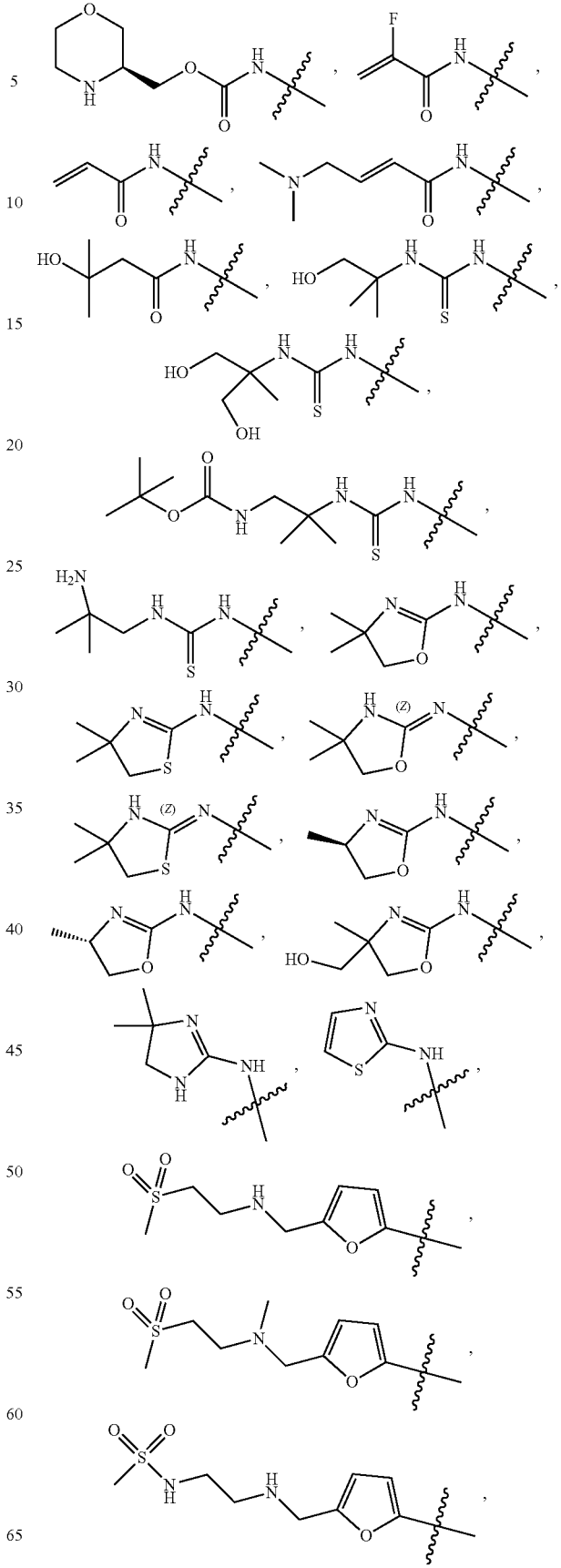

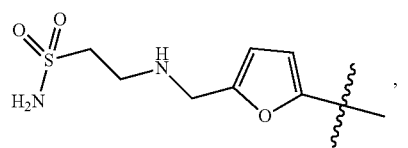,
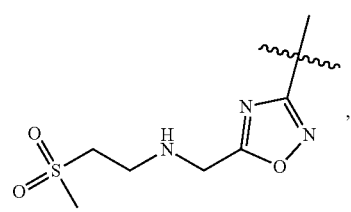,
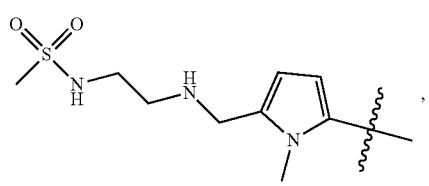,
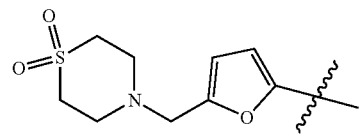,
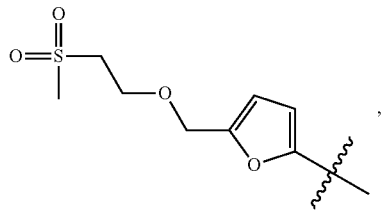,
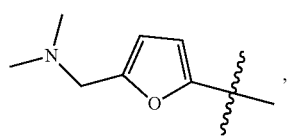,
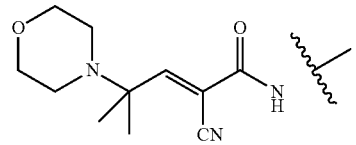,
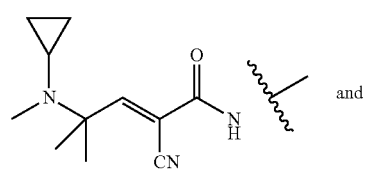 and
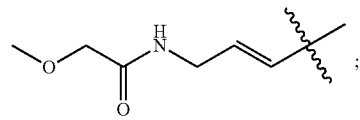;
and/or, when m is 2, the compound I is represented by any one of the following structures:
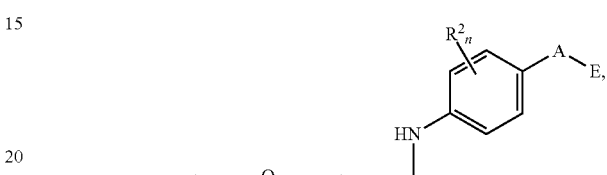
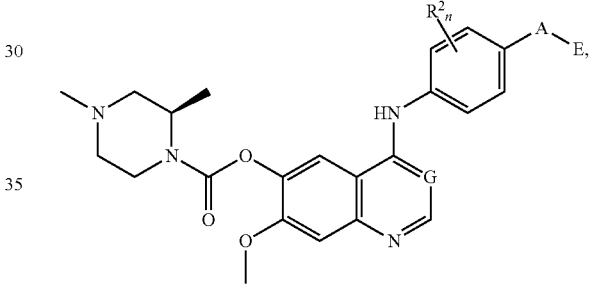
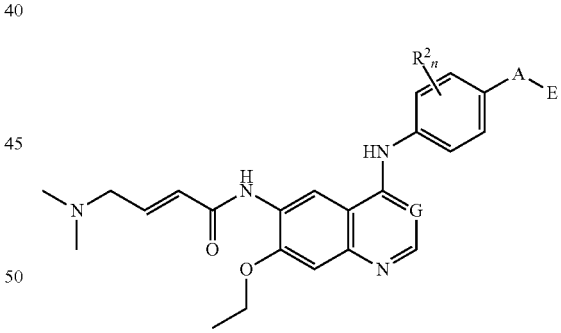
and
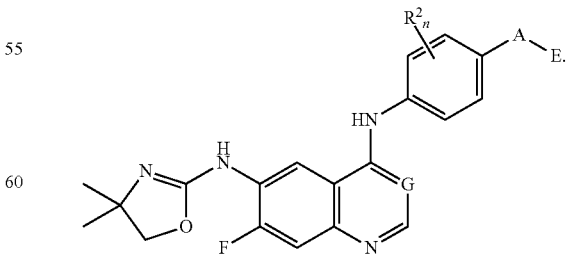
8. The nitrogenous heterocyclic compound as defined in claim 1, wherein, the compound I is any one of the following compounds:

223
224
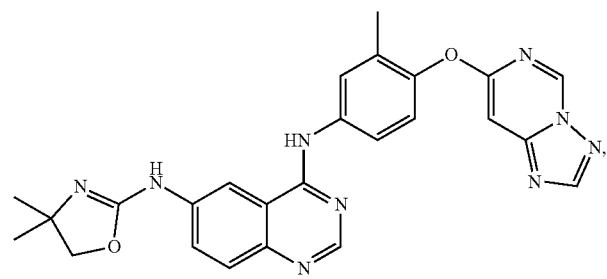
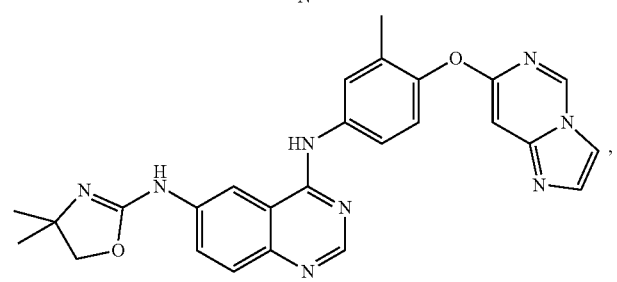
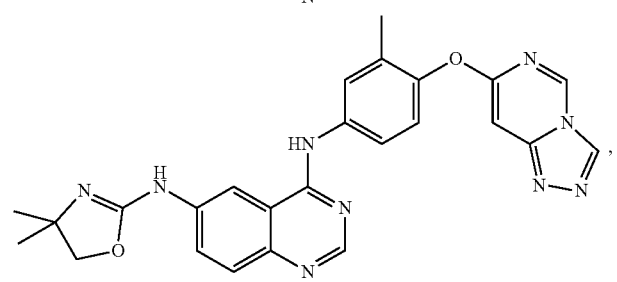, 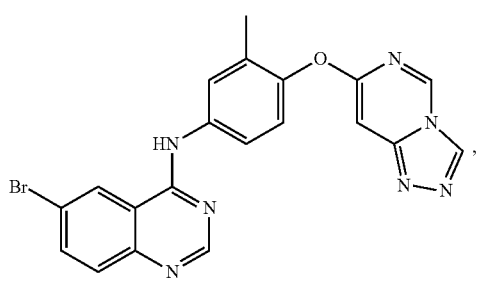
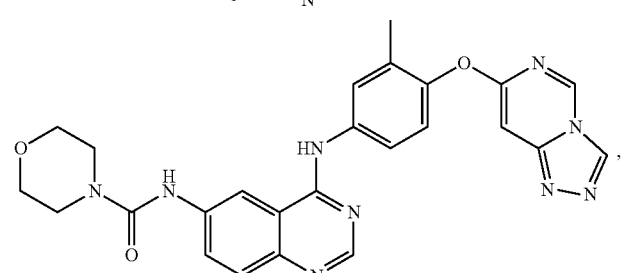
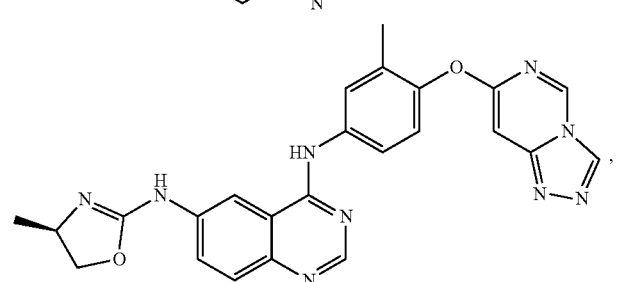
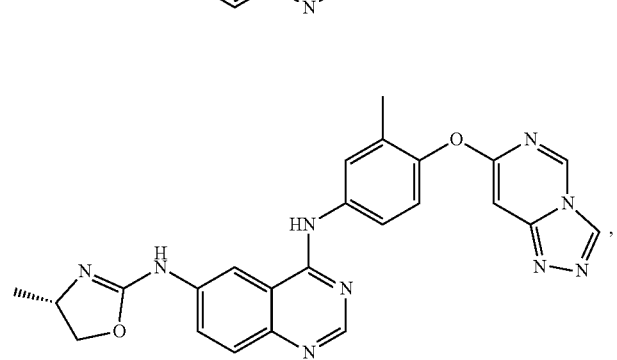

-continued
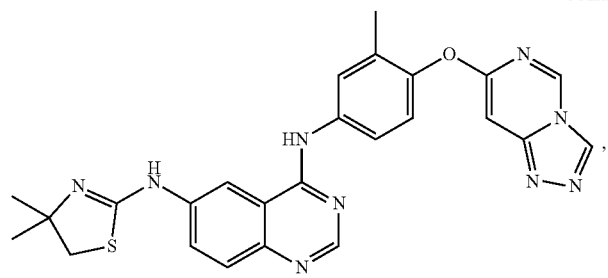
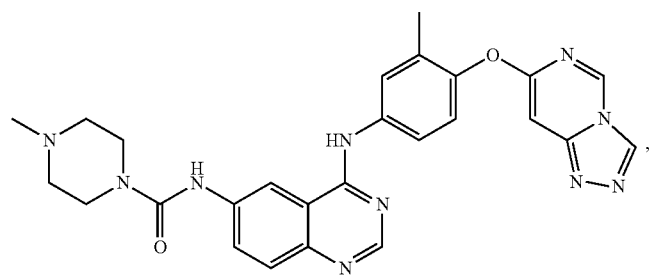
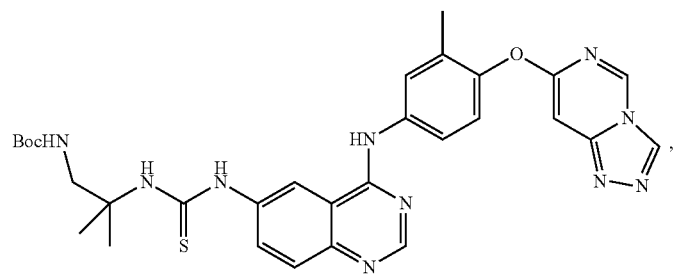
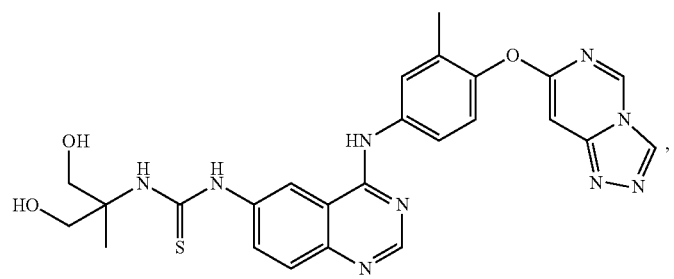
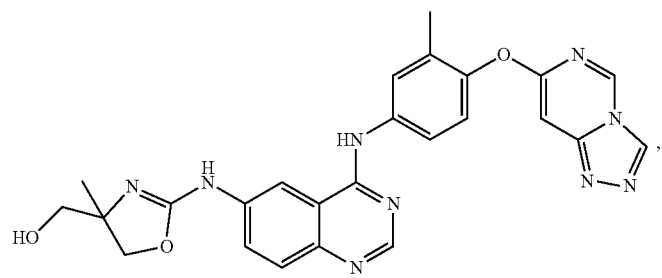
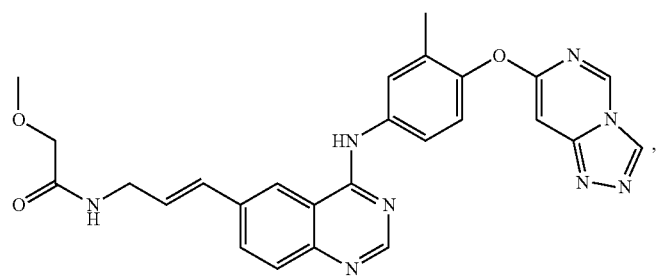

-continued
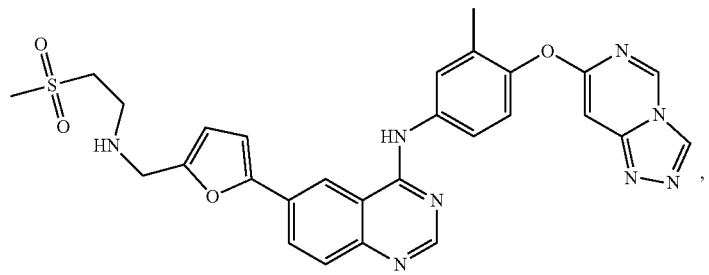
,
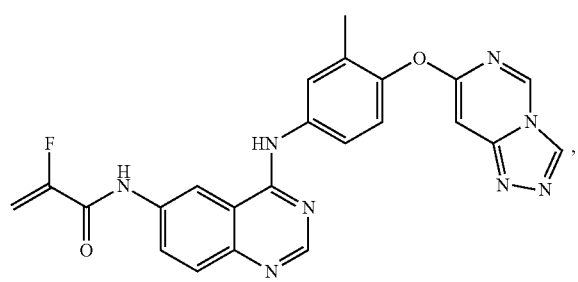
,
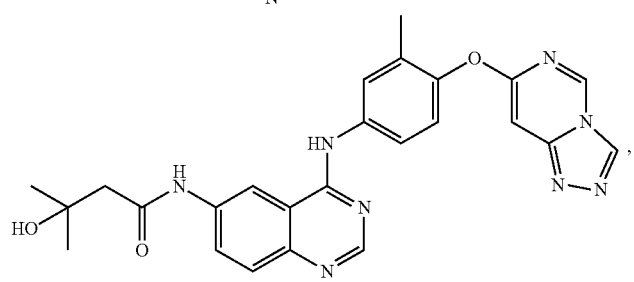
,
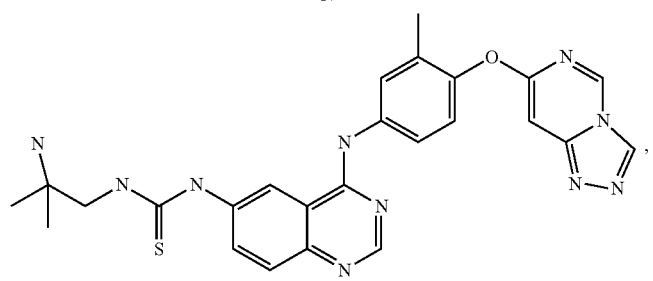
,
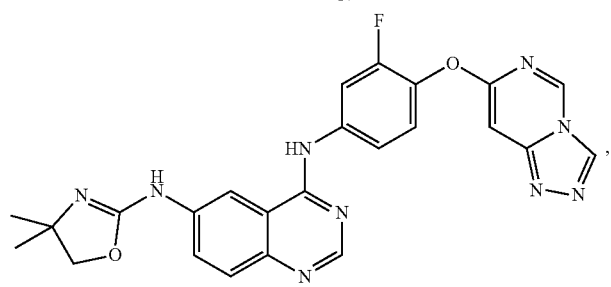
,
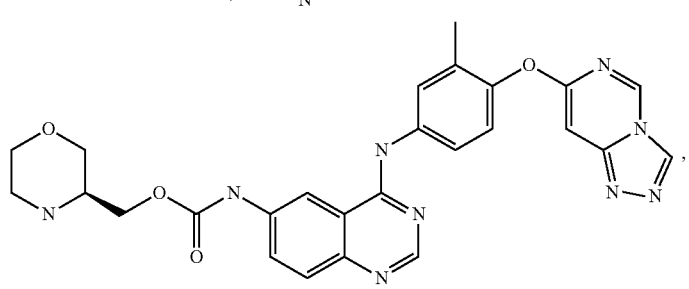
, -continued
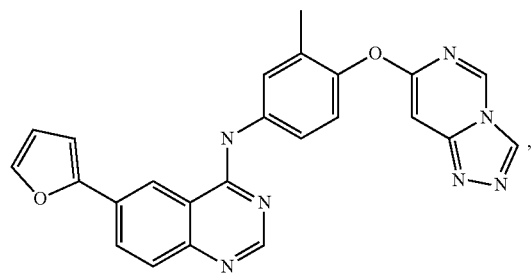
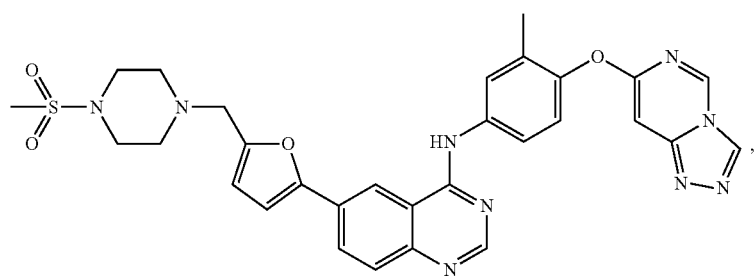
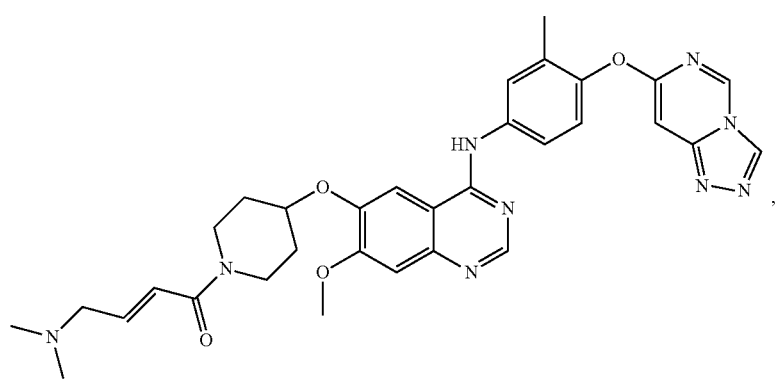
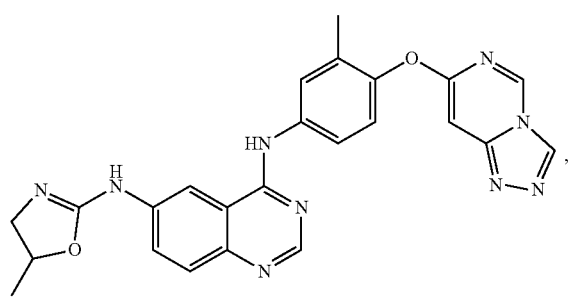
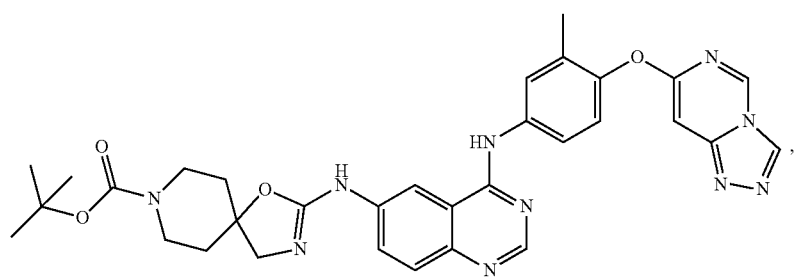

-continued
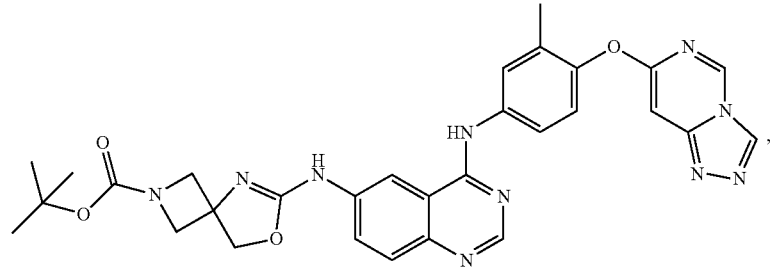
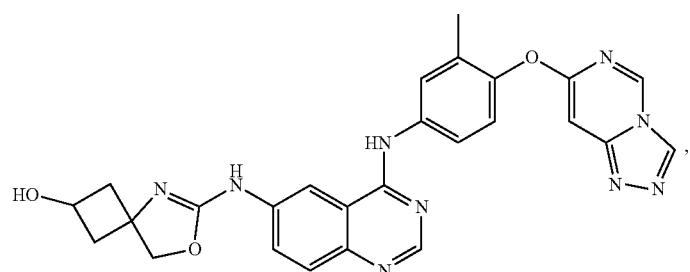
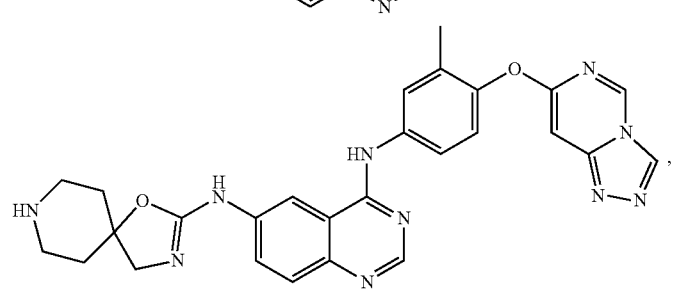
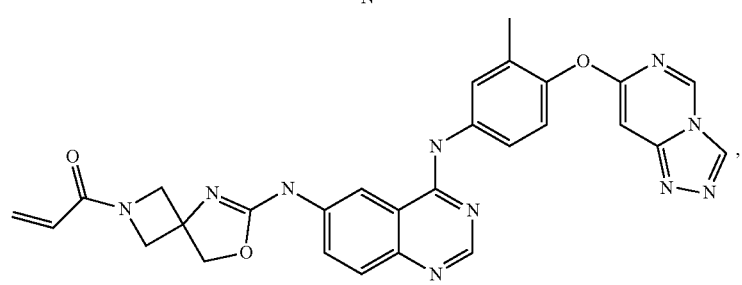
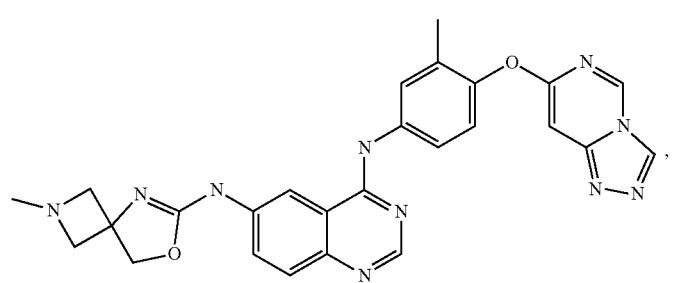
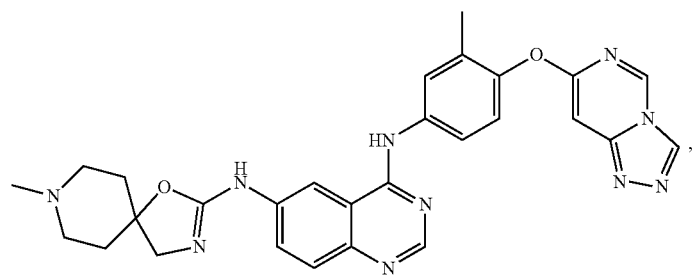

-continued
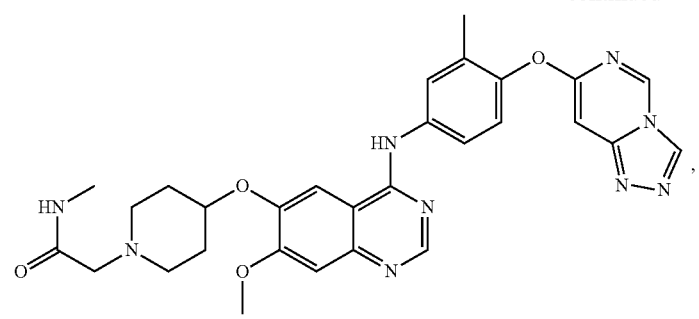
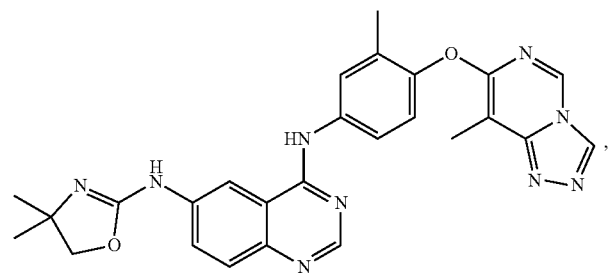
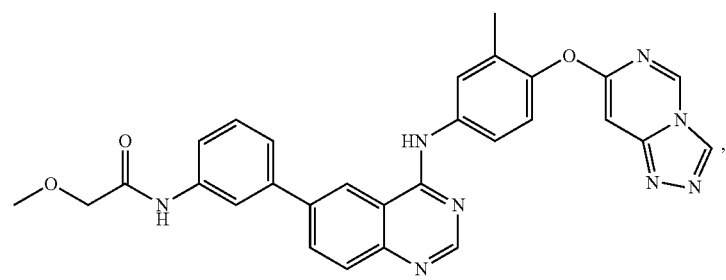
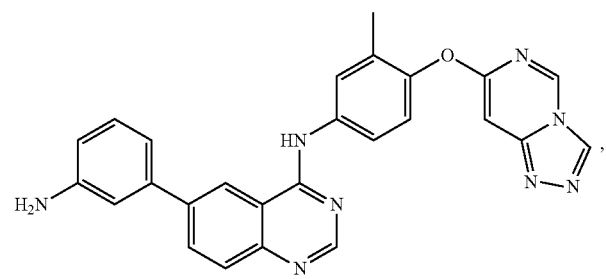
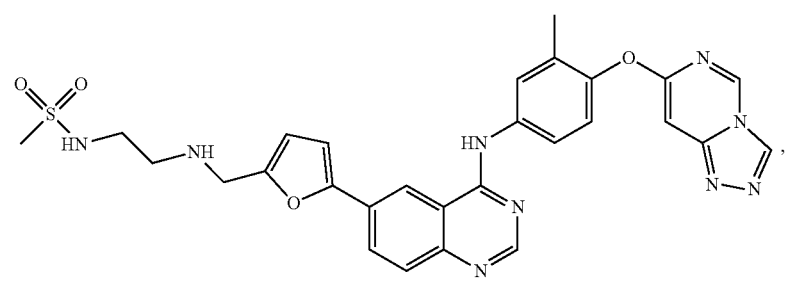
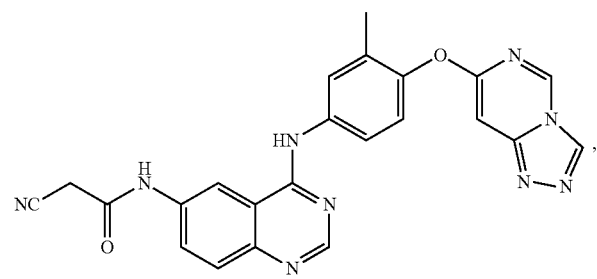

-continued
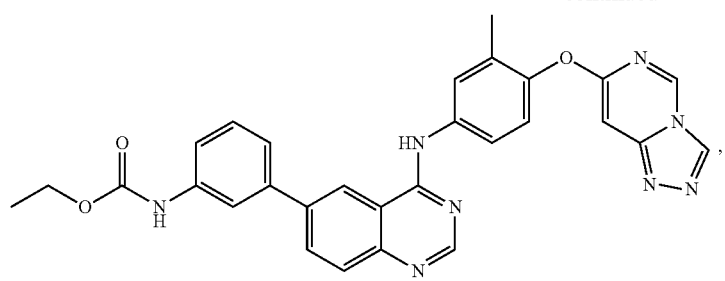
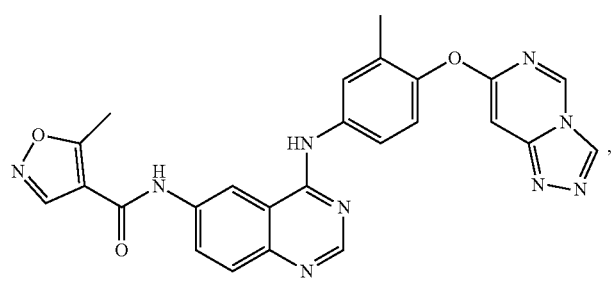
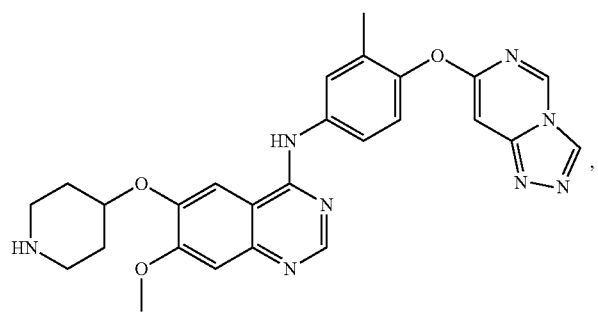
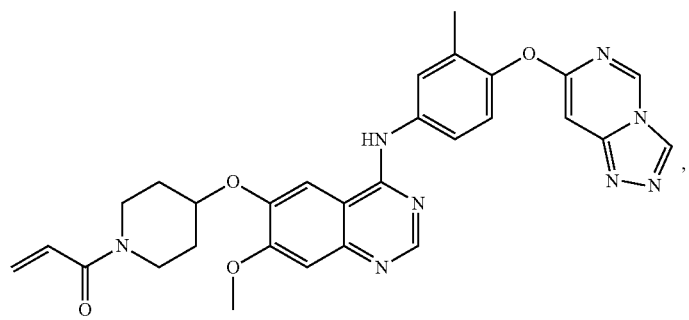
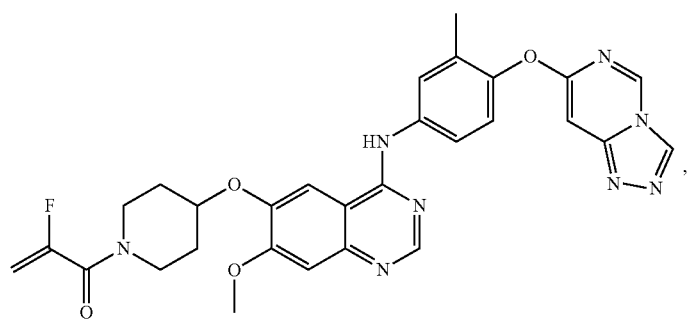

-continued
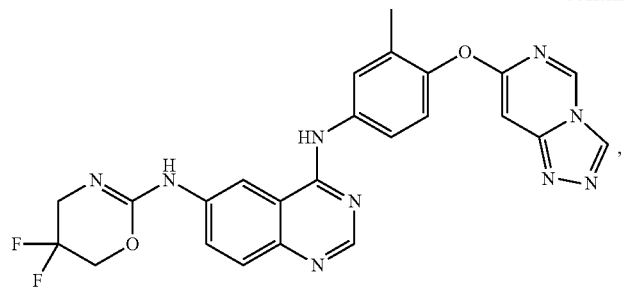
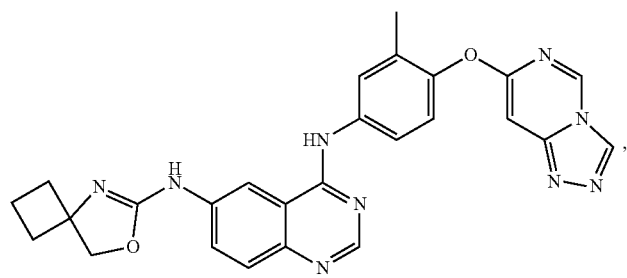
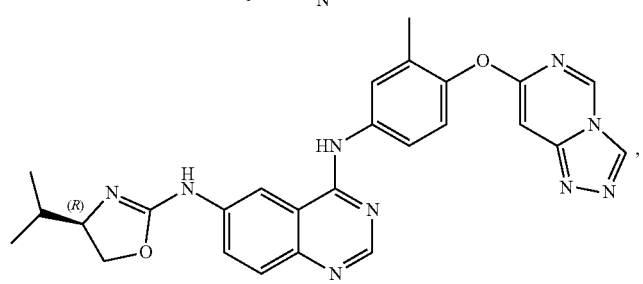
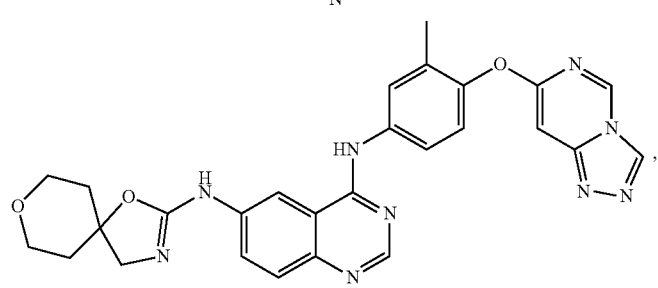
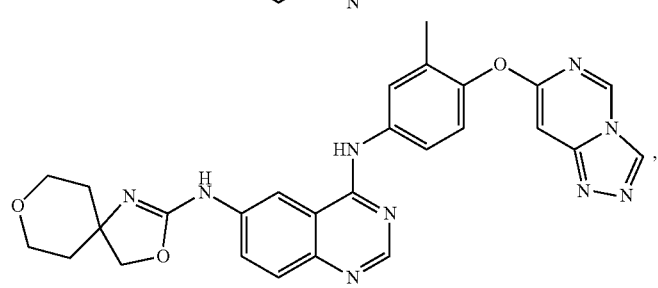
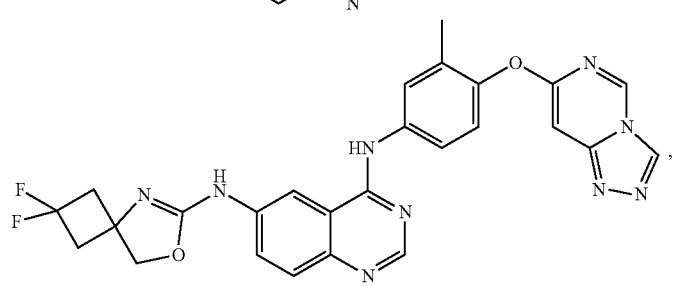

-continued
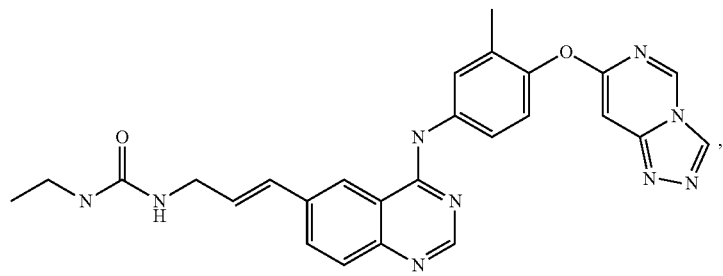
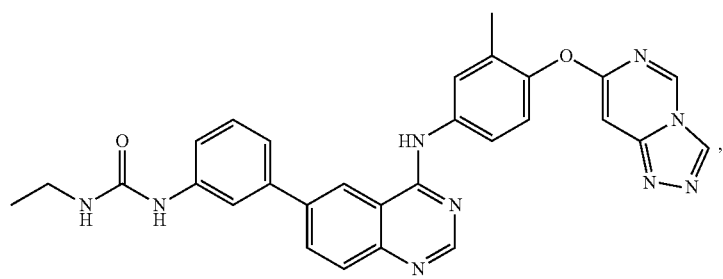
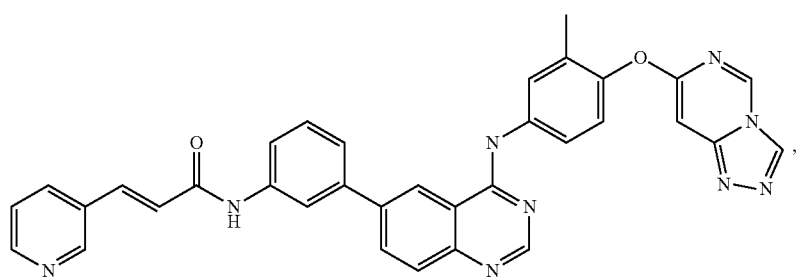
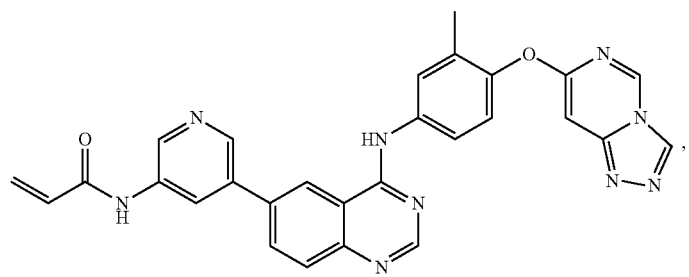
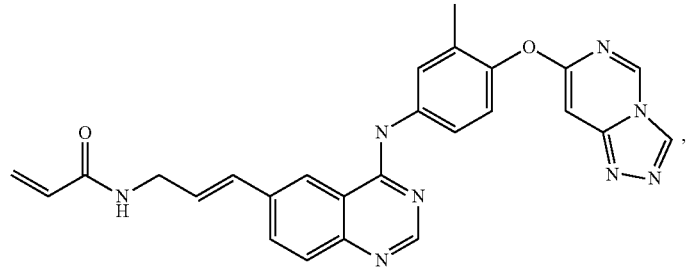
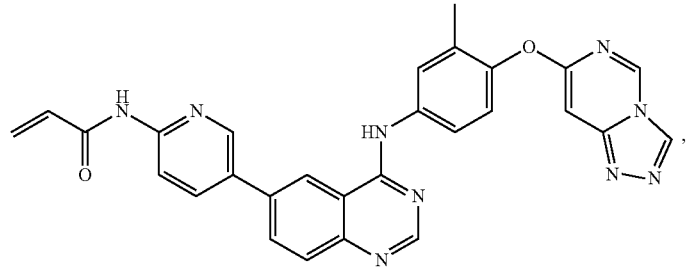

-continued
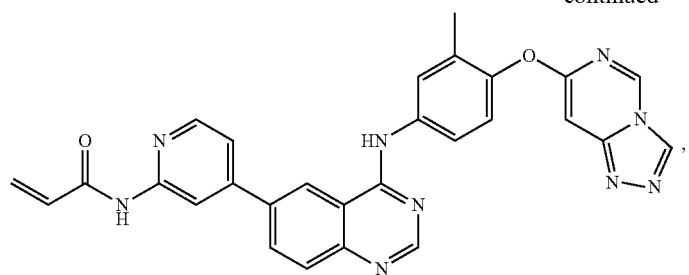
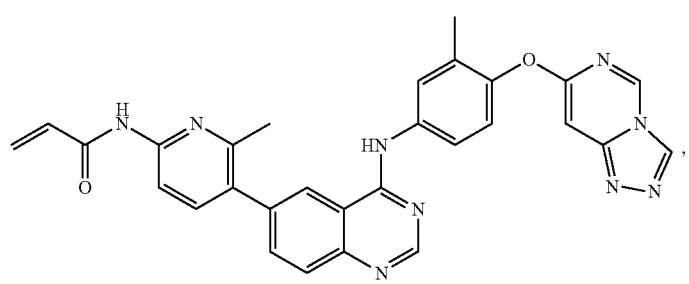
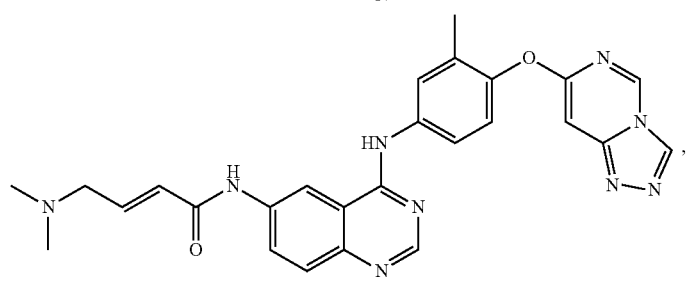
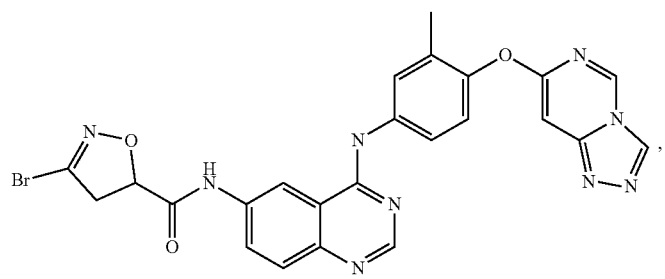
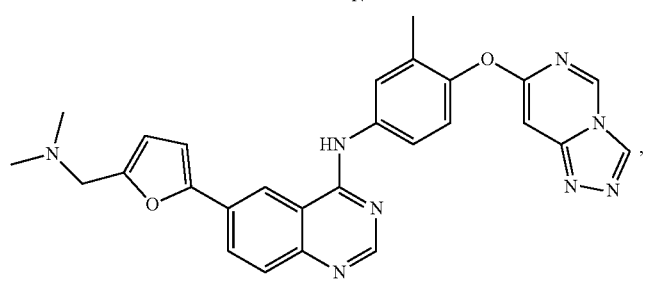
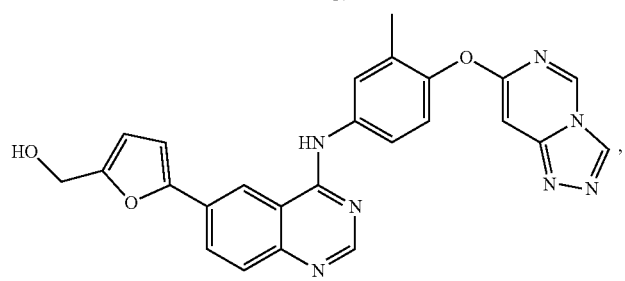

-continued
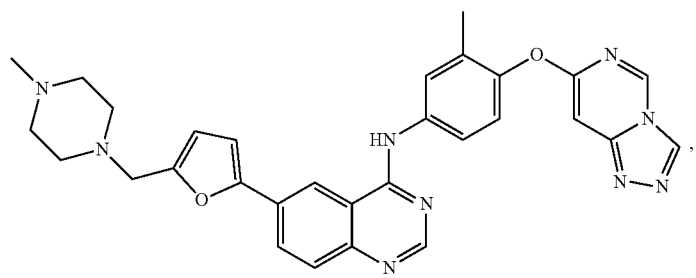
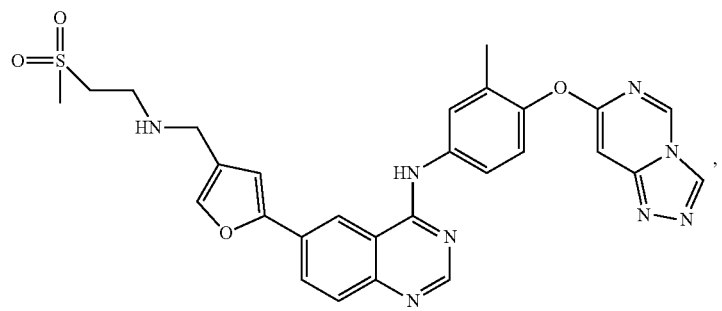
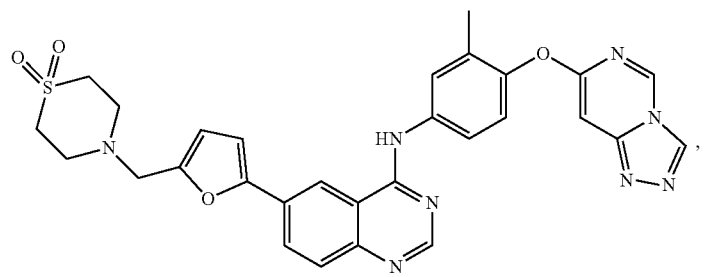
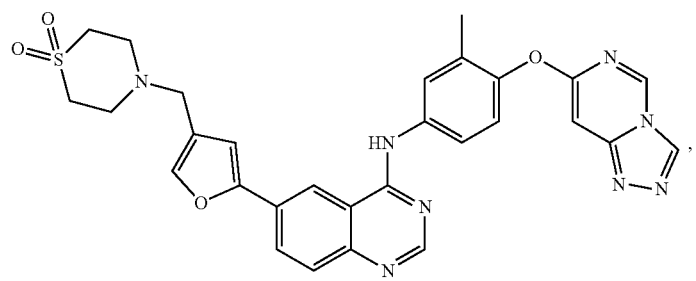
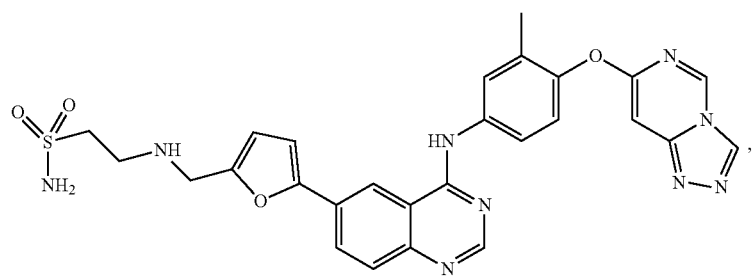
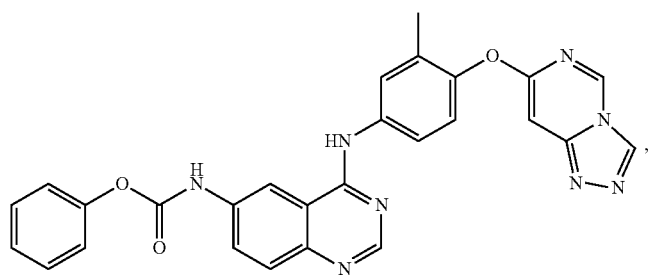

-continued
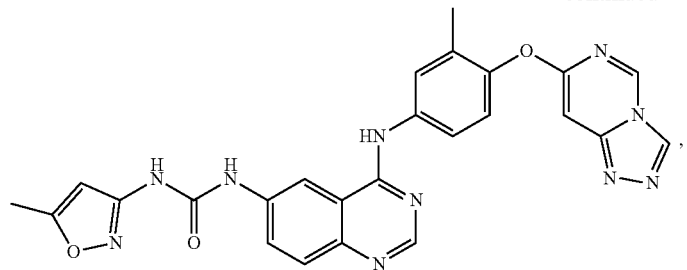
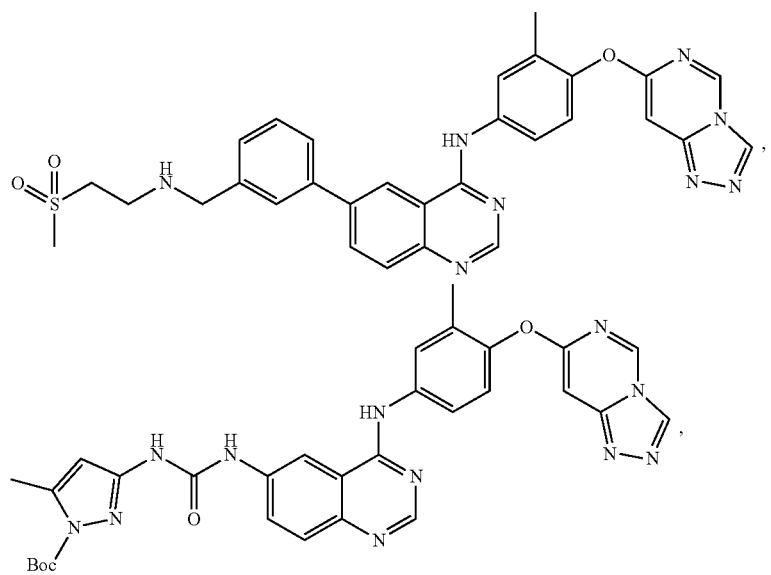
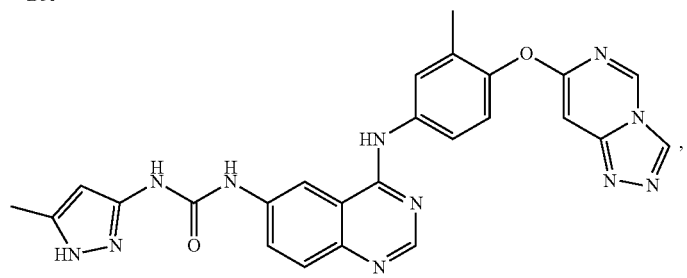
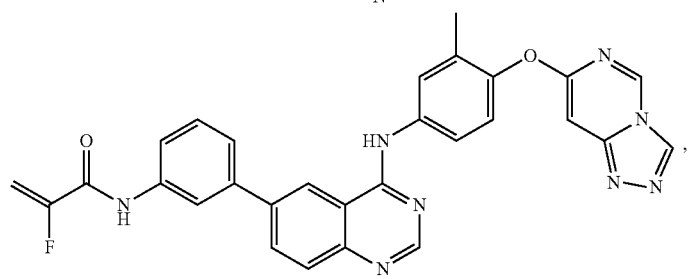
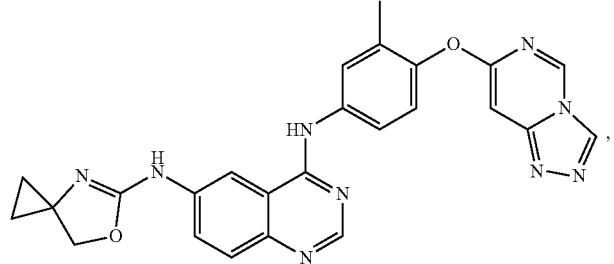

-continued
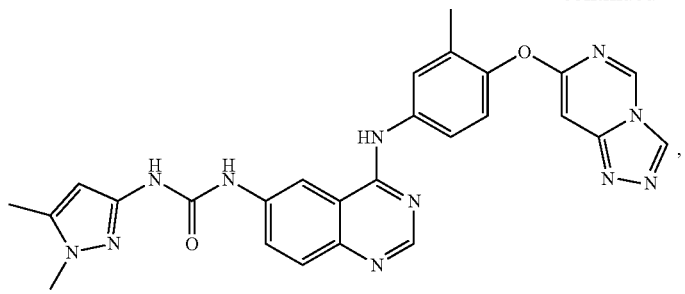
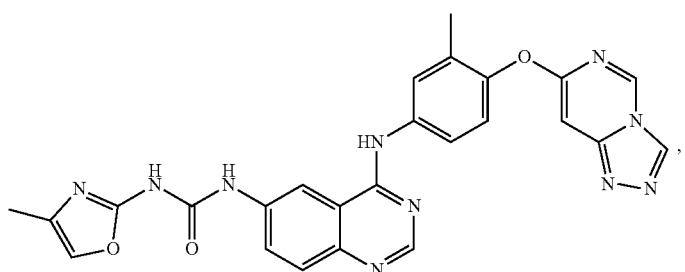
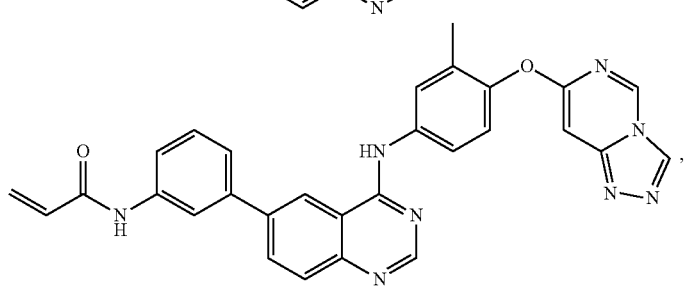
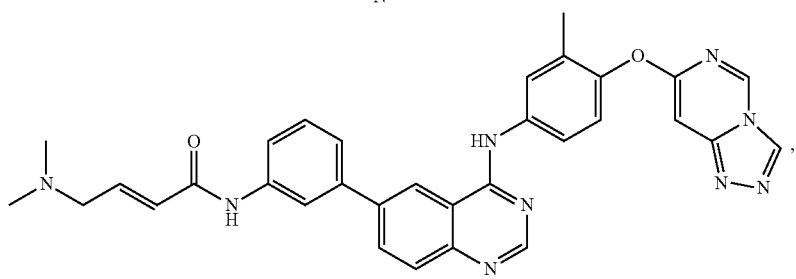
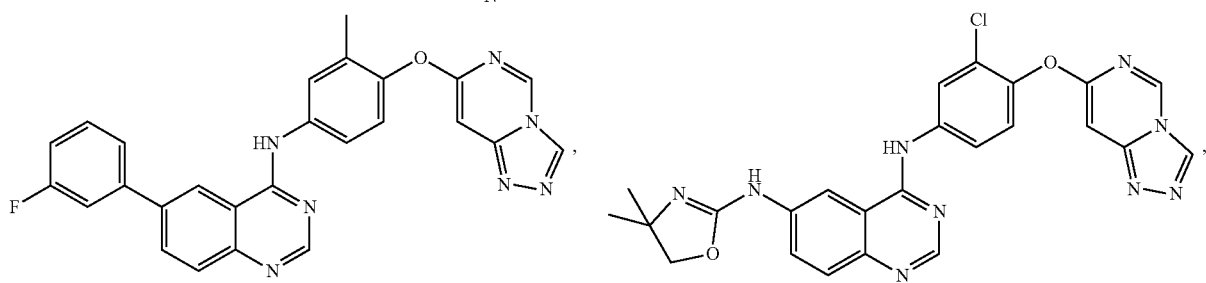
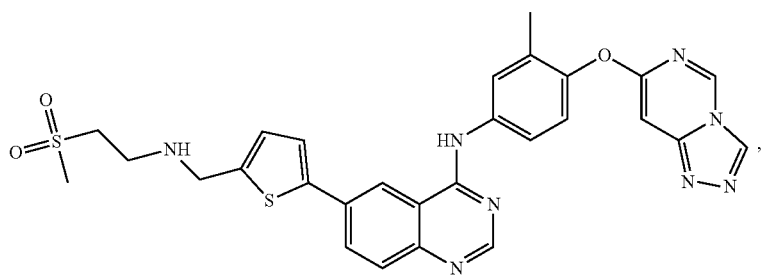

249
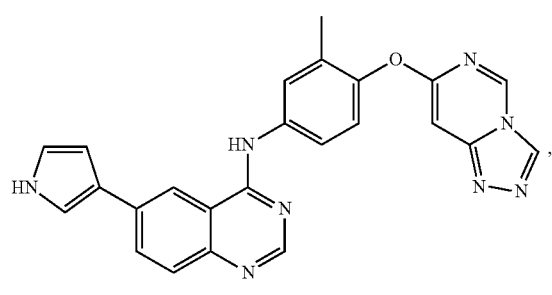
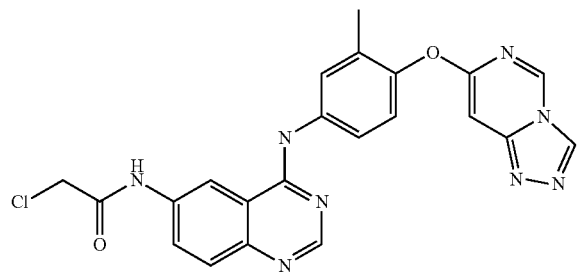
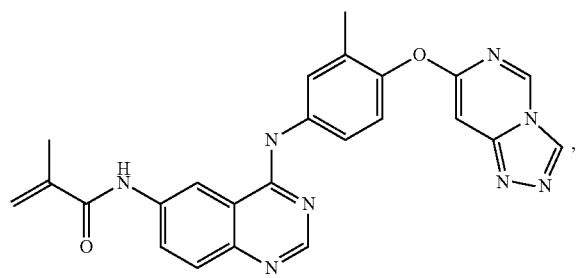
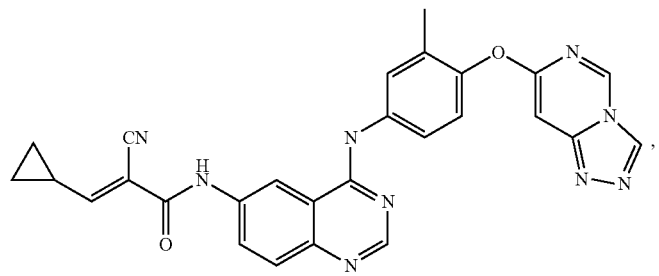
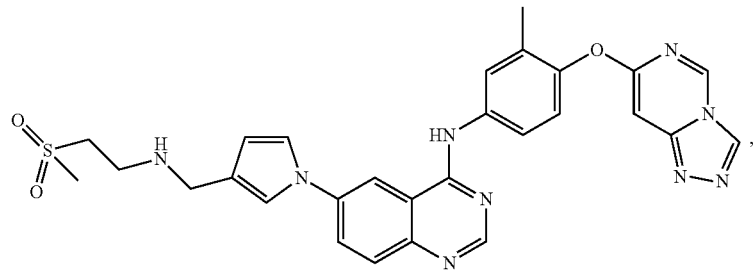
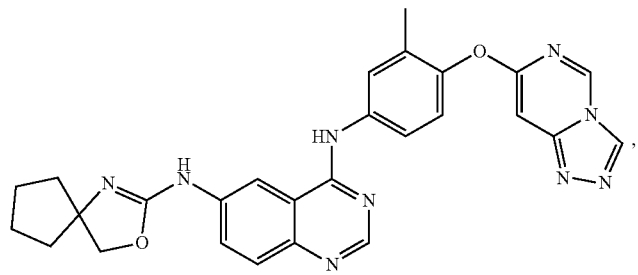
250
-continued
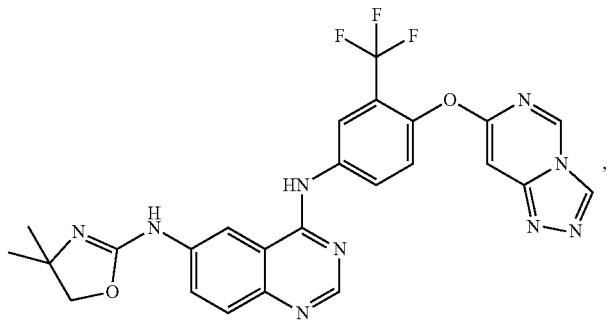
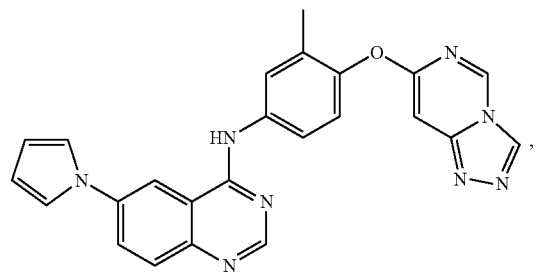

251
-continued
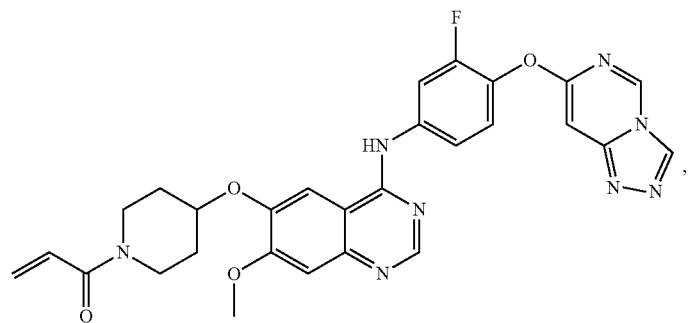
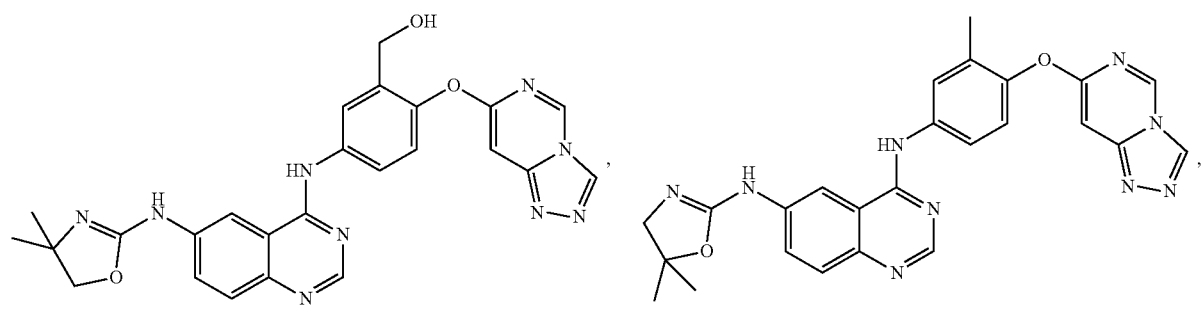
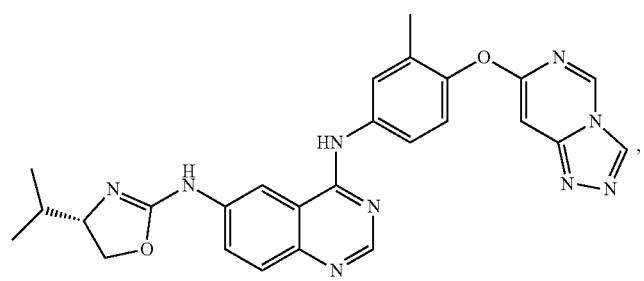
252
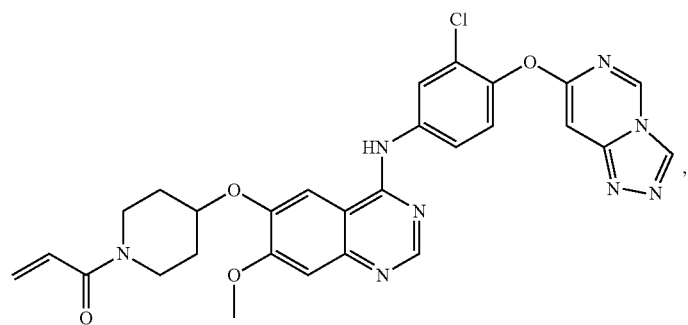
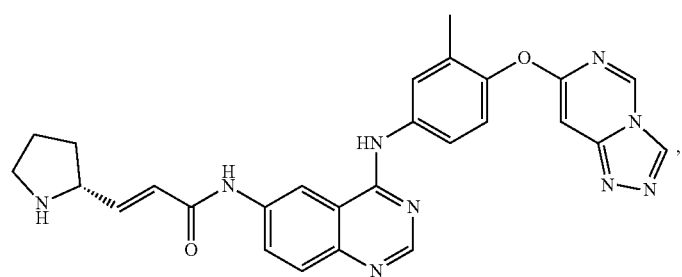

-continued
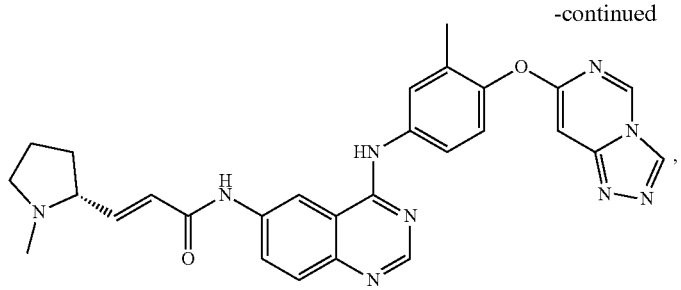
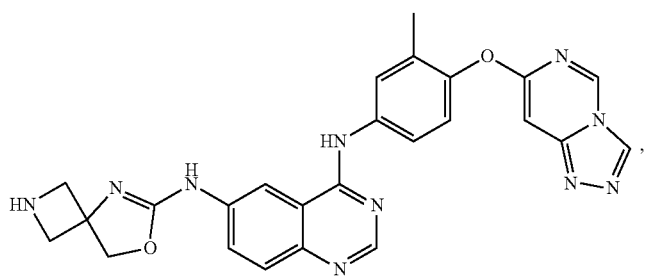
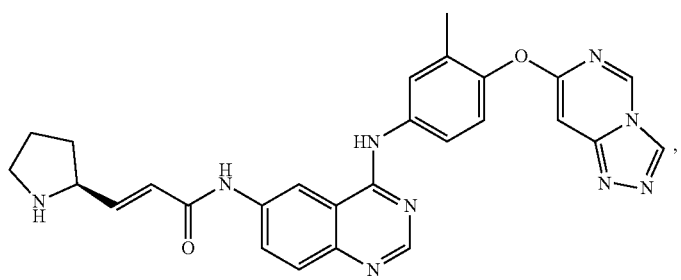
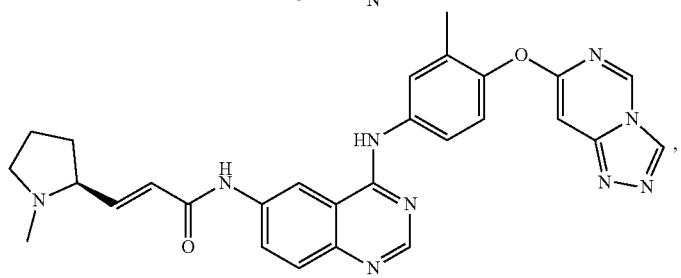
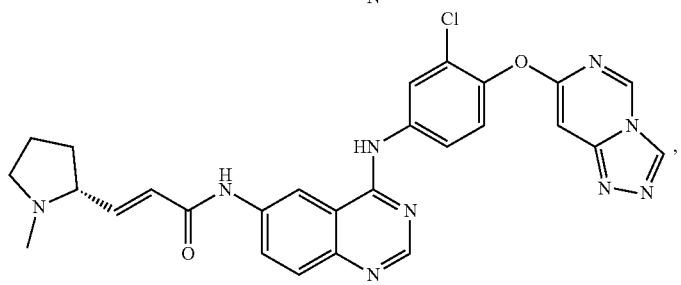
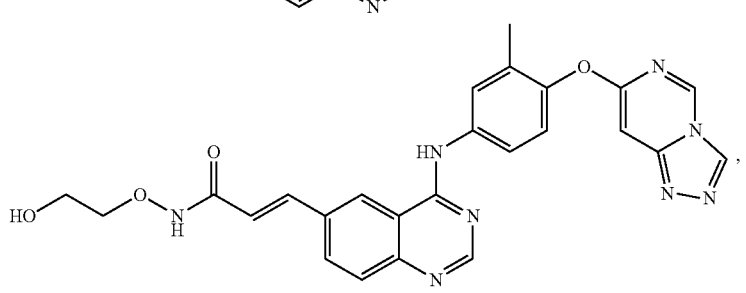

-continued
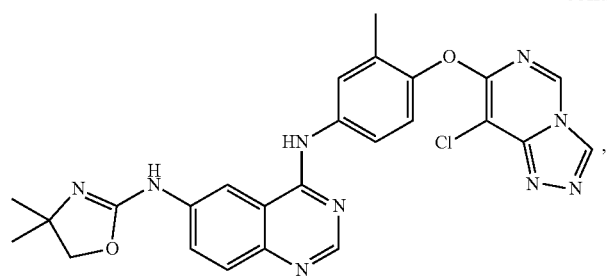
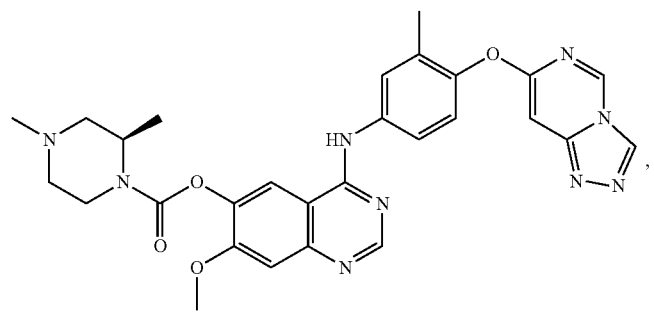
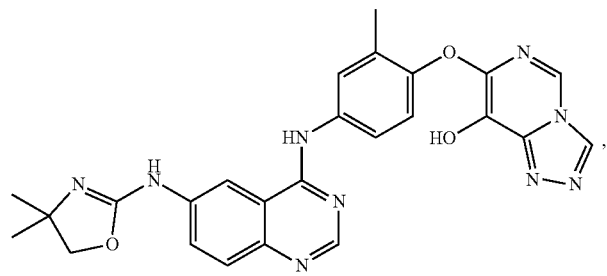
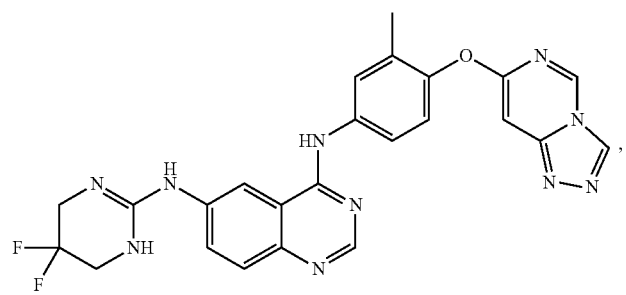
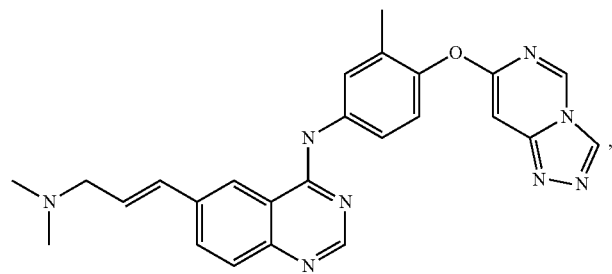
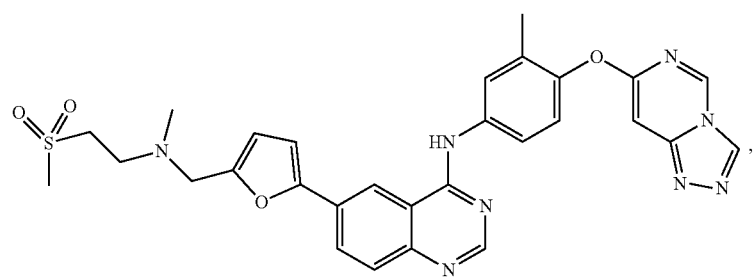

-continued
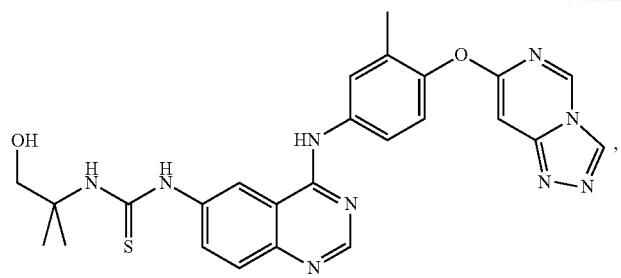
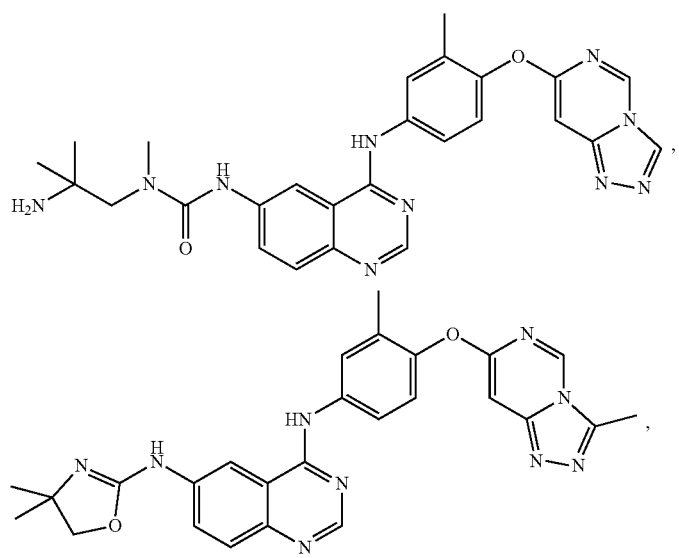
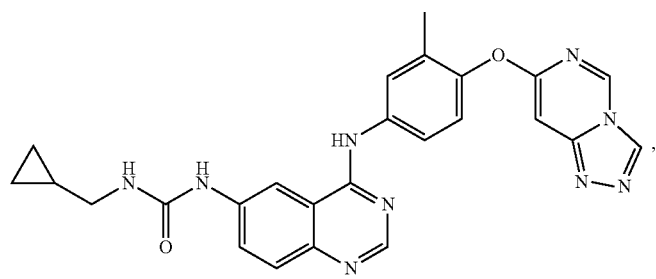
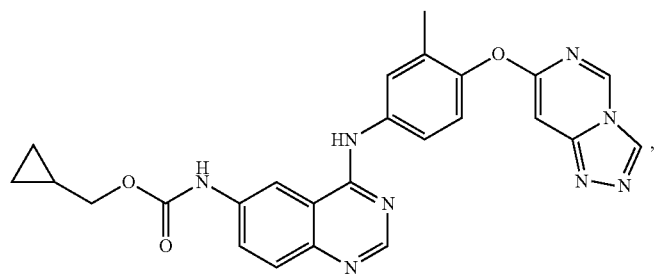
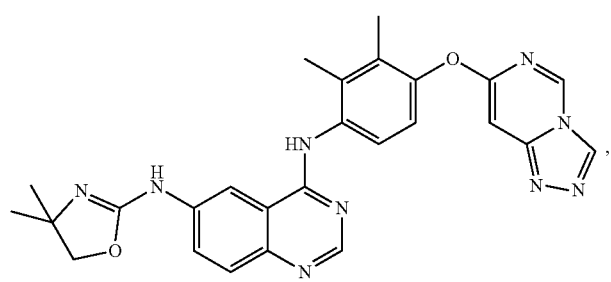

-continued
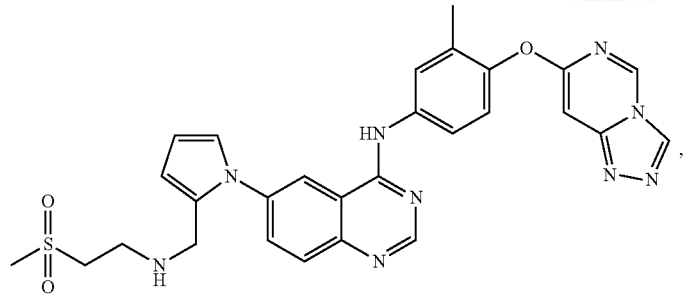
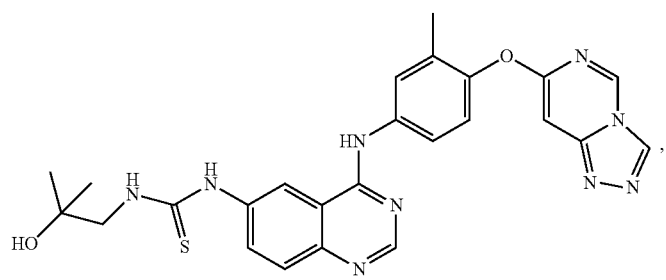
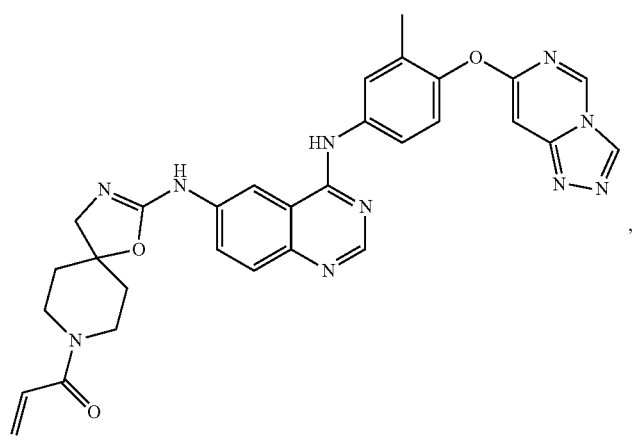
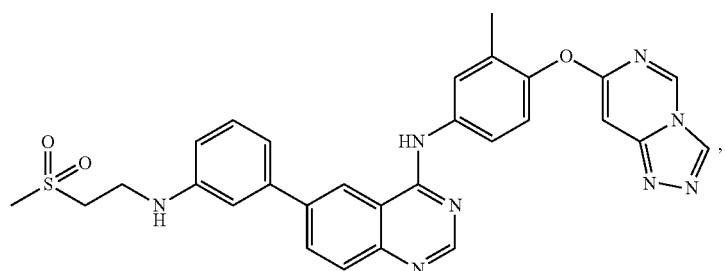
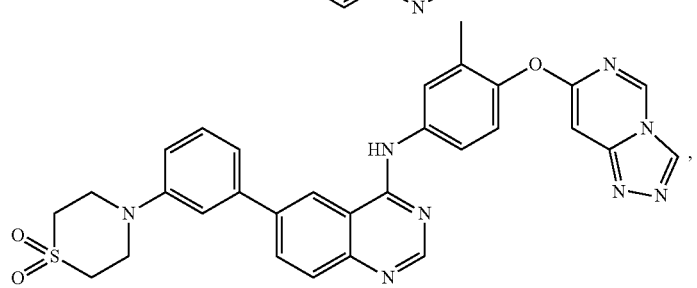

-continued
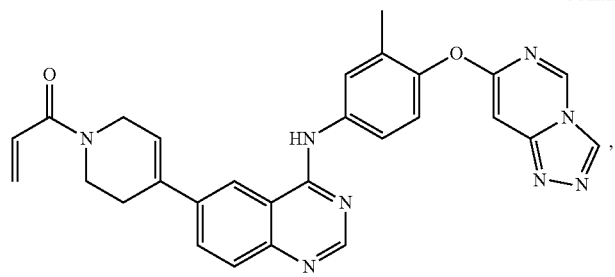
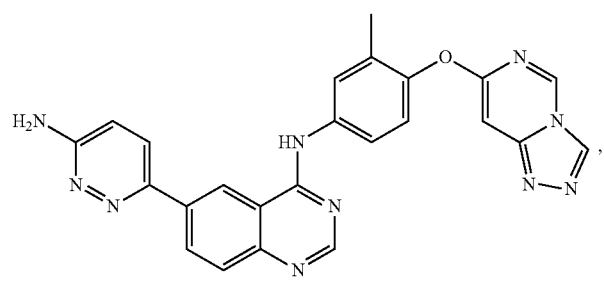
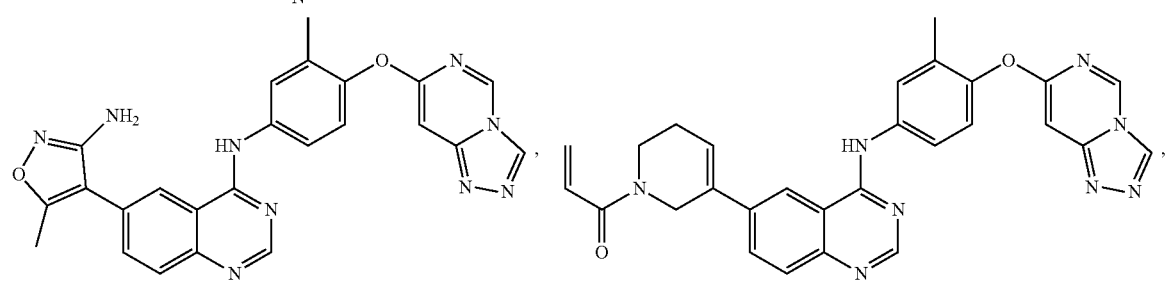
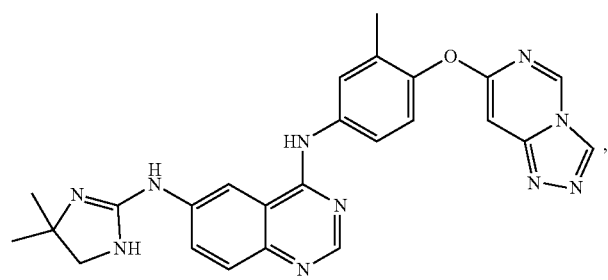
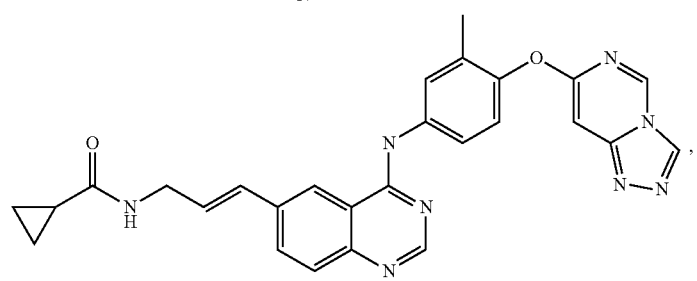
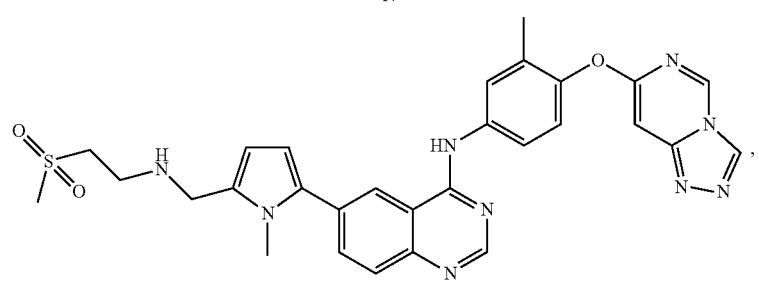

263
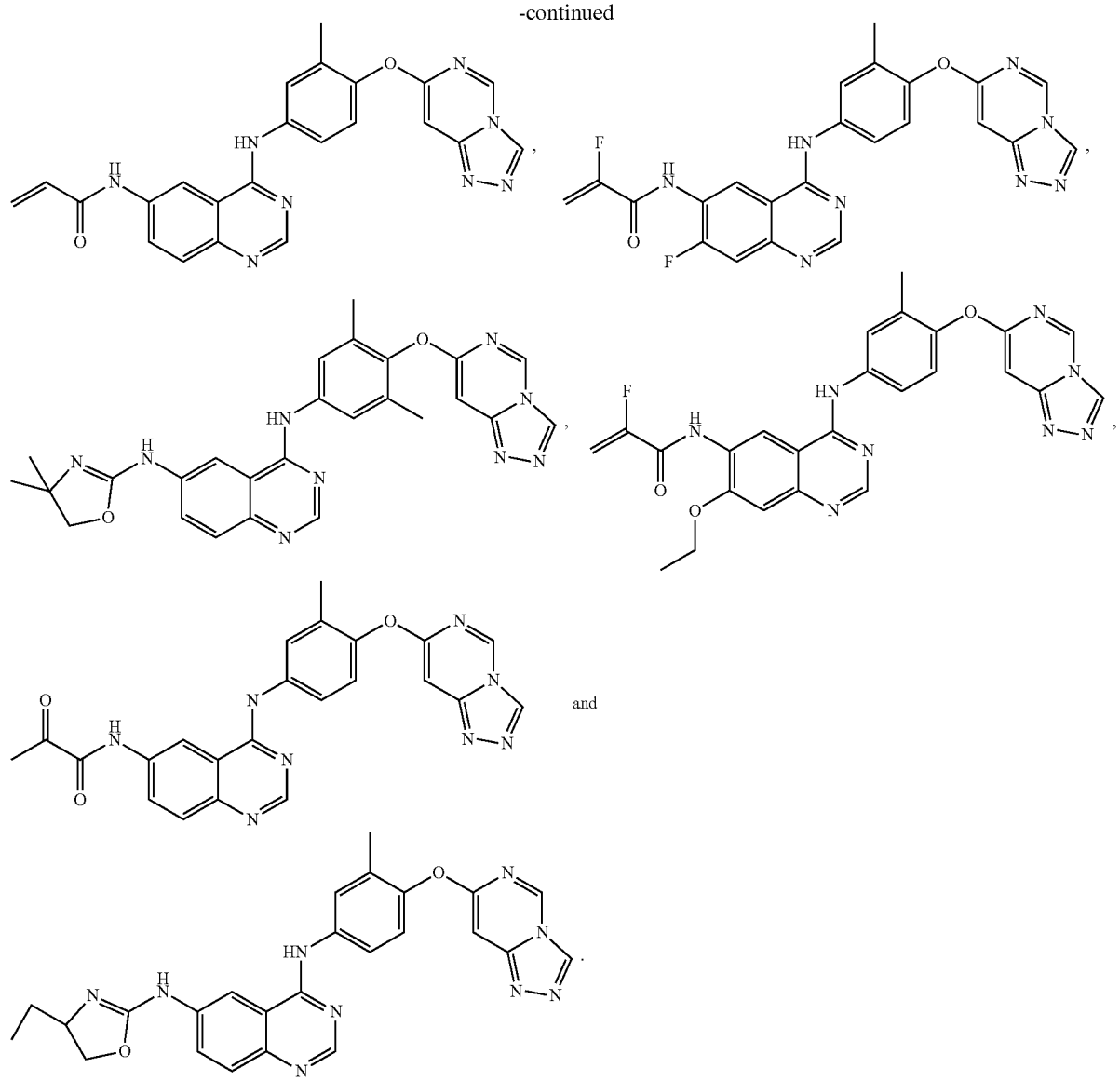
264
-continued
9. Compound 3, 3', 6, 9, 12, 32 or 33 as shown below:
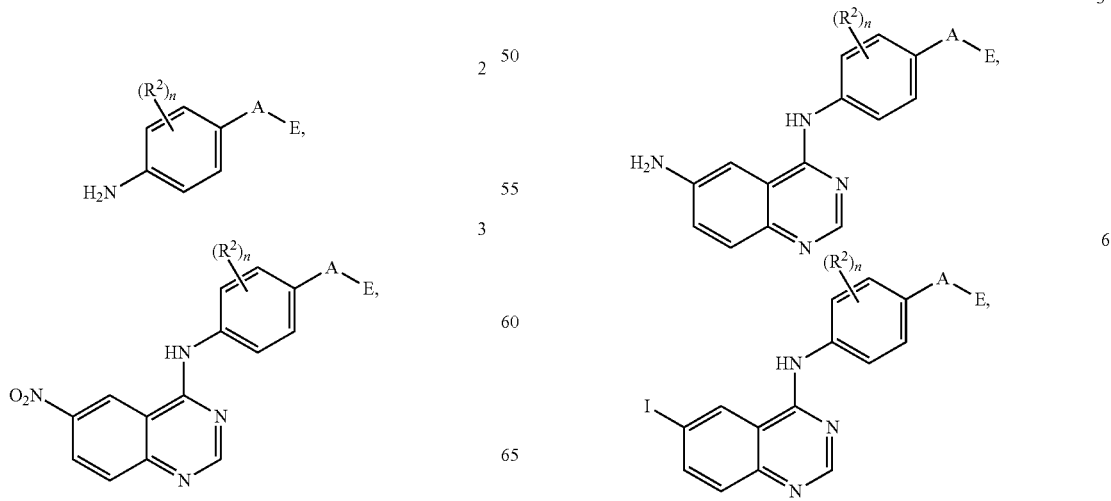

-continued
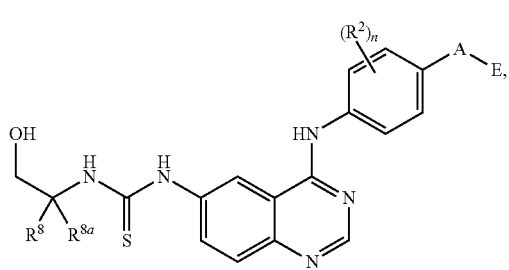
9
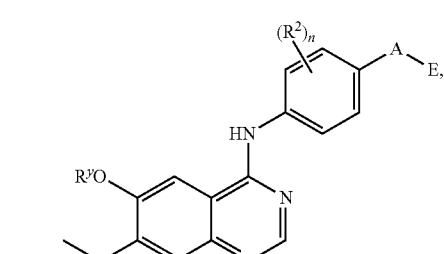
12
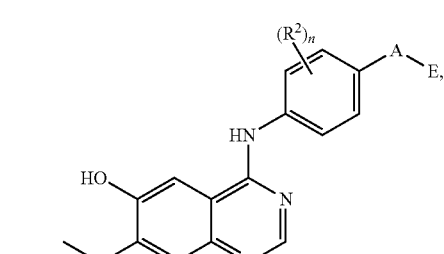
32
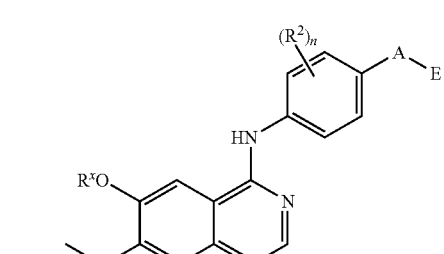
33
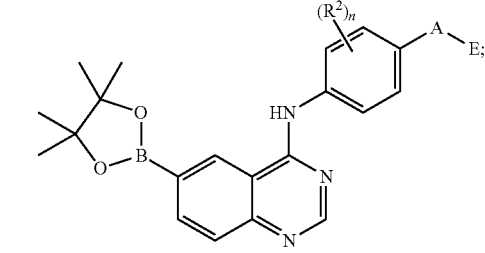
wherein, A E, n, $R^2$, $R^8$ and $R^{8a}$ are defined as claim 1; $R^y$ is a hydroxy protecting group; $R^xO$— is a leaving group.
10. Compound 2, 3, 3', 6, 9, 12, 32 or 33 as shown below:
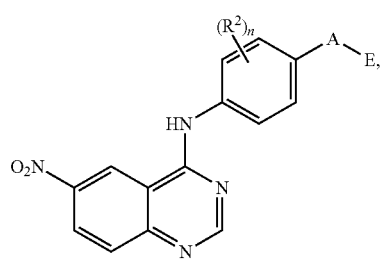
3
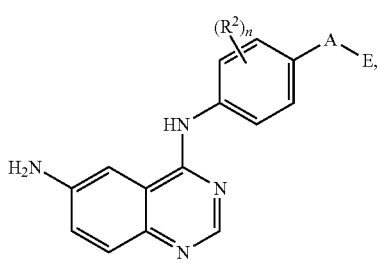
3'
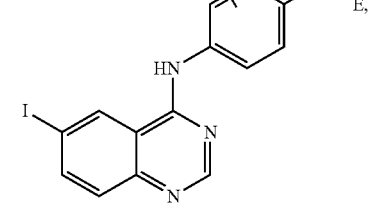
6
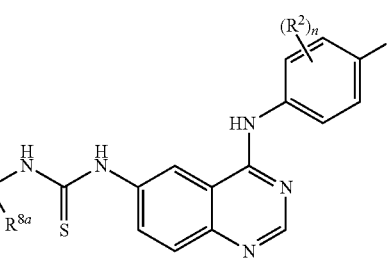
9
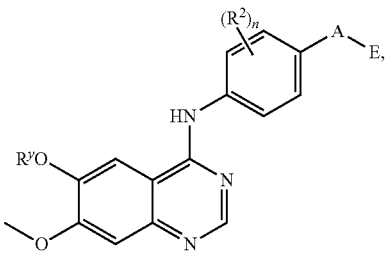
12
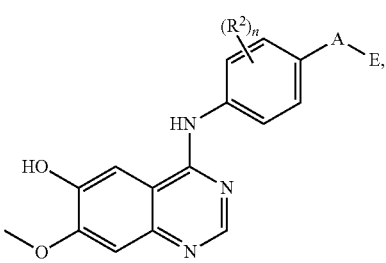
32

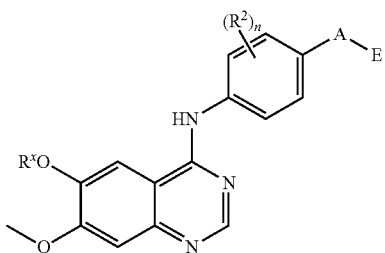

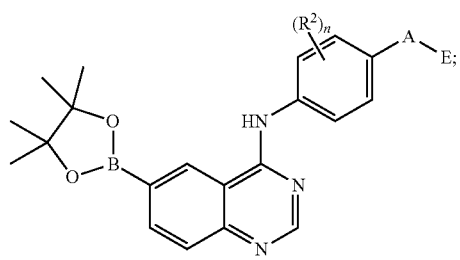

wherein, A, E, n, R², R⁸ and R⁸ᵃ are defined as claim 1; Rʸ is a hydroxy protecting group; RˣO— is a leaving group;

compound 2 is selected from 4-([1,2,4]triazolo[4,3-c]pyrimidin-7-yloxy)-3-methylaniline, 4-(imidazo[1,2-c]pyrimidin-7-yloxy)-3-methylaniline and 3-fluoro-4-([1,2,4]triazolo[4,3-c]pyrimidin-7-yloxy)aniline;

compound 3 is selected from the group consisting of

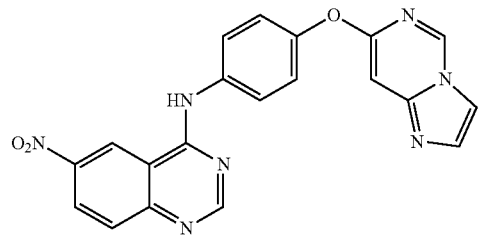

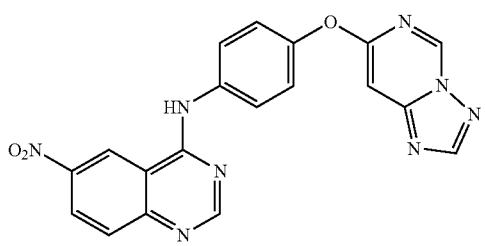

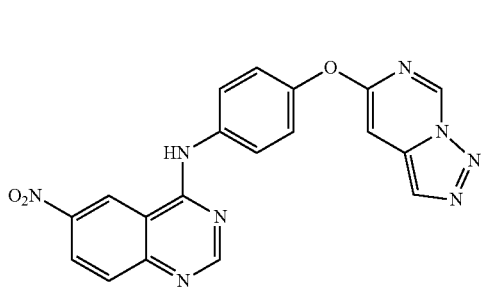

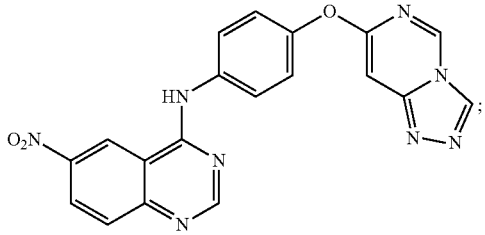

compound 3' is selected from the group consisting of

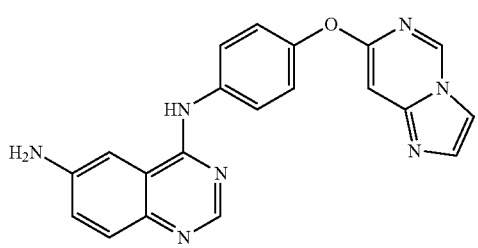

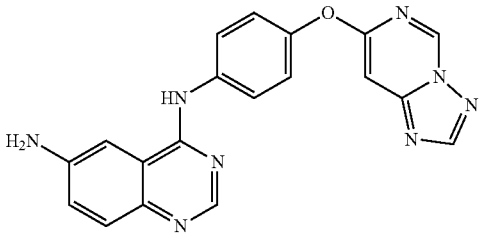

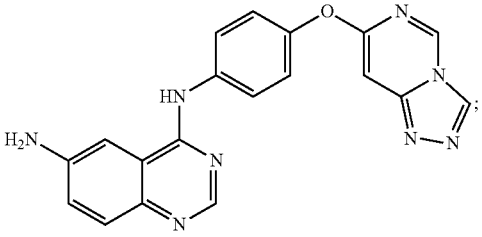

compound 6 is N-(4-([1,2,4]triazolo[4,3-c]pyrimidin-7-yloxy)-3-methylphenyl)-6-iodoquinazolin-4-amine;

compound 9 is 1-(1-hydroxy-2-methylpropan-2-yl)-3-(4-((4-(imidazo[1,2-c]pyrimidin-7-yloxy)-3-methylphenyl)amino)quinazolin-6-yl)thiourea or 1-(4-((4-([1,2,4]triazolo[4,3-c]pyrimidin-7-yloxy)-3-methylphenyl)amino)quinazolin-6-yl)-3-(1-hydroxy-2-methylpropan-2-yl)thiourea.

11. A composition, comprising the nitrogenous heterocyclic compound, the pharmaceutically acceptable salt, the enantiomer, the diastereomer, the tautomer or the solvate thereof as defined in claim 1, and at least one kind of pharmaceutically excipient.

12. A method for preparing the compound I as defined in claim 1, which is any one of schemes 1-8;

scheme 1 comprising the following step: conducting an amidation reaction of compound 3' with a carboxylic acid to give compound 4; or, conducting a substitution reaction of compound 3' with an amine or an alcohol in the presence of a thio agent or carbonyldiimidazole to give compound 4;

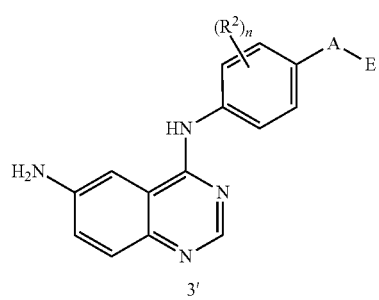

3'

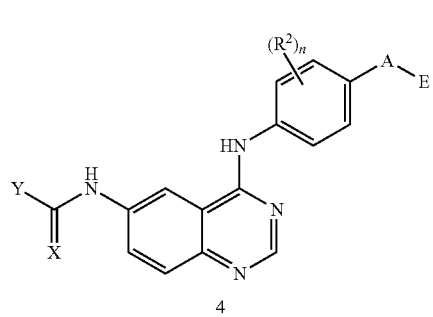

4 wherein,

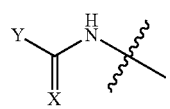

is —NR$^{15}$C(=O)OR$^{18}$, —NR$^{15}$C(=O)SR$^{18}$, —NR$^{15}$C(=O)R$^{16}$, NR$^{15}$C(=O)NR$^{16}$R$^{17}$, —NR$^{15}$C(=S)NR$^{16}$R$^{17}$ or —NR$^{15}$C(=S)R$^{16}$ as defined in claim 1;

scheme 2 comprising the following step: conducting a coupling reaction of compound 6 with R$^{15}$NH$_2$ in an organic solvent in the presence of a palladium catalyst, a phosphine ligand and a base to give the compound 31; or scheme 2 comprising the following step: conducting a coupling reaction of compound 6 with "boronic acid, olefin, or organotin compound" in the presence of a palladium catalyst to give compound 7;

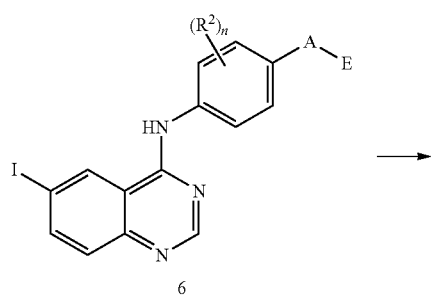

6

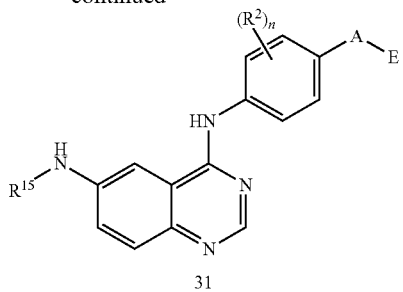

31

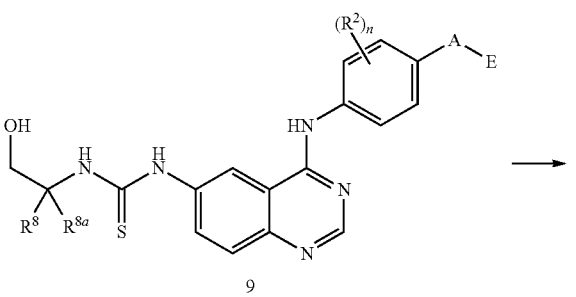

6

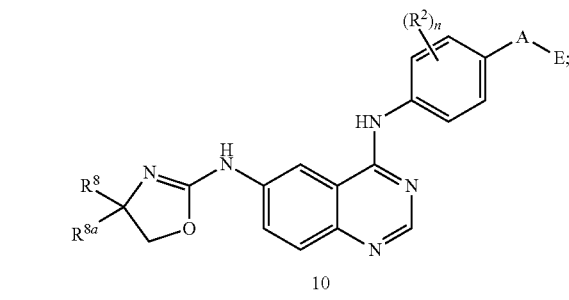

7 scheme 3 comprising the following step: conducting a cyclization reaction of compound 9 to give compound 10;

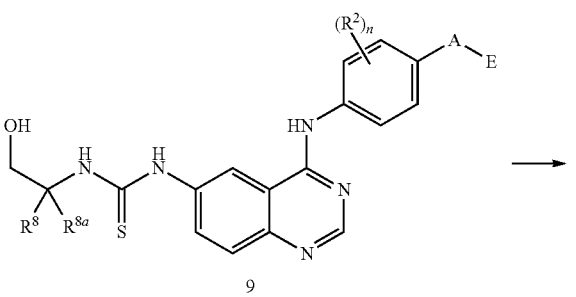

9

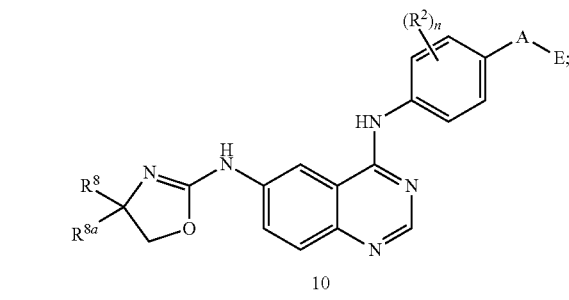

10 scheme 4 comprising the following step: conducting a cyclization reaction of compound 20 and compound 2 in an organic solvent in the presence of an acid to give compound 10;

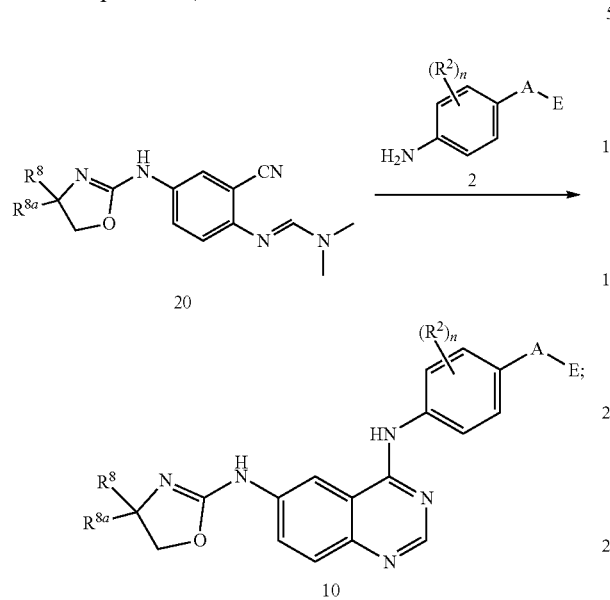

scheme 5 comprising the following step: conducting a substitution reaction of

with compound 32 in the presence of triphosgene and a base in an organic solvent to give compound 13;

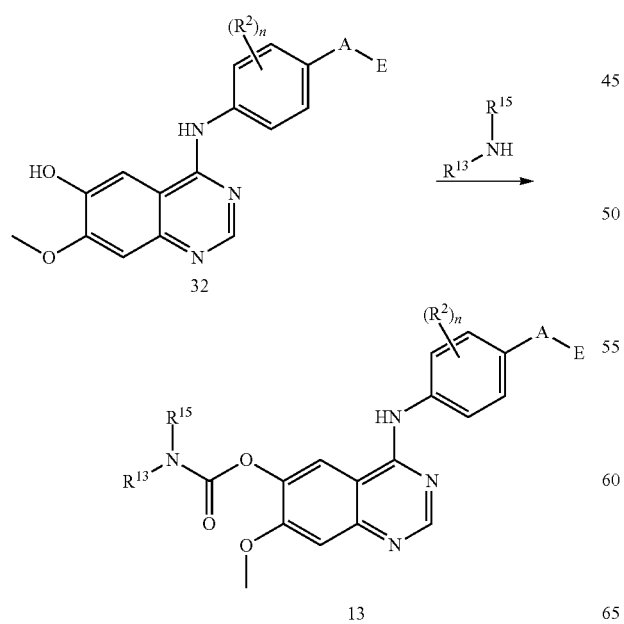

scheme 6 comprising the following step: conducting a substitution reaction of compound 32 with $R^{15}$—$X^1$ to give compound 13';

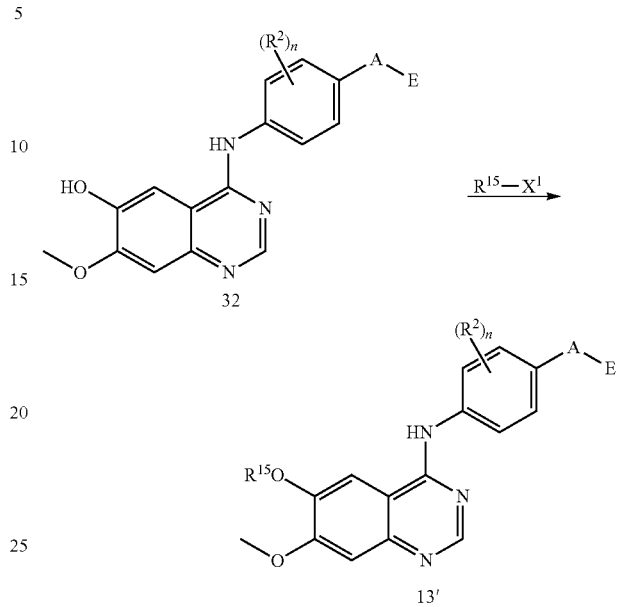

wherein, $X^1$ is H or a leaving group;

scheme 7 comprising the following step: conducting a substitution reaction of compound 33 with $R^{15}$—OH to give the compound 13';

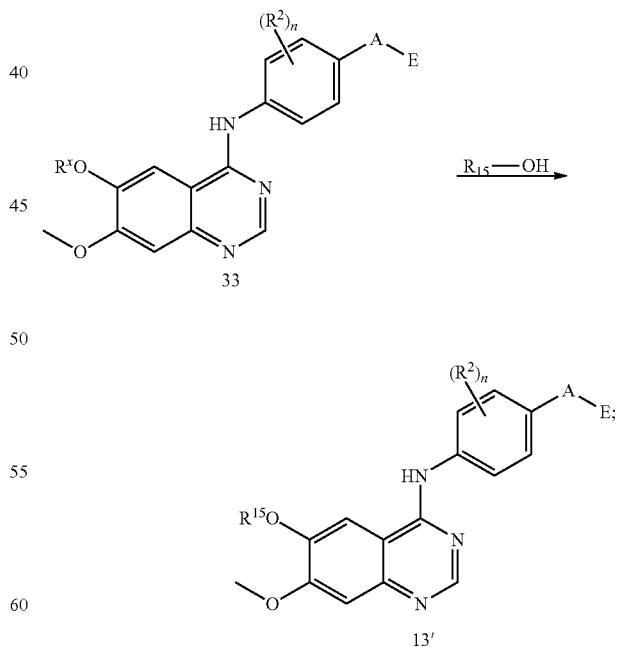

wherein, $R^xO$— is a leaving group;

scheme 8 comprising the following step: conducting a cyclization reaction of compound 9 in the presence of DIAD and PPh$_3$ to give compound 21;

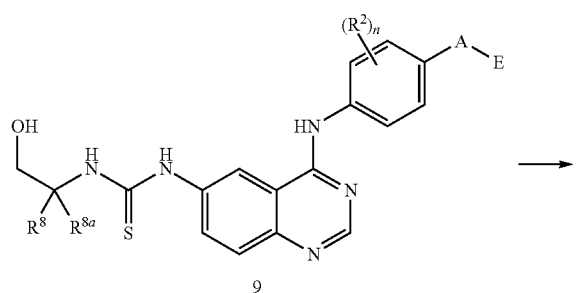

9

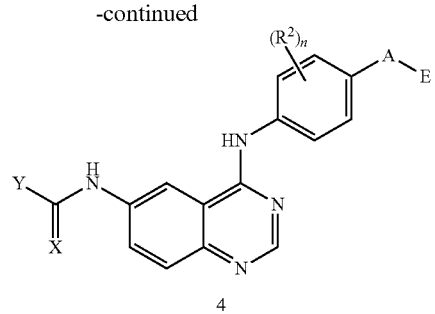

4

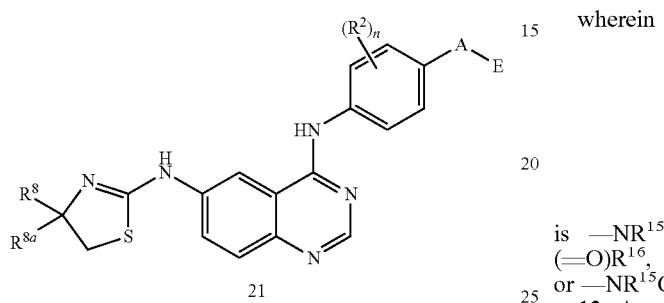

21 scheme 9 comprising the following step: conducting a cyclization reaction of compound 25 and compound 2 in the presence of an acid in an organic solvent to give compound 4;

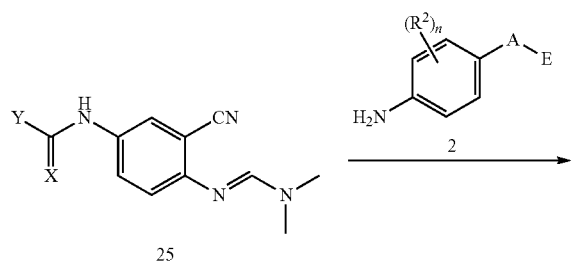

25 wherein is —NR$^{15}$C(=O)OR$^{18}$, —NR$^{15}$C(=O)SR$^{18}$, —NR$^{15}$C(=O)R$^{16}$, NR$^{15}$C(=O)NR$^{16}$R$^{17}$, —NR$^{15}$C(=S)NR$^{16}$R$^{17}$ or —NR$^{15}$C(=S)R$^{16}$ as defined in claim 1.

13. A process for manufacturing EGFR and/or ErbB2 receptor tyrosine kinase inhibitors by employing the nitrogenous heterocyclic compound, the pharmaceutically acceptable salt, the enantiomer, the diastereomer, the tautomer or the solvate thereof as defined in claim 1.

14. The process as defined in claim 13, wherein the EGFR and/or ErbB2 receptor tyrosine kinase inhibitors refer to selective inhibitor for ErbB2 receptor tyrosine kinases.

15. A method for treating a patient in need of a medicament for inhibiting EGFR and/or ErbB2 receptor tyrosine kinase, comprising administering to the patient a medicament comprising an effective amount of the nitrogenous heterocyclic compound, the pharmaceutically acceptable salt, the enantiomer, the diastereomer, the tautomer or the solvate thereof as defined in claim 1.

16. The method as defined in claim 15, wherein the "inhibiting EGFR and/or ErbB2 receptor tyrosine kinase" refers to selectively inhibiting ErbB2 receptor tyrosine kinase.

17. The method as defined in claim 16, wherein the selectively inhibiting ErbB2 receptor tyrosine kinase is used to treat breast cancer or gastric cancer.

* * * * *